US012599583B2

(12) United States Patent
Ahmed et al.

(10) Patent No.: US 12,599,583 B2
(45) Date of Patent: Apr. 14, 2026

(54) SMALL MOLECULE GRB2 STABILIZERS FOR RAS MAP KINASE INHIBITION

(71) Applicants: Board of Regents, The University of Texas System, Austin, TX (US); Board of Trustees of the University of Arkansas, Little Rock, AR (US)

(72) Inventors: Zamal Ahmed, Houston, TX (US); John A. Tainer, Houston, TX (US); Darin E. Jones, Little Rock, AR (US)

(73) Assignees: Board of Regents, The University of Texas System, Austin, TX (US); Board of Trustees of the University of Arkansas, Little Rock, AR (US)

( * ) Notice: Subject to any disclaimer, the term of this patent is extended or adjusted under 35 U.S.C. 154(b) by 1041 days.

(21) Appl. No.: 17/439,148

(22) PCT Filed: Mar. 13, 2020

(86) PCT No.: PCT/US2020/022722
§ 371 (c)(1),
(2) Date: Sep. 14, 2021

(87) PCT Pub. No.: WO2020/186202
PCT Pub. Date: Sep. 17, 2020

(65) Prior Publication Data

US 2022/0151991 A1 May 19, 2022

Related U.S. Application Data

(60) Provisional application No. 62/818,502, filed on Mar. 14, 2019.

(51) Int. Cl.
*A61K 31/404* (2006.01)
*A61K 31/4184* (2006.01)
(Continued)

(52) U.S. Cl.
CPC ........ *A61K 31/404* (2013.01); *A61K 31/4184* (2013.01); *A61K 31/423* (2013.01);
(Continued)

(58) Field of Classification Search
None
See application file for complete search history.

(56) References Cited

U.S. PATENT DOCUMENTS 6,410,529 B1 6/2002 Chan et al.
8,431,572 B2 4/2013 Schadt et al.
(Continued)

FOREIGN PATENT DOCUMENTS

CN 103373971 A * 10/2013 ........... C07D 217/22
EP 0193051 A2 9/1986
(Continued)

OTHER PUBLICATIONS

Meanwell NA. Tactical Applications to Address Developability Problems. Tactics in Contemporary Drug Design. Jan. 28, 2014;9:283-381 (Year: 2014).*

(Continued)

*Primary Examiner* — Jeffrey S Lundgren
*Assistant Examiner* — Anthony Joseph Seitz
(74) *Attorney, Agent, or Firm* — pH IP Law

(57) ABSTRACT

The present disclosure compounds of the formula (I-A) or (I), wherein the variables are defined herein, as well as pharmaceutical compositions thereof. The present disclosure also provides methods for the use of said compounds and/or pharmaceutical compositions, such as in the treatment of cancer. The present disclosure also provides methods for the use of compounds of the formula (III), wherein the variables are defined herein.

(Continued)

(I-A)

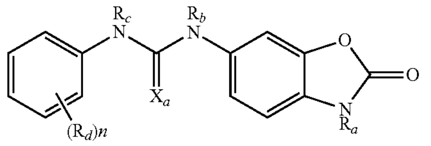

(I)

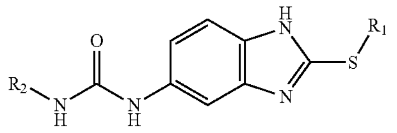

(III)

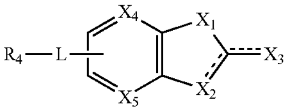

16 Claims, 15 Drawing Sheets

(51) Int. Cl.

| | |
|---|---|
| ***A61K 31/423*** | (2006.01) |
| ***A61K 31/5377*** | (2006.01) |
| ***A61P 35/00*** | (2006.01) |
| ***C07D 209/34*** | (2006.01) |
| ***C07D 235/26*** | (2006.01) |
| ***C07D 235/28*** | (2006.01) |
| ***C07D 263/58*** | (2006.01) |
| ***C07D 405/12*** | (2006.01) |
| ***C07D 409/12*** | (2006.01) |

(52) U.S. Cl.

CPC .......... *A61K 31/5377* (2013.01); *A61P 35/00* (2018.01); *C07D 209/34* (2013.01); *C07D 235/26* (2013.01); *C07D 235/28* (2013.01); *C07D 263/58* (2013.01); *C07D 405/12* (2013.01); *C07D 409/12* (2013.01)

(56) References Cited

U.S. PATENT DOCUMENTS

| | | | | |
|---|---|---|---|---|
| 2009/0239841 | A1 | 9/2009 | Hutchison et al. | |
| 2010/0179146 | A1 | 7/2010 | Huang et al. | |
| 2017/0182010 | A1 | 6/2017 | Piomelli et al. | |
| 2023/0366033 | A1 * | 11/2023 | Tainer .................. | A61K 31/502 |

FOREIGN PATENT DOCUMENTS

| | | | | | |
|---|---|---|---|---|---|
| WO | WO 2012/088491 | A2 | | 6/2012 | |
| WO | WO-2019043217 | A1 | * | 3/2019 | ........... C07D 235/26 |

OTHER PUBLICATIONS

Brown, Bioisosteres in Medicinal Chemistry, 2012 (Year: 2012).*

Gülkok, et al., (2012). Synthesis of some new urea and thiourea derivatives and evaluation of their antimicrobial activities. Turkish Journal of Chemistry 36 (2): 279-291 (Year: 2012).*

CAS Reg No. 1223984-74-4 (Year: 2012).*

Extended European Search Report issued in European Patent Application No. 20770574.0, dated Mar. 10, 2023.

Gülkok, Y. et al., "Synthesis of some new urea and thiourea derivatives and evaluation of their antimicrobial activities," *Turkish Journal of Chemistry*, 36 (2012): 279-291.

Kolasa, K. et al., "Wstepne Badania Farmakologiczne Orsodkowego Dzialania Pochodnych Fenylowych I Piperydynometylowej Benzoksazolonu-2," *Ann Univ Mariae Curie Sklodowska Med*, 36 (1981): 73-81. (Polish Language) (see reference C1 for the degree of relevance found by a foreign office).

PCT International Preliminary Report on Patentability issued in International Patent Application No. PCT/US2020/022722, mailed Sep. 23, 2021.

PCT International Search Report and Written Opinion issued in International Patent Application No. PCT/US2020/022722, mailed Jul. 27, 2020.

Partial Supplementary European Search Report issued in European Patent Application No. 20770574.0, dated Dec. 12, 2022.

Pubchem-CID: 50796823, create date Feb. 22, 2011; pp. 1-8.

Wang, T. et al., "Discovery of novel CDK8 inhibitors using multiple crystal structures in docking-based virtual screening," *European Journal of Medicinal Chemistry*, 129 (2017): 275-285.

* cited by examiner

GRB002(<700nM)

GRB001 (25uM)

GRB003 (>100uM)

GRB004 (50uM)

GRB005 (50uM)

GRB008 (NB)

GRB011 (NB)

GRB006 (>100uM)

GRB009 (>100uM)

GRB010 (>100uM)

C

ITC Control

| Cell-lines | K-RAS Status | TP53 Status | Other relavant driver mutations |
|---|---|---|---|
| PC3 cells | WT | WT | ALK F1174L; BRAF Q257K |
| HEK293T | WT | WT | |
| NIH-3T3 | WT | WT | |
| OVCAR-5 | G12V | | ERCC2 R616P; EX01 E828A; RNF43 W302C |
| OVCAR-8 | P121H | | ERBB2 G776V; PARP16 G199V |
| A549 | G12S | | SMARCA4 Q729fs*4 (Homo) |
| MDA-MB-231 | G13D | R280K | BRAF G464V; NF2 E231* |
| H1975 | WT | R273H | EGFR (heterozygous) T790M and L858R |
| H1299 | WT | NULL | N-RAS Q61K |

FIG. 15

SMALL MOLECULE GRB2 STABILIZERS FOR RAS MAP KINASE INHIBITION

The present application is a national phase application under 35 U.S.C. § 371 of International Application No. PCT/US2020/022722, filed Mar. 13, 2020, which claims the priority benefit of U.S. Provisional Application Ser. No. 62/818,502, filed Mar. 14, 2019, the entire contents of each of which are hereby incorporated by reference.

BACKGROUND

I. Field of the Invention

The present disclosure relates in general to the field of chemistry and medicine, specifically to compositions of matter and methods of their use in medical indications, such as cancer.

II. Description of Related Art

The growth factor receptor tyrosine kinases such as EGFR are potent inducers of cell proliferation. Ligands binding to receptor induces receptor-dimerization and activation, which in turn recruit intracellular molecules for downstream signal transduction. A key signaling pathway activated by RTKs is the Ras signaling cascade. GRB2 is a cytoplasmic adapter protein constitutively bound to the mammalian homologue of *drosophila* son of sevenless (SOS), and a guanine exchange factor (GEF) for Ras. All RTKs recruit GRB2 either directly or indirectly to their early signaling complex (ESC) as a way to position SOS-GEF at a close proximity to Ras for activating the Ras-MAP kinase cascade.

It has previously shown that under high protein concentration GRB2 could form dimers. Additionally, under physiological conditions there is a monomer dimer equilibrium where only the monomeric GRB2 (mGRB2) is capable of binding to SOS and activate MAP kinase, while the dimeric GRB2 (dGRB2) is inhibitory to this process (Ahmed et al., 2015). This has inspired development of an entirely new type of small molecule inhibitors for GRB2 function. Since the dimeric GRB2 is the autoinhibited form, it was reasoned that the design of small molecule therapeutics capable of stabilizing the dimer interface and thereby inhibiting the cellular proliferative signal would provide a new avenue for RAS/MAP kinase activity in many cancers, for which there currently exists a significant need.

SUMMARY

The present disclosure provides compounds for the treatment and/or prevention of diseases or disorders, such as cancer. These small molecules stabilize dimeric GRB2, which leads to inhibition of RAS and downstream RTK signaling.

In some aspects, the present disclosure provides compounds of the formula:

(I-A)

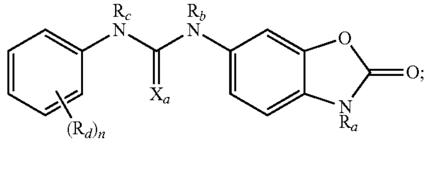

wherein:

n is 2, 3, 4, or 5;

$X_a$ is O or S;

$R_a$ is hydrogen; or alkyl$_{(C\leq12)}$, aralkyl$_{(C\leq12)}$, heteroaralkyl$_{(C\leq12)}$, or a substituted version of any of these groups;

$R_b$ and $R_c$ are each independently hydrogen, alkyl$_{(C\leq12)}$, or substituted alkyl$_{(C\leq12)}$; and $R_d$ is in each instance independently halo, hydroxy, cyano, nitro, alkyl$_{(C\leq12)}$, substituted alkyl$_{(C\leq12)}$, alkoxy$_{(C\leq12)}$, or substituted alkoxy$_{(C\leq12)}$; or a compound of the formula:

(I)

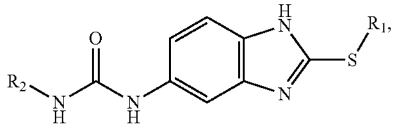

wherein:

$R_1$ is hydrogen; or alkyl$_{(C\leq12)}$, aralkyl$_{(C\leq12)}$, heteroaralkyl$_{(C\leq12)}$, or a substituted version of any of these groups; and $R_2$ is aralkyl$_{(C\leq12)}$, heteroaryl$_{(C\leq12)}$, heteroaralkyl$_{(C\leq12)}$, or a substituted version of any of these groups; or a group of the formula:

(Ia)

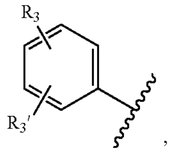

wherein:

$R_3$ is hydrogen, hydroxy, halo, amino, nitro, cyano, carboxy, or mercapto; or alkyl$_{(C\leq12)}$, alkoxy$_{(C\leq12)}$, alkylamino$_{(C\leq12)}$, dialkylamino$_{(C\leq12)}$, acyl$_{(C\leq12)}$, acyloxy$_{(C\leq12)}$, amido$_{(C\leq12)}$, or a substituted version of any of these groups; or —C(O)NR$_{3a}$R$_{3b}$, wherein:

$R_{3a}$ and $R_{3b}$ are each independently hydrogen, alkyl$_{(C\leq12)}$, or substituted alkyl$_{(C\leq12)}$;

$R_3$' is hydrogen, hydroxy, halo, amino, nitro, cyano, carboxy, or mercapto; or alkyl$_{(C\leq12)}$, alkylamino$_{(C\leq12)}$, dialkylamino$_{(C\leq12)}$, acyl$_{(C\leq12)}$, acyloxy$_{(C\leq12)}$, amido$_{(C\leq12)}$, or a substituted version of any of these groups; or —C(O)NR$_{3c}$R$_{3d}$, wherein:

$R_{3c}$ and $R_{3d}$ are each independently hydrogen, alkyl$_{(C\leq12)}$, or substituted alkyl$_{(C\leq12)}$; or $R_3$ and $R_3$' are taken together and are alkenediyl$_{(C\leq12)}$ or substituted alkenediyl$_{(C\leq12)}$;

or a pharmaceutically acceptable salt and/or tautomer of either of these formulae.

In some embodiments, the compounds are further defined as:

(I-A)

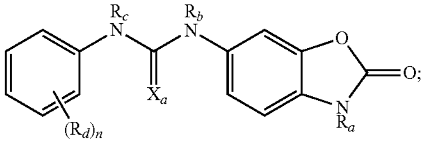

wherein:

n is 2, 3, 4, or 5;

$X_a$ is O or S;

$R_a$ is hydrogen; or alkyl$_{(C\leq 12)}$, aralkyl$_{(C\leq 12)}$, heteroaralkyl$_{(C\leq 12)}$, or a substituted version of any of these groups;

$R_b$ and $R_c$ are each independently hydrogen, alkyl$_{(C\leq 12)}$, or substituted alkyl$_{(C\leq 12)}$; and $R_d$ is in each instance independently halo, hydroxy, cyano, nitro, alkyl$_{(C\leq 12)}$, substituted alkyl$_{(C\leq 12)}$, alkoxy$_{(C\leq 12)}$, or substituted alkoxy$_{(C\leq 12)}$;

or a pharmaceutically acceptable salt and/or tautomer thereof.

In further embodiments, the compounds are further defined as:

(I-B)

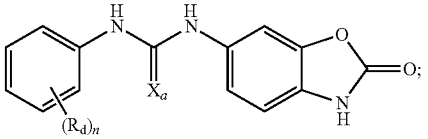

wherein:

n is 2, 3, 4, or 5;

$X_a$ is O or S; and $R_d$ is in each instance independently halo, hydroxy, cyano, nitro, alkyl$_{(C\leq 12)}$, substituted alkyl$_{(C\leq 12)}$, alkoxy$_{(C\leq 12)}$, or substituted alkoxy$_{(C\leq 12)}$;

or a pharmaceutically acceptable salt and/or tautomer thereof.

In some embodiments, $X_a$ is O. In other embodiments, $X_a$ is S. In some embodiments, n is 2 or 3. In some embodiments, n is 2. In other embodiments, n is 3. In some embodiments, $R_d$ is hydroxy. In other embodiments, $R_d$ is halo, such as chloro or fluoro. In still other embodiments, $R_d$ is alkyl$_{(C\leq 12)}$ or substituted alkyl$_{(C\leq 12)}$. In some embodiments, $R_d$ is alkyl$_{(C\leq 12)}$, such as methyl. In yet other embodiments, $R_d$ is alkoxy$_{(C\leq 12)}$ or substituted alkoxy$_{(C\leq 12)}$. In some embodiments, alkoxy$_{(C\leq 12)}$, such as methoxy.

In some embodiments, the compound is defined as:

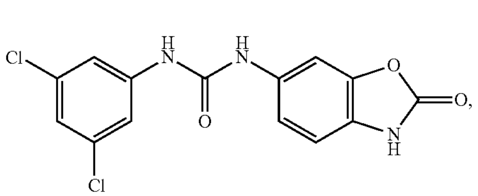

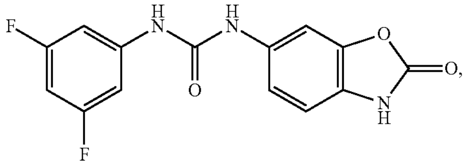

-continued

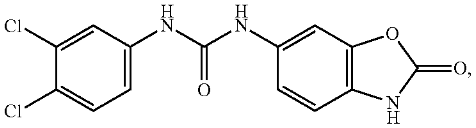

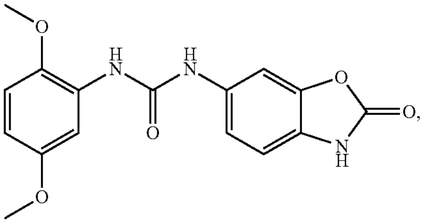

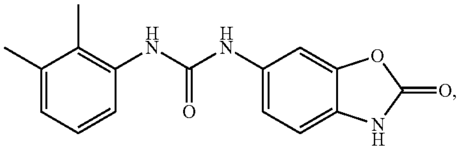

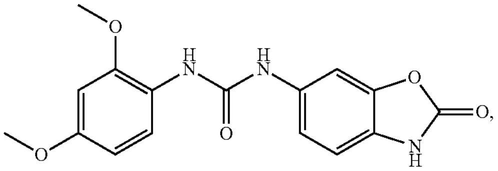

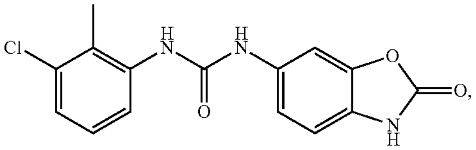

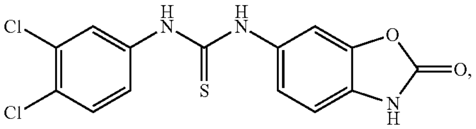

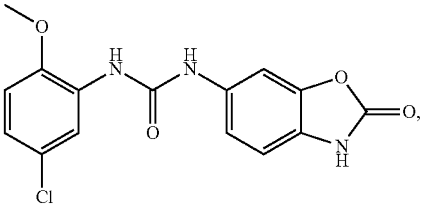

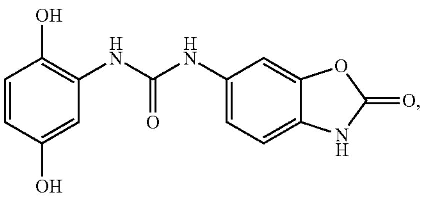

or

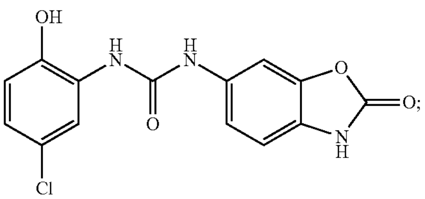

or a pharmaceutically acceptable salt and/or tautomer thereof.

In some embodiments, the compounds are of the formula:

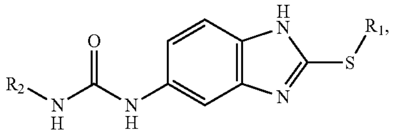

(I)

wherein:

$R_1$ is hydrogen; or alkyl$_{(C\le12)}$, aralkyl$_{(C\le12)}$, heteroaralkyl$_{(C\le12)}$, or a substituted version of any of these groups; and $R_2$ is aralkyl$_{(C\le12)}$, heteroaryl$_{(C\le12)}$, heteroaralkyl$_{(C\le12)}$, or a substituted version of any of these groups; or a group of the formula:

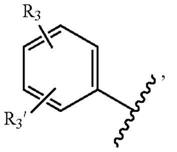

(Ia)

wherein:

$R_3$ is hydrogen, hydroxy, halo, amino, nitro, cyano, carboxy, or mercapto; or alkyl$_{(C\le12)}$, alkoxy$_{(C\le12)}$, alkylamino$_{(C\le12)}$, dialkylamino$_{(C\le12)}$, acyl$_{(C\le12)}$, acyloxy$_{(C\le12)}$, amido$_{(C\le12)}$, or a substituted version of any of these groups; or —C(O)NR$_{3a}$R$_{3b}$, wherein:

$R_{3a}$ and $R_{3b}$ are each independently hydrogen, alkyl$_{(C\le12)}$, or substituted alkyl$_{(C\le12)}$;

$R_3$' is hydrogen, hydroxy, halo, amino, nitro, cyano, carboxy, or mercapto; or alkyl$_{(C\le12)}$, alkylamino$_{(C\le12)}$, dialkylamino$_{(C\le12)}$, acyl$_{(C\le12)}$, acyloxy$_{(C\le12)}$, amido$_{(C\le12)}$, or a substituted version of any of these groups; or —C(O)NR$_{3c}$R$_{3d}$, wherein:

$R_{3c}$ and $R_{3d}$ are each independently hydrogen, alkyl$_{(C\le12)}$, or substituted alkyl$_{(C\le12)}$; or $R_3$ and $R_3$' are taken together and are alkenediyl $_{(C\le12)}$ or substituted alkenediyl$_{(C\le12)}$;

or a pharmaceutically acceptable salt and/or tautomer thereof.

In some embodiments, the compounds are further defined as:

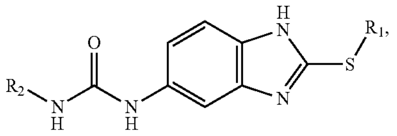

(I)

wherein:

$R_1$ is hydrogen; or alkyl$_{(C\le12)}$, aralkyl$_{(C\le12)}$, heteroaralkyl$_{(C\le12)}$, or a substituted version of any of these groups; and $R_2$ is aralkyl$_{(C\le12)}$, or a substituted version of any of these groups; or a group of the formula:

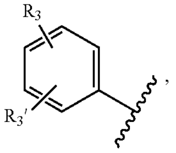

(Ia)

wherein:

$R_3$ is hydrogen, hydroxy, halo, amino, nitro, cyano, carboxy, or mercapto; or alkyl$_{(C\le12)}$, alkoxy$_{(C\le12)}$, alkylamino$_{(C\le12)}$, dialkylamino$_{(C\le12)}$, acyl$_{(C\le12)}$, acyloxy$_{(C\le12)}$, amido$_{(C\le12)}$, or a substituted version of any of these groups; or —C(O)NR$_{3a}$R$_{3b}$, wherein:

$R_{3a}$ and $R_{3b}$ are each independently hydrogen, alkyl$_{(C\le12)}$, or substituted alkyl$_{(C\le12)}$;

$R_3$' is hydrogen, hydroxy, halo, amino, nitro, cyano, carboxy, or mercapto; or alkyl$_{(C\le12)}$, alkylamino$_{(C\le12)}$, dialkylamino$_{(C\le12)}$, acyl$_{(C\le12)}$, acyloxy$_{(C\le12)}$, amido$_{(C\le12)}$, or a substituted version of any of these groups; or —C(O)NR$_{3c}$R$_{3d}$, wherein:

$R_{3c}$ and $R_{3d}$ are each independently hydrogen, alkyl$_{(C\le12)}$, or substituted alkyl$_{(C\le12)}$; or $R_3$ and $R_3$' are taken together and are alkenediyl $_{(C\le12)}$ or substituted alkenediyl$_{(C\le12)}$;

or a pharmaceutically acceptable salt and/or tautomer thereof.

In further embodiments, the compounds are further defined as:

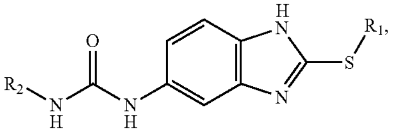

(I)

wherein:

$R_1$ is hydrogen; or alkyl$_{(C\le12)}$, substituted alkyl$_{(C\le12)}$, aralkyl$_{(C\le12)}$, or substituted aralkyl$_{(C\le12)}$; and $R_2$ is aralkyl$_{(C\le12)}$ or substituted aralkyl$_{(C\le12)}$; or a group of the formula:

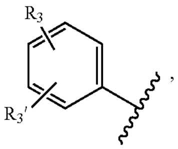

(Ia)

wherein:

$R_3$ is hydrogen, hydroxy, halo, amino, nitro, cyano, carboxy, or mercapto; or alkyl$_{(C\le12)}$, alkoxy$_{(C\le12)}$, alkylamino$_{(C\le12)}$, dialkylamino$_{(C\le12)}$, acyl$_{(C\le12)}$, acyloxy$_{(C\le12)}$, amido$_{(C\le12)}$, or a substituted version of any of these groups; or —C(O)NR$_{3a}$R$_{3b}$, wherein:

R$_{3a}$ and R$_{3b}$ are each independently hydrogen, alkyl$_{(C\leq12)}$, or substituted alkyl$_{(C\leq12)}$;

R$_3$' is hydrogen, hydroxy, halo, amino, nitro, cyano, carboxy, or mercapto; or alkyl$_{(C\leq12)}$, alkylamino$_{(C\leq12)}$, dialkylamino$_{(C\leq12)}$, acyl$_{(C\leq12)}$, acyloxy$_{(C\leq12)}$, amido$_{(C\leq12)}$, or a substituted version of any of these groups; or —C(O)NR$_{3c}$R$_{3d}$, wherein:

R$_{3c}$ and R$_{3d}$ are each independently hydrogen, alkyl$_{(C\leq12)}$, or substituted alkyl$_{(C\leq12)}$; or R$_3$ and R$_3$' are taken together and are alkenediyl$_{(C\leq12)}$ or substituted alkenediyl$_{(C\leq12)}$;

or a pharmaceutically acceptable salt and/or tautomer thereof.

In some embodiments, R$_2$ is aralkyl$_{(C\leq12)}$ or substituted aralkyl$_{(C\leq12)}$. In further embodiments, R$_2$ is substituted aralkyl$_{(C\leq12)}$, such as 4-fluorobenzyl.

In other embodiments, the compounds are further defined as:

(II)

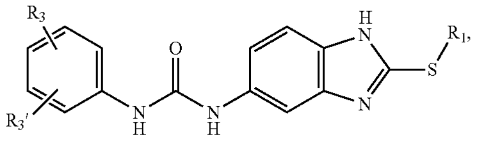

wherein:

R$_1$ is hydrogen; or alkyl$_{(C\leq12)}$, substituted alkyl$_{(C\leq12)}$, aralkyl$_{(C\leq12)}$, or substituted aralkyl$_{(C\leq12)}$; and R$_3$ is hydrogen, hydroxy, halo, amino, nitro, cyano, carboxy, or mercapto; or alkyl$_{(C\leq12)}$, alkoxy$_{(C\leq12)}$, alkylamino$_{(C\leq12)}$, dialkylamino$_{(C\leq12)}$, acyl$_{(C\leq12)}$, acyloxy$_{(C\leq12)}$, amido$_{(C\leq12)}$, or a substituted version of any of these groups; or —C(O)NR$_{3a}$R$_{3b}$, wherein:

R$_{3a}$ and R$_{3b}$ are each independently hydrogen, alkyl$_{(C\leq12)}$, or substituted alkyl$_{(C\leq12)}$;

R$_3$' is hydrogen, hydroxy, halo, amino, nitro, cyano, carboxy, or mercapto; or alkyl$_{(C\leq12)}$, alkylamino$_{(C\leq12)}$, dialkylamino$_{(C\leq12)}$, acyl$_{(C\leq12)}$, acyloxy$_{(C\leq12)}$, amido$_{(C\leq12)}$, or a substituted version of any of these groups; or —C(O)NR$_{3c}$R$_{3d}$, wherein:

R$_{3c}$ and R$_{3d}$ are each independently hydrogen, alkyl$_{(C\leq12)}$, or substituted alkyl$_{(C\leq12)}$; or R$_3$ and R$_3$' are taken together and are alkenediyl$_{(C\leq12)}$ or substituted alkenediyl$_{(C\leq12)}$;

or a pharmaceutically acceptable salt and/or tautomer thereof.

In some embodiments, R$_1$ is hydrogen. In other embodiments, R$_1$ is aralkyl$_{(C\leq12)}$ or substituted aralkyl$_{(C\leq12)}$. In further embodiments, R$_1$ is substituted aralkyl$_{(C\leq12)}$, such as 4-fluorobenzyl. In some embodiments, R$_3$ is hydrogen. In other embodiments, R$_3$ is cyano. In still other embodiments, R$_3$ is halo, such as fluoro. In yet other embodiments, R$_3$ is alkyl$_{(C\leq12)}$ or substituted alkyl$_{(C\leq12)}$. In further embodiments, R$_3$ is alkyl$_{(C\leq12)}$, such as methyl. In still other embodiments, R$_3$ is alkoxy$_{(C\leq12)}$ or substituted alkoxy$_{(C\leq12)}$. In further embodiments, R$_3$ is alkoxy$_{(C\leq12)}$, such as methoxy. In still other embodiments, R$_3$ is acyl$_{(C\leq12)}$ or substituted acyl$_{(C\leq12)}$. In further embodiments, R$_3$ is acyl$_{(C\leq12)}$, such as acetyl. In some embodiments, R$_3$' is hydrogen. In other embodiments, R$_3$' is cyano. In still other embodiments, R$_3$' is halo, such as fluoro. In yet other embodiments, R$_3$' is alkyl$_{(C\leq12)}$ or substituted alkyl$_{(C\leq12)}$. In further embodiments, R$_3$' is alkyl$_{(C\leq12)}$, such as methyl. In still other embodiments, R$_3$' is acyl$_{(C\leq12)}$ or substituted acyl$_{(C\leq12)}$. In further embodiments, R$_3$' is acyl$_{(C\leq12)}$, such as acetyl.

In some embodiments, the compounds are further defined as:

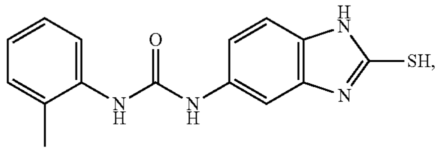

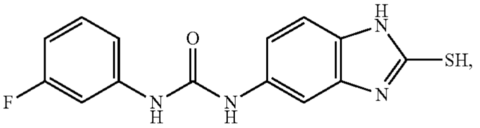

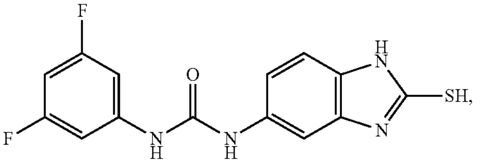

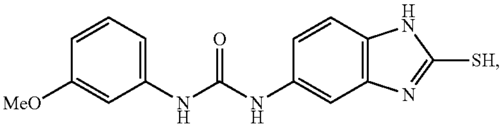

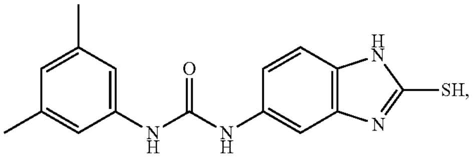

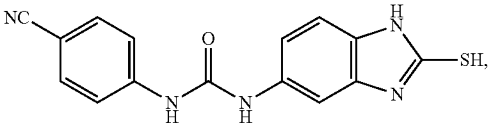

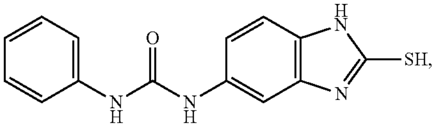

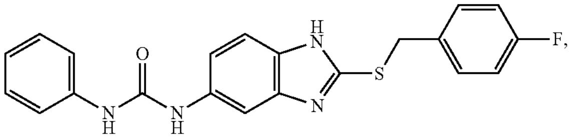

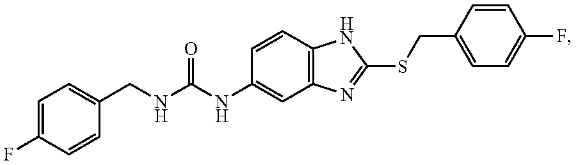

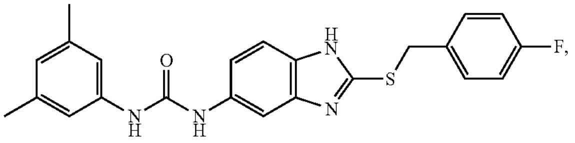

-continued

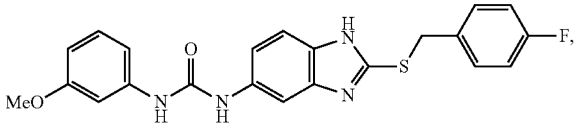

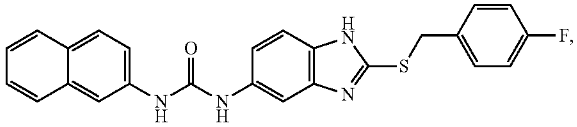

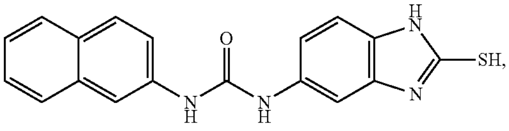

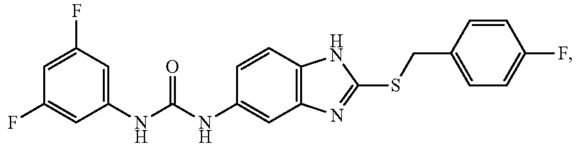

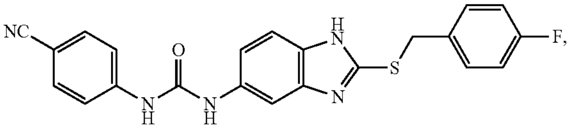

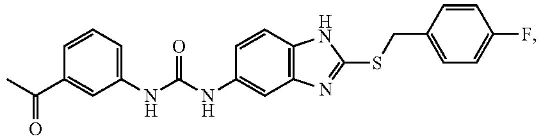
or

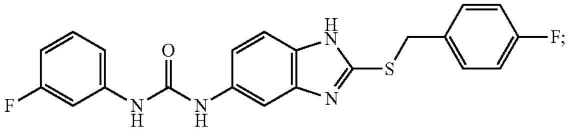

or a pharmaceutically acceptable salt and/or tautomer thereof.

In further embodiments, the compounds are further defined as:

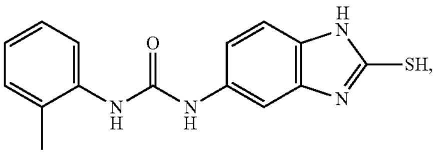

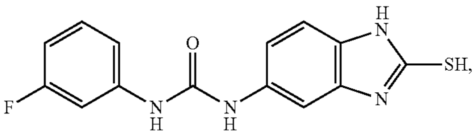

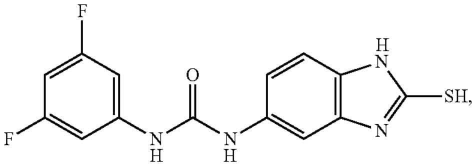

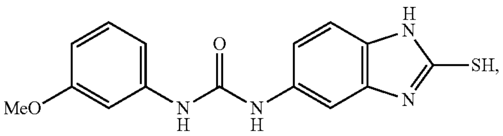

-continued

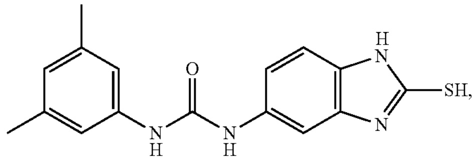

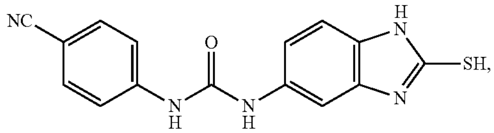

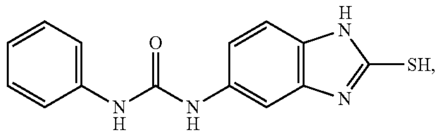
or

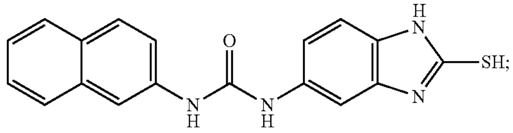

or a pharmaceutically acceptable salt and/or tautomer thereof.

In still further embodiments, the compounds are further defined as:

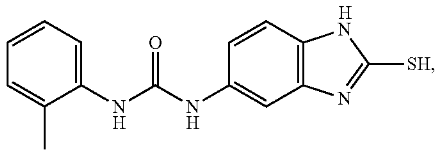

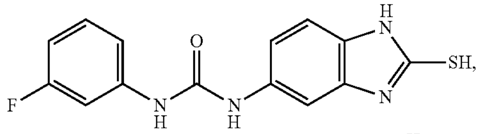
or

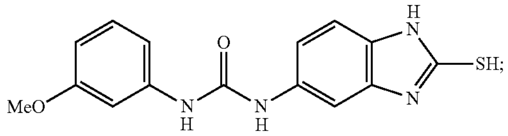

or a pharmaceutically acceptable salt and/or tautomer thereof.

In other embodiments, the compounds are further defined as:

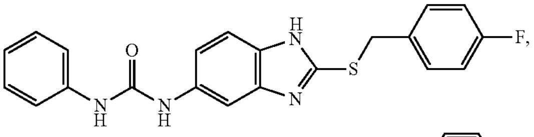

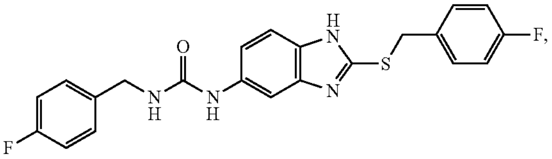

-continued
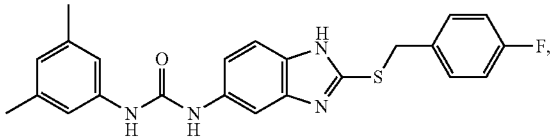
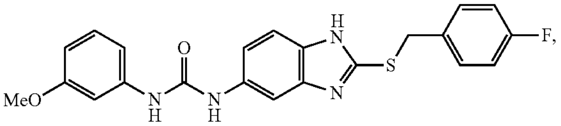
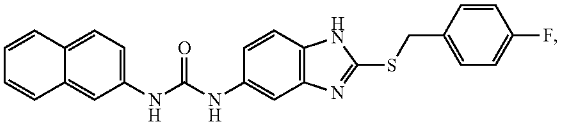
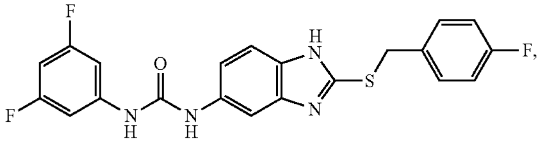
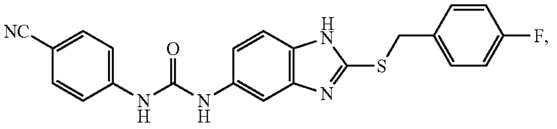
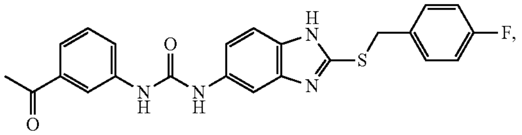
or
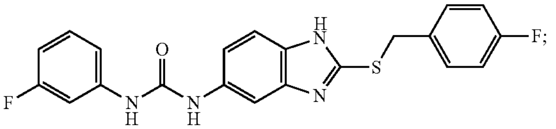
or a pharmaceutically acceptable salt and/or tautomer thereof.
In another aspect, the present disclosure provides compounds of the formula:
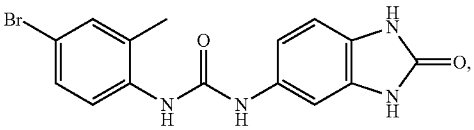
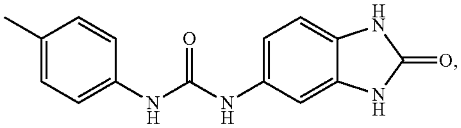
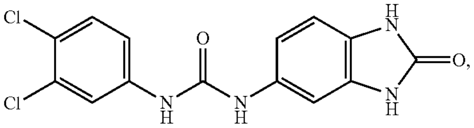
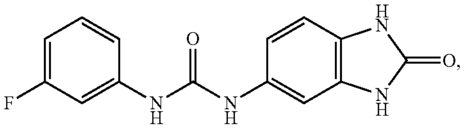
-continued
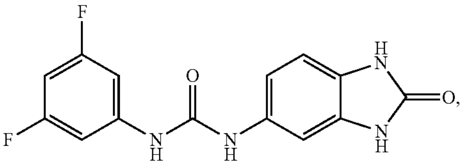
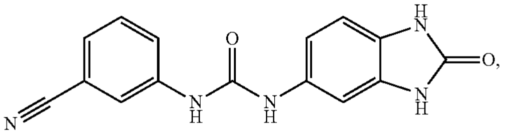
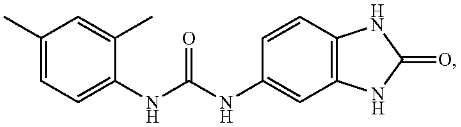
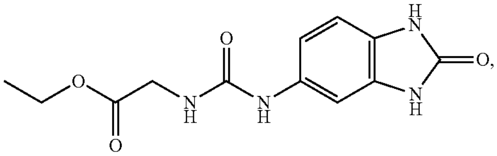
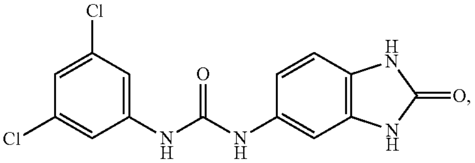
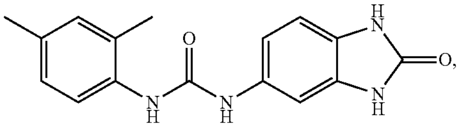
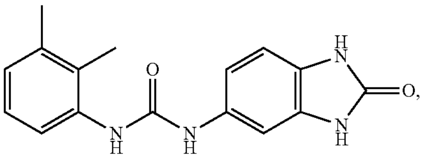
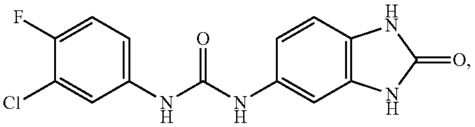
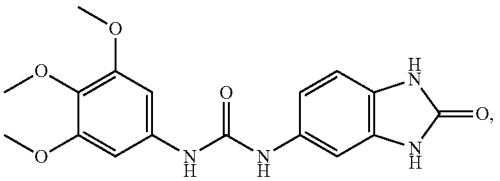
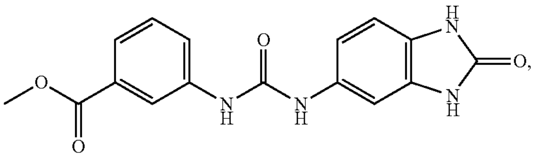
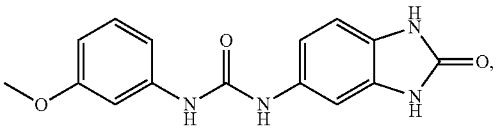

-continued
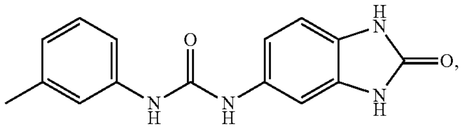
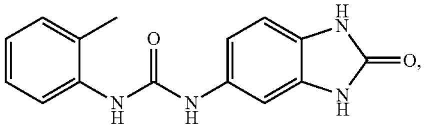
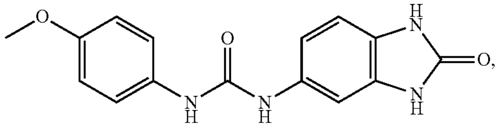
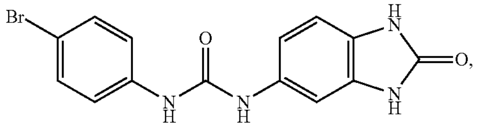
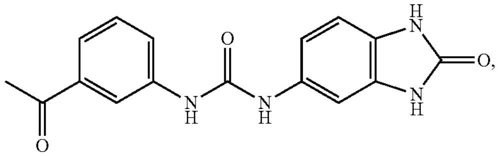
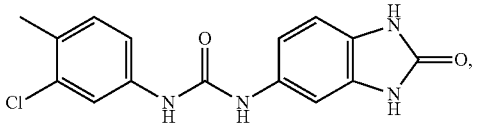
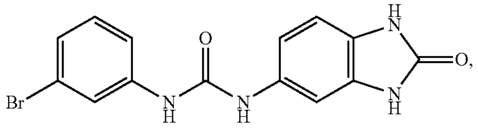
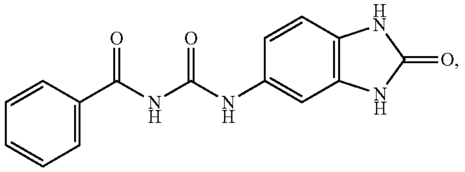
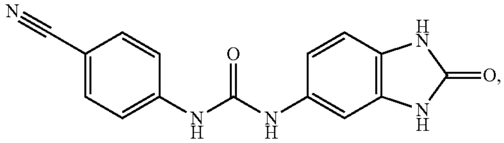
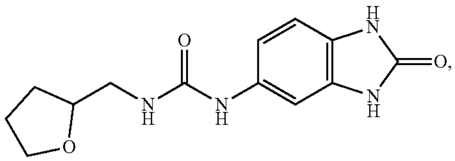
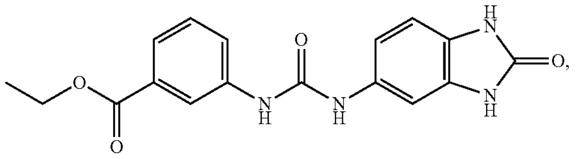
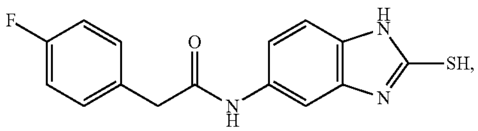
-continued
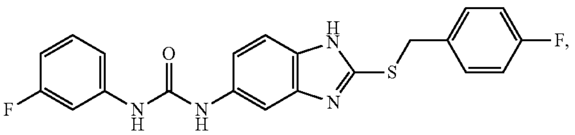
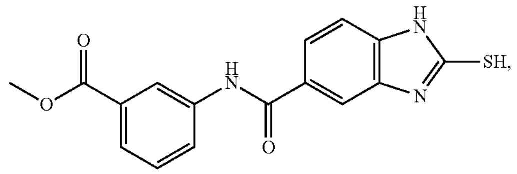
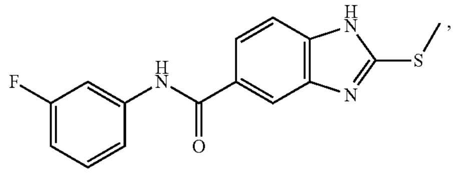
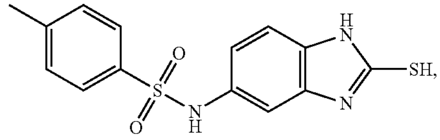
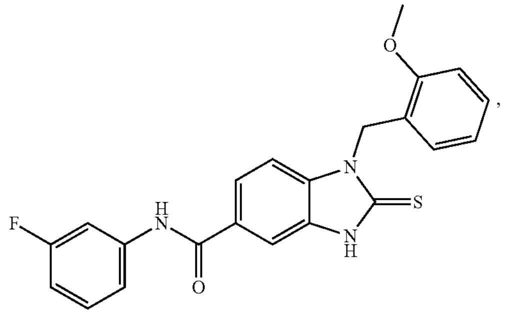
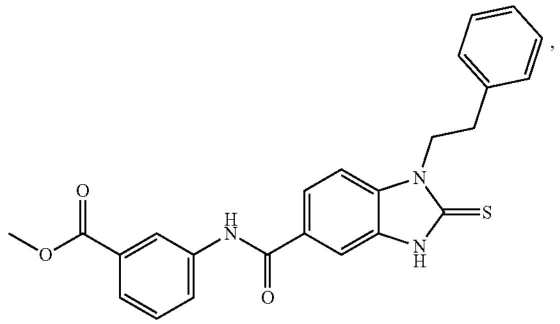
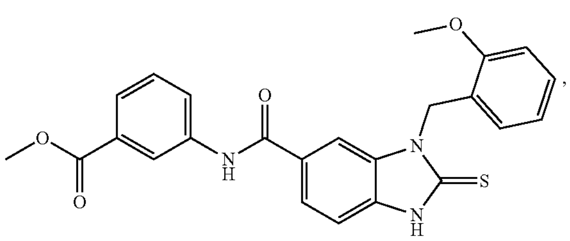

-continued
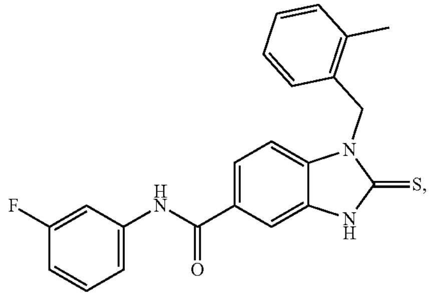
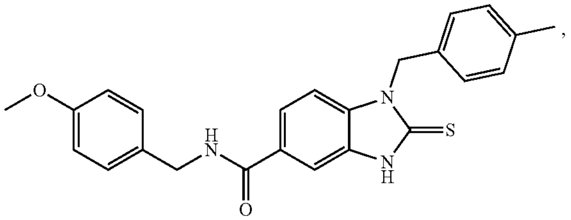
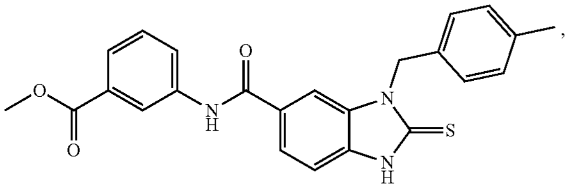
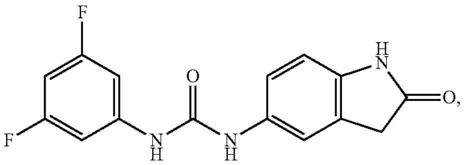
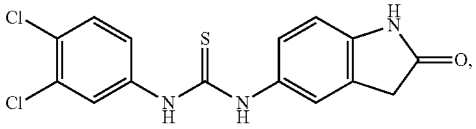
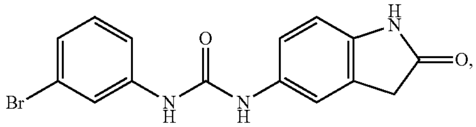
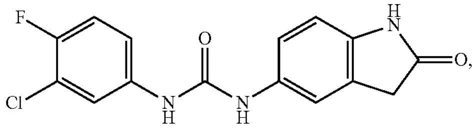
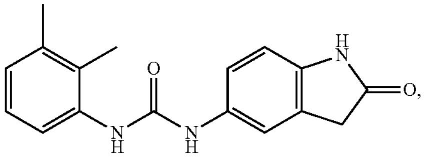
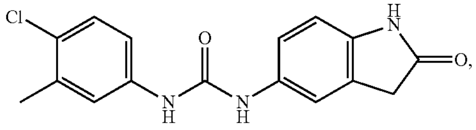
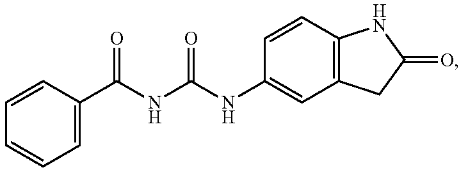
-continued
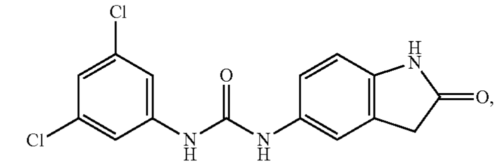
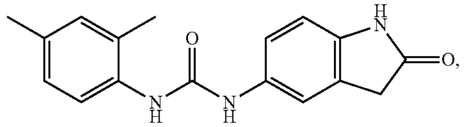
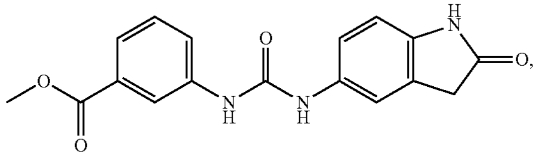
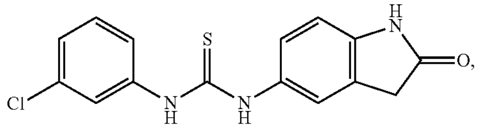
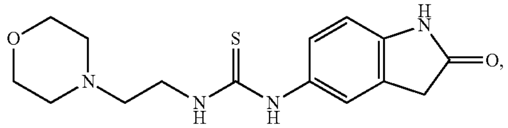
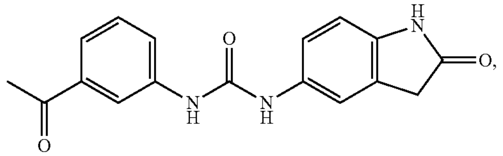
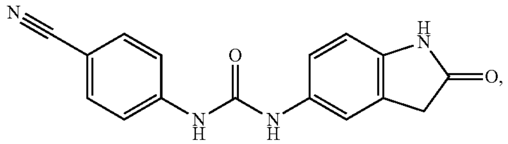
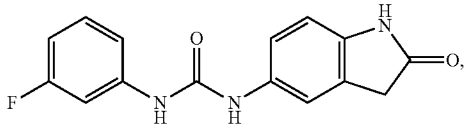
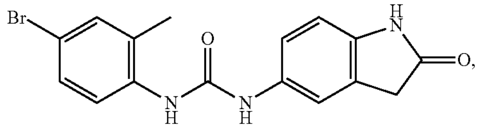
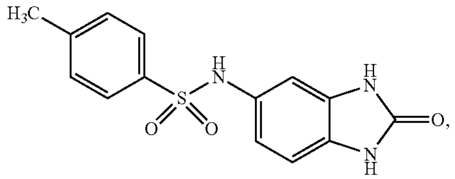
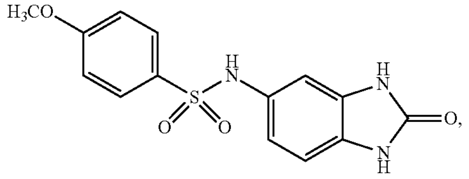

-continued
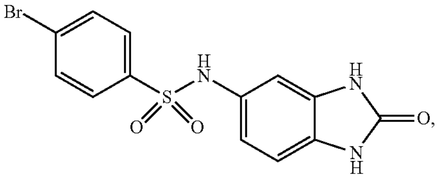
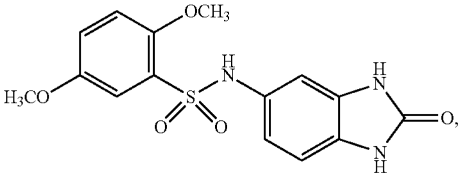
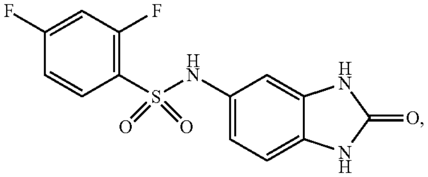
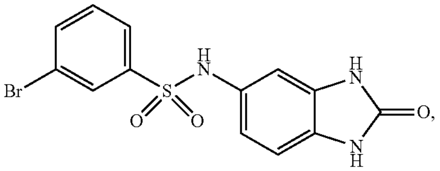
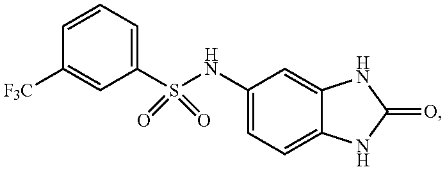
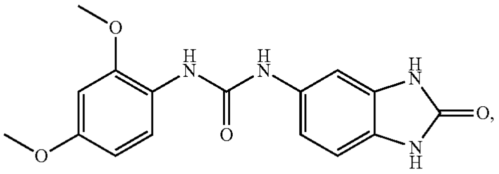
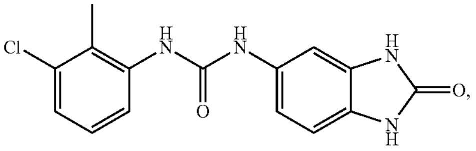
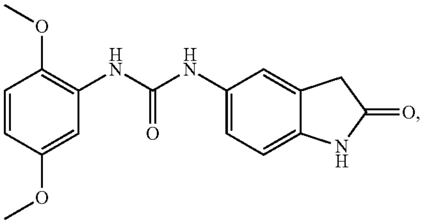
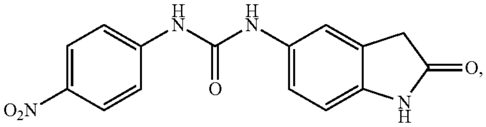
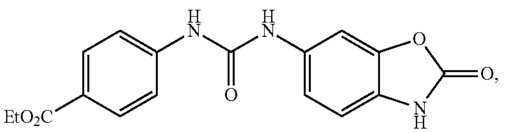
-continued
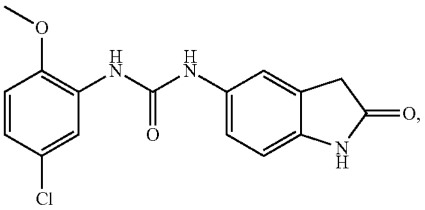
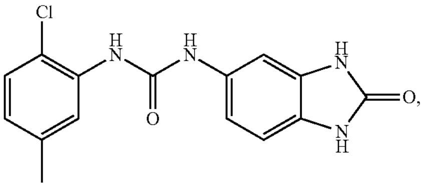
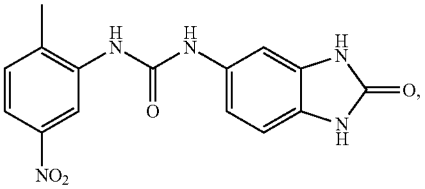
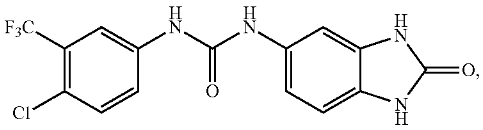
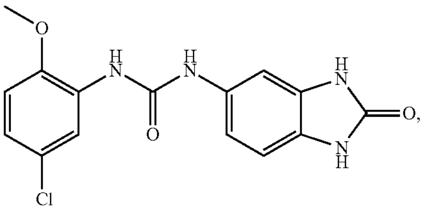
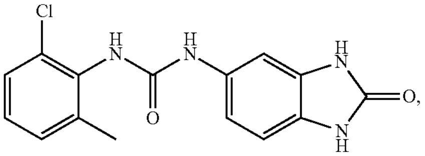
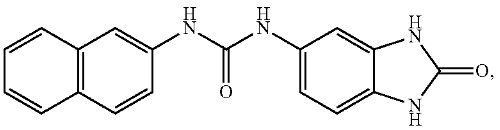
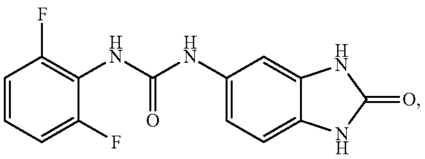
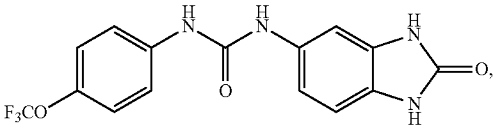
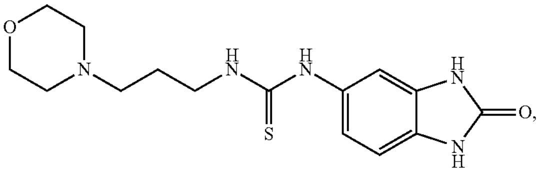

-continued
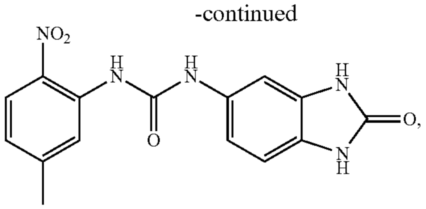
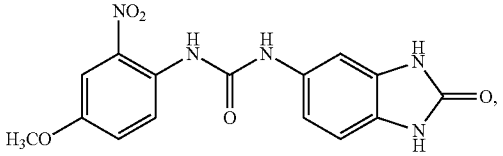
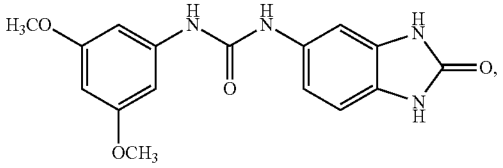
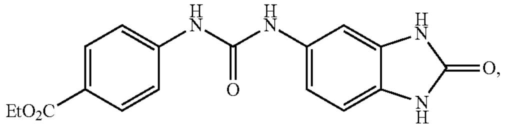
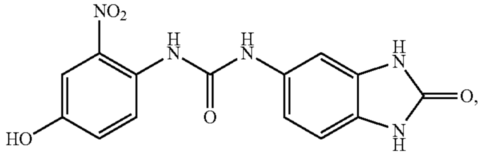
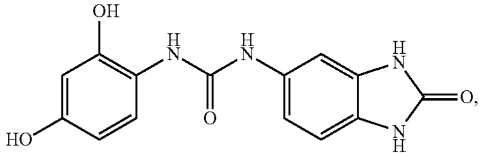
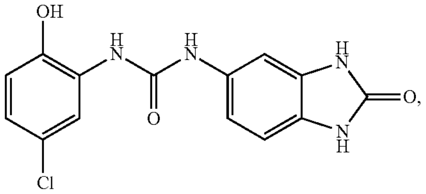
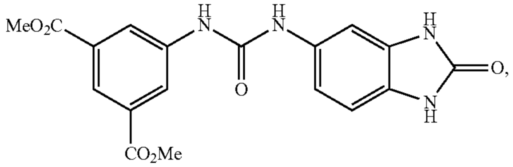
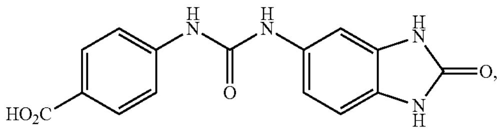
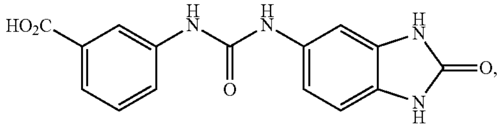
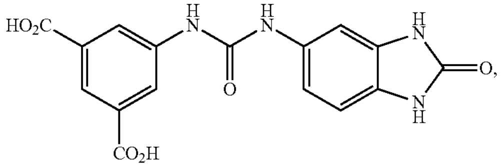
-continued
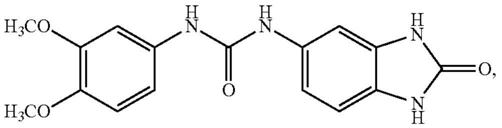
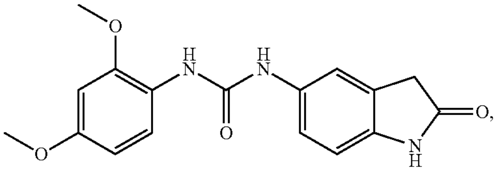
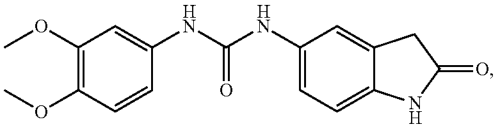
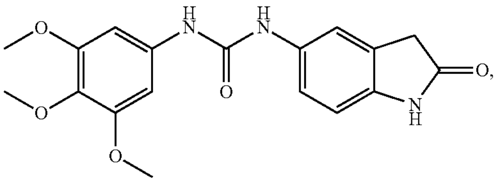
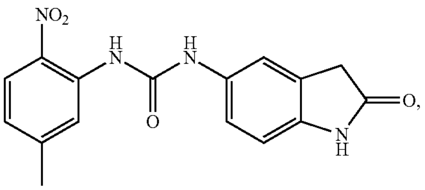
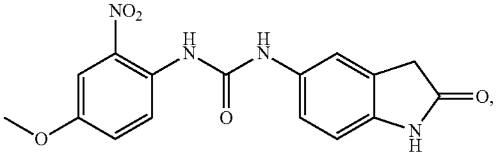
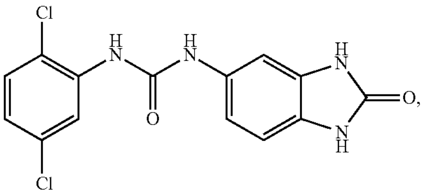
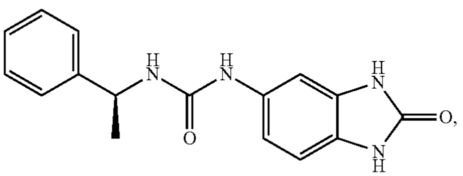
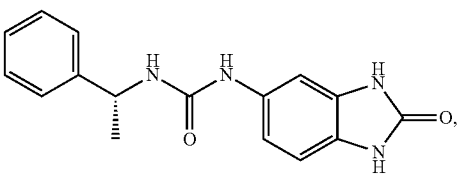
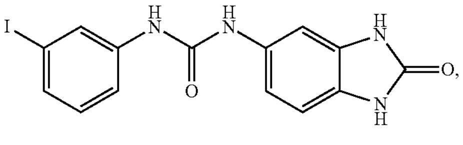

-continued

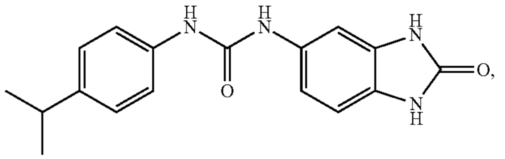

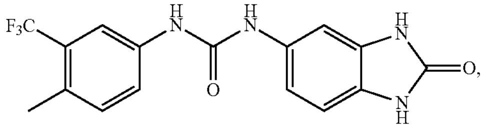

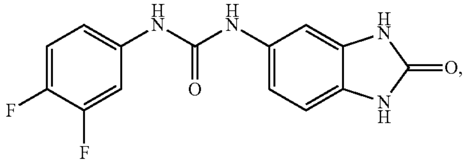

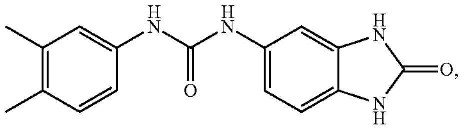

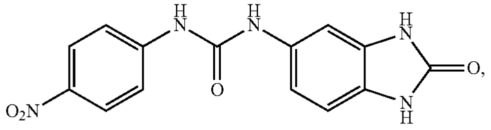

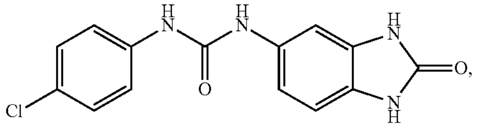

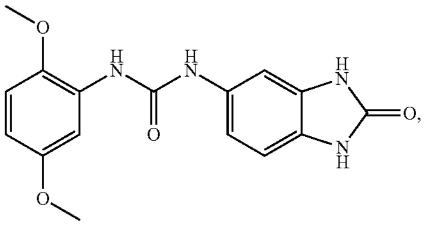

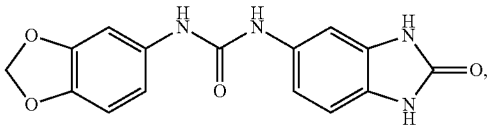

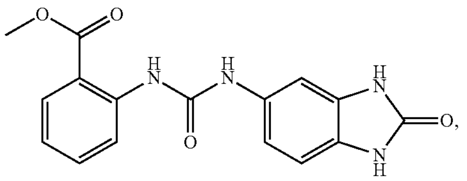

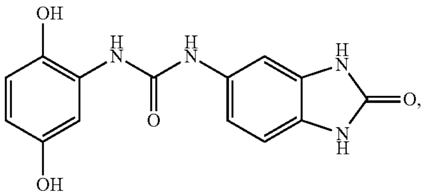

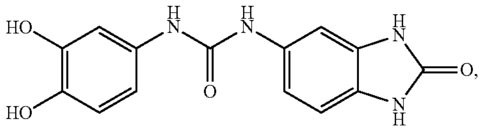

-continued

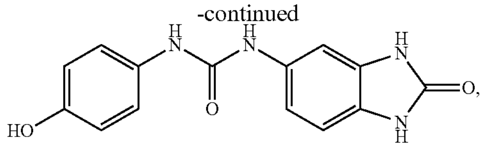

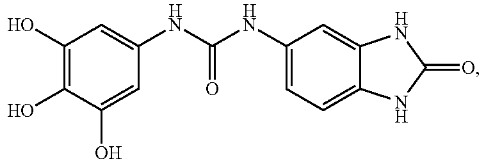

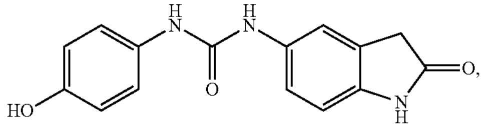

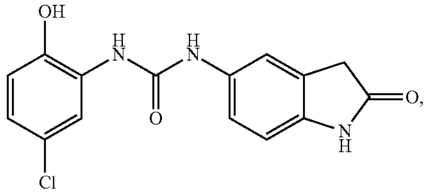

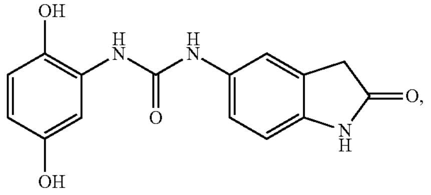

or

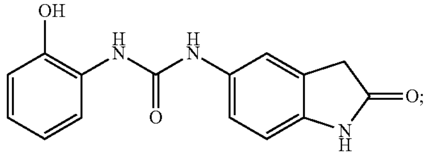

or a pharmaceutically acceptable salt and/or tautomer thereof.

In still another aspect, the present disclosure provides pharmaceutical compositions comprising:

a) a compound of the present disclosure; and b) an excipient or a pharmaceutically acceptable carrier.

In some embodiments, the composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in cremes, in lipid compositions, via a catheter, via a lavage, via continuous infusion, via infusion, via inhalation, via injection, via local delivery, or via localized perfusion.

In yet another aspect, the present disclosure provides methods of treating or preventing a disease or disorder in a patient in need thereof comprising administering to the patient a therapeutically effective amount of a compound or composition of the present disclosure. In some embodiments, the disease or disorder is cancer. In further embodiments, the cancer is a KRAS-positive cancer. In some embodiments, the cancer is ovarian cancer, lung cancer, or breast cancer. In further embodiments, the cancer is breast cancer, such as triple negative breast cancer. In some embodiments, the patient is a mammal, such as a human. In some embodiments, administering comprises intravenous, intra-arterial, intra-tumoral, subcutaneous, topical or intraperitoneal administration. In some embodiments, administering comprises local, regional, systemic, or continual administration. In some embodiments, the methods further comprise administering to the patient a second anti-cancer therapy. In further embodiments, the second anti-cancer therapy is surgery, chemotherapy, radiotherapy, hormonal therapy, toxin therapy, immunotherapy, and cryotherapy. In some embodiments, the second anti-cancer therapy is provided prior to administering said compound. In some embodiments, the second anti-cancer therapy is provided after administering said compound. In some embodiments, the second anti-cancer therapy is provided at the same time as said compound.

In still another aspect, the present disclosure provides methods of treating or preventing a disease or disorder in a patient in need thereof comprising administering to the patient a therapeutically effective amount of a compound of the formula:

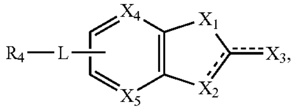

(III)

wherein:

$X_1$ is —$CH_2$—, —NH—, or —O—;

$X_2$ is —N= or —$NR_{x2}$—, wherein:

$R_{x2}$ is hydrogen; or alkyl$_{(C\leq12)}$, aralkyl$_{(C\leq12)}$, heteroaralkyl$_{(C\leq12)}$, or a substituted version of any of these groups;

$X_3$ is oxo, =S, or —$SR_{x3}$, wherein:

$R_{x3}$ is hydrogen; or alkyl$_{(C\leq12)}$, aralkyl$_{(C\leq12)}$, heteroaralkyl$_{(C\leq12)}$, or a substituted version of any of these groups;

$X_4$ and $X_5$ are each independently —CH= or —N=;

L is —NHC(O)NH—, —NHC(S)NH—, —C(O)NH—, —C(O)NHC(O)NH—, or —$S(O)_2NH$—; and $R_4$ is 1,3-benzodioxol-5-yl; or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -alkanediyl$_{(C\leq12)}$-$R_{4a}$, -arendiyl$_{(C\leq12)}$-alkoxy$_{(C\leq12)}$, or a substituted version of any of these groups, wherein:

$R_{4a}$ is carboxy; or cycloalkyl$_{(C\leq12)}$, heterocycloalkyl$_{(C\leq12)}$, —C(O)-alkoxy$_{(C\leq12)}$, or a substituted version of any of these groups;

or a pharmaceutically acceptable salt and/or tautomer thereof.

In some embodiments, the compound is of the formula:

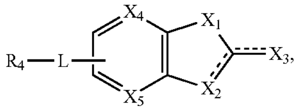

(III)

wherein:

$X_1$ is —$CH_2$—, —NH—, or —O—;

$X_2$ is —N= or —$NR_{x2}$—, wherein:

$R_{x2}$ is hydrogen; or alkyl$_{(C\leq12)}$, aralkyl$_{(C\leq12)}$, heteroaralkyl$_{(C\leq12)}$, or a substituted version of any of these groups;

$X_3$ is oxo, =S, or —$SR_{x3}$, wherein:

$R_{x3}$ is hydrogen; or alkyl$_{(C\leq12)}$, aralkyl$_{(C\leq12)}$, heteroaralkyl$_{(C\leq12)}$, or a substituted version of any of these groups;

$X_4$ and $X_5$ are each independently —CH= or —N=;

L is —NHC(O)NH—, —NHC(S)NH—, —C(O)NH—, —C(O)NHC(O)NH—, or —$S(O)_2NH$—; and $R_4$ is 1,3-benzodioxol-5-yl; or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -alkanediyl$_{(C\leq12)}$-$R_{4a}$, or a substituted version of any of these groups, wherein:

$R_{4a}$ is carboxy; or cycloalkyl$_{(C\leq12)}$, heterocycloalkyl$_{(C\leq12)}$, —C(O)-alkoxy$_{(C\leq12)}$, or a substituted version of any of these groups;

or a pharmaceutically acceptable salt and/or tautomer thereof.

In some embodiments, the disease or disorder is cancer. In further embodiments, the cancer is a KRAS-positive cancer. In some embodiments, the cancer is ovarian cancer, lung cancer, or breast cancer. In further embodiments, the cancer is breast cancer, such as triple negative breast cancer. In some embodiments, the patient is a mammal, such as a human. In some embodiments, administering comprises intravenous, intra-arterial, intra-tumoral, subcutaneous, topical or intraperitoneal administration. In some embodiments, administering comprises local, regional, systemic, or continual administration. In some embodiments, the methods further comprise administering to the patient a second anti-cancer therapy. In further embodiments, the second anti-cancer therapy is surgery, chemotherapy, radiotherapy, hormonal therapy, toxin therapy, immunotherapy, and cryotherapy. In some embodiments, the second anti-cancer therapy is provided prior to administering said compound. In some embodiments, the second anti-cancer therapy is provided after administering said compound. In some embodiments, the second anti-cancer therapy is provided at the same time as said compound.

In yet another aspect, the present disclosure provides methods of inhibiting RTK-induced MAP kinase comprising contacting a cell with a compound of the formula:

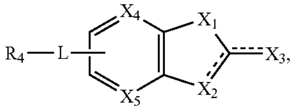

(III)

wherein:

$X_1$ is —$CH_2$—, —NH—, or —O—;

$X_2$ is —N= or —$NR_{x2}$—, wherein:

$R_{x2}$ is hydrogen; or alkyl$_{(C\leq12)}$, aralkyl$_{(C\leq12)}$, heteroaralkyl$_{(C\leq12)}$, or a substituted version of any of these groups;

$X_3$ is oxo, =S, or —$SR_{x3}$, wherein:

$R_{x3}$ is hydrogen; or alkyl$_{(C\leq12)}$, aralkyl$_{(C\leq12)}$, heteroaralkyl$_{(C\leq12)}$, or a substituted version of any of these groups;

$X_4$ and $X_5$ are each independently —CH= or —N=;

L is —NHC(O)NH—, —NHC(S)NH—, —C(O)NH—, —C(O)NHC(O)NH—, or —$S(O)_2NH$—; and $R_4$ is 1,3-benzodioxol-5-yl; or alkyl$_{(C\le 12)}$, aryl$_{(C\le 12)}$, aralkyl$_{(C\le 12)}$, heteroaryl$_{(C\le 12)}$, heteroaralkyl$_{(C\le 12)}$, -alkanediyl$_{(C\le 12)}$-$R_{4a}$, -arendiyl$_{(C\le 12)}$-alkoxy$_{(C\le 12)}$, or a substituted version of any of these groups, wherein:

$R_{4a}$ is carboxy; or cycloalkyl$_{(C\le 12)}$, heterocycloalkyl$_{(C\le 12)}$, —C(O)-alkoxy$_{(C\le 12)}$, or a substituted version of any of these groups;

or a pharmaceutically acceptable salt and/or tautomer thereof.

In some embodiments, the compound is of the formula:

(III)

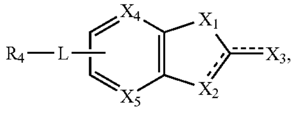

wherein:

$X_1$ is —$CH_2$—, —NH—, or —O—;

$X_2$ is —N= or —$NR_{x2}$—, wherein:

$R_{x2}$ is hydrogen; or alkyl$_{(C\le 12)}$, aralkyl$_{(C\le 12)}$, heteroaralkyl$_{(C\le 12)}$, or a substituted version of any of these groups;

$X_3$ is oxo, =S, or —$SR_{x3}$, wherein:

$R_{x3}$ is hydrogen; or alkyl$_{(C\le 12)}$, aralkyl$_{(C\le 12)}$, heteroaralkyl$_{(C\le 12)}$, or a substituted version of any of these groups;

$X_4$ and $X_5$ are each independently —CH= or —N=;

L is —NHC(O)NH—, —NHC(S)NH—, —C(O)NH—, —C(O)NHC(O)NH—, or —$S(O)_2NH$—; and $R_4$ is 1,3-benzodioxol-5-yl; or alkyl$_{(C\le 12)}$, aryl$_{(C\le 12)}$, aralkyl$_{(C\le 12)}$, heteroaryl$_{(C\le 12)}$, heteroaralkyl$_{(C\le 12)}$, -alkanediyl$_{(C\le 12)}$-$R_{4a}$, or a substituted version of any of these groups, wherein:

$R_{4a}$ is carboxy; or cycloalkyl$_{(C\le 12)}$, heterocycloalkyl$_{(C\le 12)}$, —C(O)-alkoxy$_{(C\le 12)}$, or a substituted version of any of these groups;

or a pharmaceutically acceptable salt and/or tautomer thereof.

In still another aspect, the present disclosure provides methods of stabilizing dimeric GRB2 in a cell comprising contacting the cell with an effective amount of a compound of the formula:

(III)

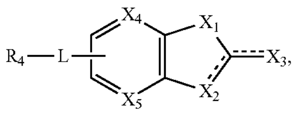

wherein:

$X_1$ is —$CH_2$—, —NH—, or —O—;

$X_2$ is —N= or —$NR_{x2}$—, wherein:

$R_{x2}$ is hydrogen; or alkyl$_{(C\le 12)}$, aralkyl$_{(C\le 12)}$, heteroaralkyl$_{(C\le 12)}$, or a substituted version of any of these groups;

$X_3$ is oxo, =S, or —$SR_{x3}$, wherein:

$R_{x3}$ is hydrogen; or alkyl$_{(C\le 12)}$, aralkyl$_{(C\le 12)}$, heteroaralkyl$_{(C\le 12)}$, or a substituted version of any of these groups;

$X_4$ and $X_5$ are each independently —CH= or —N=;

L is —NHC(O)NH—, —NHC(S)NH—, —C(O)NH—, —C(O)NHC(O)NH—, or —$S(O)_2NH$—; and $R_4$ is 1,3-benzodioxol-5-yl; or alkyl$_{(C\le 12)}$, aryl$_{(C\le 12)}$, aralkyl$_{(C\le 12)}$, heteroaryl$_{(C\le 12)}$, heteroaralkyl$_{(C\le 12)}$, -alkanediyl$_{(C\le 12)}$-$R_{4a}$, -arendiyl$_{(C\le 12)}$-alkoxy$_{(C\le 12)}$, or a substituted version of any of these groups, wherein:

$R_{4a}$ is carboxy; or cycloalkyl$_{(C\le 12)}$, heterocycloalkyl$_{(C\le 12)}$, —C(O)-alkoxy$_{(C\le 12)}$, or a substituted version of any of these groups;

or a pharmaceutically acceptable salt and/or tautomer thereof.

In some embodiments, the compound is further defined as:

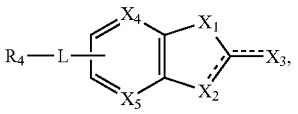

wherein:

$X_1$ is —$CH_2$—, —NH—, or —O—;

$X_2$ is —N= or —$NR_{x2}$—, wherein:

$R_{x2}$ is hydrogen; or alkyl$_{(C\le 12)}$, aralkyl$_{(C\le 12)}$, heteroaralkyl$_{(C\le 12)}$, or a substituted version of any of these groups;

$X_3$ is oxo, =S, or —$SR_{x3}$, wherein:

$R_{x3}$ is hydrogen; or alkyl$_{(C\le 12)}$, aralkyl$_{(C\le 12)}$, heteroaralkyl$_{(C\le 12)}$, or a substituted version of any of these groups;

$X_4$ and $X_5$ are each independently —CH= or —N=;

L is —NHC(O)NH—, —NHC(S)NH—, —C(O)NH—, —C(O)NHC(O)NH—, or —$S(O)_2NH$—; and $R_4$ is 1,3-benzodioxol-5-yl; or alkyl$_{(C\le 12)}$, aryl$_{(C\le 12)}$, aralkyl$_{(C\le 12)}$, heteroaryl$_{(C\le 12)}$, heteroaralkyl$_{(C\le 12)}$, -alkanediyl$_{(C\le 12)}$-$R_{4a}$, or a substituted version of any of these groups, wherein:

$R_{4a}$ is carboxy; or cycloalkyl$_{(C\le 12)}$, heterocycloalkyl$_{(C\le 12)}$, —C(O)-alkoxy$_{(C\le 12)}$, or a substituted version of any of these groups;

or a pharmaceutically acceptable salt and/or tautomer thereof.

With respect to any of the previous three aspects, the compound may in some embodiments be further defined as:

(IV)

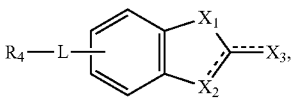

wherein:

$X_1$ is —$CH_2$—, —NH—, or —O—;

$X_2$ is —N= or —$NR_{x2}$—, wherein:

$R_{x2}$ is hydrogen; or alkyl$_{(C\le 12)}$, aralkyl$_{(C\le 12)}$, heteroaralkyl$_{(C\le 12)}$, or a substituted version of any of these groups;

$X_3$ is oxo, =S, or —$SR_{x3}$, wherein:

$R_{x3}$ is hydrogen; or alkyl$_{(C\le 12)}$, aralkyl$_{(C\le 12)}$, heteroaralkyl$_{(C\le 12)}$, or a substituted version of any of these groups;

L is —NHC(O)NH—, —NHC(S)NH—, —C(O)NH—, —C(O)NHC(O)NH—, or —$S(O)_2NH$—; and $R_4$ is 1,3-benzodioxol-5-yl; or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -alkanediyl$_{(C\leq12)}$-$R_{4a}$, or a substituted version of any of these groups, wherein:

$R_{4a}$ is carboxy; or cycloalkyl$_{(C\leq12)}$, heterocycloalkyl$_{(C\leq12)}$, —C(O)-alkoxy$_{(C\leq12)}$, or a substituted version of any of these groups;

or a pharmaceutically acceptable salt and/or tautomer thereof.

In further embodiments, the compound is further defined as:

(V)

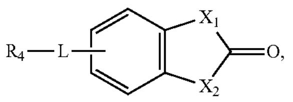

wherein:

$X_1$ is —$CH_2$—, —NH—, or —O—;

$X_2$ is —$NR_{x2}$—, wherein:

$R_{x2}$ is hydrogen; or alkyl$_{(C\leq12)}$, aralkyl$_{(C\leq12)}$, heteroaralkyl$_{(C\leq12)}$, or a substituted version of any of these groups;

$X_3$ is oxo, =S, or —$SR_{x3}$, wherein:

$R_{x3}$ is hydrogen; or alkyl$_{(C\leq12)}$, aralkyl$_{(C\leq12)}$, heteroaralkyl$_{(C\leq12)}$, or a substituted version of any of these groups;

L is —NHC(O)NH—, —NHC(S)NH—, —C(O)NH—, —C(O)NHC(O)NH—, or —$S(O)_2NH$—; and $R_4$ is 1,3-benzodioxol-5-yl; or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -alkanediyl$_{(C\leq12)}$-$R_{4a}$, or a substituted version of any of these groups, wherein:

$R_{4a}$ is carboxy; or cycloalkyl$_{(C\leq12)}$, heterocycloalkyl$_{(C\leq12)}$, —C(O)-alkoxy$_{(C\leq12)}$, or a substituted version of any of these groups;

or a pharmaceutically acceptable salt and/or tautomer thereof.

In still further embodiments, the compounds are further defined as:

(VI)

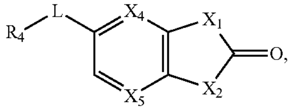

wherein:

$X_1$ is —$CH_2$—, —NH—, or —O—;

$X_2$ is —$NR_{x2}$—, wherein:

$R_{x2}$ is hydrogen; or alkyl$_{(C\leq12)}$, aralkyl$_{(C\leq12)}$, heteroaralkyl$_{(C\leq12)}$, or a substituted version of any of these groups;

L is —NHC(O)NH—, —NHC(S)NH—, —C(O)NH—, —C(O)NHC(O)NH—, or —$S(O)_2NH$—; and $R_4$ is 2H-1,3-benzodioxolyl; or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -alkanediyl$_{(C\leq12)}$-$R_{4a}$, or a substituted version of any of these groups, wherein:

$R_{4a}$ is carboxy; or cycloalkyl$_{(C\leq12)}$, heterocycloalkyl$_{(C\leq12)}$, —C(O)-alkoxy$_{(C\leq12)}$, or a substituted version of any of these groups;

or a pharmaceutically acceptable salt and/or tautomer thereof.

In some embodiments, $X_1$ is —O—. In other embodiments, $X_1$ is —$CH_2$— or —NH—. In some embodiments, $R_{x2}$ is hydrogen. In other embodiments, $R_{x2}$ is alkyl$_{(C\leq12)}$ or substituted alkyl$_{(C\leq12)}$. In further embodiments, $R_{x2}$ is alkyl$_{(C\leq12)}$, such as methyl or ethyl.

In some embodiments, the compound is further defined as:

(VII)

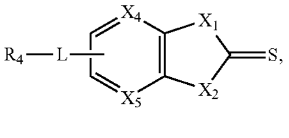

wherein:

$X_1$ is —$CH_2$—, —NH—, or —O—;

$X_2$ is —$NR_{x2}$—, wherein:

$R_{x2}$ is hydrogen; or alkyl$_{(C\leq12)}$, aralkyl$_{(C\leq12)}$, heteroaralkyl$_{(C\leq12)}$, or a substituted version of any of these groups;

L is —NHC(O)NH—, —NHC(S)NH—, —C(O)NH—, —C(O)NHC(O)NH—, or —$S(O)_2NH$—; and $R_4$ is 2H-1,3-benzodioxolyl; or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -alkanediyl$_{(C\leq12)}$-$R_{4a}$, or a substituted version of any of these groups, wherein:

$R_{4a}$ is carboxy; or cycloalkyl$_{(C\leq12)}$, heterocycloalkyl$_{(C\leq12)}$, —C(O)-alkoxy$_{(C\leq12)}$, or a substituted version of any of these groups;

or a pharmaceutically acceptable salt and/or tautomer thereof.

In some embodiments, $X_1$ is —$CH_2$— or —NH—. In other embodiments, $X_1$ is —O—.

In some embodiments, the compound is further defined as:

(VIII)

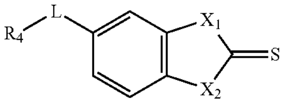

or (IX)

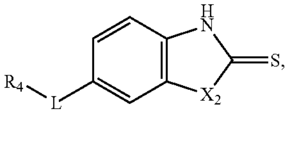

wherein:

$X_2$ is —$NR_{x2}$—, wherein:

$R_{x2}$ is hydrogen; or alkyl$_{(C\leq12)}$, aralkyl$_{(C\leq12)}$, heteroaralkyl$_{(C\leq12)}$, or a substituted version of any of these groups;

L is —NHC(O)NH—, —NHC(S)NH—, —C(O)NH—, —C(O)NHC(O)NH—, or —$S(O)_2NH$—; and $R_4$ is 1,3-benzodioxol-5-yl; or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -alkanediyl$_{(C\leq12)}$-$R_{4a}$, or a substituted version of any of these groups, wherein:

$R_{4a}$ is carboxy; or cycloalkyl$_{(C\leq12)}$, heterocycloalkyl$_{(C\leq12)}$, —C(O)-alkoxy$_{(C\leq12)}$, or a substituted version of any of these groups;

or a pharmaceutically acceptable salt and/or tautomer thereof.

In some embodiments, $R_{x2}$ is aralkyl$_{(C\leq12)}$ or substituted aralkyl$_{(C\leq12)}$. In further embodiments, $R_{x2}$ is aralkyl$_{(C\leq12)}$, such as methylbenzyl, 2-methylbenzyl, 4-methylbenzyl, or phenethyl. In other embodiments, $R_{x2}$ is substituted aralkyl$_{(C\leq12)}$, such as 2-methoxybenzyl.

In some embodiments, the compound is further defined as:

(X)

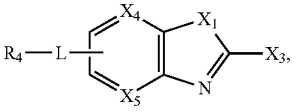

wherein:

$X_1$ is —$CH_2$—, —NH—, or —O—;

$X_3$ is —$SR_{x3}$, wherein:

$R_{x3}$ is hydrogen; or alkyl$_{(C\leq12)}$, aralkyl$_{(C\leq12)}$, heteroaralkyl$_{(C\leq12)}$, or a substituted version of any of these groups;

L is —NHC(O)NH—, —NHC(S)NH—, —C(O)NH—, —C(O)NHC(O)NH—, or —$S(O)_2NH$—; and $R_4$ is 1,3-benzodioxol-5-yl; or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -alkanediyl$_{(C\leq12)}$-$R_{4a}$, or a substituted version of any of these groups, wherein:

$R_{4a}$ is carboxy; or cycloalkyl$_{(C\leq12)}$, heterocycloalkyl$_{(C\leq12)}$, —C(O)-alkoxy$_{(C\leq12)}$, or a substituted version of any of these groups;

or a pharmaceutically acceptable salt and/or tautomer thereof.

In some embodiments, the compound is further defined as:

(XI)

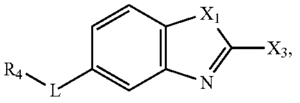

wherein:

$X_1$ is —$CH_2$—, —NH—, or —O—;

$X_3$ is —$SR_{x3}$, wherein:

$R_{x3}$ is hydrogen; or alkyl$_{(C\leq12)}$, aralkyl$_{(C\leq12)}$, heteroaralkyl$_{(C\leq12)}$, or a substituted version of any of these groups;

L is —NHC(O)NH—, —NHC(S)NH—, —C(O)NH—, —C(O)NHC(O)NH—, or —$S(O)_2NH$—; and $R_4$ is 1,3-benzodioxol-5-yl; or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -alkanediyl$_{(C\leq12)}$-$R_{4a}$, or a substituted version of any of these groups, wherein:

$R_{4a}$ is carboxy; or cycloalkyl$_{(C\leq12)}$, heterocycloalkyl$_{(C\leq12)}$, —C(O)-alkoxy$_{(C\leq12)}$, or a substituted version of any of these groups;

or a pharmaceutically acceptable salt and/or tautomer thereof.

In some embodiments, $X_1$ is —O—. In other embodiments, $X_1$ is —$CH_2$— or —NH—. In some embodiments, $R_{x3}$ is hydrogen. In other embodiments, $R_{x3}$ is alkyl$_{(C\leq12)}$ or substituted alkyl$_{(C\leq12)}$. In further embodiments, $R_{x3}$ is alkyl$_{(C\leq12)}$, such as methyl. In still other embodiments, $R_{x3}$ is aralkyl$_{(C\leq12)}$ or substituted aralkyl$_{(C\leq12)}$. In further embodiments, $R_{x3}$ is substituted aralkyl$_{(C\leq12)}$, such as 4-fluorobenzyl. In some embodiments, L is —NHC(O)NH—, —NHC(S)NH—, —C(O)NH—, or —C(O)NHC(O)NH—. In some embodiments, $R_4$ is-arendiyl$_{(C\leq12)}$-alkoxy$_{(C\leq12)}$ or substituted -arendiyl$_{(C\leq12)}$-alkoxy$_{(C\leq12)}$. In some embodiments, $R_4$ is substituted -arendiyl$_{(C\leq12)}$-alkoxy$_{(C\leq12)}$, such as 4-trifluoromethoxyphenyl. In some embodiments, $R_4$ is 1,3-benzodioxol-5-yl. In other embodiments, $R_4$ is heteroaryl$_{(C\leq12)}$ or substituted heteroaryl$_{(C\leq12)}$. In further embodiments, $R_4$ is heteroaryl$_{(C\leq12)}$, such as 2-thienyl. In still other embodiments, $R_4$ is aralkyl$_{(C\leq12)}$ or substituted aralkyl$_{(C\leq12)}$. In further embodiments, $R_4$ is aralkyl$_{(C\leq12)}$, such as benzyl. In yet other embodiments, $R_4$ is substituted aralkyl$_{(C\leq12)}$, such as 4-fluorobenzyl or 4-methoxybenzyl. In still other embodiments, $R_4$ is -alkanediyl$_{(C\leq12)}$-$R_{4a}$. In some embodiments, $R_{4a}$ is —C(O)-alkoxy$_{(C\leq12)}$, such as —$CH_2CO_2CH_3$. In other embodiments, $R_{4a}$ is heterocycloalkyl$_{(C\leq12)}$, such as tetrahydrofuran-2-ylmethyl or 2-(4-morpholinyl)ethyl. In other embodiments, $R_4$ is aryl$_{(C\leq12)}$ or substituted aryl$_{(C\leq12)}$. In further embodiments, $R_4$ is aryl$_{(C\leq12)}$, such as phenyl, 2-methylphenyl, 3-methylphenyl, 4-methylphenyl, 2,3-dimethylphenyl, 2,4-dimethylphenyl, 3,5-dimethylphenyl, or 2-naphthalenyl. In other embodiments, $R_4$ is substituted aryl$_{(C\leq12)}$, such as 3-fluorophenyl, 4-fluorophenyl, 3-chlorophenyl, 4-chlorophenyl, 3-bromophenyl, 4-bromophenyl, 3-cyanophenyl, 4-cyanophenyl, 2-methoxyphenyl, 3-methoxyphenyl, 4-methoxyphenyl, 3-trifluoromethylphenyl, 3-acetylphenyl, 3-(methoxycarbonyl)phenyl, 3-(ethoxycarbonyl)phenyl, 3,4-dichlorophenyl, 3,5-dichlorophenyl, 3,5-difluorophenyl, 3,4,5-trimethoxyphenyl, 4-bromo-2-methylphenyl, 4-bromo-2-methylphenyl, 3-chloro-4-methylphenyl, 3-chloro-4-fluorophenyl, or 4-chloro-3-methylphenyl.

In some embodiments, the compound is further defined as:

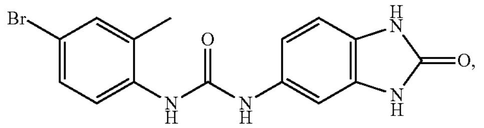

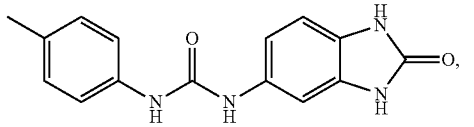

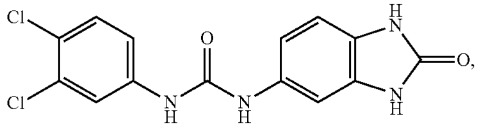

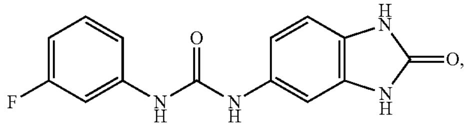

-continued
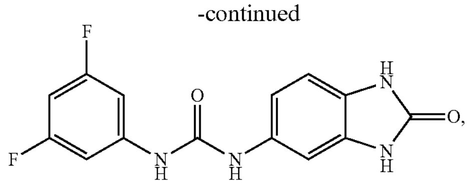
,
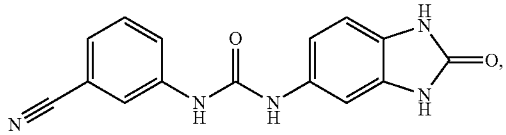
,
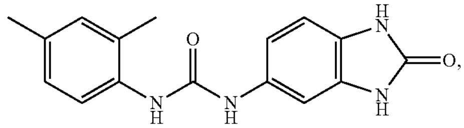
,
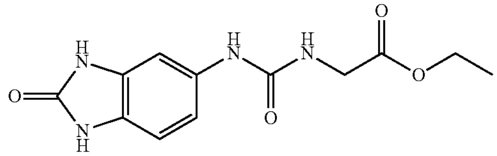
,
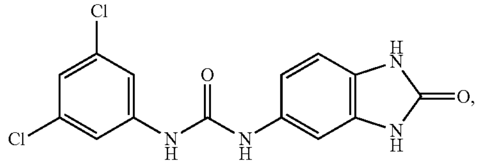
,
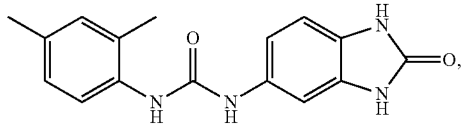
,
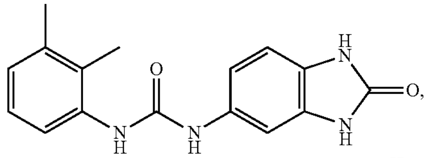
,
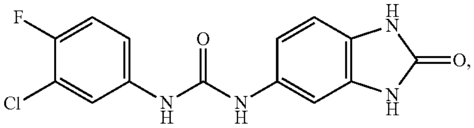
,
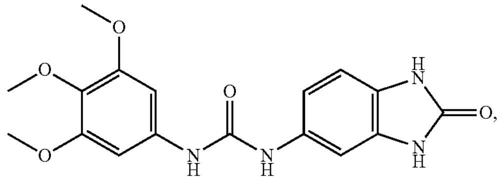
,
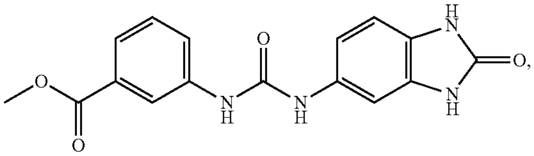
,
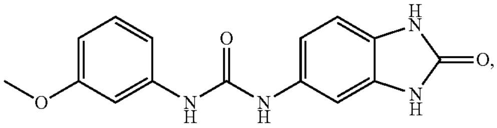
,
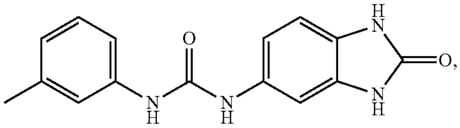
,
-continued
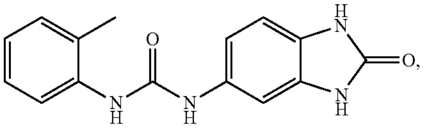
,
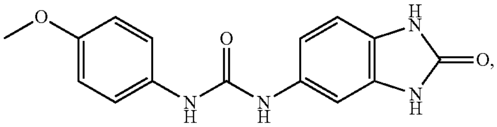
,
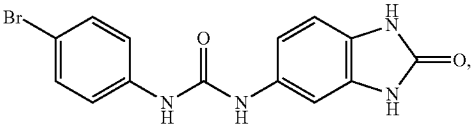
,
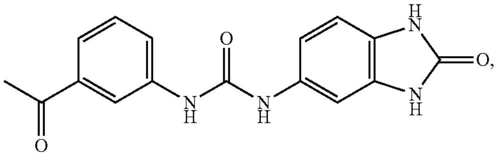
,
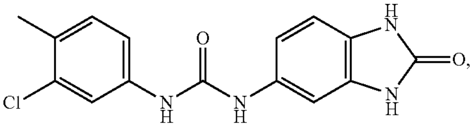
,
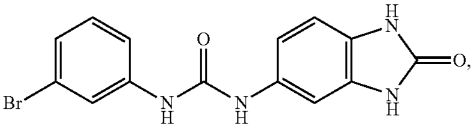
,
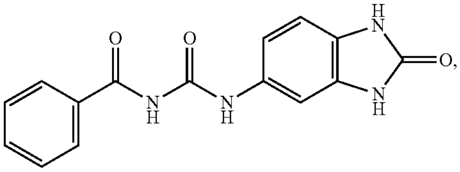
,
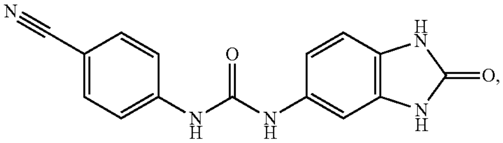
,
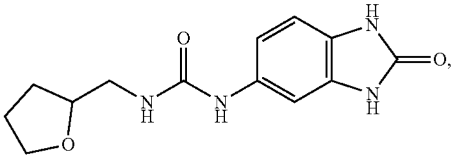
,
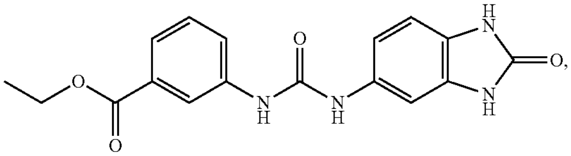
,
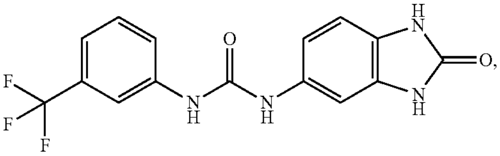
,
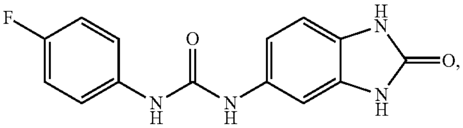
, -continued
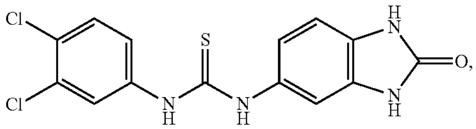,
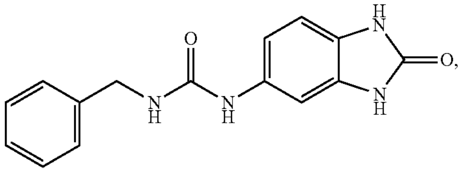,
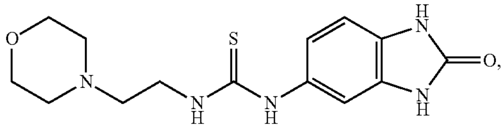,
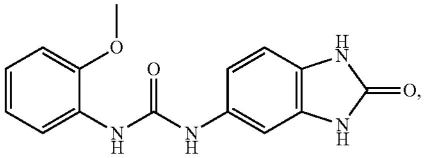,
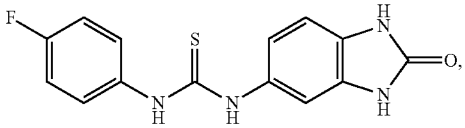,
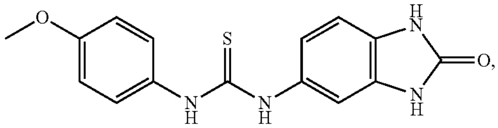,
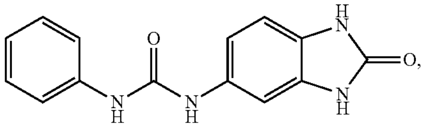,
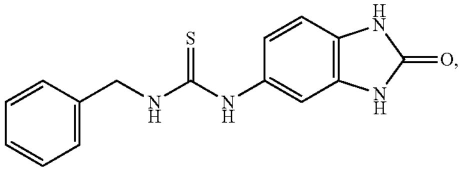,
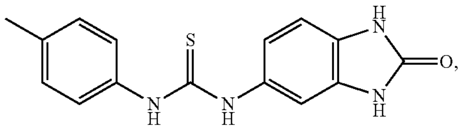,
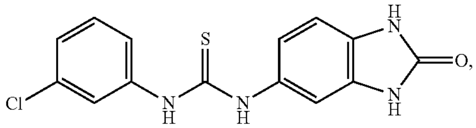,
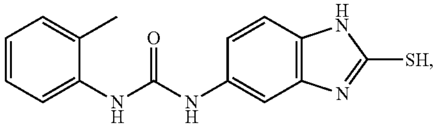,
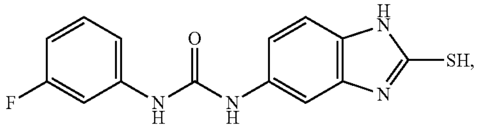,
-continued
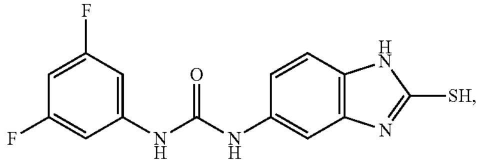,
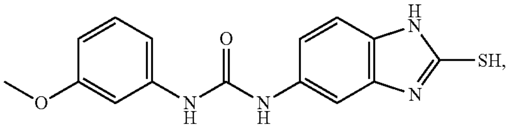,
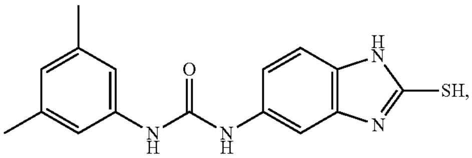,
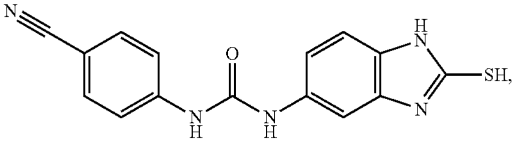,
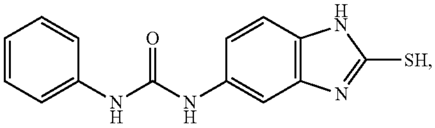,
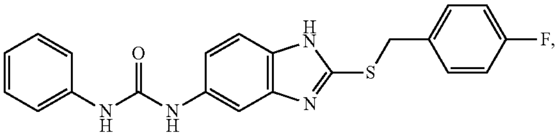,
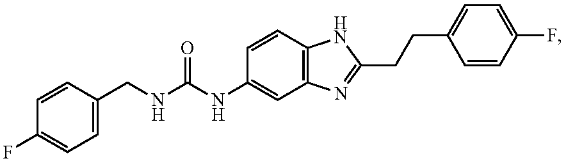,
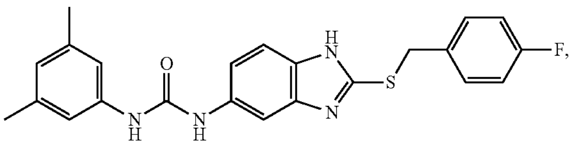,
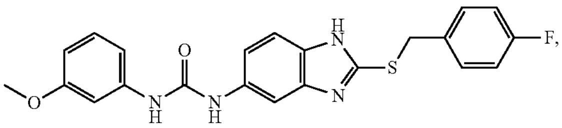,
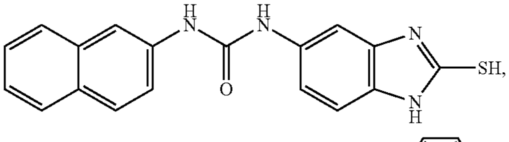,
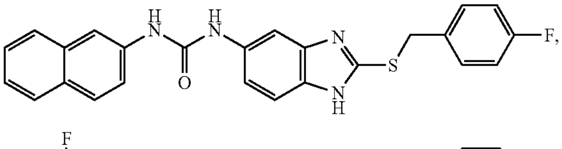,
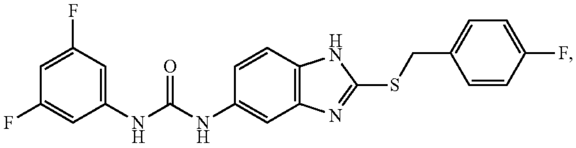, -continued
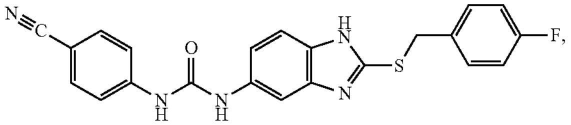
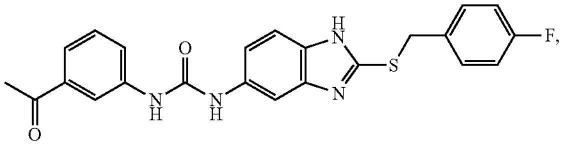
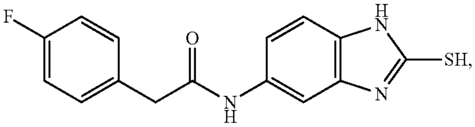
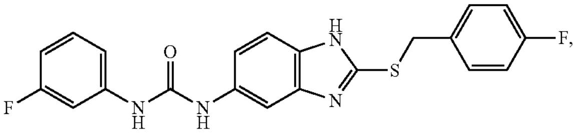
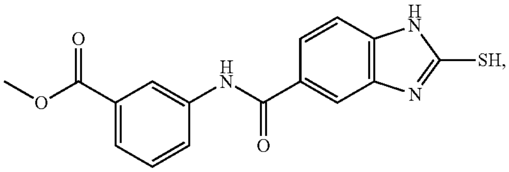
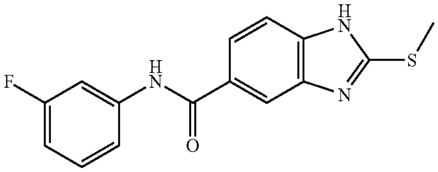
,
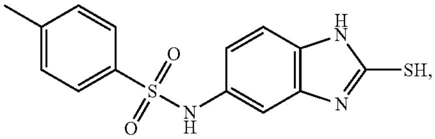
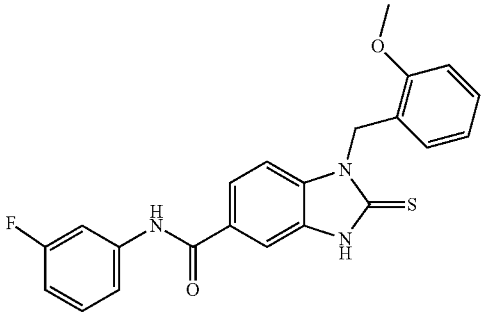
,
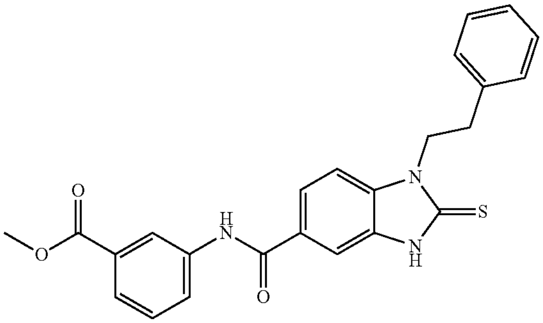
,
-continued
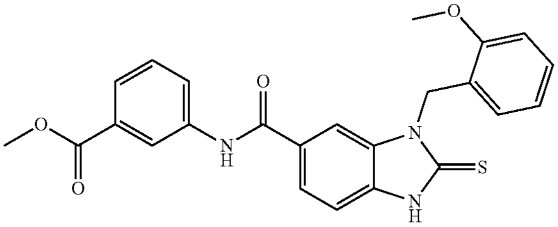
,
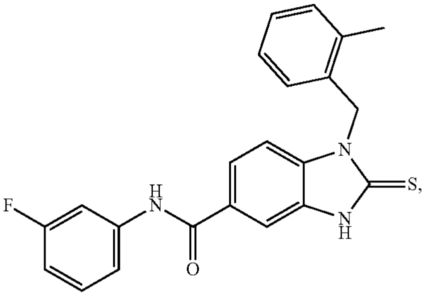
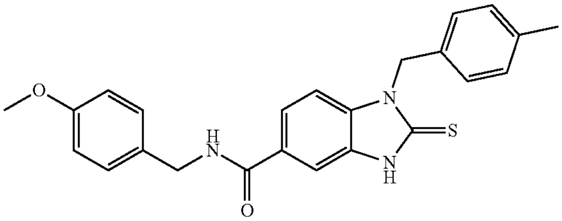
,
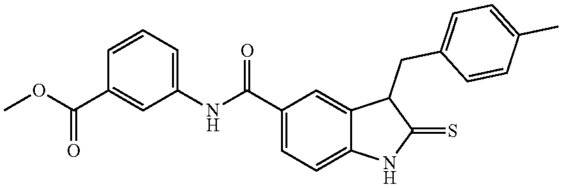
,
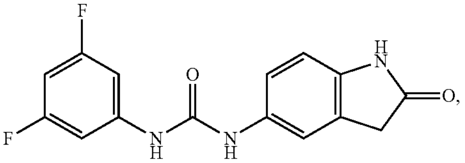
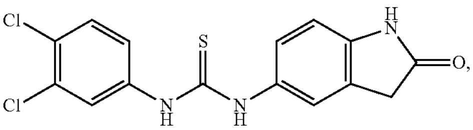
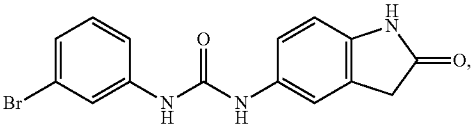
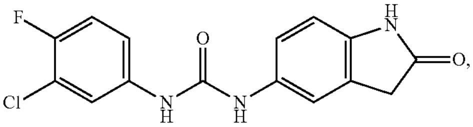
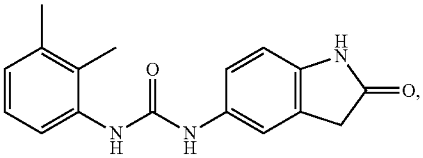

-continued
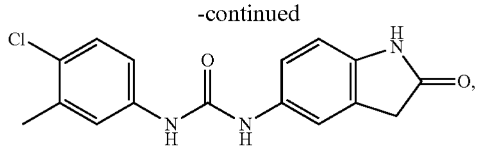
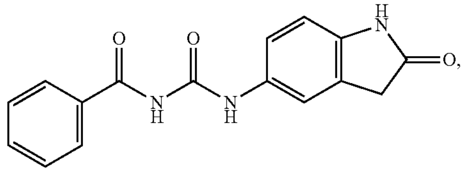
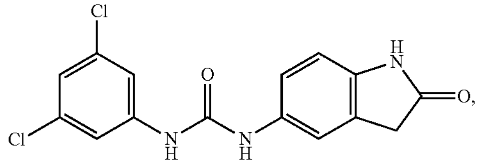
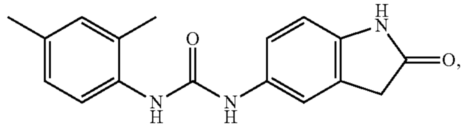
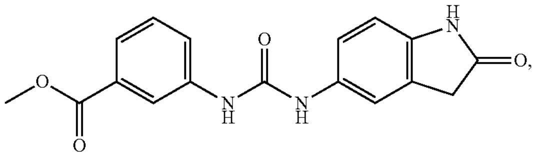
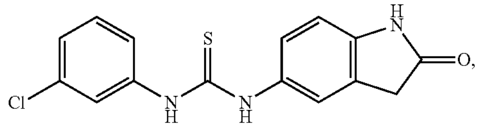
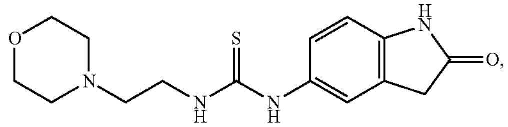
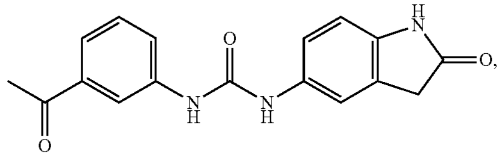
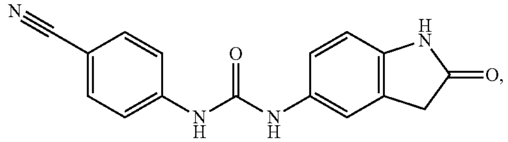
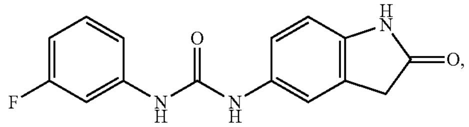
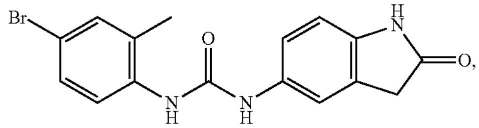
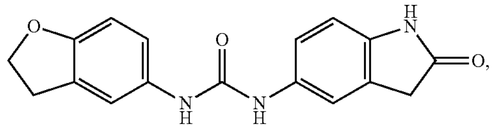
-continued
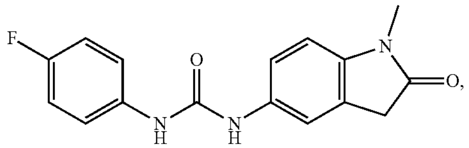
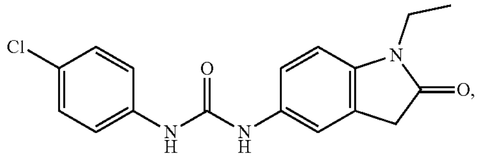
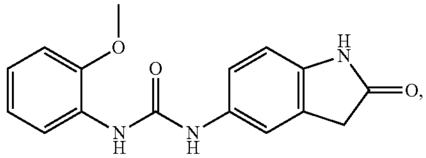
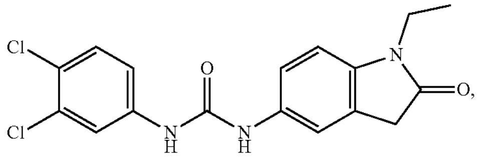
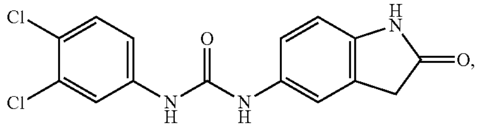
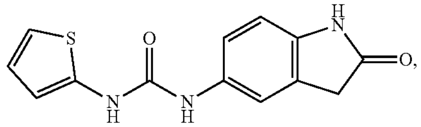
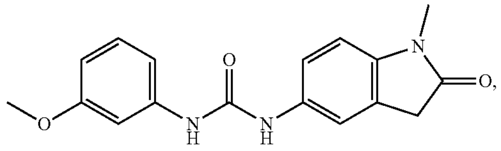
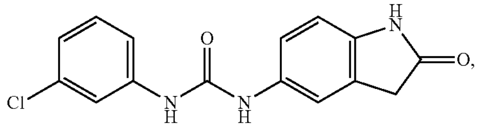
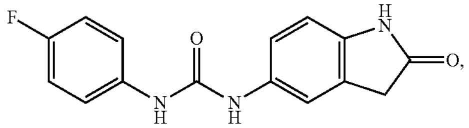
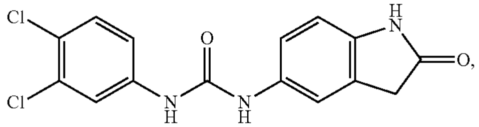
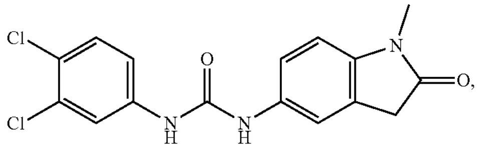
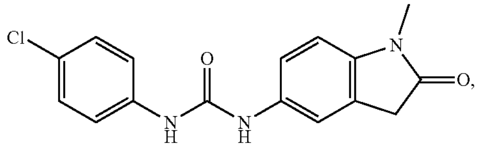

-continued
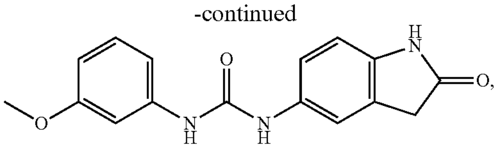,
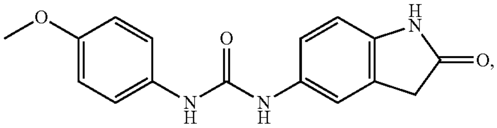,
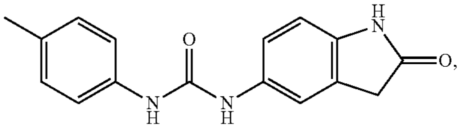,
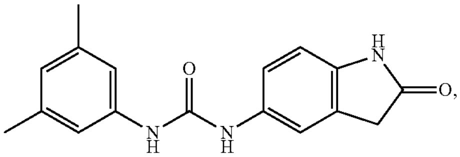,
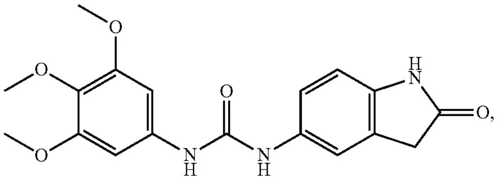,
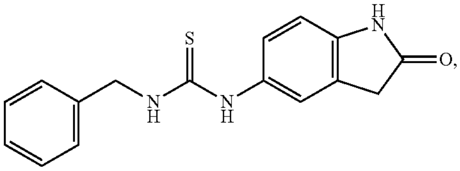,
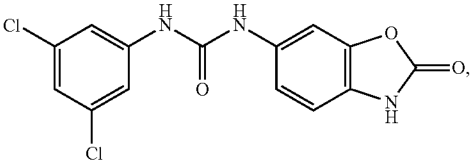,
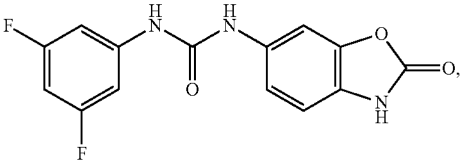,
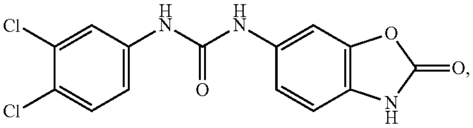,
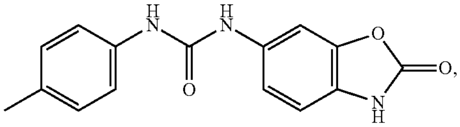,
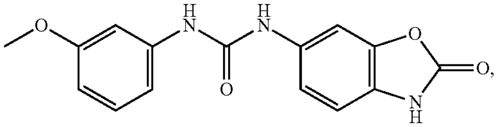,
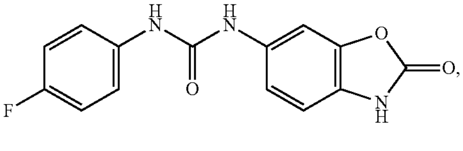,
-continued
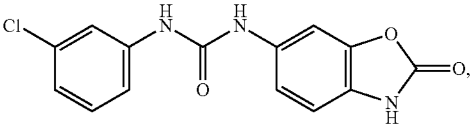,
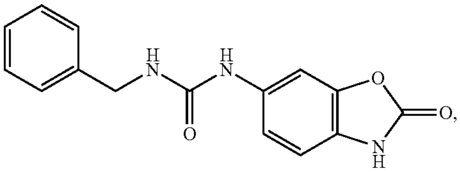,
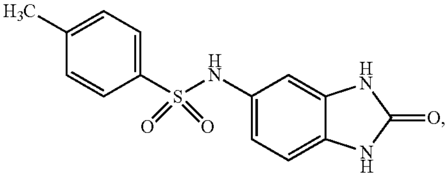,
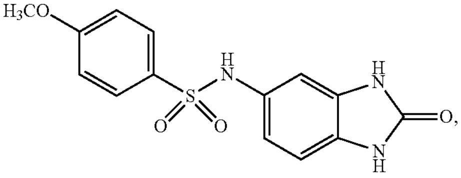,
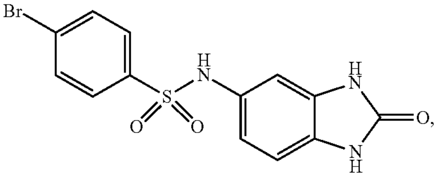,
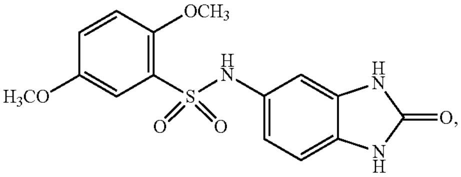,
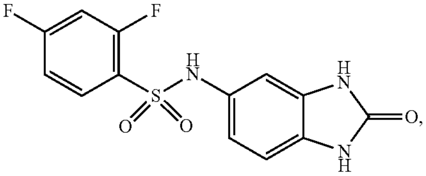,
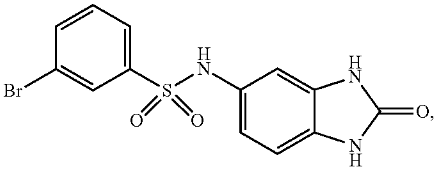,
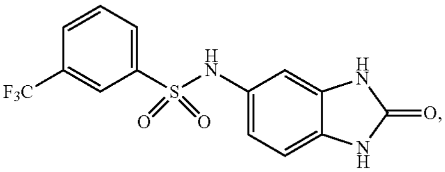,
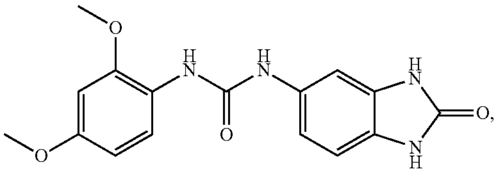, -continued
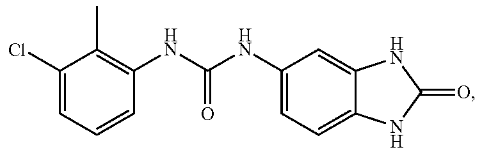
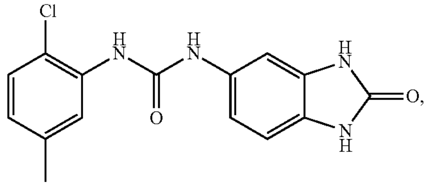
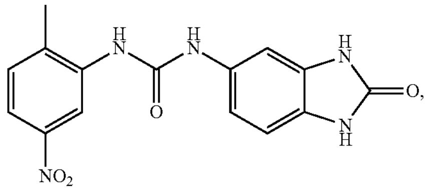
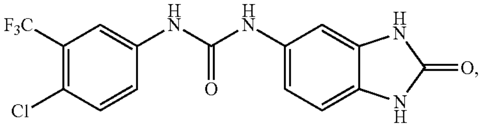
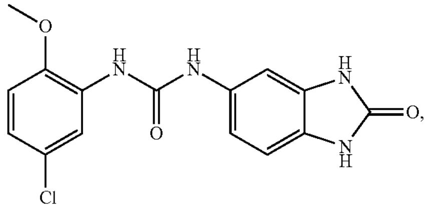
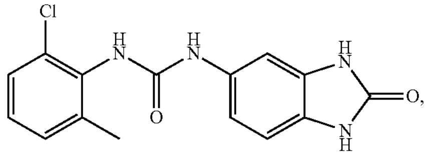
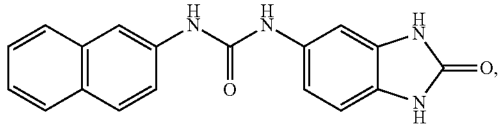
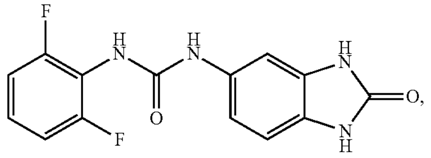
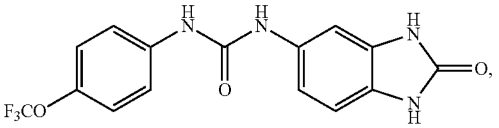
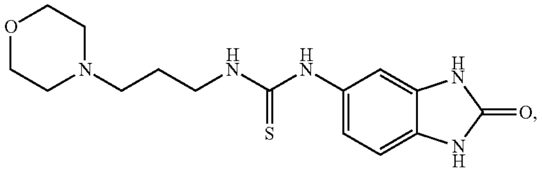
-continued
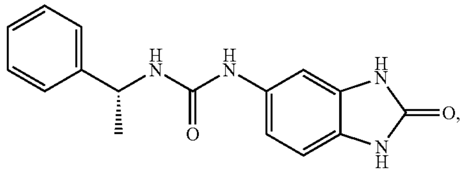
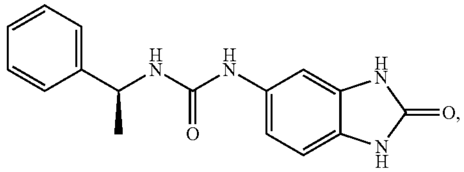
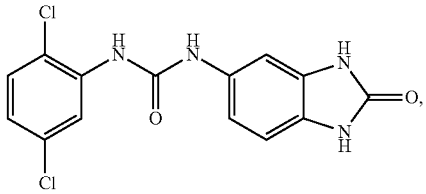
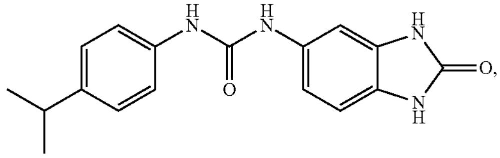
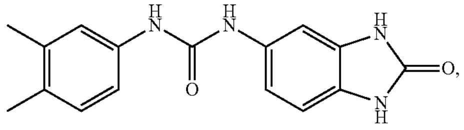
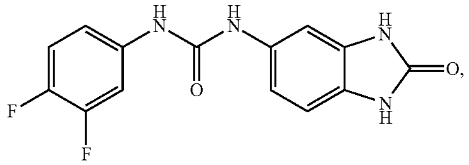
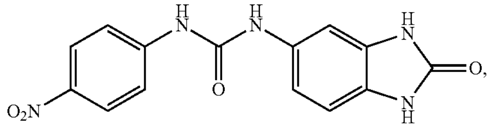
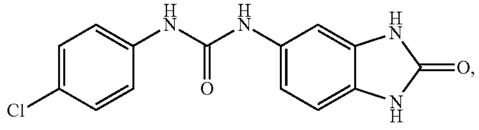
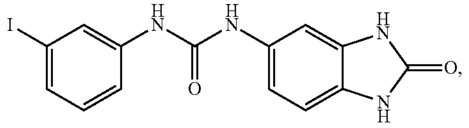
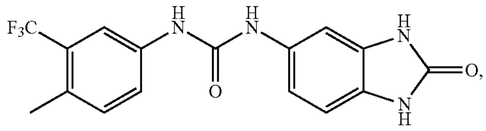
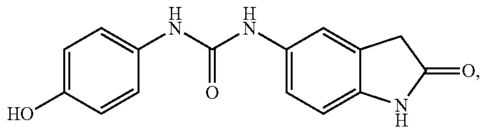

-continued
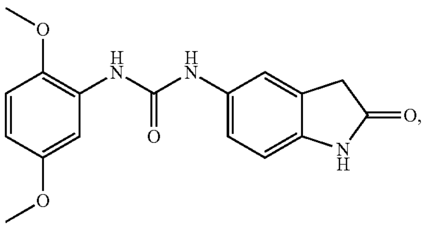
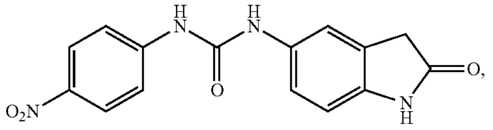
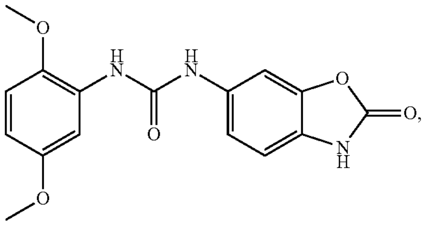
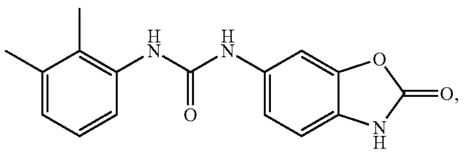
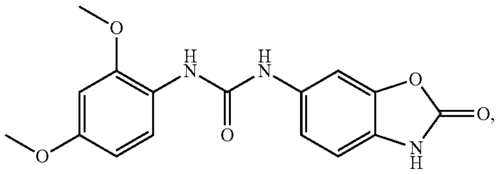
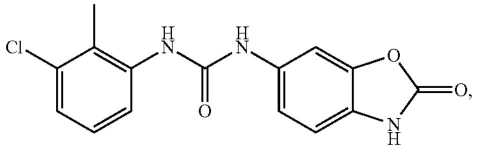
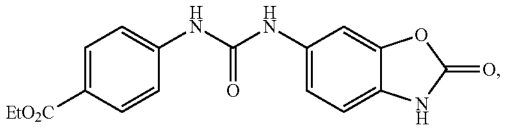
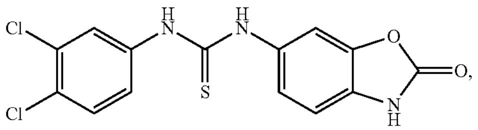
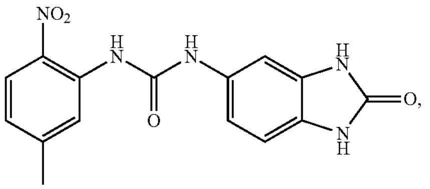
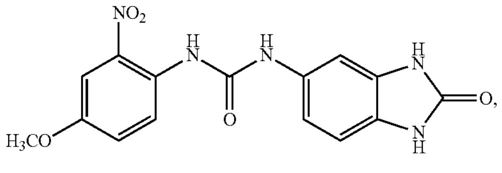
-continued
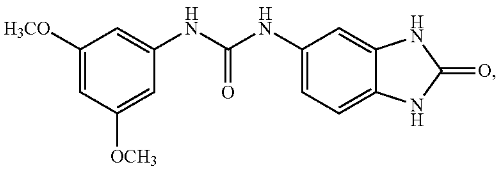
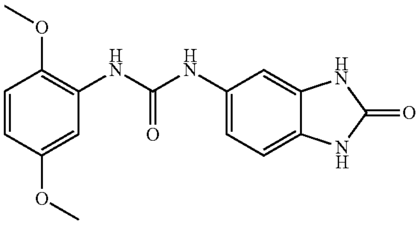
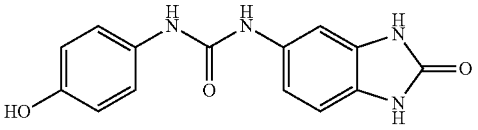
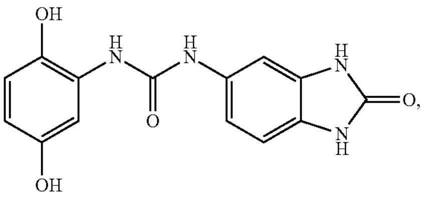
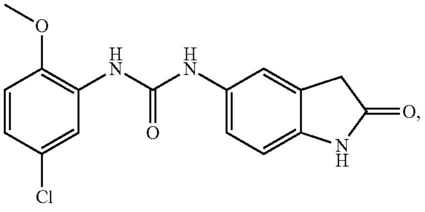
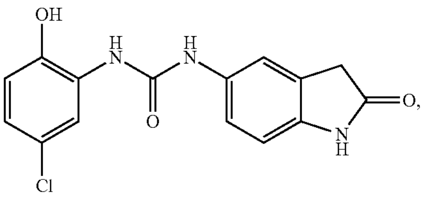
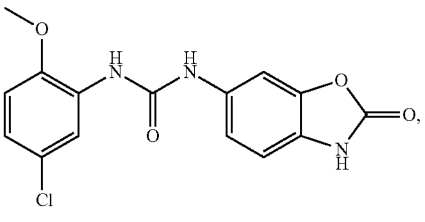
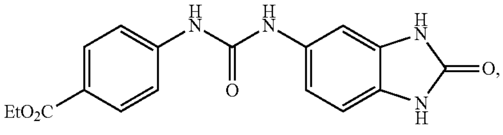
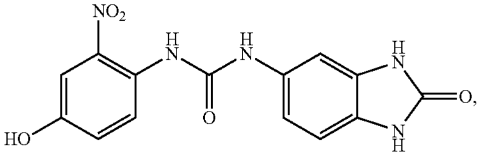

-continued
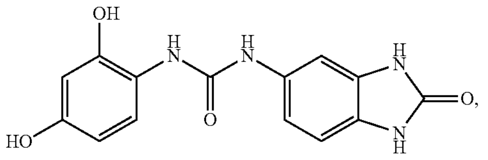
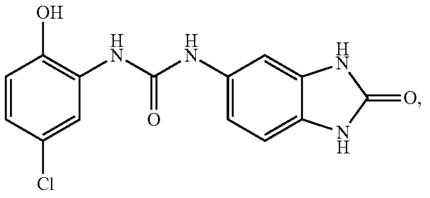
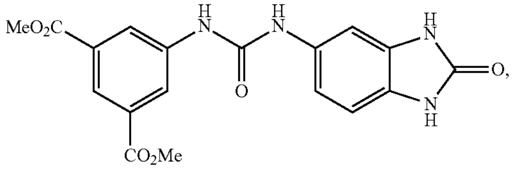
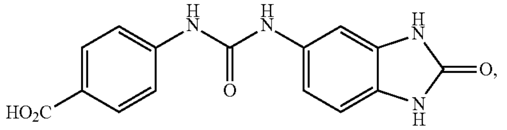
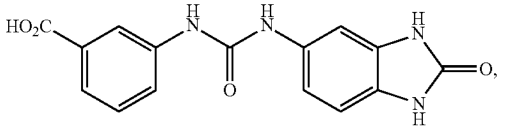
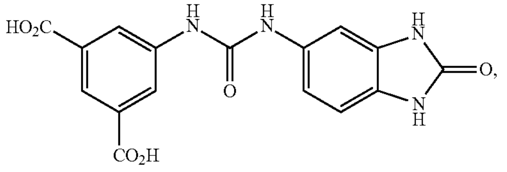
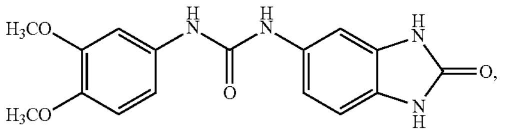
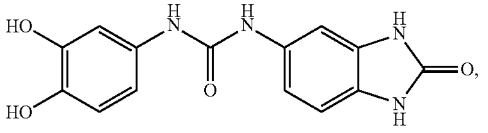
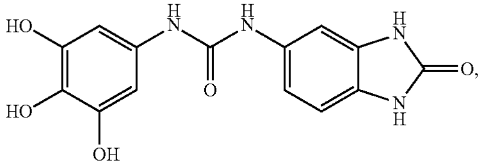
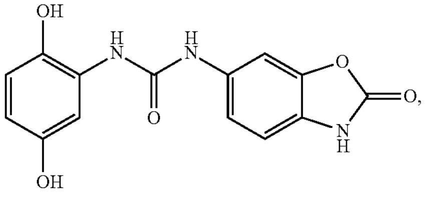
-continued
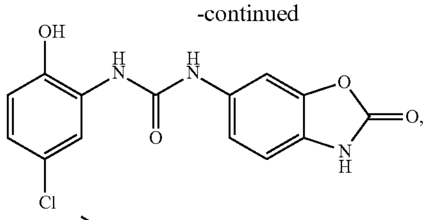
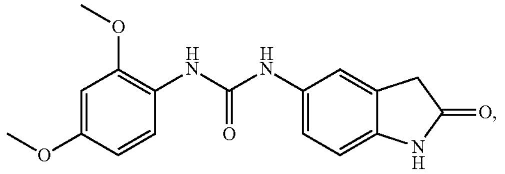
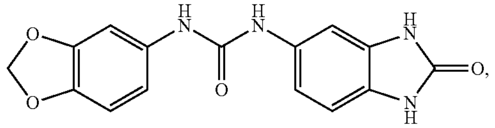
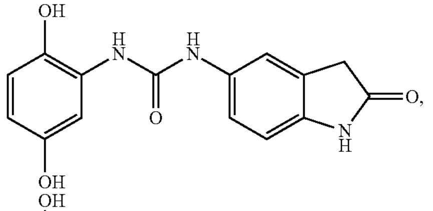
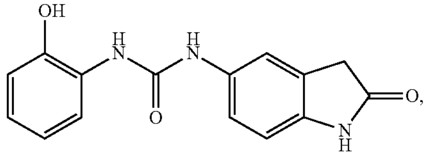
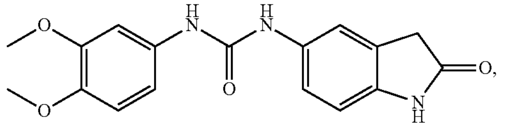
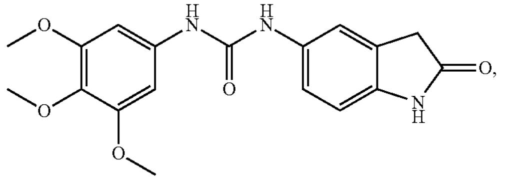
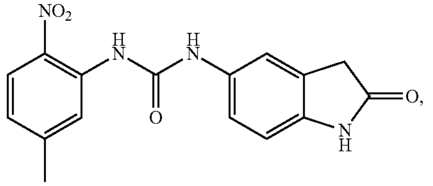
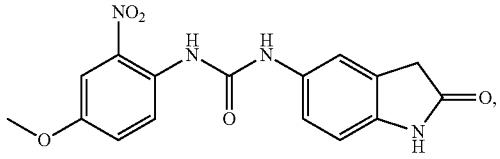
or
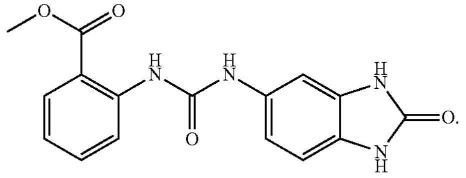
The use of the word “a” or “an” when used in conjunction with the term “comprising” in the claims and/or the specification may mean "one," but it is also consistent with the meaning of "one or more," "at least one," and "one or more than one."

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. The skilled artisan will understand that typically there is no limit on the number of items or terms in any combination, unless otherwise apparent from the context.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

For a more complete understanding of the features and advantages of the present disclosure, reference is now made to the detailed description of the disclosure along with the accompanying figures and in which:

FIG. 111B shows quantitation of the observed fragmented nucleus in FIG. 10 by Series-1 GRB001 analogues, where GRB002 and GRB005 showing highest level of fragmented nucleus, a early indication of apoptosis. FIG. 11C shows inhibition of EGF induced ERK activation by GRB001 compound in OVCAR5 and OVCAR8 cells.

FIG. 14B shows binding isotherm of GRB092 with 527±367 nM Kd. FIG. 14C shows a control ITC isotherm generated by injecting GRB092 into buffer in the absence of GRB2 proteins.

FIG. 15 shows mutational status of GRB2 inhibitor tested cell-lines.

FIG. 16A shows a representative anisotropy measurement of no-binding (NB) data for compound GRB038. FIG. 16B shows a representative anisotropy measurement with GBR093 inducing GRB2 dimerization at a EC50 of 15.5 μM. Note that NB represent compounds inability to induce GRB2 dimerization.

DETAILED DESCRIPTION

Figures 1A, 1B, 1C:
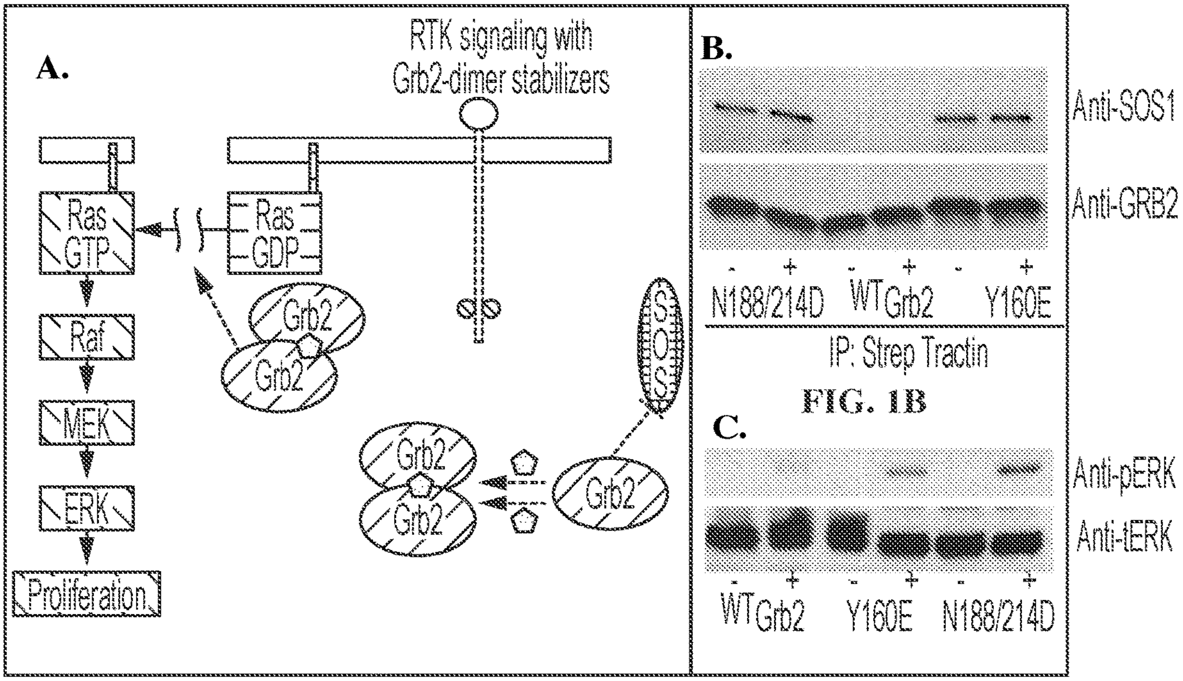
FIGS. 1A-1C show a schematic overview of how dimer stabilizing small molecule would inhibit SOS binding and Ras/MAPK activation (FIG. 1A); pull-down experiments demonstrating only the monomeric GRB2 binds SOS (FIG. 1B); and overexpression of a monomeric GRB2 enhances Ras/MAPK signaling (FIG. 1C). Monomeric GRB2 (Y160E and N188/214D) binds SOS but not the dimeric (WT).
Figure 2:
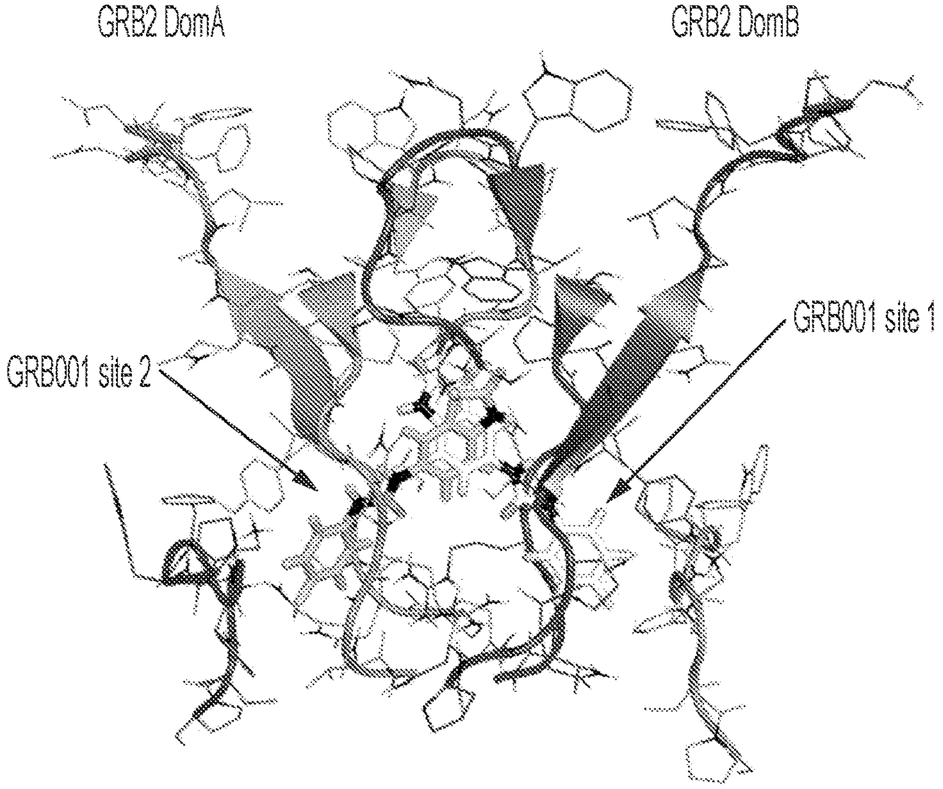
FIG. 2 shows identification of GRB2 dimer interface binding molecule. GRB001 able to bind GRB2 in two different conformations.
Figure 3:
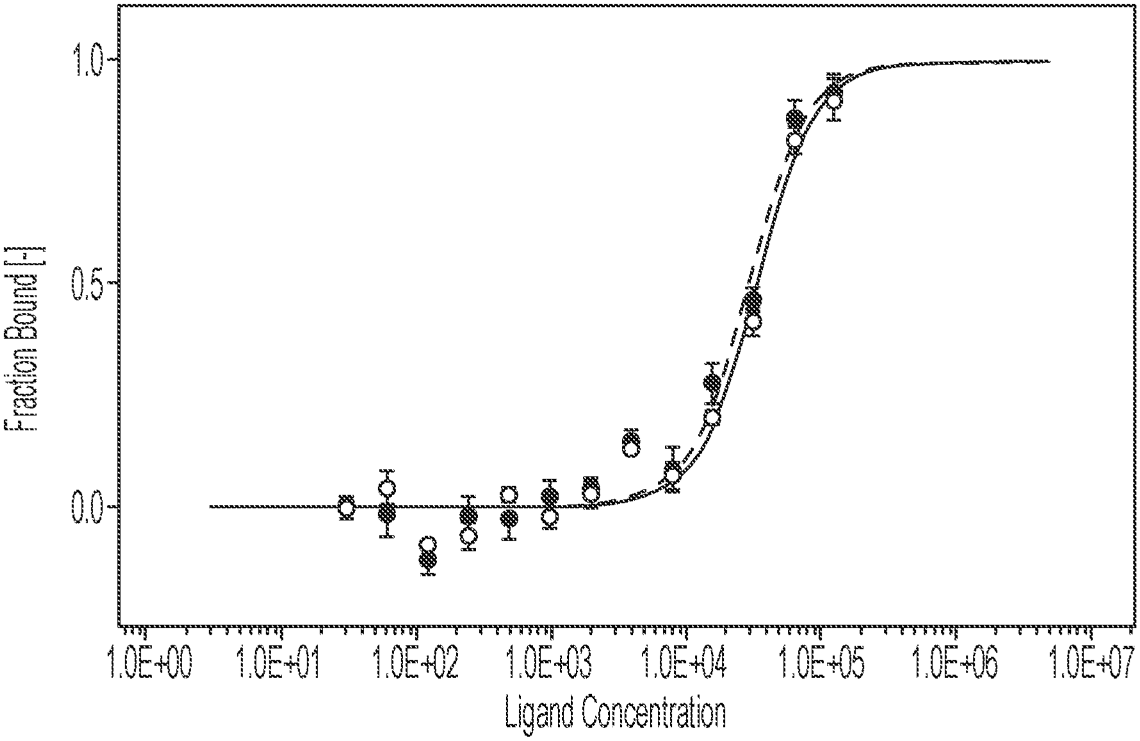
FIG. 3 shows GRB001 binding to GRB2 by MST. In vitro binding of GRB001 to GRB2 with 50 μM $K_d$.
Figure 4:
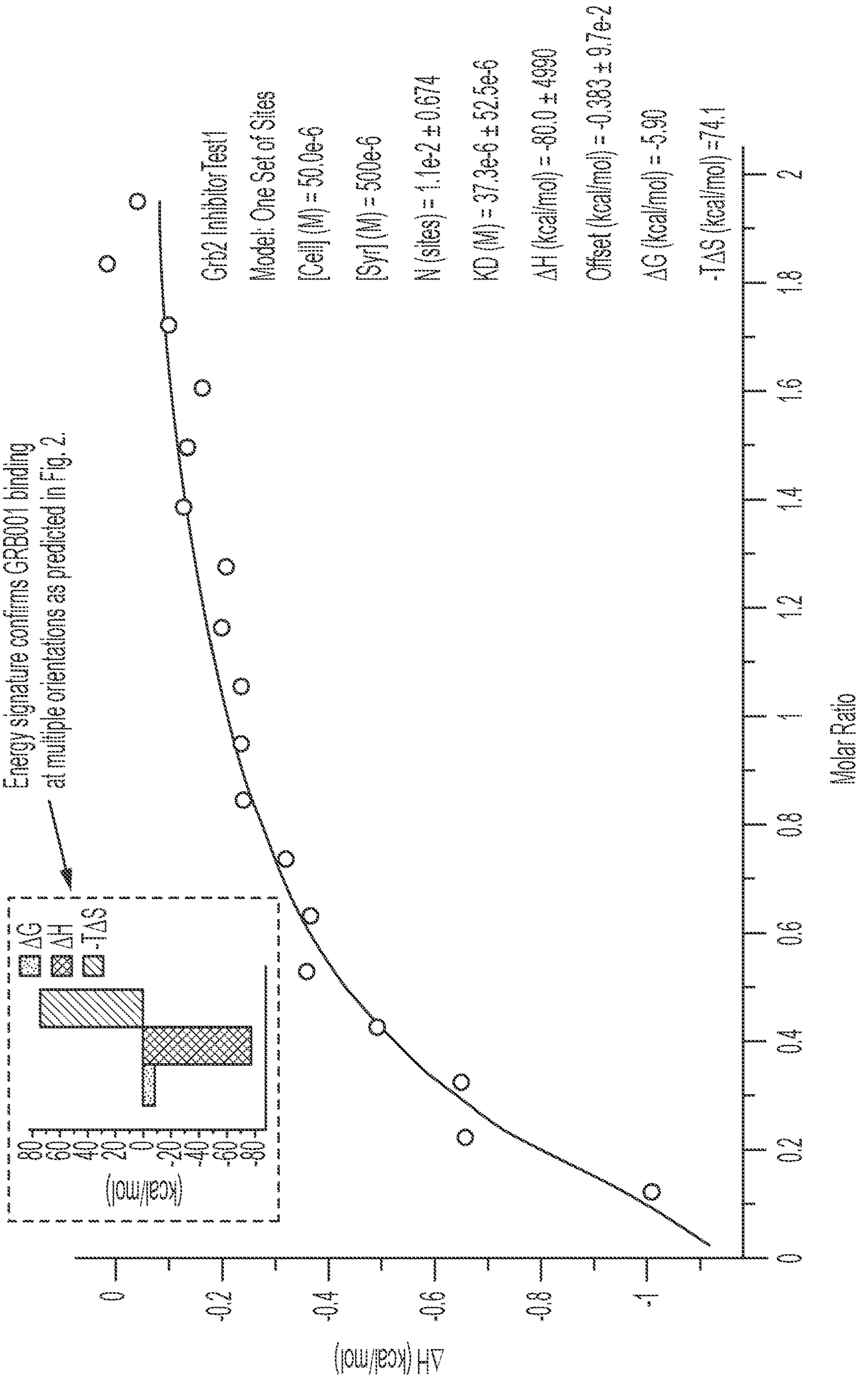
FIG. 4 shows GRB001 binding to GRB2 by ITC. Validation of in vitro binding of GRB001 to GRB2 with ITC as an alternative technique. $K_d$=37 μM+/−50 μM. GRB001 is able to bind GRB2 in two different conformations as reflected by the energy signature (inset).
Figure 5:
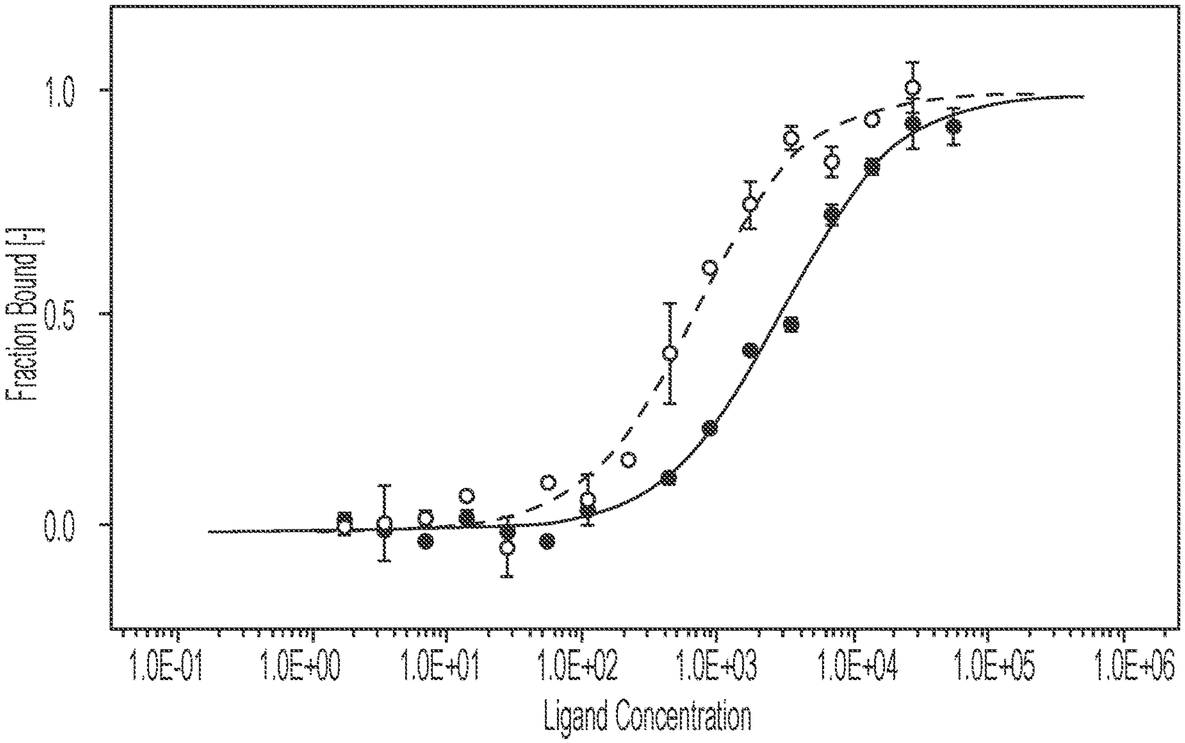
FIG. 5 shows GRB001 stabilizes the GRB2 dimer interface. Measurements of GRB2 monomer dimer equilibrium in the absence (lower, darker line) or presence of 100 μM GRB001 (upper, lighter line). The results show GRB001 induce a Kd shift favoring dimerization at lower GRB2 concentrations.
Figures 6A, 6B, 6C, 6D:
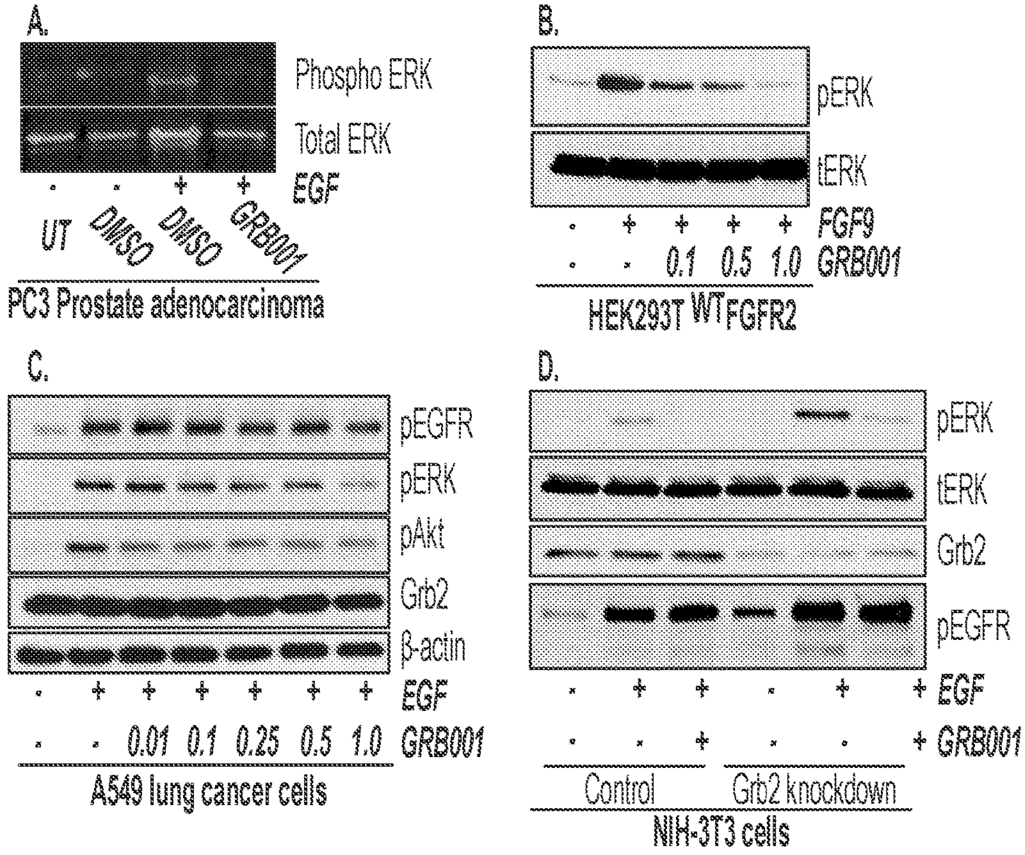
FIG. 6A-6D show GRB001 inhibits EGF and FGF induced MAPK activation. GRB001 inhibits RTK induced Ras signaling in multiple cancer cell-lines. GRB001 inhibits RAS/ERK activation while EGFR is fully active (FIG. 6D, top panel and the corresponding active EGFR in bottom panel)
Figure 7:
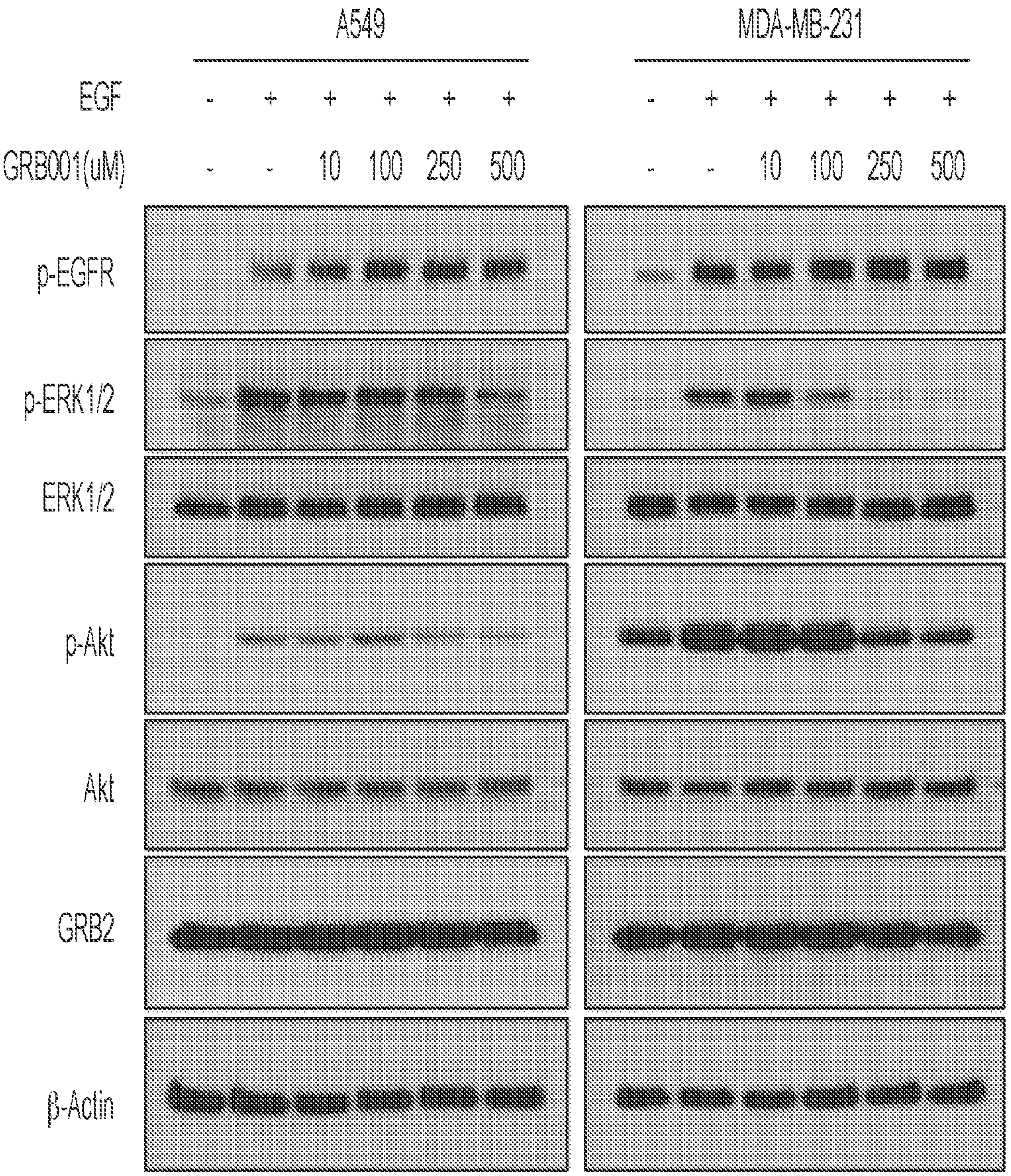
FIG. 7 shows GRB001 inhibits EGF induced MAPK activation. GRB001 inhibits RTK induced Ras signaling in MDA-MB-231 triple negative breast cancer cells with G13D k-Ras mutation and in A549 (lung adenocarcinoma) cells with G12S KRAS mutation.
Figures 8A, 8B:
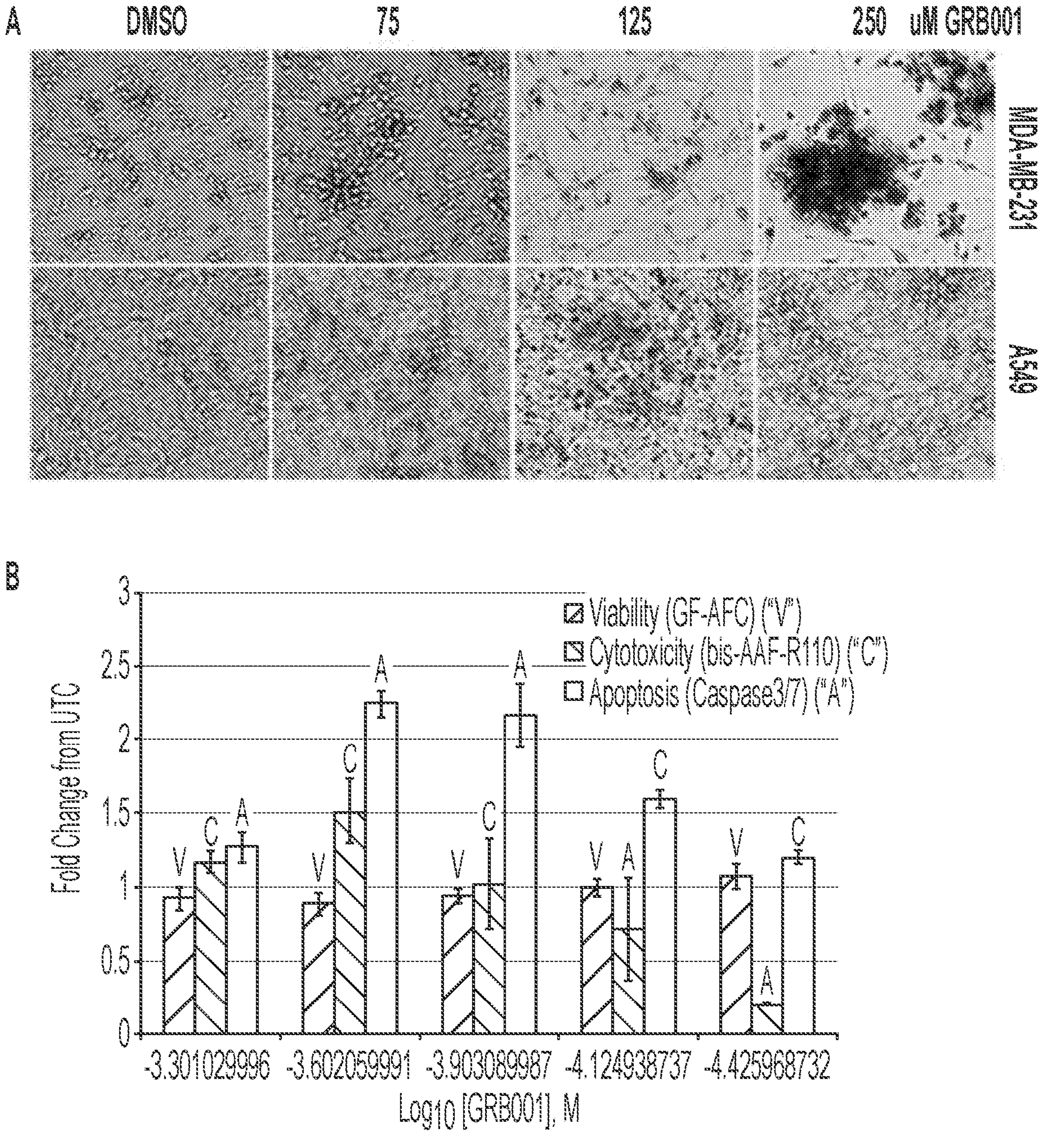
FIGS. 8A & 8B show GRB001 induces apoptosis in tumor cells (MDA-MB-231 TNBC and A549 lung cancer cells, FIG. 8A). GRB001 specifically kills triple negative breast cancer cells through caspase 3/7 mediated apoptosis (FIG. 8B).
Figure 9:
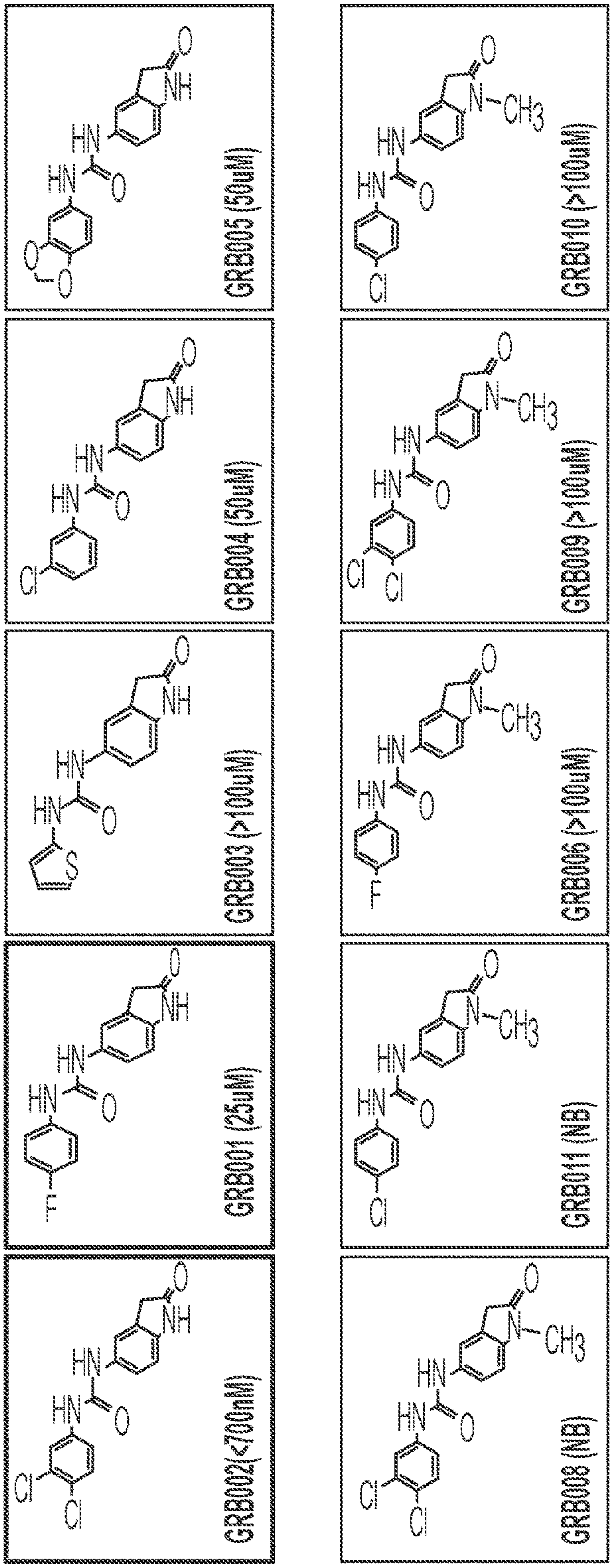
FIG. 9 shows modified derivatives of the original GRB001 compounds also called Series-1 compounds.
Figure 10:
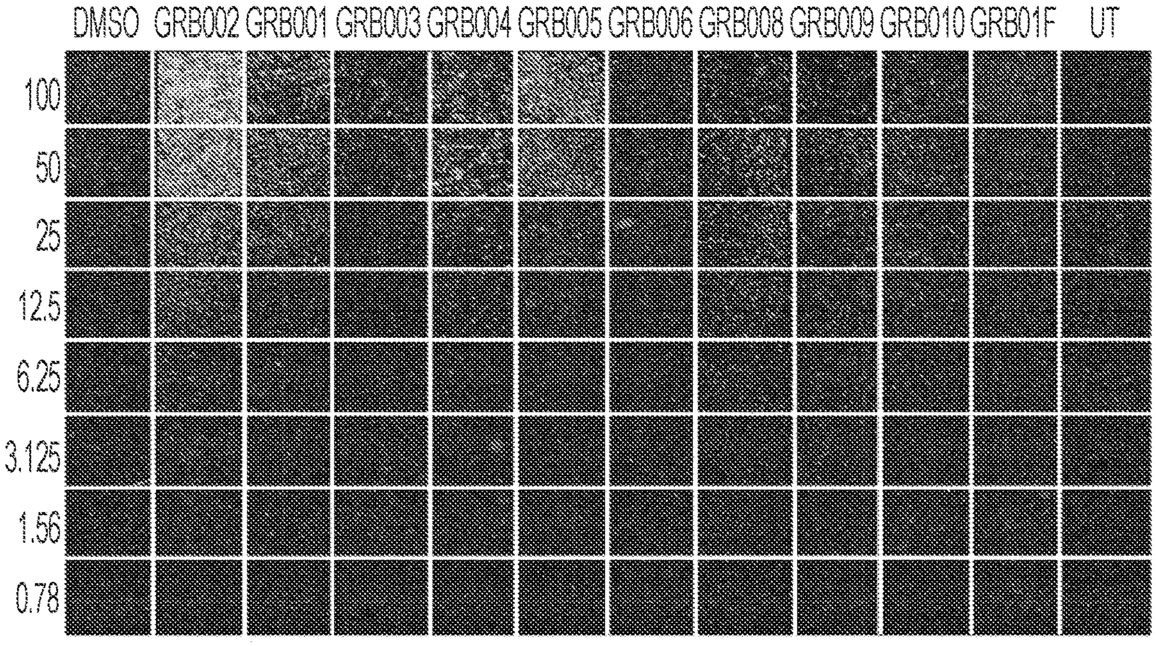
FIG. 10 shows testing of Series-1 compounds in high-throughput assay demonstrating that GRB001 derivatives induce nuclear fragmentation of OVCAR5 cells. The intensity of the red color represents nuclear condensation indicative of apoptotic cells.
Figure 11A:
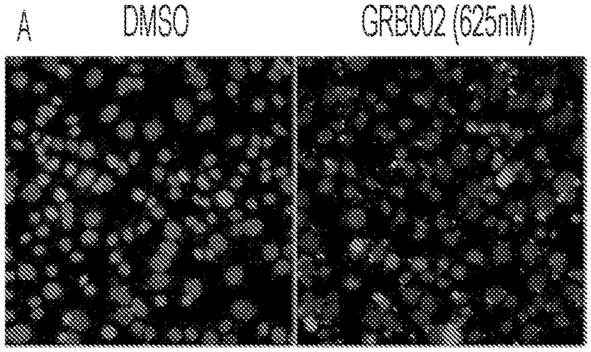
FIGS. 11A-11C shows high resolution image of GRB002 inducing nuclear fragmentation of OVCAR5 cells with 500 nM compound (FIG. 11A).
Figure 11B:
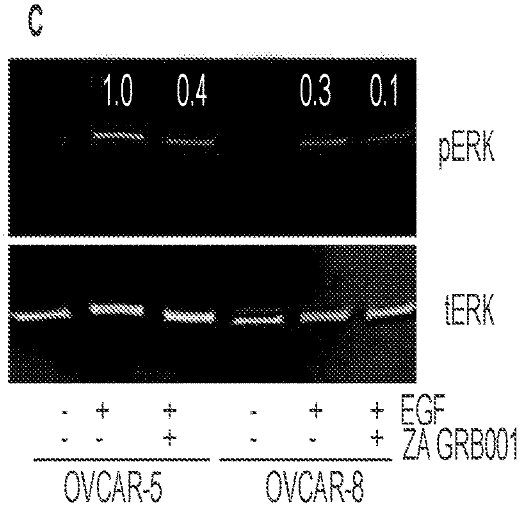
Figures 11A, 11B, 11C:
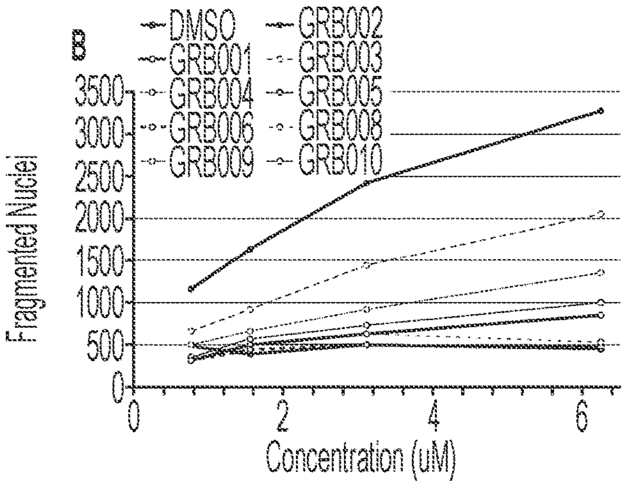
Figure 12:
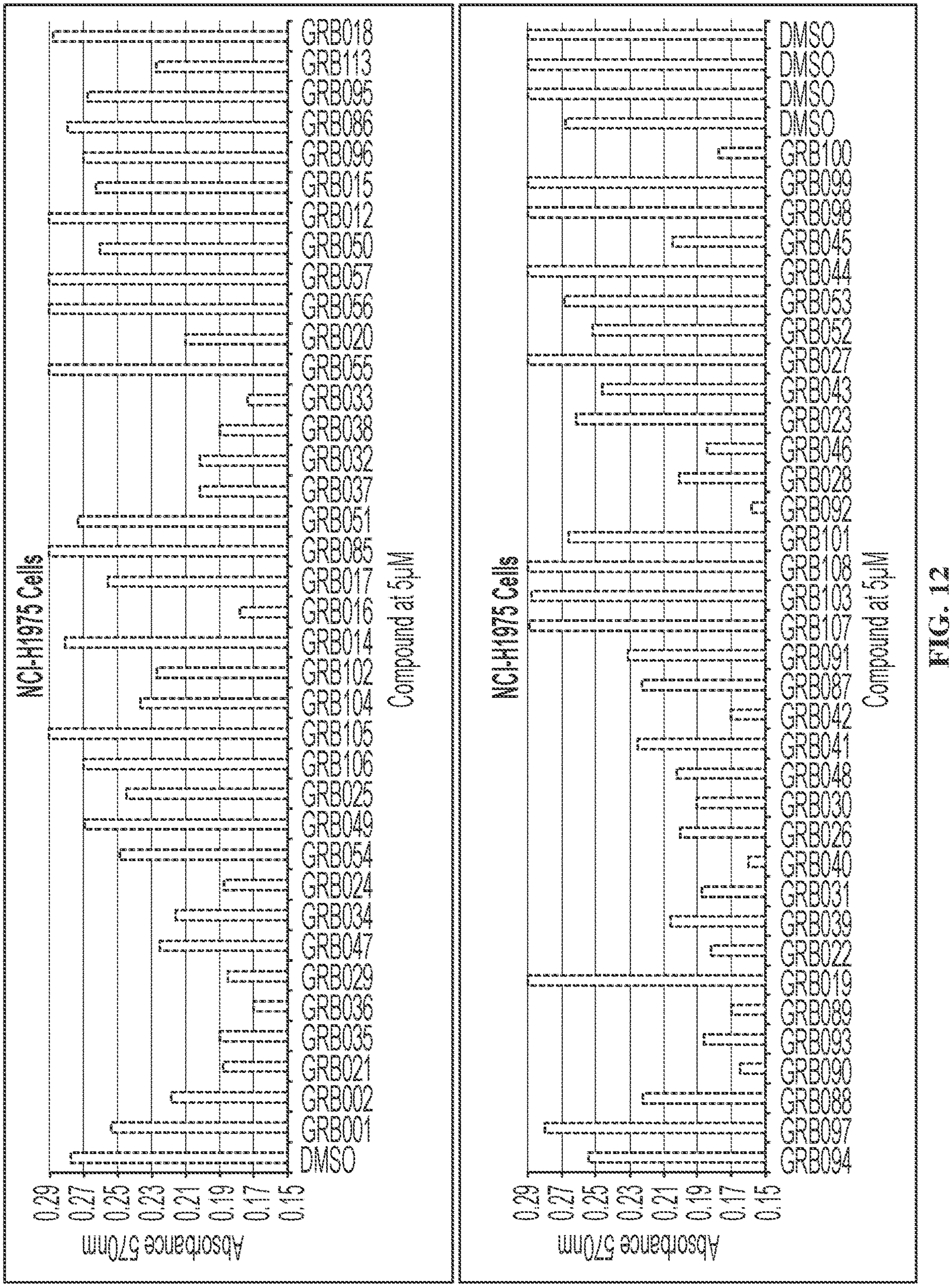
FIG. 12 shows in vivo cellular activity using MTT assay for a selection of GRB001 analogues in H1975 Lung adenocarcinoma cells bearing T790M EGFR gatekeeper mutation and are treatment resistant to current standard care. A number of the compounds disclosed herein kill these cells.
Figure 13:
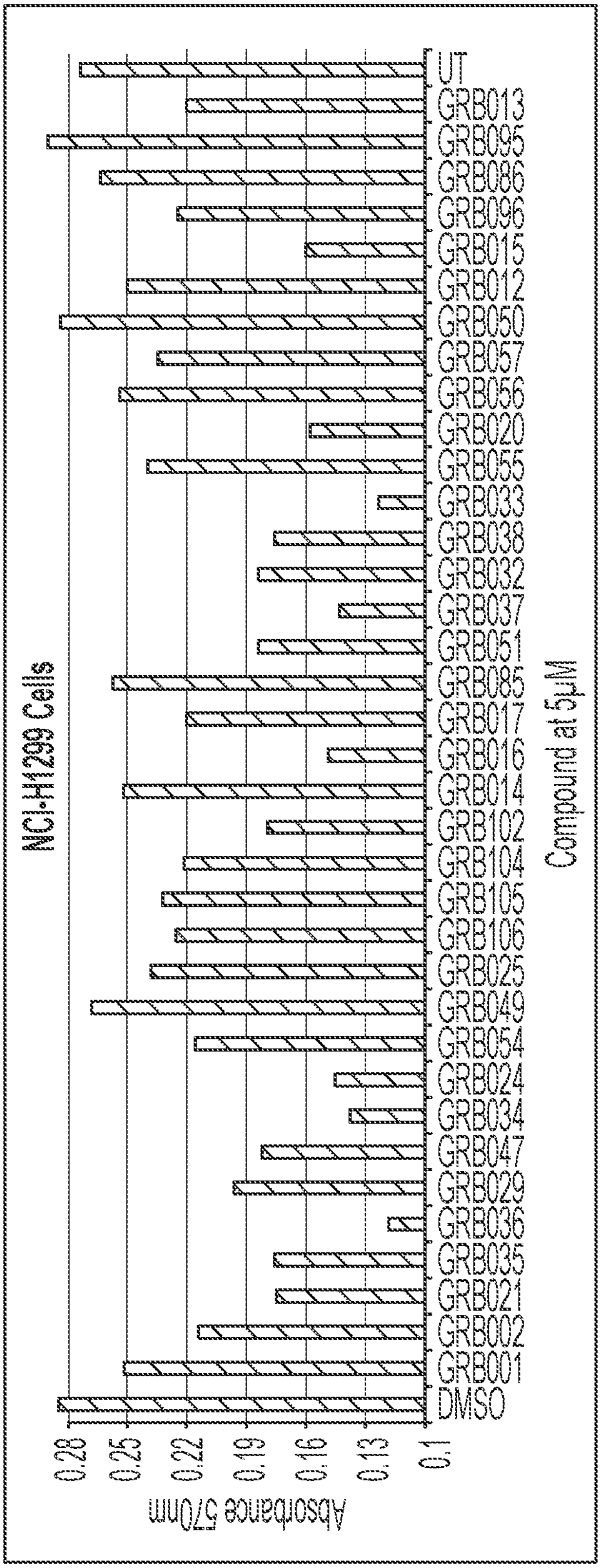
FIG. 13 shows MTT cell viability assay shows GRB2 inhibitors sensitizes NCI-H1299 a p53 null non-small cell lung cancer cells that are resistant to ionizing radiation. Treatment of these cells with ionizing radiation with GRB2 compounds leads to widespread cell death.
Figure 14A:
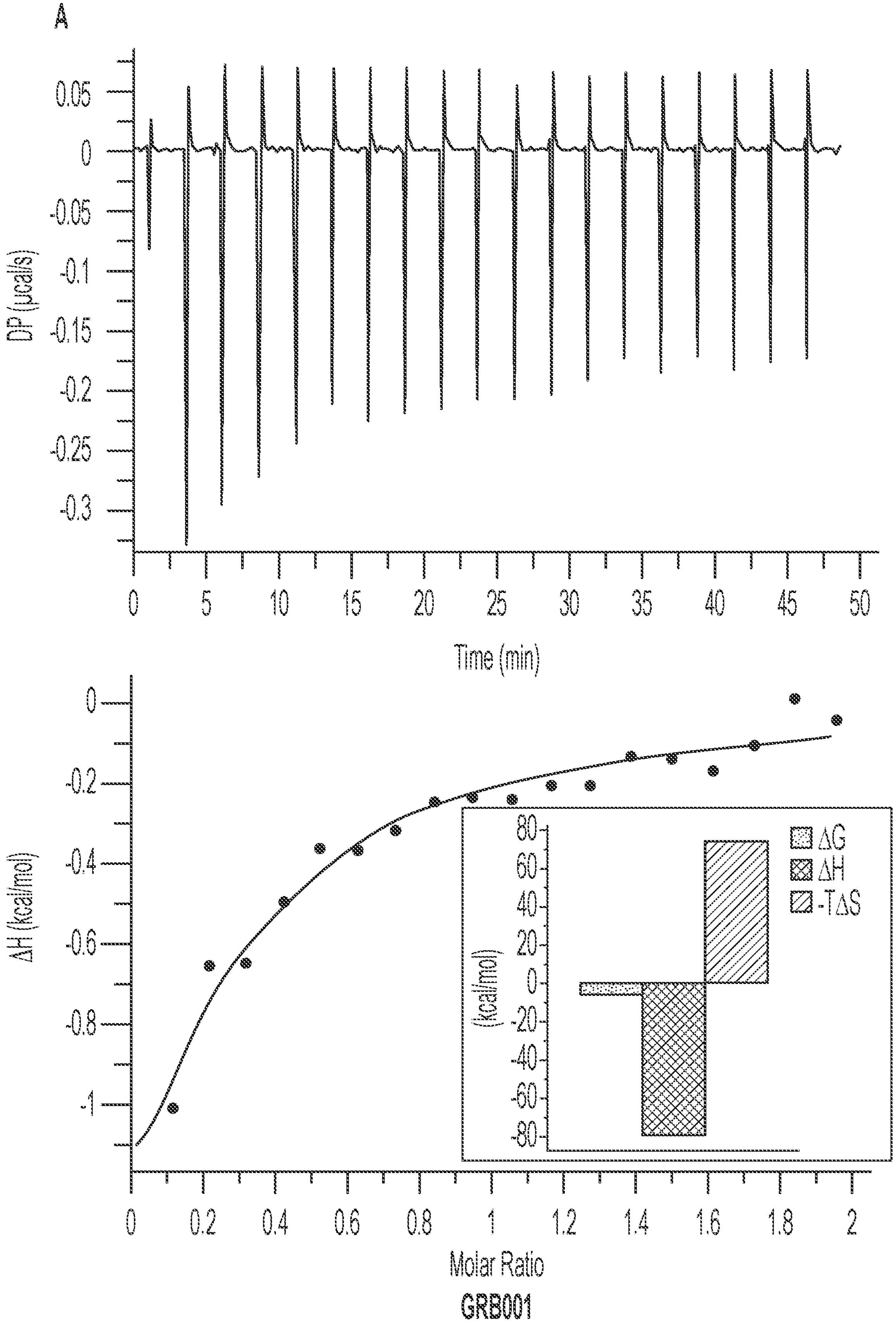
FIGS. 14A-14C show ITC binding isotherm of GRB001 binding to GRB2 as in FIG. 4 (FIG. 14A).
Figure 14B:
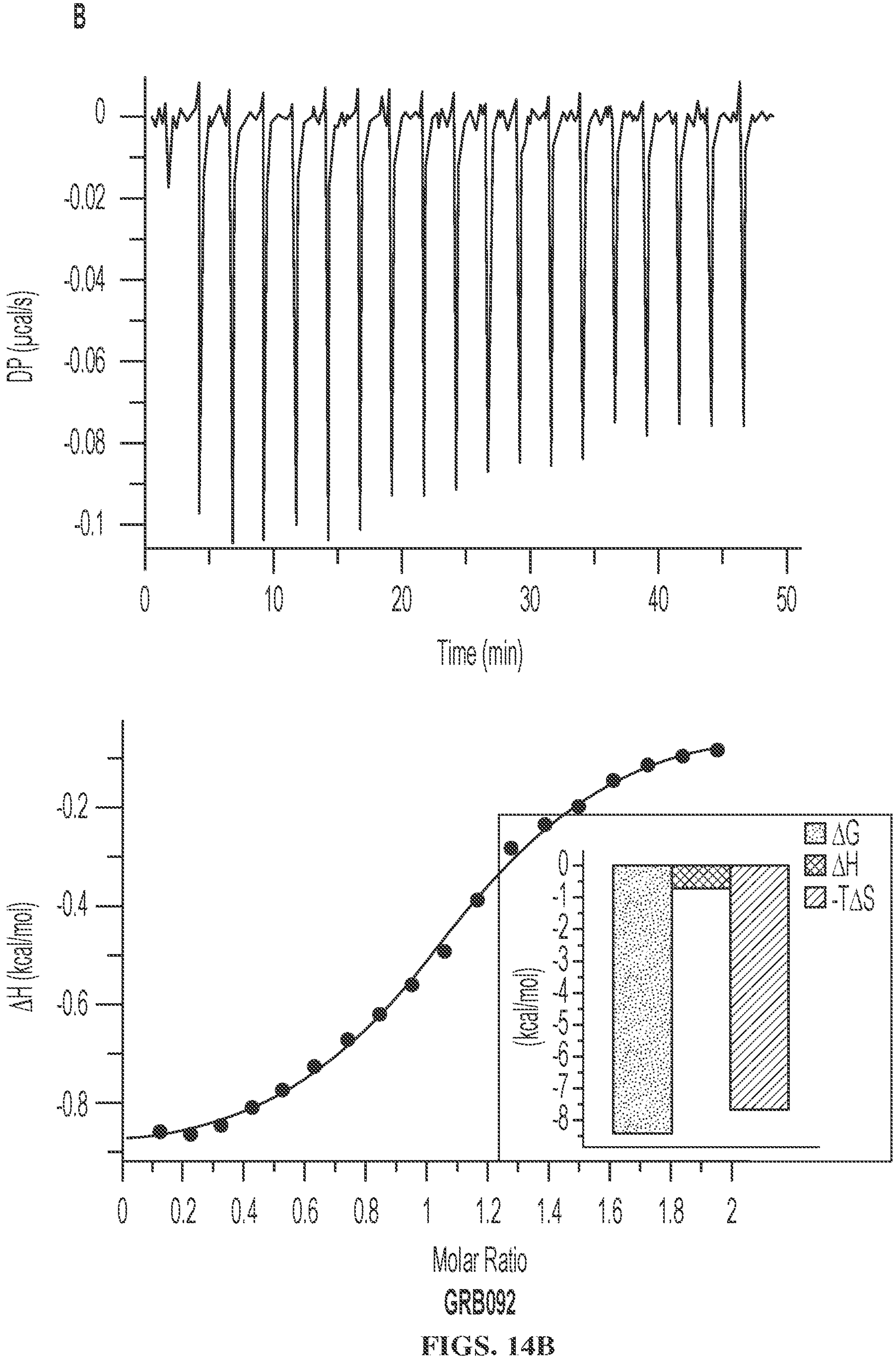
Figure 14C:
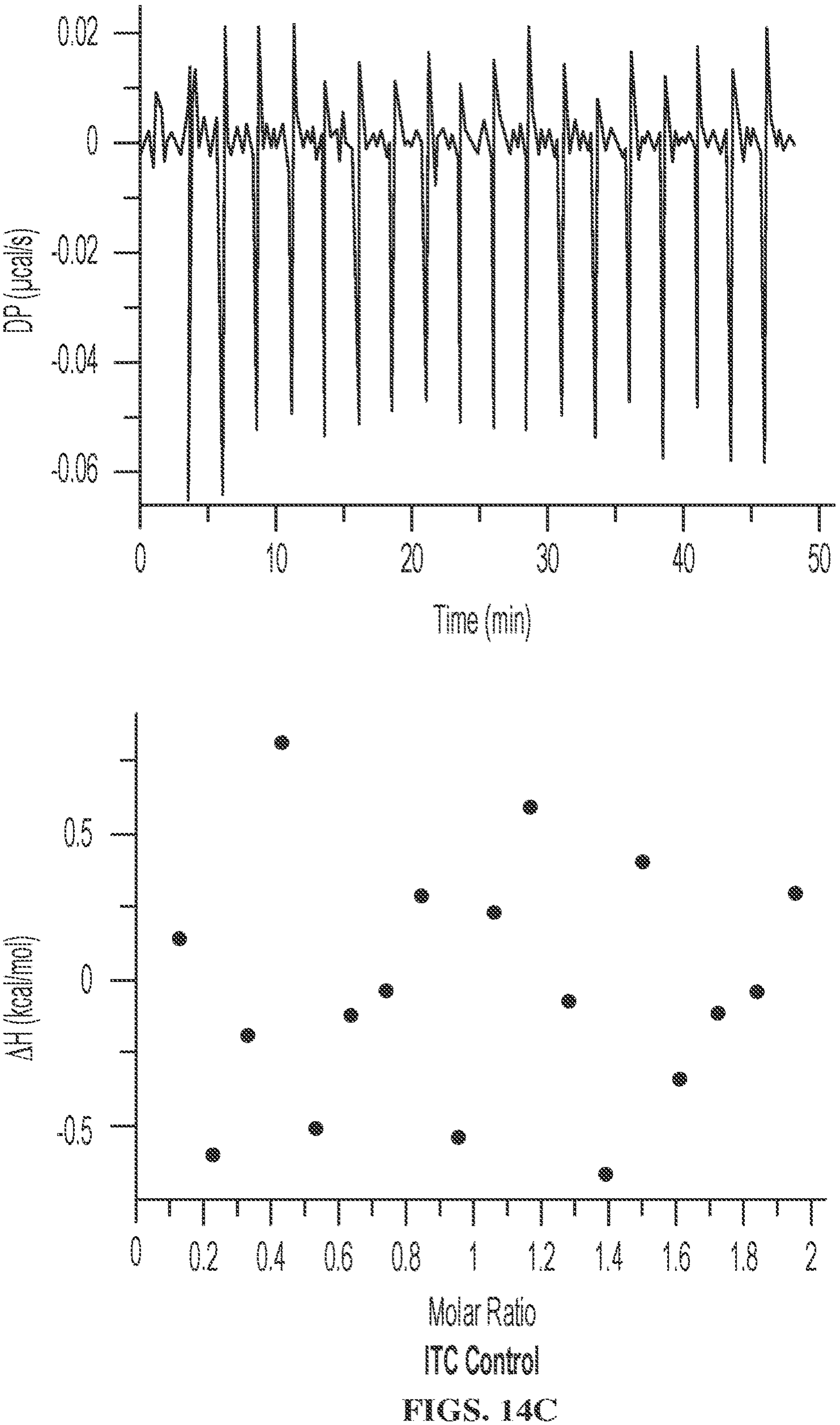

The present disclosure relates to small molecule stabilizers of dimeric GRB2. These compounds may be used to inhibit RTK-induced MAP kinase in various cancers, such as KRAS-positive cancers. These compounds may show one or more preferential properties relative to those known in the art, such as improved efficacy. These and other details are described below.

I. COMPOUNDS OF THE PRESENT DISCLOSURE

The compounds of the present disclosure may be depicted by a structural formula as shown below in Table 1.

TABLE 1

Compound IDs and structures of the compounds of the present disclosure.

| ID | Structure |
|---|---|
| GRB001 | 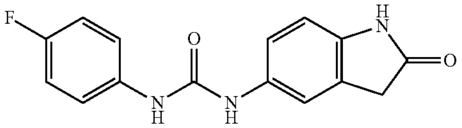 [SMILES: O=C1Cc2cc(NC(=O)Nc3ccc(F)cc3)ccc2N1] |
| GRB002 | 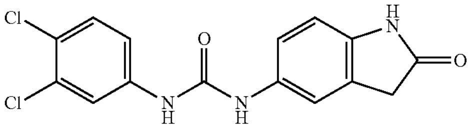 |
| GRB003 | 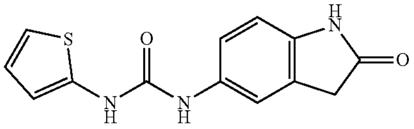 [SMILES: O=C1Cc2cc(NC(=O)Nc3cccs3)ccc2N1] |
| GRB004 | 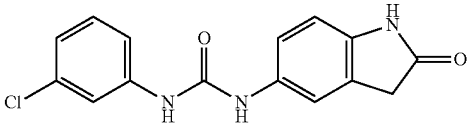 [SMILES: O=C1Cc2cc(NC(=O)Nc3cccc(Cl)c3)ccc2N1] |
| GRB005 | 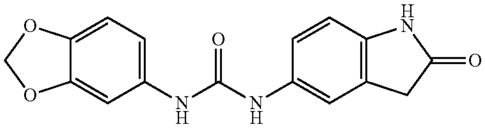 [SMILES: O=C1Cc2cc(NC(=O)Nc3ccc4c(c3)OCO4)ccc2N1] |
| GRB006 | 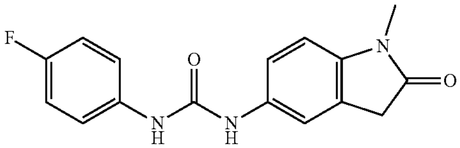 [SMILES: CN1C(=O)Cc2cc(NC(=O)Nc3ccc(F)cc3)ccc21] |
| GRB007 | 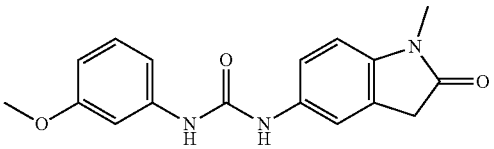 [SMILES: COc1cccc(NC(=O)Nc2ccc3c(c2)CC(=O)N3C)c1] |
| GRB008 | 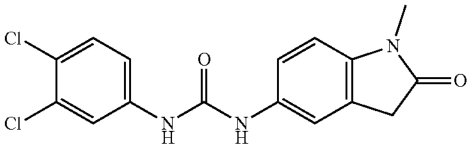 [SMILES: CN1C(=O)Cc2cc(NC(=O)Nc3ccc(Cl)c(Cl)c3)ccc21] |

TABLE 1-continued

Compound IDs and structures of the compounds of the present disclosure.

| ID | Structure |
|---|---|
| GRB009 | 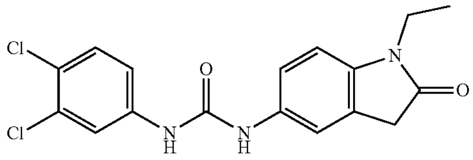 [SMILES: CCN1C(=O)Cc2cc(NC(=O)Nc3ccc(Cl)c(Cl)c3)ccc21] |
| GRB010 | 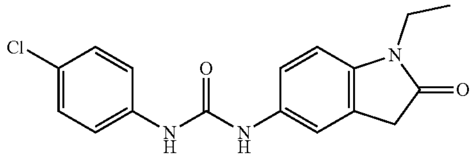 [SMILES: CCN1C(=O)Cc2cc(NC(=O)Nc3ccc(Cl)cc3)ccc21] |
| GRB011 | 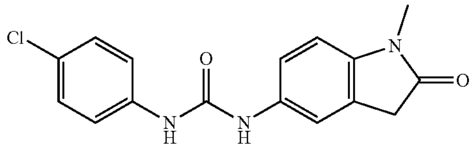 [SMILES: CN1C(=O)Cc2cc(NC(=O)Nc3ccc(Cl)cc3)ccc21] |
| GRB012 | 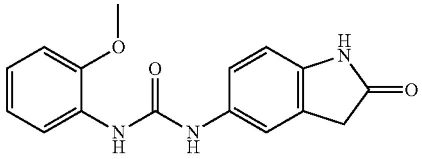 [SMILES: COc1ccccc1NC(=O)Nc1ccc2c(c1)CC(=O)N2] |
| GRB013 | 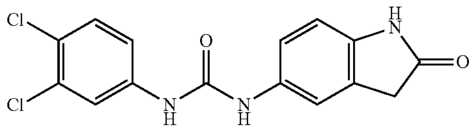 |
| GRB014 | 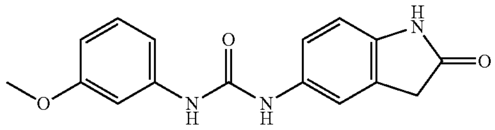 [SMILES: COc1cccc(NC(=O)Nc2ccc3c(c2)CC(=O)N3)c1] |
| GRB015 | 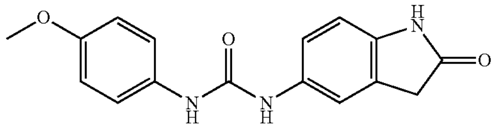 [SMILES: COc1ccc(NC(=O)Nc2ccc3c(c2)CC(=O)N3)cc1] |
| GRB016 | 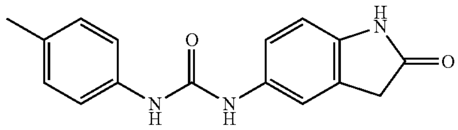 |
| GRB017 | 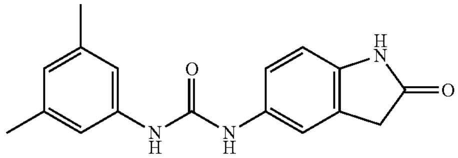 [SMILES: Cc1cc(C)cc(NC(=O)Nc2ccc3c(c2)CC(=O)N3)c1] |

TABLE 1-continued
Compound IDs and structures of the compounds of the present disclosure.
| ID | Structure |
|---|---|
| GRB018 | 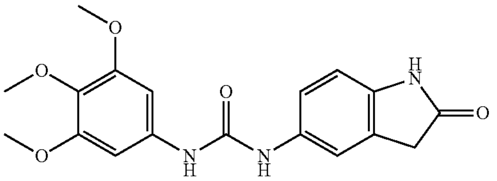 [SMILES: COc1cc(NC(=O)Nc2ccc3c(c2)CC(=O)N3)cc(OC)c1OC] |
| GRB019 | 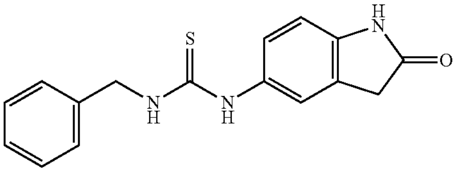 [SMILES: O=C1Cc2cc(NC(=S)NCc3ccccc3)ccc2N1] |
| GRB020 | 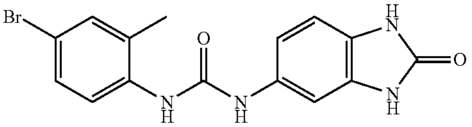 [SMILES: Cc1cc(Br)ccc1NC(=O)Nc1ccc2[nH]c(=O)[nH]c2c1] |
| GRB021 | 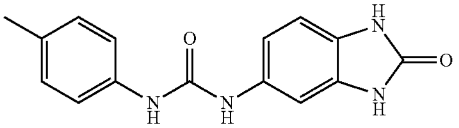 [SMILES: Cc1ccc(NC(=O)Nc2ccc3[nH]c(=O)[nH]c3c2)cc1] |
| GRB022 | 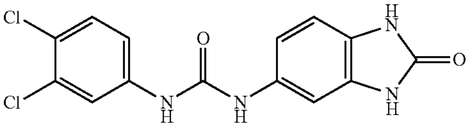 [SMILES: O=C(Nc1ccc(Cl)c(Cl)c1)Nc1ccc2[nH]c(=O)[nH]c2c1] |
| GRB023 | 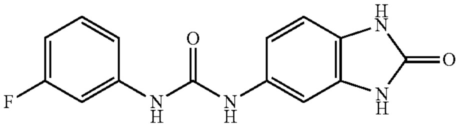 |
| GRB024 | 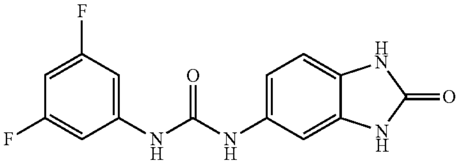 [SMILES: O=C(Nc1cc(F)cc(F)c1)Nc1ccc2[nH]c(=O)[nH]c2c1] |
| GRB025 | 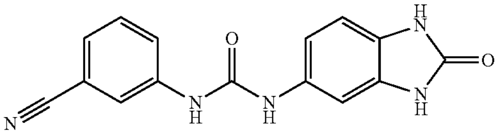 [SMILES: N#Cc1cccc(NC(=O)Nc2ccc3[nH]c(=O)[nH]c3c2)c1] |
| GRB026 | 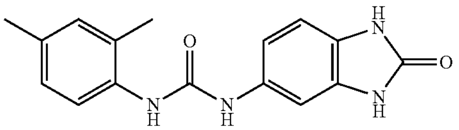 |
| GRB027 | 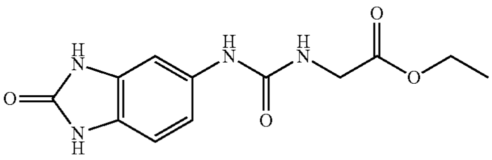 [SMILES: CCOC(=O)CNC(=O)Nc1ccc2[nH]c(=O)[nH]c2c1] |
| GRB028 | 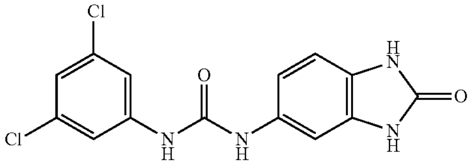 [SMILES: O=C(Nc1cc(Cl)cc(Cl)c1)Nc1ccc2[nH]c(=O)[nH]c2c1] |
| GRB029 | 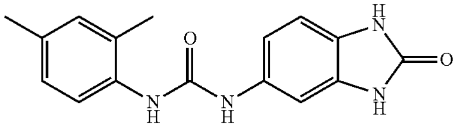 [SMILES: Cc1ccc(NC(=O)Nc2ccc3[nH]c(=O)[nH]c3c2)c(C)c1] |
| GRB030 | 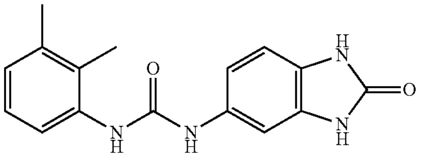 [SMILES: Cc1cccc(NC(=O)Nc2ccc3[nH]c(=O)[nH]c3c2)c1C] |
| GRB031 | 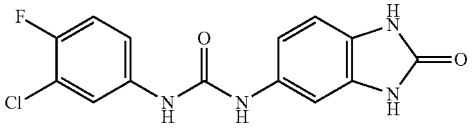 |
| GRB032 | 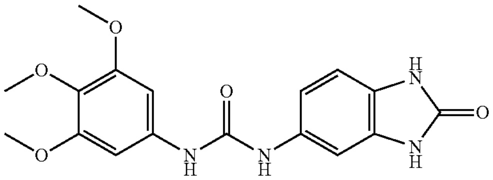 [SMILES: COc1cc(NC(=O)Nc2ccc3[nH]c(=O)[nH]c3c2)cc(OC)c1OC] |
| GRB033 | 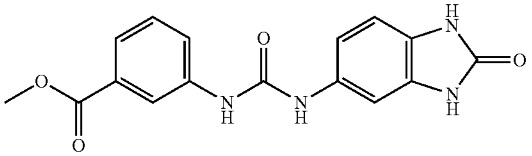 [SMILES: COC(=O)c1cccc(NC(=O)Nc2ccc3[nH]c(=O)[nH]c3c2)c1] |
| GRB034 | 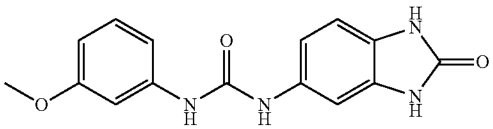 [SMILES: COc1cccc(NC(=O)Nc2ccc3[nH]c(=O)[nH]c3c2)c1] |
| GRB035 | 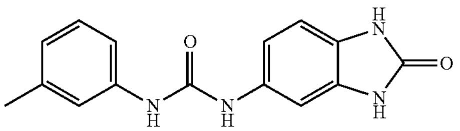 [SMILES: Cc1cccc(NC(=O)Nc2ccc3[nH]c(=O)[nH]c3c2)c1] |
| GRB036 | 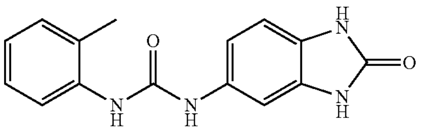 [SMILES: Cc1ccccc1NC(=O)Nc1ccc2[nH]c(=O)[nH]c2c1] |
| GRB037 | 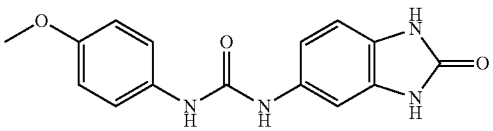 |

TABLE 1-continued
Compound IDs and structures of the compounds of the present disclosure.
| ID | Structure |
| --- | --- |
| GRB038 | 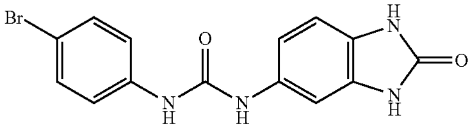 [SMILES: O=C(Nc1ccc(Br)cc1)Nc1ccc2[nH]c(=O)[nH]c2c1] |
| GRB039 | 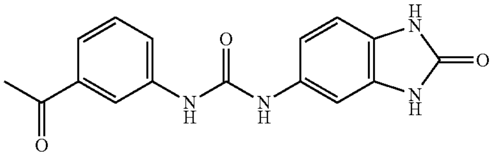 |
| GRB040 | 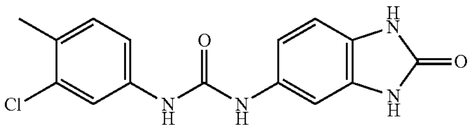 |
| GRB041 | 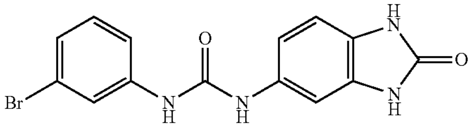 |
| GRB042 | 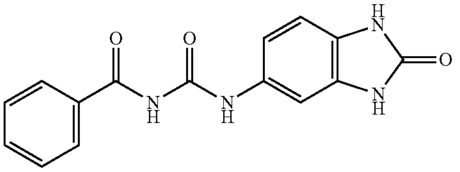 [SMILES: O=C(NC(=O)c1ccccc1)Nc1ccc2[nH]c(=O)[nH]c2c1] |
| GRB043 | 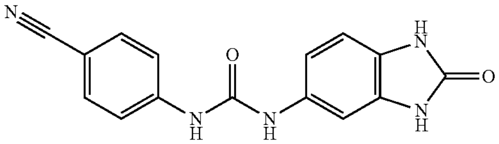 |
| GRB044 | 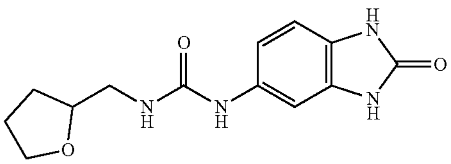 [SMILES: O=C(NCC1CCCO1)Nc1ccc2[nH]c(=O)[nH]c2c1] |
| GRB045 | 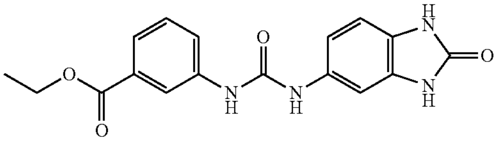 [SMILES: CCOC(=O)c1cccc(NC(=O)Nc2ccc3[nH]c(=O)[nH]c3c2)c1] |
| GRB046 | 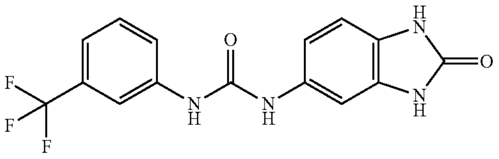 [SMILES: O=C(Nc1cccc(C(F)(F)F)c1)Nc1ccc2[nH]c(=O)[nH]c2c1] |
TABLE 1-continued
Compound IDs and structures of the compounds of the present disclosure.
| ID | Structure |
| --- | --- |
| GRB047 | 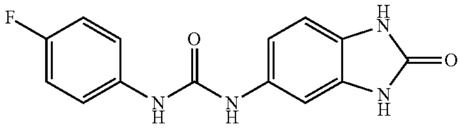 [SMILES: O=C(Nc1ccc(F)cc1)Nc1ccc2[nH]c(=O)[nH]c2c1] |
| GRB048 | 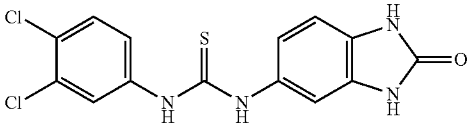 |
| GRB049 | 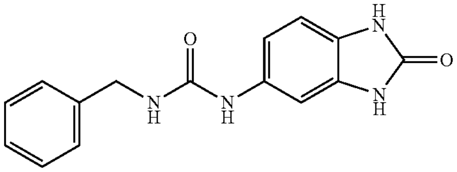 [SMILES: O=C(NCc1ccccc1)Nc1ccc2[nH]c(=O)[nH]c2c1] |
| GRB050 | 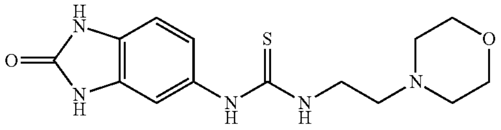 [SMILES: O=c1[nH]c2ccc(NC(=S)NCCN3CCOCC3)cc2[nH]1] |
| GRB051 | 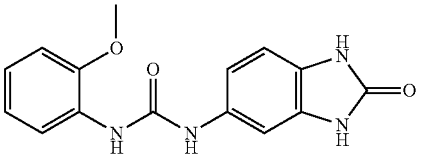 [SMILES: COc1ccccc1NC(=O)Nc1ccc2[nH]c(=O)[nH]c2c1] |
| GRB052 | 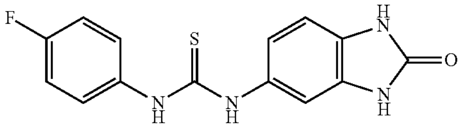 [SMILES: O=c1[nH]c2ccc(NC(=S)Nc3ccc(F)cc3)cc2[nH]1] |
| GRB053 | 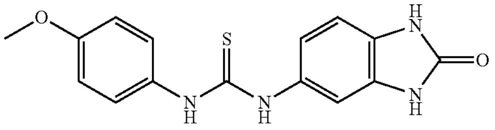 [SMILES: COc1ccc(NC(=S)Nc2ccc3[nH]c(=O)[nH]c3c2)cc1] |
| GRB054 | 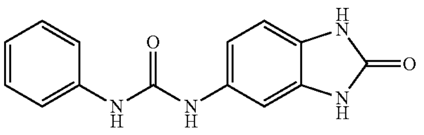 [SMILES: O=C(Nc1ccccc1)Nc1ccc2[nH]c(=O)[nH]c2c1] |
| GRB055 | 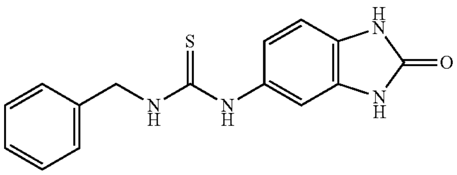 [SMILES: O=c1[nH]c2ccc(NC(=S)NCc3ccccc3)cc2[nH]1] |
| GRB056 | 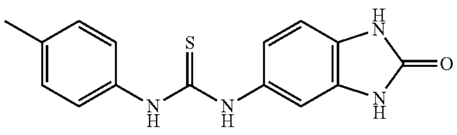 |

TABLE 1-continued
Compound IDs and structures of the compounds of the present disclosure.
| ID | Structure |
|---|---|
| GRB057 | 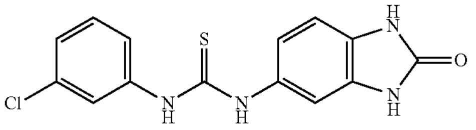 [SMILES: O=c1[nH]c2ccc(NC(=S)Nc3cccc(Cl)c3)cc2[nH]1] |
| GRB058 | 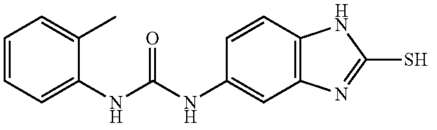 [SMILES: Cc1ccccc1NC(=O)Nc1ccc2[nH]c(S)nc2c1] |
| GRB059 | 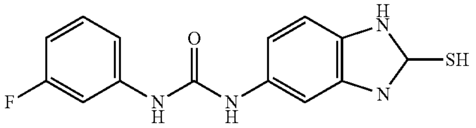 [SMILES: O=C(Nc1cccc(F)c1)Nc1ccc2c(c1)NC(S)N2] |
| GRB060 | 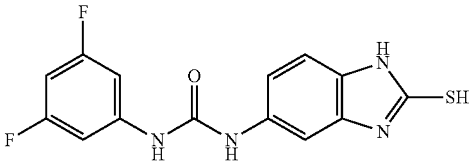 [SMILES: O=C(Nc1cc(F)cc(F)c1)Nc1ccc2[nH]c(S)nc2c1] |
| GRB061 | 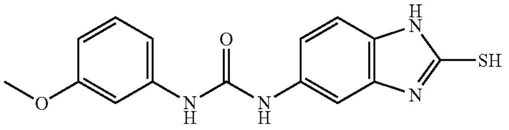 [SMILES: COc1cccc(NC(=O)Nc2ccc3[nH]c(S)nc3c2)c1] |
| GRB062 | 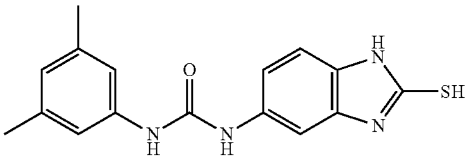 [SMILES: Cc1cc(C)cc(NC(=O)Nc2ccc3[nH]c(S)nc3c2)c1] |
| GRB063 | 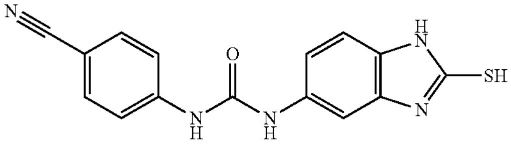 [SMILES: N#Cc1ccc(NC(=O)Nc2ccc3[nH]c(S)nc3c2)cc1] |
| GRB064 | 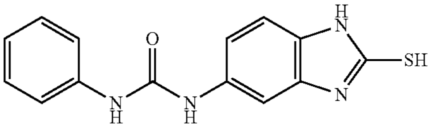 [SMILES: O=C(Nc1ccccc1)Nc1ccc2[nH]c(S)nc2c1] |
| GRB065 | 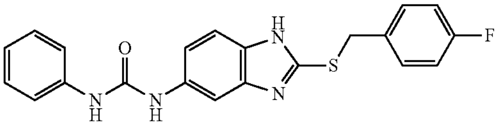 [SMILES: O=C(Nc1ccccc1)Nc1ccc2[nH]c(SCc3ccc(F)cc3)nc2c1] |
| GRB066 | 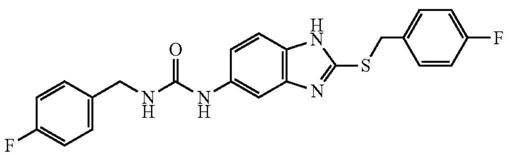 [SMILES: O=C(NCc1ccc(F)cc1)Nc1ccc2[nH]c(SCc3ccc(F)cc3)nc2c1] |
| GRB067 | 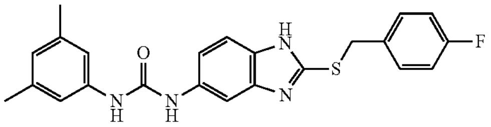 [SMILES: Cc1cc(C)cc(NC(=O)Nc2ccc3[nH]c(SCc4ccc(F)cc4)nc3c2)c1] |
| GRB068 | 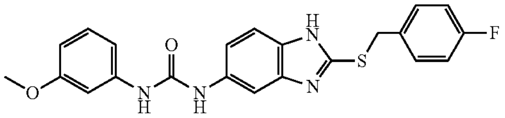 [SMILES: COc1cccc(NC(=O)Nc2ccc3[nH]c(SCc4ccc(F)cc4)nc3c2)c1] |
| GRB069 | 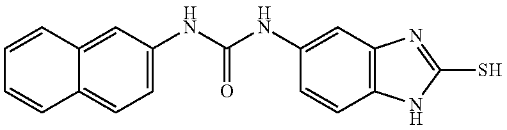 [SMILES: O=C(Nc1ccc2ccccc2c1)Nc1ccc2[nH]c(S)nc2c1] |
| GRB070 | 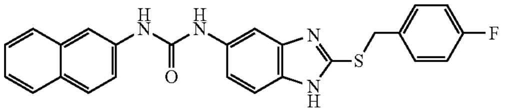 [SMILES: O=C(Nc1ccc2ccccc2c1)Nc1ccc2[nH]c(SCc3ccc(F)cc3)nc2c1] |
| GRB071 | 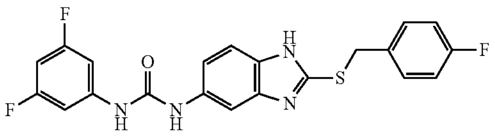 [SMILES: O=C(Nc1cc(F)cc(F)c1)Nc1ccc2[nH]c(SCc3ccc(F)cc3)nc2c1] |
| GRB072 | 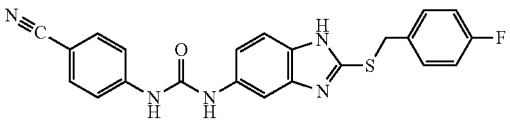 [SMILES: N#Cc1ccc(NC(=O)Nc2ccc3[nH]c(SCc4ccc(F)cc4)nc3c2)cc1] |
| GRB073 | 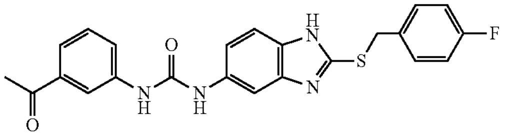 [SMILES: CC(=O)c1cccc(NC(=O)Nc2ccc3[nH]c(SCc4ccc(F)cc4)nc3c2)c1] |
| GRB074 | 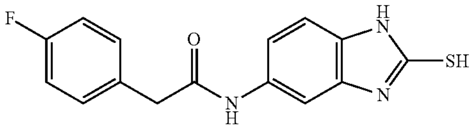 [SMILES: O=C(Cc1ccc(F)cc1)Nc1ccc2[nH]c(S)nc2c1] |
| GRB075 | 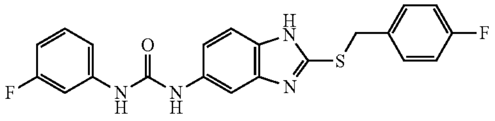 [SMILES: O=C(Nc1cccc(F)c1)Nc1ccc2[nH]c(SCc3ccc(F)cc3)nc2c1] |
| GRB076 | 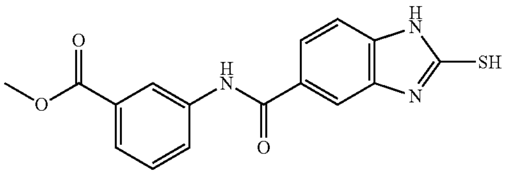 [SMILES: COC(=O)c1cccc(NC(=O)c2ccc3[nH]c(S)nc3c2)c1] |

TABLE 1-continued
Compound IDs and structures of the compounds of the present disclosure.
| ID | Structure |
|---|---|
| GRB077 | 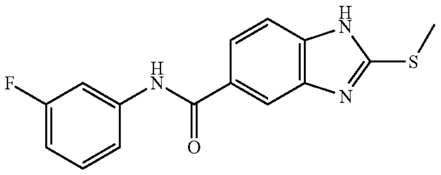 [SMILES: CSc1nc2cc(C(=O)Nc3cccc(F)c3)ccc2[nH]1] |
| GRB078 | 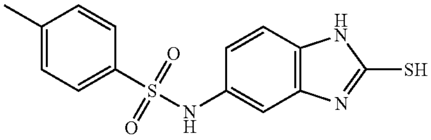 [SMILES: Cc1ccc(S(=O)(=O)Nc2ccc3[nH]c(S)nc3c2)cc1] |
| GRB079 | 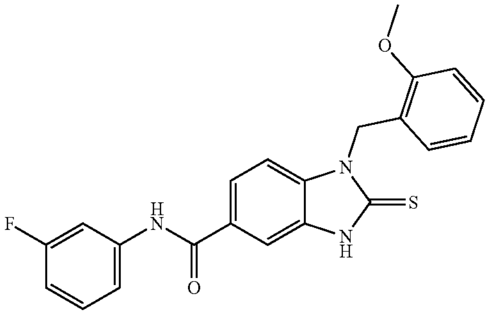 [SMILES: COc1ccccc1Cn1c(=S)[nH]c2cc(C(=O)Nc3cccc(F)c3)ccc21] |
| GRB080 | 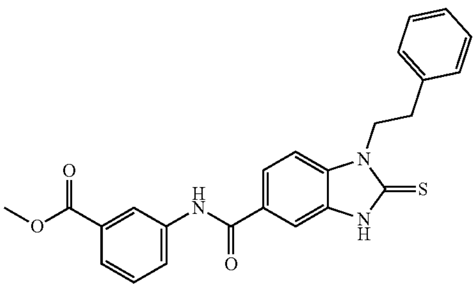 [SMILES: COC(=O)c1cccc(NC(=O)c2ccc3c(c2)[nH]c(=S)n3CCc2ccccc2)c1] |
| GRB081 | 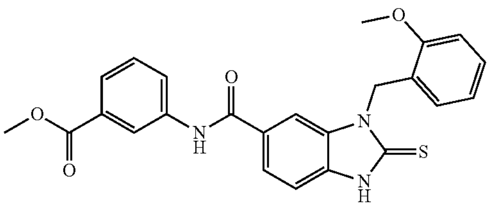 [SMILES: COC(=O)c1cccc(NC(=O)c2ccc3[nH]c(=S)n(Cc4ccccc4OC)c3c2)c1] |
| GRB082 | 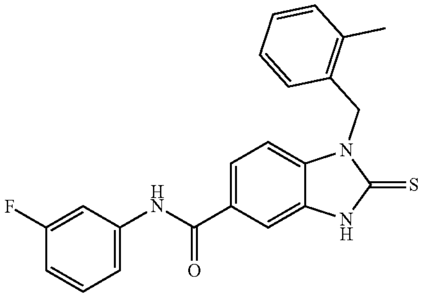 [SMILES: Cc1ccccc1Cn1c(=S)[nH]c2cc(C(=O)Nc3cccc(F)c3)ccc21] |
TABLE 1-continued
Compound IDs and structures of the compounds of the present disclosure.
| ID | Structure |
|---|---|
| GRB083 | 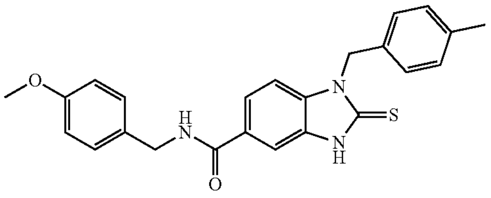 |
| GRB084 | 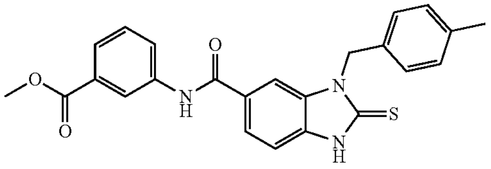 |
| GRB085 | 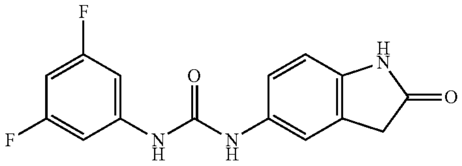 [SMILES: O=C1Cc2cc(NC(=O)Nc3cc(F)cc(F)c3)ccc2N1] |
| GRB086 | 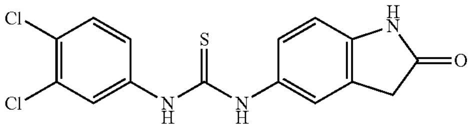 [SMILES: O=C1Cc2cc(NC(=S)Nc3ccc(Cl)c(Cl)c3)ccc2N1] |
| GRB087 | 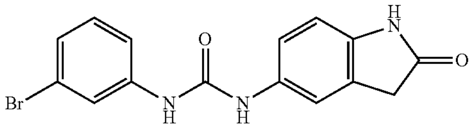 |
| GRB088 | 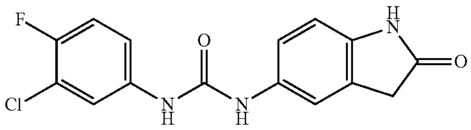 [SMILES: O=C1Cc2cc(NC(=O)Nc3ccc(F)c(Cl)c3)ccc2N1] |
| GRB089 | 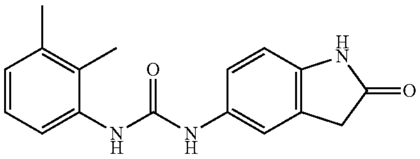 [SMILES: Cc1cccc(NC(=O)Nc2ccc3c(c2)CC(=O)N3)c1C] |
| GRB090 | 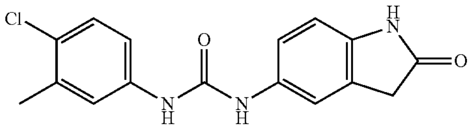 [SMILES: Cc1cc(NC(=O)Nc2ccc3c(c2)CC(=O)N3)ccc1Cl] |
| GRB091 | 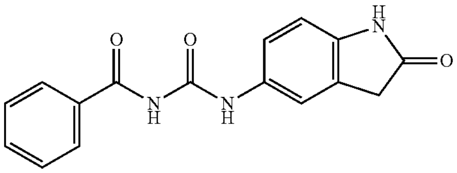 [SMILES: O=C1Cc2cc(NC(=O)NC(=O)c3ccccc3)ccc2N1] |

TABLE 1-continued
| Compound IDs and structures of the compounds of the present disclosure. | |
|---|---|
| ID | Structure |
| GRB092 | 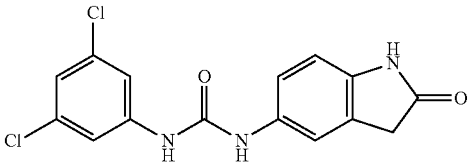 [SMILES: O=C1Cc2cc(NC(=O)Nc3cc(Cl)cc(Cl)c3)ccc2N1] |
| GRB093 | 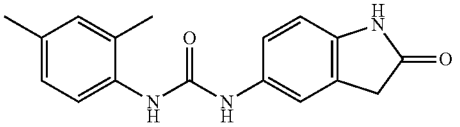 [SMILES: Cc1ccc(NC(=O)Nc2ccc3c(c2)CC(=O)N3)c(C)c1] |
| GRB094 | 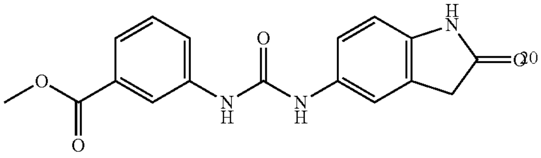 |
| GRB095 | 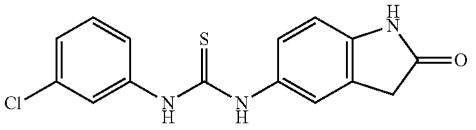 [SMILES: O=C1Cc2cc(NC(=S)Nc3cccc(Cl)c3)ccc2N1] |
| GRB096 | 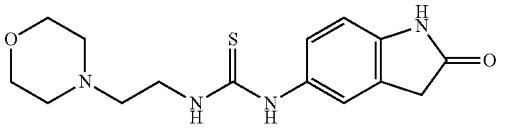 [SMILES: O=C1Cc2cc(NC(=S)NCCN3CCOCC3)ccc2N1] |
| GRB097 | 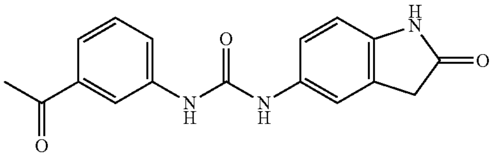 [SMILES: CC(=O)c1cccc(NC(=O)Nc2ccc3c(c2)CC(=O)N3)c1] |
| GRB098 | 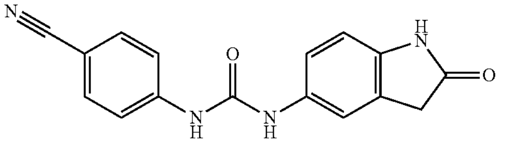 [SMILES: N#Cc1ccc(NC(=O)Nc2ccc3c(c2)CC(=O)N3)cc1] |
| GRB099 | 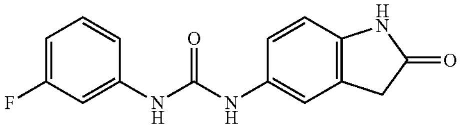 [SMILES: O=C1Cc2cc(NC(=O)Nc3cccc(F)c3)ccc2N1] |
| GRB100 | 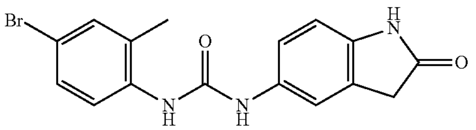 [SMILES: Cc1cc(Br)ccc1NC(=O)Nc1ccc2c(c1)CC(=O)N2] |
| GRB101 | 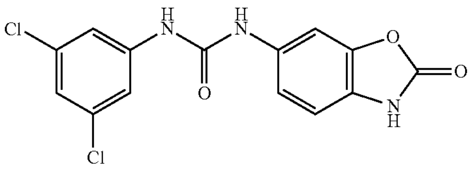 [SMILES: O=C(Nc1cc(Cl)cc(Cl)c1)Nc1ccc2[nH]c(=O)oc2c1] |
TABLE 1-continued
| Compound IDs and structures of the compounds of the present disclosure. | |
|---|---|
| ID | Structure |
| GRB102 | 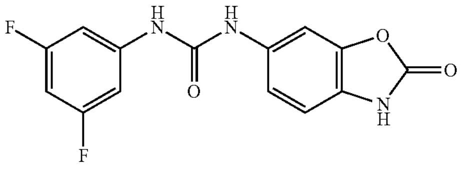 [SMILES: O=C(Nc1cc(F)cc(F)c1)Nc1ccc2[nH]c(=O)oc2c1] |
| GRB103 | 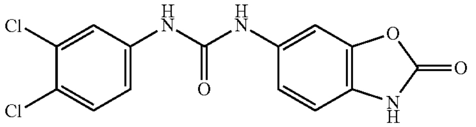 [SMILES: O=C(Nc1ccc(Cl)c(Cl)c1)Nc1ccc2[nH]c(=O)oc2c1] |
| GRB104 | 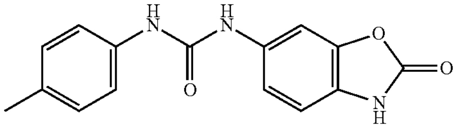 [SMILES: Cc1ccc(NC(=O)Nc2ccc3[nH]c(=O)oc3c2)cc1] |
| GRB105 | 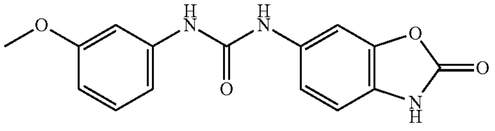 [SMILES: COc1cccc(NC(=O)Nc2ccc3[nH]c(=O)oc3c2)c1] |
| GRB106 | 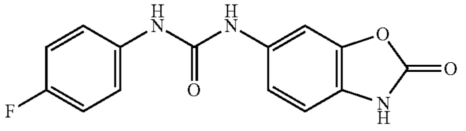 [SMILES: O=C(Nc1ccc(F)cc1)Nc1ccc2[nH]c(=O)oc2c1] |
| GRB107 | 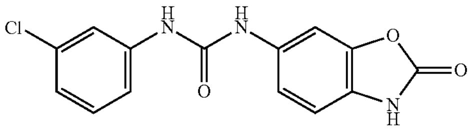 [SMILES: O=C(Nc1cccc(Cl)c1)Nc1ccc2[nH]c(=O)oc2c1] |
| GRB108 | 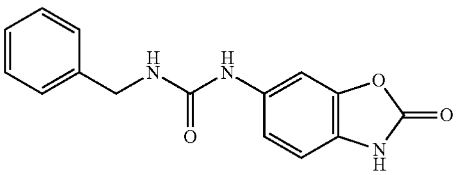 [SMILES: O=C(NCc1ccccc1)Nc1ccc2[nH]c(=O)oc2c1] |
| GRB111 | 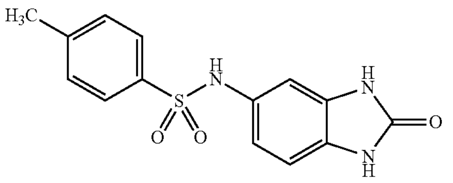 [SMILES: Cc1ccc(S(=O)(=O)Nc2ccc3[nH]c(=O)[nH]c3c2)cc1] |
| GRB112 | 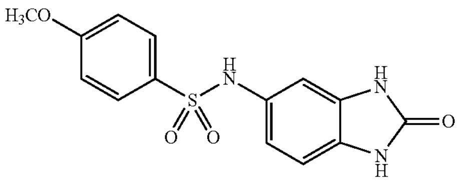 [SMILES: COc1ccc(S(=O)(=O)Nc2ccc3[nH]c(=O)[nH]c3c2)cc1] |

TABLE 1-continued
Compound IDs and structures of the compounds of the present disclosure.
| ID | Structure |
|---|---|
| GRB113 | 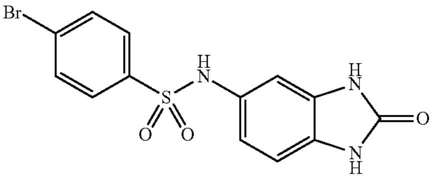 [SMILES: O=c1[nH]c2ccc(NS(=O)(=O)c3ccc(Br)cc3)cc2[nH]1] |
| GRB114 | 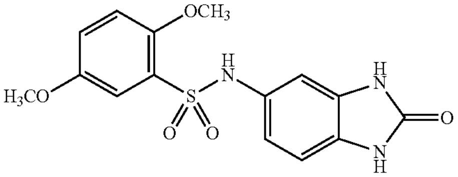 [SMILES: COc1ccc(OC)c(S(=O)(=O)Nc2ccc3[nH]c(=O)[nH]c3c2)c1] |
| GRB115 | 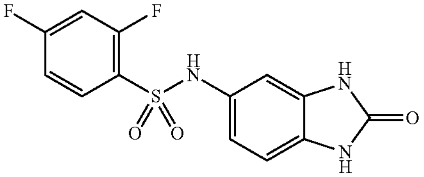 [SMILES: O=c1[nH]c2ccc(NS(=O)(=O)c3ccc(F)cc3F)cc2[nH]1] |
| GRB116 | 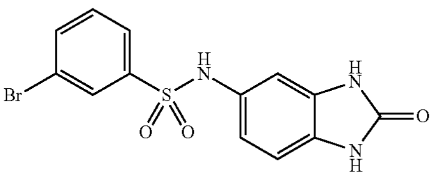 [SMILES: O=c1[nH]c2ccc(NS(=O)(=O)c3cccc(Br)c3)cc2[nH]1] |
| GRB117 | 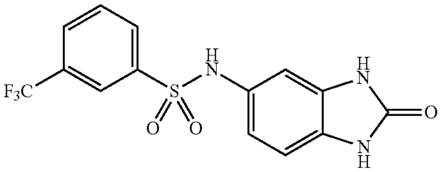 [SMILES: O=c1[nH]c2ccc(NS(=O)(=O)c3cccc(C(F)(F)F)c3)cc2[nH]1] |
| GRB121 | 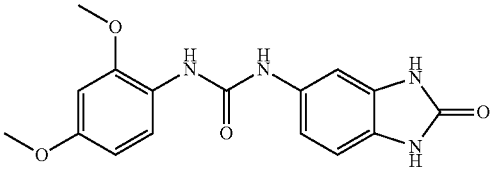 |
| GRB122 | 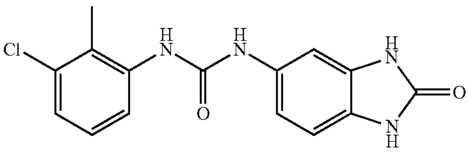 [SMILES: Cc1c(Cl)cccc1NC(=O)Nc1ccc2[nH]c(=O)[nH]c2c1] |
| GRB123 | 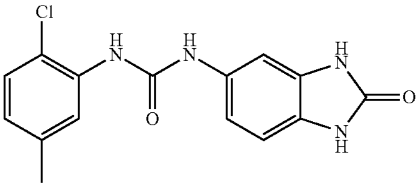 [SMILES: Cc1ccc(Cl)c(NC(=O)Nc2ccc3[nH]c(=O)[nH]c3c2)c1] |
TABLE 1-continued
Compound IDs and structures of the compounds of the present disclosure.
| ID | Structure |
|---|---|
| GRB124 | 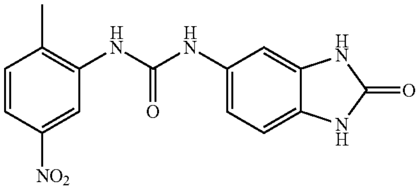 [SMILES: Cc1ccc([N+](=O)[O-])cc1NC(=O)Nc1ccc2[nH]c(=O)[nH]c2c1] |
| GRB125 | 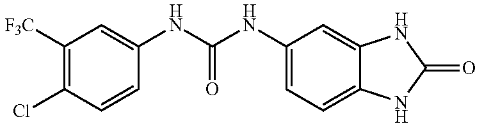 [SMILES: O=C(Nc1ccc(Cl)c(C(F)(F)F)c1)Nc1ccc2[nH]c(=O)[nH]c2c1] |
| GRB126 | 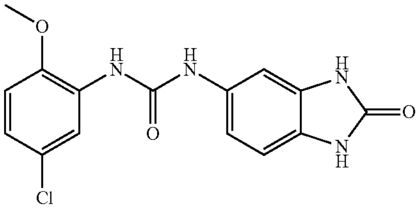 [SMILES: COc1ccc(Cl)cc1NC(=O)Nc1ccc2[nH]c(=O)[nH]c2c1] |
| GRB127 | 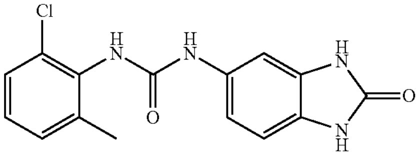 [SMILES: Cc1cccc(Cl)c1NC(=O)Nc1ccc2[nH]c(=O)[nH]c2c1] |
| GRB128 | 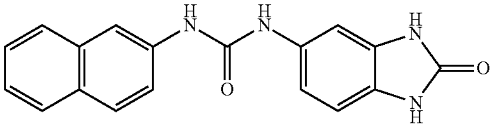 [SMILES: O=C(Nc1ccc2ccccc2c1)Nc1ccc2[nH]c(=O)[nH]c2c1] |
| GRB129 | 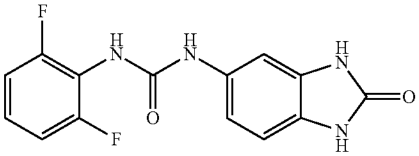 [SMILES: O=C(Nc1ccc2[nH]c(=O)[nH]c2c1)Nc1c(F)cccc1F] |
| GRB130 | 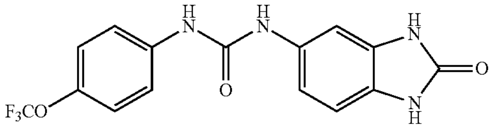 [SMILES: O=C(Nc1ccc(OC(F)(F)F)cc1)Nc1ccc2[nH]c(=O)[nH]c2c1] |
| GRB131 | 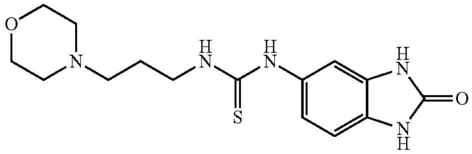 [SMILES: O=c1[nH]c2ccc(NC(=S)NCCCN3CCOCC3)cc2[nH]1] |
| GRB134 | 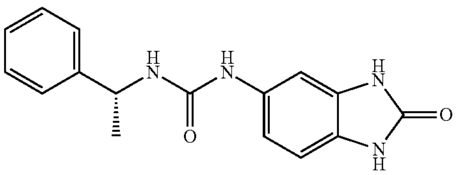 [SMILES: C[C@@H](NC(=O)Nc1ccc2[nH]c(=O)[nH]c2c1)c1ccccc1] |

TABLE 1-continued
Compound IDs and structures of the compounds of the present disclosure.
| ID | Structure |
| --- | --- |
| GRB135 | 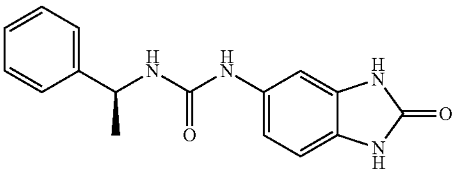 [SMILES: C[C@H](NC(=O)Nc1ccc2[nH]c(=O)[nH]c2c1)c1ccccc1] |
| GRB136 | 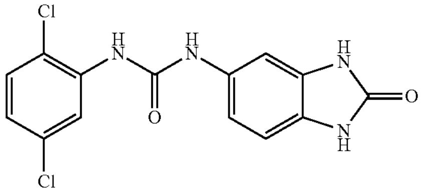 [SMILES: O=C(Nc1ccc2[nH]c(=O)[nH]c2c1)Nc1cc(Cl)ccc1Cl] |
| GRB137 | 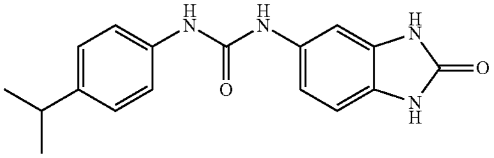 [SMILES: CC(C)c1ccc(NC(=O)Nc2ccc3[nH]c(=O)[nH]c3c2)cc1] |
| GRB138 | 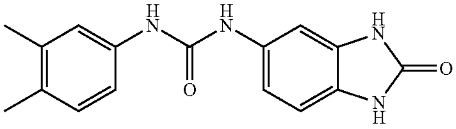 [SMILES: Cc1ccc(NC(=O)Nc2ccc3[nH]c(=O)[nH]c3c2)cc1C] |
| GRB139 | 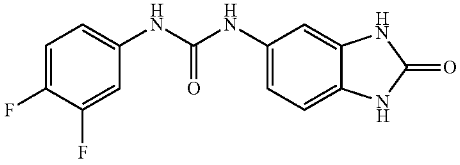 [SMILES: O=C(Nc1ccc(F)c(F)c1)Nc1ccc2[nH]c(=O)[nH]c2c1] |
| GRB140 | 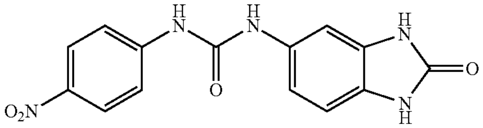 [SMILES: O=C(Nc1ccc([N+](=O)[O-])cc1)Nc1ccc2[nH]c(=O)[nH]c2c1] |
| GRB141 | 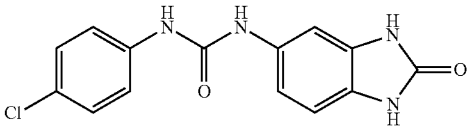 [SMILES: O=C(Nc1ccc(Cl)cc1)Nc1ccc2[nH]c(=O)[nH]c2c1] |
| GRB142 | 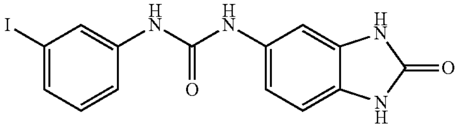 [SMILES: O=C(Nc1cccc(I)c1)Nc1ccc2[nH]c(=O)[nH]c2c1] |
| GRB143 | 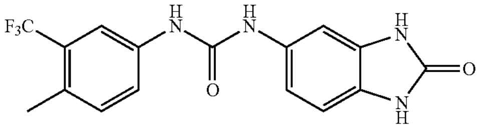 [SMILES: Cc1ccc(NC(=O)Nc2ccc3[nH]c(=O)[nH]c3c2)cc1C(F)(F)F] |
TABLE 1-continued
Compound IDs and structures of the compounds of the present disclosure.
| ID | Structure |
| --- | --- |
| GRB144 | 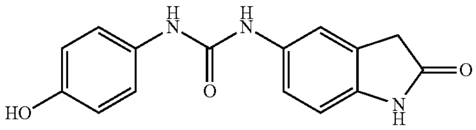 [SMILES: O=C1Cc2cc(NC(=O)Nc3ccc(O)cc3)ccc2N1] |
| GRB145 | 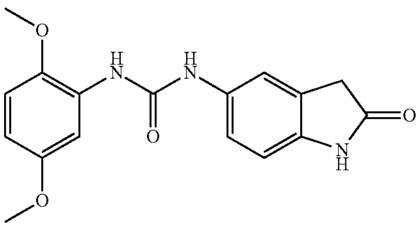 |
| GRB146 | 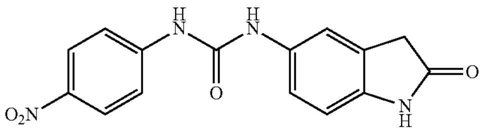 [SMILES: O=C1Cc2cc(NC(=O)Nc3ccc([N+](=O)[O-])cc3)ccc2N1] |
| GRB147 | 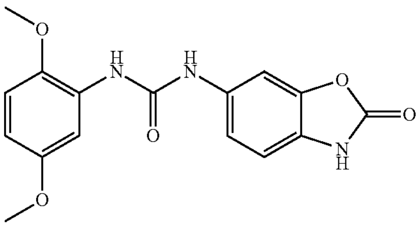 [SMILES: COc1ccc(OC)c(NC(=O)Nc2ccc3[nH]c(=O)oc3c2)c1] |
| GRB148 | 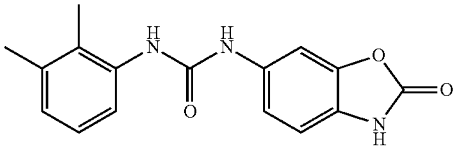 [SMILES: Cc1cccc(NC(=O)Nc2ccc3[nH]c(=O)oc3c2)c1C] |
| GRB149 | 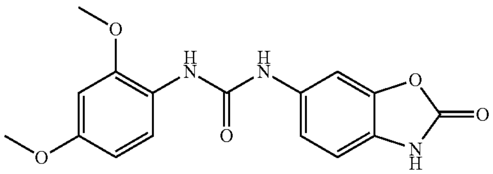 [SMILES: COc1ccc(NC(=O)Nc2ccc3[nH]c(=O)oc3c2)c(OC)c1] |
| GRB150 | 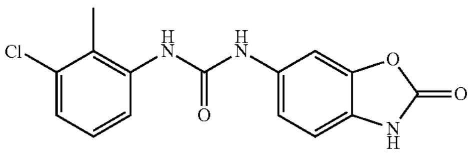 [SMILES: Cc1c(Cl)cccc1NC(=O)Nc1ccc2[nH]c(=O)oc2c1] |
| GRB151 | 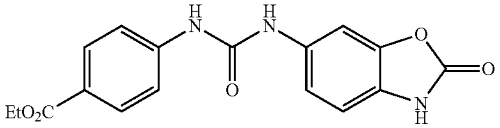 [SMILES: CCOC(=O)c1ccc(NC(=O)Nc2ccc3[nH]c(=O)oc3c2)cc1] |
| GRB152 | 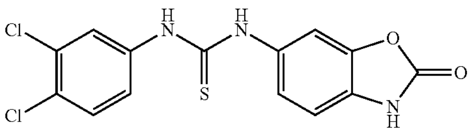 [SMILES: O=c1[nH]c2ccc(NC(=S)Nc3ccc(Cl)c(Cl)c3)cc2o1] |

TABLE 1-continued
Compound IDs and structures of the compounds of the present disclosure.
| ID | Structure |
|---|---|
| GRB153 | 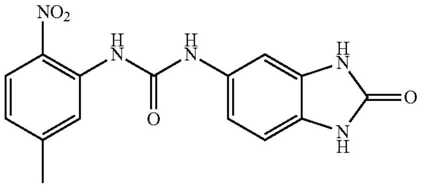 [SMILES: Cc1ccc([N+](=O)[O-])c(NC(=O)Nc2ccc3[nH]c(=O)[nH]c3c2)c1] |
| GRB154 | 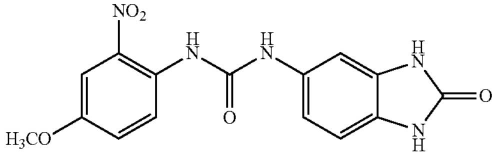 [SMILES: COc1ccc(NC(=O)Nc2ccc3[nH]c(=O)[nH]c3c2)c([N+](=O)[O-])c1] |
| GRB155 | 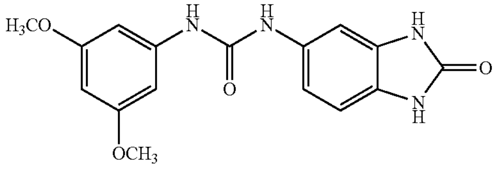 [SMILES: COc1cc(NC(=O)Nc2ccc3[nH]c(=O)[nH]c3c2)cc(OC)c1] |
| GRB156 | 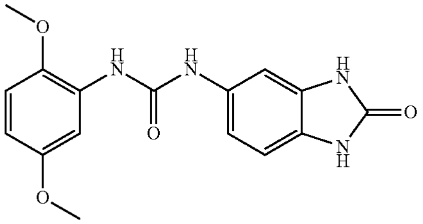 [SMILES: COc1ccc(OC)c(NC(=O)Nc2ccc3[nH]c(=O)[nH]c3c2)c1] |
| GRB157 | 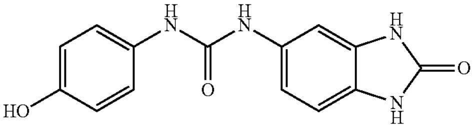 [SMILES: O=C(Nc1ccc(O)cc1)Nc1ccc2[nH]c(=O)[nH]c2c1] |
| GRB158 | 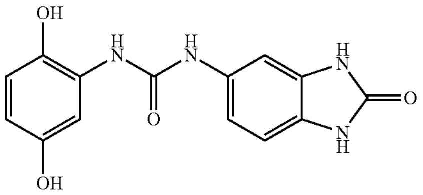 [SMILES: O=C(Nc1ccc2[nH]c(=O)[nH]c2c1)Nc1cc(O)ccc1O] |
| GRB159 | 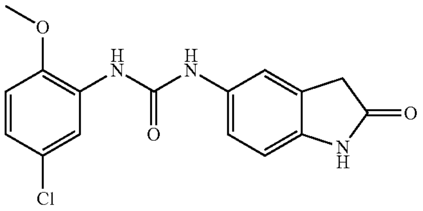 [SMILES: COc1ccc(Cl)cc1NC(=O)Nc1ccc2c(c1)CC(=O)N2] |
| GRB160 | 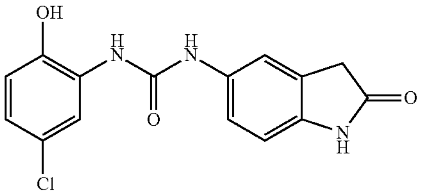 [SMILES: O=C1Cc2cc(NC(=O)Nc3cc(Cl)ccc3O)ccc2N1] |
TABLE 1-continued
Compound IDs and structures of the compounds of the present disclosure.
| ID | Structure |
|---|---|
| GRB161 | 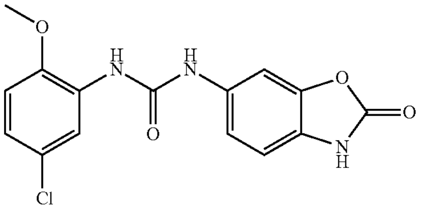 [SMILES: COc1ccc(Cl)cc1NC(=O)Nc1ccc2[nH]c(=O)oc2c1] |
| GRB163 | 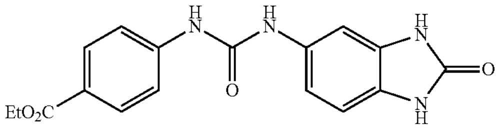 [SMILES: CCOC(=O)c1ccc(NC(=O)Nc2ccc3[nH]c(=O)[nH]c3c2)cc1] |
| GRB164 | 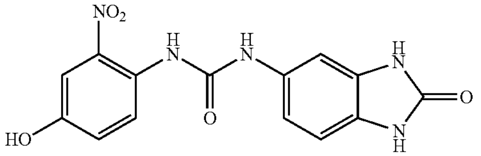 [SMILES: O=C(Nc1ccc2[nH]c(=O)[nH]c2c1)Nc1ccc(O)cc1[N+](=O)[O-]] |
| GRB165 | 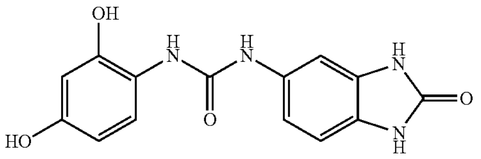 [SMILES: O=C(Nc1ccc2[nH]c(=O)[nH]c2c1)Nc1ccc(O)cc1O] |
| GRB166 | 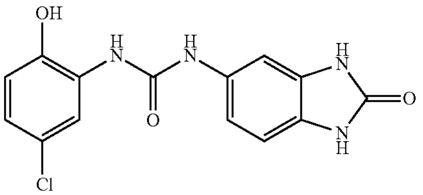 [SMILES: O=C(Nc1ccc2[nH]c(=O)[nH]c2c1)Nc1cc(Cl)ccc1O] |
| GRB167 | 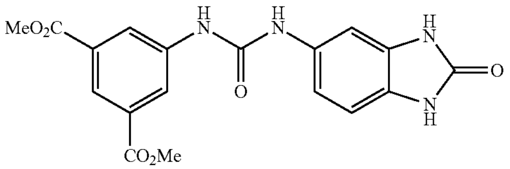 [SMILES: COC(=O)c1cc(NC(=O)Nc2ccc3[nH]c(=O)[nH]c3c2)cc(C(=O)OC)c1] |
| GRB168 | 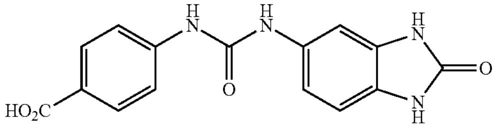 |
| GRB169 | 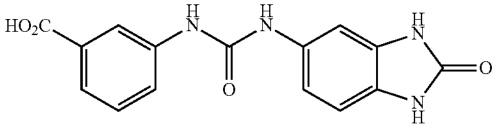 [SMILES: O=C(Nc1cccc(C(=O)O)c1)Nc1ccc2[nH]c(=O)[nH]c2c1] |
| GRB170 | 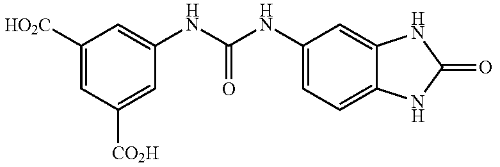 [SMILES: O=C(Nc1cc(C(=O)O)cc(C(=O)O)c1)Nc1ccc2[nH]c(=O)[nH]c2c1] |

TABLE 1-continued

Compound IDs and structures of the compounds of the present disclosure.

| ID | Structure |
|---|---|
| GRB171 | 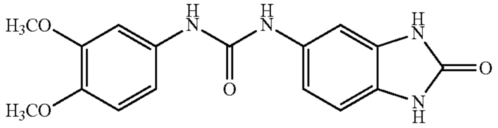 [SMILES: COc1ccc(NC(=O)Nc2ccc3[nH]c(=O)[nH]c3c2)cc1OC] |
| GRB172 | 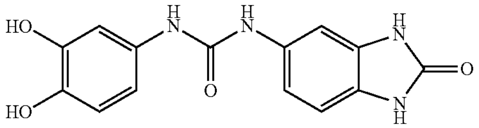 [SMILES: O=C(Nc1ccc(O)c(O)c1)Nc1ccc2[nH]c(=O)[nH]c2c1] |
| GRB173 | 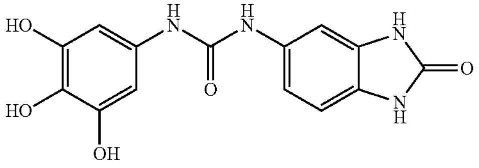 [SMILES: O=C(Nc1cc(O)c(O)c(O)c1)Nc1ccc2[nH]c(=O)[nH]c2c1] |
| GRB174 | 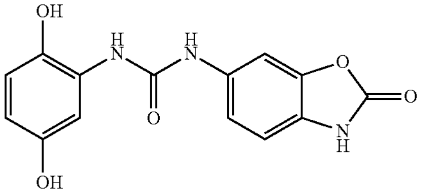 [SMILES: O=C(Nc1ccc2[nH]c(=O)oc2c1)Nc1cc(O)ccc1O] |
| GRB175 | 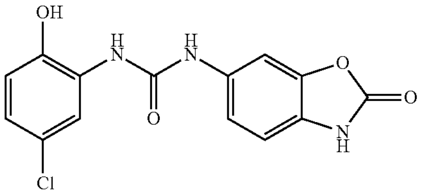 [SMILES: O=C(Nc1ccc2[nH]c(=O)oc2c1)Nc1cc(Cl)ccc1O] |
| GRB181 | 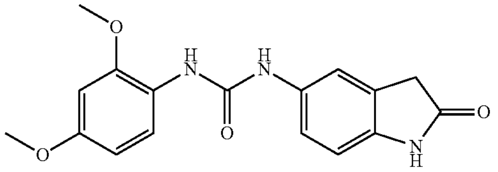 [SMILES: COc1ccc(NC(=O)Nc2ccc3c(c2)CC(=O)N3)c(OC)c1] |
| GRB182 | 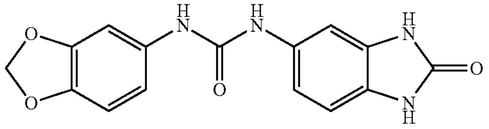 [SMILES: O=C(Nc1ccc2c(c1)OCO2)Nc1ccc2[nH]c(=O)[nH]c2c1] |
| GRB183 | 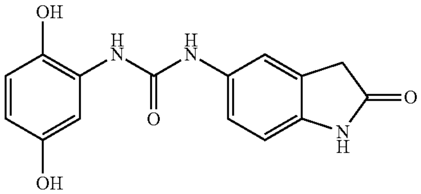 [SMILES: O=C1Cc2cc(NC(=O)Nc3cc(O)ccc3O)ccc2N1] |
| GRB184 | 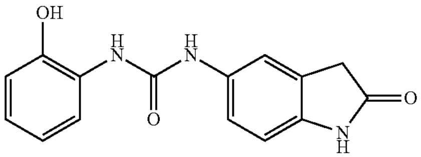 [SMILES: O=C1Cc2cc(NC(=O)Nc3ccccc3O)ccc2N1] |

TABLE 1-continued

Compound IDs and structures of the compounds of the present disclosure.

| ID | Structure |
|---|---|
| GRB185 | 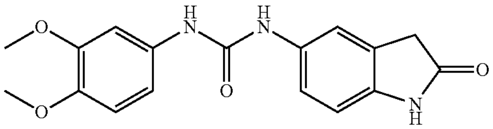 [SMILES: COc1ccc(NC(=O)Nc2ccc3c(c2)CC(=O)N3)cc1OC] |
| GRB186 | 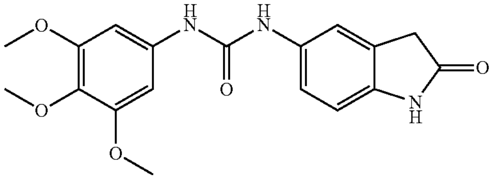 [SMILES: COc1cc(NC(=O)Nc2ccc3c(c2)CC(=O)N3)cc(OC)c1OC] |
| GRB187 | 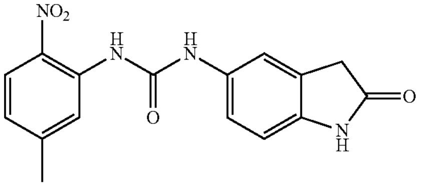 [SMILES: Cc1ccc([N+](=O)[O-])c(NC(=O)Nc2ccc3c(c2)CC(=O)N3)c1] |
| GRB188 | 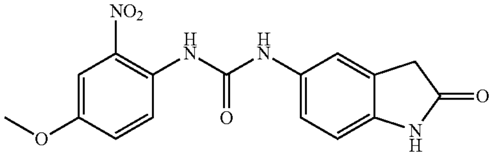 [SMILES: COc1ccc(NC(=O)Nc2ccc3c(c2)CC(=O)N3)c([N+](=O)[O-])c1] |
| GRB189 | 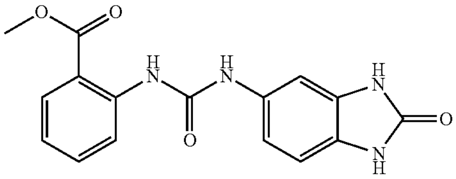 [SMILES: COC(=O)c1ccccc1NC(=O)Nc1ccc2[nH]c(=O)[nH]c2c1] |

The compounds of the present disclosure are shown, for example, above, in the summary section, and in the claims below. They may be made using the synthetic methods outlined in the Examples section. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

All the compounds of the present disclosure may in some embodiments be used for the prevention and treatment of one or more diseases or disorders discussed herein or otherwise. In some embodiments, one or more of the compounds characterized or exemplified herein as an intermediate, a metabolite, and/or prodrug, may nevertheless also be useful for the prevention and treatment of one or more diseases or disorders. As such unless explicitly stated to the contrary, all the compounds of the present disclosure are deemed "active compounds" and "therapeutic compounds" that are contemplated for use as active pharmaceutical ingredients (APIs). Actual suitability for human or veterinary use is typically determined using a combination of clinical trial protocols and regulatory procedures, such as those administered by the Food and Drug Administration (FDA). In the United States, the FDA is responsible for protecting the public health by assuring the safety, effectiveness, quality, and security of human and veterinary drugs, vaccines and other biological products, and medical devices.

In some embodiments, the compounds of the present disclosure have the advantage that they may be more efficacious than, be less toxic than, be longer acting than, be more potent than, produce fewer side effects than, be more easily absorbed than, more metabolically stable than, more lipophilic than, more hydrophilic than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

Compounds of the present disclosure may contain one or more asymmetrically-substituted carbon or nitrogen atom and may be isolated in optically active or racemic form.

Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the S or the R configuration. In some embodiments, the present compounds may contain two or more atoms which have a defined stereochemical orientation.

Chemical formulas used to represent compounds of the present invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, isotopes of fluorine include $^{18}F$, and isotopes of carbon include $^{13}C$ and $^{14}C$.

In some embodiments, compounds of the present disclosure function as prodrugs or can be derivatized to function as prodrugs. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the compounds employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a patient, cleaves to form a hydroxy, amino, or carboxylic acid, respectively.

In some embodiments, compounds of the present disclosure exist in salt or non-salt form. With regard to the salt form(s), in some embodiments the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will be appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present disclosure.

II. CHEMICAL DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —$CO_2H$); "halo" means independently —F, —Cl, —Br or —I; "amino" means —$NH_2$; "hydroxyamino" means —NHOH; "nitro" means —$NO_2$; imino means=NH; "cyano" means —CN; "isocyanyl" means —N=C=O; "azido" means —$N_3$; in a monovalent context "phosphate" means —OP(O)$(OH)_2$ or a deprotonated form thereof; in a divalent context "phosphate" means —OP(O)(OH)O— or a deprotonated form thereof; "mercapto" means —SH; and "thio" means=S; "sulfonyl" means —$S(O)_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "═══" represents a single bond or a double bond. Thus, the formula

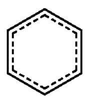

covers, for example

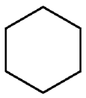, 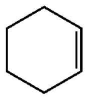, 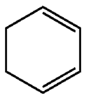, 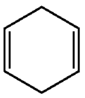, and 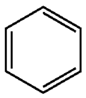.

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "〰", when drawn perpendicularly across a bond (e.g.

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "┆" means a single bond where the group attached to the thick end of the wedge is "into the page". The symbol "〰" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

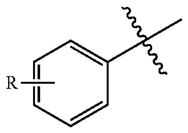

, then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

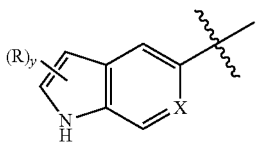

, then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" or "C=n" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C\leq8)}$", "cycloalkanediyl$_{(C\leq8)}$", "heteroaryl$_{(C\leq8)}$", and "acyl$_{(C\leq8)}$" is one, the minimum number of carbon atoms in the groups "alkenyl$_{(C\leq8)}$", "alkynyl$_{(C\leq8)}$", and "heterocycloalkyl$_{(C\leq8)}$" is two, the minimum number of carbon atoms in the group "cycloalkyl$_{(C\leq8)}$" is three, and the minimum number of carbon atoms in the groups "aryl$_{(C\leq8)}$" and "arenediyl$_{(C\leq8)}$" is six. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. Except as noted below, every carbon atom is counted to determine whether the group or compound falls with the specified number of carbon atoms. For example, the group dihexylamino is an example of a dialkylamino$_{(C=12)}$ group; however, it is not an example of a dialkylamino$_{(C=6)}$ group. Likewise, phenylethyl is an example of an aralkyl$_{(C=8)}$ group. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic $\pi$ system. An aromatic compound or chemical group may be depicted as a single resonance structure; however, depiction of one resonance structure is taken to also refer to any other resonance structure. For example:

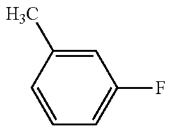

is also taken to refer to

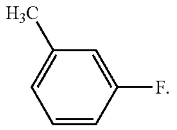

Aromatic compounds may also be depicted using a circle to represent the delocalized nature of the electrons in the fully conjugated cyclic π system, two non-limiting examples of which are shown below:

 and 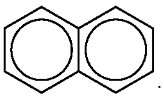.

The term "alkyl" refers to a monovalent saturated aliphatic group with a carbon atom as the point of attachment, a linear or branched acyclic structure, and no atoms other than carbon and hydrogen. The groups $-CH_3$ (Me), $-CH_2CH_3$ (Et), $-CH_2CH_2CH_3$ (n-Pr or propyl), $-CH(CH_3)_2$ (i-Pr, $^i$Pr or isopropyl), $-CH_2CH_2CH_2CH_3$ (n-Bu), $-CH(CH_3)CH_2CH_3$ (sec-butyl), $-CH_2CH(CH_3)_2$ (isobutyl), $-C(CH_3)_3$ (tert-butyl, t-butyl, t-Bu or $^t$Bu), and $-CH_2C(CH_3)_3$ (neo-pentyl) are non-limiting examples of alkyl groups. The term "alkanediyl" refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups $-CH_2-$ (methylene), $-CH_2CH_2-$, $-CH_2C(CH_3)_2CH_2-$, and $-CH_2CH_2CH_2-$ are non-limiting examples of alkanediyl groups. The term "alkylidene" refers to the divalent group $=CRR'$ in which R and R' are independently hydrogen or alkyl. Non-limiting examples of alkylidene groups include: $=CH_2$, $=CH(CH_2CH_3)$, and $=C(CH_3)_2$. An "alkane" refers to the class of compounds having the formula H—R, wherein R is alkyl as this term is defined above.

The term "cycloalkyl" refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: $-CH(CH_2)_2$ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" refers to a divalent saturated aliphatic group with two carbon atoms as points of attachment, no carbon-carbon double or triple bonds, and no atoms other than carbon and hydrogen. The group

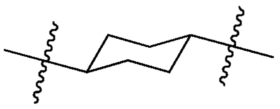 [SMILES: *C1CCC(*)CC1]

is a non-limiting example of cycloalkanediyl group. A "cycloalkane" refers to the class of compounds having the formula H—R, wherein R is cycloalkyl as this term is defined above.

The term "aryl" refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, $-C_6H_4CH_2CH_3$ (ethylphenyl), naphthyl, and a monovalent group derived from biphenyl (e.g., 4-phenylphenyl). The term "arenediyl" refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

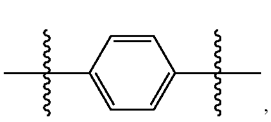, 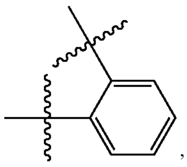,

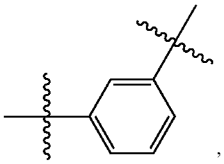,

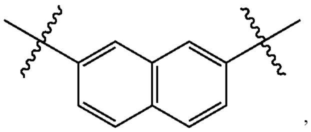,

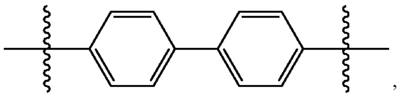, and

-continued

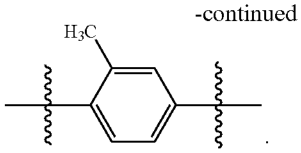

An "arene" refers to the class of compounds having the formula H—R, wherein R is aryl as that term is defined above. Benzene and toluene are non-limiting examples of arenes.

The term "aralkyl" refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl.

The term "heteroaryl" refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused; however, the term heteroaryl does not preclude the presence of one or more alkyl or aryl groups (carbon number limitation permitting) attached to one or more ring atoms. Non-limiting examples of heteroaryl groups include benzoxazolyl, benzimidazolyl, furanyl, imidazolyl (Im), indolyl, indazolyl (Im), isoxazolyl, methylpyridinyl, oxazolyl, oxadiazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes.

The term "heteroaralkyl" refers to the monovalent group -alkanediyl-heteroaryl, in which the terms alkanediyl and heteroaryl are each used in a manner consistent with the definitions provided above. Non-limiting examples are: pyridinylmethyl and 2-quinolinyl-ethyl.

The term "heterocycloalkyl" refers to a monovalent non-aromatic group with a carbon atom or nitrogen atom as the point of attachment, said carbon atom or nitrogen atom forming part of one or more non-aromatic ring structures, each with three to eight ring atoms, wherein at least one of the ring atoms of the non-aromatic ring structure(s) is nitrogen, oxygen or sulfur, and wherein the heterocycloalkyl group consists of no atoms other than carbon, hydrogen, nitrogen, oxygen and sulfur. If more than one ring is present, the rings are fused. As used herein, the term does not preclude the presence of one or more alkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group.

The term "acyl" refers to the group —C(O)R, in which R is a hydrogen, alkyl, cycloalkyl, or aryl as those terms are defined above. The groups, —CHO, —$C(O)CH_3$ (acetyl, Ac), —$C(O)CH_2CH_3$, —$C(O)CH(CH_3)_2$, —$C(O)CH(CH_2)_2$, —$C(O)C_6H_5$, and —$C(O)C_6H_4CH_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group.

The term "alkoxy" refers to the group —OR, in which R is an alkyl, as that term is defined above. Non-limiting examples include: —$OCH_3$ (methoxy), —$OCH_2CH_3$ (ethoxy), —$OCH_2CH_2CH_3$, —$OCH(CH_3)_2$ (isopropoxy), or —$OC(CH_3)_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group.

When a chemical group is used with the "substituted" modifier, one or more hydrogen atom has been replaced, independently at each instance, by —OH, —F, —Cl, —Br, —I, —$NH_2$, —$NO_2$, —$CO_2H$, —$CO_2CH_3$, —$CO_2CH_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$C(O)NHCH_3$, —$C(O)N(CH_3)_2$, —$OC(O)CH_3$, —$NHC(O)CH_3$, —$S(O)_2OH$, or —$S(O)_2NH_2$. For example, the following groups are non-limiting examples of substituted alkyl groups: —$CH_2OH$, —$CH_2Cl$, —$CF_3$, —$CH_2CN$, —$CH_2C(O)OH$, —$CH_2C(O)OCH_3$, —$CH_2C(O)NH_2$, —$CH_2C(O)CH_3$, —$CH_2OCH_3$, —$CH_2OC(O)CH_3$, —$CH_2NH_2$, —$CH_2N(CH_3)_2$, and —$CH_2CH_2Cl$. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —$CH_2Cl$ is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —$CH_2F$, —$CF_3$, and —$CH_2CF_3$ are non-limiting examples of fluoroalkyl groups. Non-limiting examples of substituted aralkyls are: (3-chlorophenyl)-methyl, and 2-chloro-2-phenyl-eth-1-yl. The groups, —$C(O)CH_2CF_3$, —$CO_2H$ (carboxyl), —$CO_2CH_3$ (methylcarboxyl), —$CO_2CH_2CH_3$, —$C(O)NH_2$ (carbamoyl), and —$CON(CH_3)_2$, are non-limiting examples of substituted acyl groups. The groups —$NHC(O)OCH_3$ and —$NHC(O)NHCH_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects or patients.

An "active ingredient" (AI) or active pharmaceutical ingredient (API) (also referred to as an active compound, active substance, active agent, pharmaceutical agent, agent, biologically active molecule, or a therapeutic compound) is the ingredient in a pharmaceutical drug that is biologically active.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient, is sufficient to effect such treatment or prevention of the disease as those terms are defined below.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds disclosed herein which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical preparation, pharmaceutical composition, pharmaceutical formulation, pharmaceutical product, medicinal product, medicine, medication, medicament, or simply a drug, agent, or preparation) is a composition used to diagnose, cure, treat, or prevent disease, which comprises an active pharmaceutical ingredient (API) (defined above) and optionally contains one or more inactive ingredients, which are also referred to as excipients (defined above).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present disclosure. The prodrug itself may or may not also have activity with respect to a given target protein. For example, a compound comprising a hydroxy group may be administered as an ester that is converted by hydrolysis in vivo to the hydroxy compound. Non-limiting examples of suitable esters that may be converted in vivo into hydroxy compounds include acetates, citrates, lactates, phosphates, tartrates, malonates, oxalates, salicylates, propionates, succinates, fumarates, maleates, methylene-bis-p-hydroxynaphthoate, gentisates, isethionates, di-p-toluoyltartrates, methanesulfonates, ethanesulfonates, benzenesulfonates, p-toluenesulfonates, cyclohexylsulfamates, quinates, and esters of amino acids. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease or symptom thereof in a subject or patient that is experiencing or displaying the pathology or symptomatology of the disease.

The term "unit dose" refers to a formulation of the compound or composition such that the formulation is prepared in a manner sufficient to provide a single therapeutically effective dose of the active ingredient to a patient in a single administration. Such unit dose formulations that may be used include but are not limited to a single tablet, capsule, or other oral formulations, or a single vial with a syringeable liquid or other injectable formulations.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

III. TREATMENT OF CANCER AND OTHER HYPERPROLIFERATIVE DISEASES

While hyperproliferative diseases can be associated with any disease which causes a cell to begin to reproduce uncontrollably, the prototypical example is cancer. Psoriasis is another example. One of the key elements of cancer is that the cell's normal apoptotic cycle is interrupted and thus agents that interrupt the growth of the cells are important as therapeutic agents for treating these diseases. In some embodiments, the caffeic acid derivatives described herein may be used to decreased cell counts and as such may be used to treat a variety of cancers or other malignancies.

In some embodiments, cancer, cancer tissue, or cancer cells may be treated by the compounds, methods, and compositions disclosed herein. In some embodiments, cancer cells or tissue that may be treated include but are not limited to cells or tissue from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In some embodiments, the cancer that may be treated may be of the following histological types: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia, including hairy cell leukemia; chronic lymphocytic leukemia (CLL); acute lymphoblastic leukemia (ALL); acute myeloid leukemia (AML); and chronic myeloblastic leukemia.

In another aspect, the compounds, compositions, and methods disclosed herein may be used to treat cancer or other hyperproliferative diseases. While hyperproliferative diseases can be associated with any disease which causes a cell to begin to reproduce uncontrollably, the prototypical example is cancer. One of the elements of cancer is that the cell's normal apoptotic cycle is interrupted. As such, agents that interrupt the growth of the cells are important as therapeutic agents for treating these diseases. In this disclosure, the compounds of the present disclosure thereof may be used to lead to decreased cell counts and may be used to treat a variety of types of cancer.

In some embodiments, cancer cells that may be treated with the compounds or compositions of the present disclosure include, but are not limited to, bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, and uterus cells.

In some embodiments, tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

In certain embodiments regarding methods of treating cancer in a patient, comprising administering to the patient a pharmaceutically effective amount of a compound of the present disclosure, the pharmaceutically effective amount is 0.1-1000 mg/kg. In certain embodiments, the pharmaceutically effective amount is administered in a single dose per day. In certain embodiments, the pharmaceutically effective amount is administered in two or more doses per day. The compound may be administered by contacting a tumor cell during ex vivo purging, for example. The method of treatment may comprise any one or more of the following: a) inducing cytotoxicity in a tumor cell; b) killing a tumor cell; c) inducing apoptosis in a tumor cell; d) inducing differentiation in a tumor cell; or e) inhibiting growth in a tumor cell. The tumor cell may be any type of tumor cell, such as a brain cell. Other types of cells include, for example, a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, or a soft tissue cancer cell.

In some embodiments, treatment methods further comprise monitoring treatment progress. In some of these embodiments, the method includes the step of determining a level of changes in hematological parameters and/or cancer stem cell (CSC) analysis with cell surface proteins as diagnostic markers or diagnostic measurement (e.g., screen, assay) in a patient suffering from or susceptible to a disorder or symptoms thereof associated with cancer in which the patient has been administered a therapeutic amount of a compound or composition as described herein. The level of the marker determined in the method can be compared to known levels of marker in either healthy normal controls or in other afflicted patients to establish the patient's disease status. In some embodiments, a second level of the marker in the patient is determined at a time point later than the determination of the first level, and the two levels are compared to monitor the course of disease or the efficacy of the therapy. In some embodiments, a pre-treatment level of marker in the patient is determined prior to beginning treatment according to the methods described herein; this pre-treatment level of marker can then be compared to the level of marker in the patient after the treatment commences, to determine the efficacy of the treatment.

In some embodiments, the patient is a mammal, e.g., a primate, preferably a higher primate, e.g., a human (e.g., a patient having, or at risk of having, a disorder described herein). In some embodiments, the patient is in need of enhancing the patient's immune response. In certain embodiments, the patient is, or is at risk of being, immunocompromised. For example, in some embodiments, the patient is undergoing or has undergone a chemotherapeutic treatment and/or radiation therapy. Alternatively, or in combination, the patient is, or is at risk of being, immunocompromised as a result of an infection.

A. Breast Cancer

Breast cancer refers to cancers originating from breast tissue, most commonly from the inner lining of milk ducts or the lobules that supply the ducts with milk. Cancers originating from ducts are known as ductal carcinomas; those originating from lobules are known as lobular carcinomas. There are many different types of breast cancer, with different stages (spread), aggressiveness, and genetic makeup; survival varies greatly depending on those factors. Computerized models are available to predict survival. With best treatment and dependent on staging, 10-year disease-free survival varies from 98% to 10%. Treatment includes surgery, drugs (hormonal therapy and chemotherapy), and radiation.

Worldwide, breast cancer comprises 10.4% of all cancer incidence among women, making it the second most common type of non-skin cancer (after lung cancer) and the fifth most common cause of cancer death. In 2004, breast cancer caused 519,000 deaths worldwide (7% of cancer deaths; almost 1% of all deaths). Breast cancer is about 100 times more common in women than in men, although males tend to have poorer outcomes due to delays in diagnosis.

Some breast cancers require the hormones estrogen and progesterone to grow, and have receptors for those hormones. After surgery those cancers are treated with drugs that interfere with those hormones, usually tamoxifen, and with drugs that shut off the production of estrogen in the ovaries or elsewhere; this may damage the ovaries and end fertility. After surgery, low-risk, hormone-sensitive breast cancers may be treated with hormone therapy and radiation alone. Breast cancers without hormone receptors, or which have spread to the lymph nodes in the armpits, or which express certain genetic characteristics, are higher-risk, and are treated more aggressively. One standard regimen, popular in the U.S., is cyclophosphamide plus doxorubicin (Adriamycin), known as CA; these drugs damage DNA in the cancer, but also in fast-growing normal cells where they cause serious side effects. Sometimes a taxane drug, such as docetaxel, is added, and the regime is then known as CAT; taxane attacks the microtubules in cancer cells. An equivalent treatment, popular in Europe, is cyclophosphamide, methotrexate, and fluorouracil (CMF). Monoclonal antibodies, such as trastuzumab (Herceptin), are used for cancer cells that have the HER2 mutation. Radiation is usually added to the surgical bed to control cancer cells that were missed by the surgery, which usually extends survival, although radiation exposure to the heart may cause damage and heart failure in the following years.

While screening techniques (which are further discussed below) are useful in determining the possibility of cancer, a further testing is necessary to confirm whether a lump detected on screening is cancer, as opposed to a benign alternative such as a simple cyst.

In a clinical setting, breast cancer is commonly diagnosed using a "triple test" of clinical breast examination (breast examination by a trained medical practitioner), mammography, and fine needle aspiration cytology. Both mammography and clinical breast exam, also used for screening, can indicate an approximate likelihood that a lump is cancer, and may also identify any other lesions. Fine Needle Aspiration and Cytology (FNAC), which may be done in a doctor's office using local anaesthetic if required, involves attempting to extract a small portion of fluid from the lump. Clear fluid makes the lump highly unlikely to be cancerous, but bloody fluid may be sent off for inspection under a microscope for cancerous cells. Together, these three tools can be used to diagnose breast cancer with a good degree of accuracy.

Other options for biopsy include core biopsy, where a section of the breast lump is removed, and an excisional biopsy, where the entire lump is removed.

In addition vacuum-assisted breast biopsy (VAB) may help diagnose breast cancer among patients with a mammographically detected breast in women according to a systematic review. In this study, summary estimates for vacuum assisted breast biopsy in diagnosis of breast cancer were as follows sensitivity was 98.1% with 95% CI=0.972-0.987 and specificity was 100% with 95% CI=0.997-0.999; however, underestimate rates of atypical ductal hyperplasia (ADH) and ductal carcinoma in situ (DCIS) were 20.9% with 95% CI=0.177-0.245 and 11.2% with 95% CI=0.098-0.128 respectively.

Breast cancer screening refers to testing otherwise-healthy women for breast cancer in an attempt to achieve an earlier diagnosis. The assumption is that early detection will improve outcomes. A number of screening tests have been employed including: clinical and self breast exams, mammography, genetic screening, ultrasound, and magnetic resonance imaging.

A clinical or self breast exam involves feeling the breast for lumps or other abnormalities. Research evidence does not support the effectiveness of either type of breast exam, because by the time a lump is large enough to be found it is likely to have been growing for several years and will soon be large enough to be found without an exam. Mammographic screening for breast cancer uses x-rays to examine the breast for any uncharacteristic masses or lumps. In women at high risk, such as those with a strong family history of cancer, mammography screening is recommended at an earlier age and additional testing may include genetic screening that tests for the BRCA genes and/or magnetic resonance imaging.

Breast cancer is sometimes treated first with surgery, and then with chemotherapy, radiation, or both. Treatments are given with increasing aggressiveness according to the prognosis and risk of recurrence. Stage 1 cancers (and DCIS) have an excellent prognosis and are generally treated with lumpectomy with or without chemotherapy or radiation. Although the aggressive HER2+ cancers should also be treated with the trastuzumab (Herceptin) regime. Stage 2 and 3 cancers with a progressively poorer prognosis and greater risk of recurrence are generally treated with surgery (lumpectomy or mastectomy with or without lymph node removal), radiation (sometimes) and chemotherapy (plus trastuzumab for HER2+ cancers). Stage 4, metastatic cancer, (i.e., spread to distant sites) is not curable and is managed by various combinations of all treatments from surgery, radiation, chemotherapy and targeted therapies. These treatments increase the median survival time of stage 4 breast cancer by about 6 months.

B. Ovarian Cancer

Ovarian cancer is a cancerous growth arising from different parts of the ovary. Most (>90%) ovarian cancers are classified as "epithelial" and were believed to arise from the surface (epithelium) of the ovary. However, recent evidence suggests that the Fallopian tube could also be the source of some ovarian cancers. Since the ovaries and tubes are closely related to each other, it is hypothesized that these cells can mimic ovarian cancer. Other types arise from the egg cells (germ cell tumor) or supporting cells (sex cord/stromal).

In 2004, in the United States, 25,580 new cases were diagnosed and 16,090 women died of ovarian cancer. The risk increases with age and decreases with pregnancy. Lifetime risk is about 1.6%, but women with affected first-degree relatives have a 5% risk. Women with a mutated BRCA1 or BRCA2 gene carry a risk between 25% and 60% depending on the specific mutation. Ovarian cancer is the fifth leading cause of death from cancer in women and the leading cause of death from gynecological cancer.

Ovarian cancer causes non-specific symptoms. Early diagnosis would result in better survival, on the assumption that stage I and II cancers progress to stage III and IV cancers (but this has not been proven). Most women with ovarian cancer report one or more symptoms such as abdominal pain or discomfort, an abdominal mass, bloating, back pain, urinary urgency, constipation, tiredness and a range of other non-specific symptoms, as well as more specific symptoms such as pelvic pain, abnormal vaginal bleeding or involuntary weight loss. There can be a build-up of fluid (ascites) in the abdominal cavity.

Diagnosis of ovarian cancer starts with a physical examination (including a pelvic examination), a blood test (for CA-125 and sometimes other markers), and transvaginal ultrasound. The diagnosis must be confirmed with surgery to inspect the abdominal cavity, take biopsies (tissue samples for microscopic analysis) and look for cancer cells in the abdominal fluid. Treatment usually involves chemotherapy and surgery, and sometimes radiotherapy.

In most cases, the cause of ovarian cancer remains unknown. Older women, and in those who have a first or second degree relative with the disease, have an increased risk. Hereditary forms of ovarian cancer can be caused by mutations in specific genes (most notably BRCA1 and BRCA2, but also in genes for hereditary nonpolyposis colorectal cancer). Infertile women and those with a condition called endometriosis, those who have never been pregnant and those who use postmenopausal estrogen replacement therapy are at increased risk. Use of combined oral contraceptive pills is a protective factor. The risk is also lower in women who have had their uterine tubes blocked surgically (tubal ligation).

Ovarian cancer is classified according to the histology of the tumor, obtained in a pathology report. Histology dictates many aspects of clinical treatment, management, and prognosis. Surface epithelial-stromal tumour, also known as ovarian epithelial carcinoma, is the most common type of ovarian cancer. It includes serous tumour, endometrioid tumor and mucinous cystadenocarcinoma. Sex cord-stromal tumor, including estrogen-producing granulosa cell tumor and virilizing Sertoli-Leydig cell tumor or arrhenoblastoma, accounts for 8% of ovarian cancers. Germ cell tumor accounts for approximately 30% of ovarian tumors but only 5% of ovarian cancers, because most germ cell tumors are teratomas and most teratomas are benign (see Teratoma). Germ cell tumor tends to occur in young women and girls. The prognosis depends on the specific histology of germ cell tumor, but overall is favorable. Mixed tumors, containing elements of more than one of the above classes of tumor histology.

Ovarian cancer can also be a secondary cancer, the result of metastasis from a primary cancer elsewhere in the body. Seven percent of ovarian cancers are due to metastases while the rest are primary cancers. Common primary cancers are breast cancer and gastrointestinal cancer (a common mistake is to name all peritoneal metastases from any gastrointestinal cancer as Krukenberg cancer, but this is only the case if it originates from primary gastric cancer). Surface epithelial-stromal tumor can originate in the peritoneum (the lining of the abdominal cavity), in which case the ovarian cancer is secondary to primary peritoneal cancer, but treatment is basically the same as for primary surface epithelial-stromal tumor involving the peritoneum.

Ovarian cancer staging is by the FIGO staging system and uses information obtained after surgery, which can include a total abdominal hysterectomy, removal of (usually) both ovaries and fallopian tubes, (usually) the momentum, and pelvic (peritoneal) washings for cytopathology. The AJCC stage is the same as the FIGO stage. The AJCC staging system describes the extent of the primary Tumor (T), the absence or presence of metastasis to nearby lymph Nodes (N), and the absence or presence of distant Metastasis (M).

The AJCC/TNM staging system includes three categories for ovarian cancer, T, N and M. The T category contains three other subcategories, T1, T2 and T3, each of them being classified according to the place where the tumor has developed (in one or both ovaries, inside or outside the ovary). The T1 category of ovarian cancer describes ovarian tumors that are confined to the ovaries, and which may affect one or both of them. The sub-subcategory T1a is used to stage cancer that is found in only one ovary, which has left the capsule intact and which cannot be found in the fluid taken from the pelvis. Cancer that has not affected the capsule, is confined to the inside of the ovaries and cannot be found in the fluid taken from the pelvis but has affected both ovaries is staged as T1b. T1c category describes a type of tumor that can affect one or both ovaries, and which has grown through the capsule of an ovary or it is present in the fluid taken from the pelvis. T2 is a more advanced stage of cancer. In this case, the tumor has grown in one or both ovaries and is spread to the uterus, fallopian tubes or other pelvic tissues. Stage T2a is used to describe a cancerous tumor that has spread to the uterus or the fallopian tubes (or both) but which is not present in the fluid taken from the pelvis. Stages T2b and T2c indicate cancer that metastasized to other pelvic tissues than the uterus and fallopian tubes and which cannot be seen in the fluid taken from the pelvis, respectively tumors that spread to any of the pelvic tissues (including uterus and fallopian tubes) but which can also be found in the fluid taken from the pelvis. T3 is the stage used to describe cancer that has spread to the peritoneum. This stage provides information on the size of the metastatic tumors (tumors that are located in other areas of the body, but are caused by ovarian cancer). These tumors can be very small, visible only under the microscope (T3a), visible but not larger than 2 centimeters (T3b) and bigger than 2 centimeters (T3c).

This staging system also uses N categories to describe cancers that have or not spread to nearby lymph nodes. There are only two N categories, NO which indicates that the cancerous tumors have not affected the lymph nodes, and N1 which indicates the involvement of lymph nodes close to the tumor. The M categories in the AJCC/TNM staging system provide information on whether the ovarian cancer has metastasized to distant organs such as liver or lungs. M0 indicates that the cancer did not spread to distant organs and M1 category is used for cancer that has spread to other organs of the body. The AJCC/TNM staging system also contains a Tx and a Nx sub-category which indicates that the extent of the tumor cannot be described because of insufficient data, respectively the involvement of the lymph nodes cannot be described because of the same reason.

Ovarian cancer, as well as any other type of cancer, is also graded, apart from staged. The histologic grade of a tumor measures how abnormal or malignant its cells look under the microscope. There are four grades indicating the likelihood of the cancer to spread and the higher the grade, the more likely for this to occur. Grade 0 is used to describe non-invasive tumors. Grade 0 cancers are also referred to as borderline tumors. Grade 1 tumors have cells that are well differentiated (look very similar to the normal tissue) and are the ones with the best prognosis. Grade 2 tumors are also called moderately well differentiated and they are made up by cells that resemble the normal tissue. Grade 3 tumors have the worst prognosis and their cells are abnormal, referred to as poorly differentiated.

The signs and symptoms of ovarian cancer are most of the times absent, but when they exist they are nonspecific. In most cases, the symptoms persist for several months until the patient is diagnosed.

A prospective case-control study of 1,709 women visiting primary care clinics found that the combination of bloating, increased abdominal size, and urinary symptoms was found in 43% of those with ovarian cancer but in only 8% of those presenting to primary care clinics.

The exact cause is usually unknown. The risk of developing ovarian cancer appears to be affected by several factors. The more children a woman has, the lower her risk of ovarian cancer. Early age at first pregnancy, older age of final pregnancy and the use of low dose hormonal contraception have also been shown to have a protective effect. Ovarian cancer is reduced in women after tubal ligation.

The relationship between use of oral contraceptives and ovarian cancer was shown in a summary of results of 45 case-control and prospective studies. Cumulatively these studies show a protective effect for ovarian cancers. Women who used oral contraceptives for 10 years had about a 60% reduction in risk of ovarian cancer. (risk ratio 0.42 with statistical significant confidence intervals given the large study size, not unexpected). This means that if 250 women took oral contraceptives for 10 years, 1 ovarian cancer would be prevented. This is by far the largest epidemiological study to date on this subject (45 studies, over 20,000 women with ovarian cancer and about 80,000 controls).

The link to the use of fertility medication, such as Clomiphene citrate, has been controversial. An analysis in 1991 raised the possibility that use of drugs may increase the risk of ovarian cancer. Several cohort studies and case-control studies have been conducted since then without demonstrating conclusive evidence for such a link. It will remain a complex topic to study as the infertile population differs in parity from the "normal" population.

There is good evidence that in some women genetic factors are important. Carriers of certain mutations of the BRCA1 or the BRCA2 gene are notably at risk. The BRCA1 and BRCA2 genes account for 5%-13% of ovarian cancers and certain populations (e.g. Ashkenazi Jewish women) are at a higher risk of both breast cancer and ovarian cancer, often at an earlier age than the general population. Patients with a personal history of breast cancer or a family history of breast and/or ovarian cancer, especially if diagnosed at a young age, may have an elevated risk.

A strong family history of uterine cancer, colon cancer, or other gastrointestinal cancers may indicate the presence of a syndrome known as hereditary nonpolyposis colorectal cancer (HNPCC, also known as Lynch syndrome), which confers a higher risk for developing ovarian cancer. Patients with strong genetic risk for ovarian cancer may consider the use of prophylactic, i.e. preventative, oophorectomy after completion of childbearing.[*citation needed*] Australia being member of International Cancer Genome Consortium is leading efforts to map ovarian cancer's complete genome.

Ovarian cancer at its early stages (I/II) is difficult to diagnose until it spreads and advances to later stages (II/IV). This is because most symptoms are non-specific and thus of little use in diagnosis.

When an ovarian malignancy is included in the list of diagnostic possibilities, a limited number of laboratory tests are indicated. A complete blood count (CBC) and serum electrolyte test should be obtained in all patients.

The serum BHCG level should be measured in any female in whom pregnancy is a possibility. In addition, serum alpha-fetoprotein (AFP) and lactate dehydrogenase (LDH) should be measured in young girls and adolescents with suspected ovarian tumors because the younger the patient, the greater the likelihood of a malignant germ cell tumor.

A blood test called CA-125 is useful in differential diagnosis and in follow up of the disease, but it by itself has not been shown to be an effective method to screen for early-stage ovarian cancer due to its unacceptable low sensitivity and specificity. However, this is the only widely-used marker currently available.

Current research is looking at ways to combine tumor markers proteomics along with other indicators of disease (i.e., radiology and/or symptoms) to improve accuracy. The challenge in such an approach is that the very low population prevalence of ovarian cancer means that even testing with very high sensitivity and specificity will still lead to a number of false positive results (i.e., performing surgical procedures in which cancer is not found intra-operatively). However, the contributions of proteomics are still in the early stages and require further refining. Current studies on proteomics mark the beginning of a paradigm shift towards individually tailored therapy.

A pelvic examination and imaging including CT scan and trans-vaginal ultrasound are essential. Physical examination may reveal increased abdominal girth and/or ascites (fluid within the abdominal cavity). Pelvic examination may reveal an ovarian or abdominal mass. The pelvic examination can include a rectovaginal component for better palpation of the ovaries. For very young patients, magnetic resonance imaging may be preferred to rectal and vaginal examination.

To definitively diagnose ovarian cancer, a surgical procedure to take a look into the abdomen is required. This can be an open procedure (laparotomy, incision through the abdominal wall) or keyhole surgery (laparoscopy). During this procedure, suspicious areas will be removed and sent for microscopic analysis. Fluid from the abdominal cavity can also be analysed for cancerous cells. If there is cancer, this procedure can also determine its spread (which is a form of tumor staging).

Women who have had children are less likely to develop ovarian cancer than women who have not, and breastfeeding may also reduce the risk of certain types of ovarian cancer. Tubal ligation and hysterectomy reduce the risk and removal of both tubes and ovaries (bilateral salpingo-oophorectomy) dramatically reduces the risk of not only ovarian cancer but breast cancer also. The use of oral contraceptives (birth control pills) for five years or more decreases the risk of ovarian cancer in later life by 50%.

Tubal ligation is believed to decrease the chance of developing ovarian cancer by up to 67% while a hysterectomy may reduce the risk of getting ovarian cancer by about one-third. Moreover, according to some studies, analgesics such as acetaminophen and aspirin seem to reduce one's risks of developing ovarian cancer. Yet, the information is not consistent and more research needs to be carried on this matter.

Routine screening of women for ovarian cancer is not recommended by any professional society—this includes the U.S. Preventive Services Task Force, the American Cancer Society, the American College of Obstetricians and Gynecologists, and the National Comprehensive Cancer Network. This is because no trial has shown improved survival for women undergoing screening. Screening for any type of cancer must be accurate and reliable—it needs to accurately detect the disease and it must not give false positive results in people who do not have cancer. As yet there is no technique for ovarian screening that has been shown to fulfil these criteria. However, in some countries such as the UK, women who are likely to have an increased risk of ovarian cancer (for example if they have a family history of the disease) can be offered individual screening through their doctors, although this will not necessarily detect the disease at an early stage.

Researchers are assessing different ways to screen for ovarian cancer. Screening tests that could potentially be used alone or in combination for routine screening include the CA-125 marker and transvaginal ultrasound. Doctors can measure the levels of the CA-125 protein in a woman's blood—high levels could be a sign of ovarian cancer, but this is not always the case. And not all women with ovarian cancer have high CA-125 levels. Transvaginal ultrasound involves using an ultrasound probe to scan the ovaries from inside the vagina, giving a clearer image than scanning the abdomen. The UK Collaborative Trial of Ovarian Cancer Screening is testing a screening technique that combines CA-125 blood tests with transvaginal ultrasound.

The purpose of screening is to diagnose ovarian cancer at an early stage, when it is more likely to be treated successfully. However, the development of the disease is not fully understood, and it has been argued that early-stage cancers may not always develop into late-stage disease. With any screening technique there are risks and benefits that need to be carefully considered, and health authorities need to assess these before introducing any ovarian cancer screening programs.

The goal of ovarian cancer screening is to detect the disease at stage I. Several large studies are ongoing, but none have identified an effective technique. In 2009, however, early results from the UK Collaborative Trial of Ovarian Cancer Screening (UKCTOCS) showed that a technique combining annual CA-125 tests with ultrasound imaging did help to detect the disease at an early stage. However, it is not yet clear if this approach could actually help to save lives—the full results of the trial will be published in 2015.

Surgical treatment may be sufficient for malignant tumors that are well-differentiated and confined to the ovary. Addition of chemotherapy may be required for more aggressive tumors that are confined to the ovary. For patients with advanced disease a combination of surgical reduction with a combination chemotherapy regimen is standard. Borderline tumors, even following spread outside of the ovary, are managed well with surgery, and chemotherapy is not seen as useful.

Surgery is the preferred treatment and is frequently necessary to obtain a tissue specimen for differential diagnosis via its histology. Surgery performed by a specialist in gynecologic oncology usually results in an improved result. Improved survival is attributed to more accurate staging of the disease and a higher rate of aggressive surgical excision of tumor in the abdomen by gynecologic oncologists as opposed to general gynecologists and general surgeons.

The type of surgery depends upon how widespread the cancer is when diagnosed (the cancer stage), as well as the presumed type and grade of cancer. The surgeon may remove one (unilateral oophorectomy) or both ovaries (bilateral oophorectomy), the fallopian tubes (salpingectomy), and the uterus (hysterectomy). For some very early tumors (stage 1, low grade or low-risk disease), only the involved ovary and fallopian tube will be removed (called a "unilateral salpingo-oophorectomy," USO), especially in young females who wish to preserve their fertility.

In advanced malignancy, where complete resection is not feasible, as much tumor as possible is removed (debulking surgery). In cases where this type of surgery is successful (i.e., <1 cm in diameter of tumor is left behind ["optimal debulking" ]), the prognosis is improved compared to patients where large tumor masses (>1 cm in diameter) are left behind. Minimally invasive surgical techniques may facilitate the safe removal of very large (greater than 10 cm) tumors with fewer complications of surgery.

Chemotherapy has been a general standard of care for ovarian cancer for decades, although with highly variable protocols. Chemotherapy is used after surgery to treat any residual disease, if appropriate. This depends on the histology of the tumor; some kinds of tumor (particularly teratoma) are not sensitive to chemotherapy. In some cases, there may be reason to perform chemotherapy first, followed by surgery.

For patients with stage IIIC epithelial ovarian adenocarcinomas who have undergone successful optimal debulking, a recent clinical trial demonstrated that median survival time is significantly longer for patient receiving intraperitoneal (IP) chemotherapy. Patients in this clinical trial reported less compliance with IP chemotherapy and fewer than half of the patients received all six cycles of IP chemotherapy. Despite this high “drop-out” rate, the group as a whole (including the patients that didn’t complete IP chemotherapy treatment) survived longer on average than patients who received intravenous chemotherapy alone.

Some specialists believe the toxicities and other complications of IP chemotherapy will be unnecessary with improved IV chemotherapy drugs currently being developed.

Although IP chemotherapy has been recommended as a standard of care for the first-line treatment of ovarian cancer, the basis for this recommendation has been challenged.

Radiation therapy is not effective for advanced stages because when vital organs are in the radiation field, a high dose cannot be safely delivered. Radiation therapy is then commonly avoided in such stages as the vital organs may not be able to withstand the problems associated with these ovarian cancer treatments.

Ovarian cancer usually has a poor prognosis. It is disproportionately deadly because it lacks any clear early detection or screening test, meaning that most cases are not diagnosed until they have reached advanced stages. More than 60% of women presenting with this cancer already have stage III or stage IV cancer, when it has already spread beyond the ovaries.

Ovarian cancers shed cells into the naturally occurring fluid within the abdominal cavity. These cells can then implant on other abdominal (peritoneal) structures, included the uterus, urinary bladder, bowel and the lining of the bowel wall momentum forming new tumor growths before cancer is even suspected.

The five-year survival rate for all stages of ovarian cancer is 45.5%. For cases where a diagnosis is made early in the disease, when the cancer is still confined to the primary site, the five-year survival rate is 92.7%.

IV. PHARMACEUTICAL FORMULATIONS AND METHODS OF TREATMENT

A. Formulations

In another aspect, for administration to a patient in need of such treatment, pharmaceutical formulations (also referred to as a pharmaceutical preparations, pharmaceutical compositions, pharmaceutical products, medicinal products, medicines, medications, or medicaments) comprise a therapeutically effective amount of a compound disclosed herein formulated with one or more excipients and/or drug carriers appropriate to the indicated route of administration. In some embodiments, the compounds disclosed herein are formulated in a manner amenable for the treatment of human and/or veterinary patients. In some embodiments, formulation comprises admixing or combining one or more of the compounds disclosed herein with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, e.g., for oral administration, the pharmaceutical formulation may be tableted or encapsulated. In some embodiments, the compounds may be dissolved or slurried in water, polyethylene glycol, propylene glycol, ethanol, corn oil, cottonseed oil, peanut oil, sesame oil, benzyl alcohol, sodium chloride, and/or various buffers. In some embodiments, the pharmaceutical formulations may be subjected to pharmaceutical operations, such as sterilization, and/or may contain drug carriers and/or excipients such as preservatives, stabilizers, wetting agents, emulsifiers, encapsulating agents such as lipids, dendrimers, polymers, proteins such as albumin, nucleic acids, and buffers.

Pharmaceutical formulations may be administered by a variety of methods, e.g., orally or by injection (e.g. subcutaneous, intravenous, and intraperitoneal). Depending on the route of administration, the compounds disclosed herein may be coated in a material to protect the compound from the action of acids and other natural conditions which may inactivate the compound. To administer the active compound by other than parenteral administration, it may be necessary to coat the compound with, or co-administer the compound with, a material to prevent its inactivation. In some embodiments, the active compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The compounds disclosed herein may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

The compounds disclosed herein can be administered orally, for example, with an inert diluent or an assimilable edible carrier. The compounds and other ingredients may also be enclosed in a hard or soft-shell gelatin capsule, compressed into tablets, or incorporated directly into the patient’s diet. For oral therapeutic administration, the compounds disclosed herein may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such pharmaceutical formulations is such that a suitable dosage will be obtained.

The therapeutic compound may also be administered topically to the skin, eye, ear, or mucosal membranes. Administration of the therapeutic compound topically may include formulations of the compounds as a topical solution, lotion, cream, ointment, gel, foam, transdermal patch, or tincture. When the therapeutic compound is formulated for topical administration, the compound may be combined with one or more agents that increase the permeability of the compound through the tissue to which it is administered. In other embodiments, it is contemplated that the topical administration is administered to the eye. Such administration may be applied to the surface of the cornea, conjunctiva, or sclera. Without wishing to be bound by any theory, it is believed that administration to the surface of the eye allows the therapeutic compound to reach the posterior portion of the eye. Ophthalmic topical administration can be formulated as a solution, suspension, ointment, gel, or emulsion. Finally, topical administration may also include administration to the mucosa membranes such as the inside of the mouth. Such administration can be directly to a particular location within the mucosal membrane such as a tooth, a sore, or an ulcer. Alternatively, if local delivery to the lungs is desired the therapeutic compound may be administered by inhalation in a dry-powder or aerosol formulation.

In some embodiments, it may be advantageous to formulate parenteral compositions in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical carrier. In some embodiments, the specification for the dosage unit forms of the disclosure are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient. In some embodiments, active compounds are administered at a therapeutically effective dosage sufficient to treat a condition associated with a condition in a patient. For example, the efficacy of a compound can be evaluated in an animal model system that may be predictive of efficacy in treating the disease in a human or another animal.

In some embodiments, the effective dose range for the therapeutic compound can be extrapolated from effective doses determined in animal studies for a variety of different animals. In some embodiments, the human equivalent dose (TED) in mg/kg can be calculated in accordance with the following formula (see, e.g., Reagan-Shaw et al., *FASEB J.,* 22(3):659-661, 2008, which is incorporated herein by reference):

$$\text{HED (mg/kg)}=\text{Animal dose (mg/kg)}\times(\text{Animal } K_m/\text{Human } K_m)$$

Use of the $K_m$ factors in conversion results in HED values based on body surface area (BSA) rather than only on body mass. $K_m$ values for humans and various animals are well known. For example, the $K_m$ for an average 60 kg human (with a BSA of 1.6 $m^2$) is 37, whereas a 20 kg child (BSA 0.8 $m^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are specific to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a compound of the present disclosure or composition comprising a compound of the present disclosure administered to a patient may be determined by physical and physiological factors such as type of animal treated, age, sex, body weight, severity of condition, the type of disease being treated, previous or concurrent therapeutic interventions, idiopathy of the patient and on the route of administration. These factors may be determined by a skilled artisan. The practitioner responsible for administration will typically determine the concentration of active ingredient(s) in a composition and appropriate dose(s) for the individual patient. The dosage may be adjusted by the individual physician in the event of any complication.

In some embodiments, the therapeutically effective amount typically will vary from about 0.001 mg/kg to about 1000 mg/kg, from about 0.01 mg/kg to about 750 mg/kg, from about 100 mg/kg to about 500 mg/kg, from about 1 mg/kg to about 250 mg/kg, from about 10 mg/kg to about 150 mg/kg in one or more dose administrations daily, for one or several days (depending of course of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some embodiments, the amount is less than 10,000 mg per day with a range of 750 mg to 9,000 mg per day.

In some embodiments, the amount of the active compound in the pharmaceutical formulation is from about 2 to about 75 weight percent. In some of these embodiments, the amount if from about 25 to about 60 weight percent.

Single or multiple doses of the agents are contemplated. Desired time intervals for delivery of multiple doses can be determined by one of ordinary skill in the art employing no more than routine experimentation. As an example, patients may be administered two doses daily at approximately 12-hour intervals. In some embodiments, the agent is administered once a day.

The agent(s) may be administered on a routine schedule. As used herein a routine schedule refers to a predetermined designated period of time. The routine schedule may encompass periods of time which are identical, or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the disclosure provides that the agent(s) may be taken orally and that the timing of which is or is not dependent upon food intake. Thus, for example, the agent can be taken every morning and/or every evening, regardless of when the patient has eaten or will eat.

The following abbreviations are used in the present disclosure: GRB2, growth factor receptor-bound protein 2; mGRB2, monomeric growth factor receptor-bound protein 2; dGRB, dimeric growth factor receptor-bound protein 2; SOS, son of sevenless; RTK, Receptor tyrosine kinases;

MAP, mitogen-activated protein; SH2, Src homology 2; SH3, SRC homology 3; EGFR, epidermal growth factor receptor; TNBC, triple-negative breast cancer; NMR, nuclear magnetic resonance; LRMS, low-resolution mass spectrometry; GEF, guanine exchange factor; and ESC, early signaling complex.

V. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Results and Discussion

In response to recent insight into GRB2 molecular function (Ahmed et al., 2015), small molecule inhibitors were developed to control GRB2 activity and particularly to sever the link between GRB2 and SOS. It was found that GRB2 can be a monomer or a dimer in cells. Importantly, only monomers are capable of binding SOS and activating Ras whereas the dimers are inhibitory. This means that if GRB2 can be held at its dimeric state inside cells, it will be prevented from binding and therefore blocked from recruiting SOS to an activated RTK. From these data, it was envisioned the development of entirely new type of small molecule inhibitors for GRB2 function. Since the dimeric GRB2 is the autoinhibited form, it was reasoned that a small molecule stabilizing the dimer interface would be a valuable for inhibiting cellular proliferative signal, thus provide a new avenue for inhibiting RTK induced MAP kinase in many cancers. Moreover, analysis of the structure showed that the binding pocket at the dimer interface is unique to GRB2 alone therefore stabilizing compounds expected to be specific for GRB2 with limited cross-reactivity with other SH2 or SH3 domain bearing molecules in cells. Small molecules targeting GRB2 were developed and were shown to be capable of stabilizing synthetic GRB2 dimer conformation to keep the molecule in its dimeric state. It was found that the stabilization of dimeric GRB2 leads to inhibition of EGF-stimulated Ras/MAP without affecting the receptor tyrosine kinase activity.

Furthermore, the dual concept of 1) inhibiting of Ras-MAP kinase activity through functional GRB2 inhibitors and 2) using these compounds to selectively kills cancer cells by programmed cell death, was confirmed. These findings indicates that the current difficulties with drug-resistant mutant RTKs in cancers with uncontrolled kinase activity may be controlled by dGRB2 stabilizing molecules. Therefore, several rounds of chemical optimization were performed to increase potency and cell-permeability as well as improve activity.

Compounds were tested in HEK293T and NIH-3T3 cell-lines and a number of cancer cell-lines including PC3, OVCAR-5 cells with G12V KRAS mutation. OVCAR-8 contains ERBB2 G776V, p53 Y126 to K132 deletion and a rare P121H KRAS mutation that display RAS/MAPK activation similar to that of the ovarian cancer cell lines with classical KRAS mutations. GRB2 stabilizers were also tested and shown to be effective in triple negative MDA-MB-231 breast cancer (TNBC) cells, which bears a G13D KRAS mutation as well as p53 mutations, and A549 lung cancer cells that contain G12S KRAS mutation. TNBC cells appears to be more sensitive to the GRB2 inhibitors, which correlates with strong Ras/MAPK inhibition. This data strongly suggests a potential therapeutic value of dGRB2 stabilizers as a stand-alone treatment for EGFR and KRAS driven cancers.

Example 2—Synthetic Methods and Characterization Data

GRB058 $^1$H-NMR (400 MHz, DMSO-D6) δ 12.38 (d, J=7.3 Hz, 2H), 9.05 (s, 1H), 7.82 (t, J=7.3 Hz, 2H), 7.61 (d, J=1.8 Hz, 1H), 7.14 (dd, J=16.9, 7.8 Hz, 2H), 7.03 (d, J=8.7 Hz, 1H), 6.91-6.95 (m, 2H), 2.23-2.28 (m, 3H); $^{13}$C-NMR (101 MHz, DMSO-D6) δ 167.64, 152.68, 137.40, 135.28, 132.65, 130.17, 127.44, 127.24, 126.15, 122.61, 120.93, 113.07, 109.55, 99.40, 17.89. LRMS (ESI) $C_{15}H_{14}N_4OS$ found [M+H]: 299.1.

GRB085 $^1$H-NMR (400 MHz, DMSO-D6) δ 10.26 (s, 1H), 9.00 (s, 1H), 8.63 (s, 1H), 7.35 (s, 1H), 7.13-7.18 (m, 3H), 6.71-6.77 (m, 2H), 3.45 (s, 2H); $^{13}$C-NMR (101 MHz, DMSO-D6) δ 176.24, 163.74, 161.49, 152.41, 142.68, 138.85, 133.02, 126.27, 118.37, 116.48, 108.99, 100.90, 100.61, 96.48, 36.09. LRMS (ESI) $C_{15}H_{11}F_2N_3O_2$ found [M+H]: 304.28.

GRB087 $^1$H-NMR (400 MHz, DMSO-D6) δ 10.24 (s, 1H), 8.76 (s, 1H), 8.52 (s, 1H), 7.83 (s, 1H), 7.36 (s, 1H), 7.11-7.28 (m, 4H), 6.72 (d, J=6.9 Hz, 1H), 3.45 (s, 2H); $^{13}$C-NMR (101 MHz, DMSO-D6) δ 176.74, 153.07, 142.15, 139.19, 133.80, 131.19, 126.77, 124.62, 122.23, 120.79, 118.68, 117.39, 116.85, 109.49, 40.05, 36.62. LRMS (ESI) $C_{15}H_{12}BrN_3O_2$ found [M+H]: 348.32.

GRB089 $^1$H-NMR (400 MHz, DMSO-D6) δ 10.22 (s, 1H), 8.71 (d, J=3.2 Hz, 1H), 7.83 (s, 1H), 7.52 (d, J=5.0 Hz, 1H), 7.39 (s, 1H), 7.15 (d, J=7.3 Hz, 1H), 7.00-7.02 (m, 1H), 6.87 (s, 1H), 6.71 (q, J=4.0 Hz, 1H), 3.44 (d, J=2.3 Hz, 2H), 2.24 (d, J=3.7 Hz, 3H), 2.11 (d, J=3.7 Hz, 3H); $^{13}$C-NMR (101 MHz, DMSO-D6) δ 176.20, 153.06, 138.17, 137.16, 136.50, 133.99, 127.20, 126.22, 125.20, 124.66, 120.14, 117.50, 115.79, 108.99, 36.12, 20.37, 13.60. LRMS (ESI) $C_{17}H_{17}N_3O_2$ found [M+H]: 296.36.

GRB092 $^1$H-NMR (400 MHz, DMSO-D6) δ 10.26 (s, 1H), 8.95 (s, 1H), 8.66 (s, 1H), 7.51 (s, 2H), 7.35 (s, 1H), 7.11-7.19 (m, 2H), 6.73 (d, J=8.2 Hz, 1H), 3.45 (s, 2H); $^{13}$C-NMR (101 MHz, DMSO-D6) δ 176.23, 152.39, 142.49, 138.89, 134.04, 132.99, 126.26, 120.62, 118.46, 116.56, 116.15, 108.97, 36.08. LRMS (ESI) $C_{15}H_{11}Cl_2N_3O_2$ found [M+H]: 336.39.

GRB093 $^1$H-NMR (400 MHz, DMSO-D6) δ 10.22 (s, 1H), 8.72 (s, 1H), 7.63-7.73 (m, 2H), 7.39 (s, 1H), 7.15 (d, J=8.2 Hz, 1H), 6.91-6.96 (m, 2H), 6.71 (d, J=8.7 Hz, 1H), 3.44 (s, 2H), 2.19 (d, J=11.4 Hz, 6H); $^{13}$C-NMR (101 MHz, DMSO-D6) δ 176.20, 152.92, 138.17, 134.93, 133.96, 131.38, 130.68, 127.59, 126.55, 126.23, 121.25, 117.49, 115.79, 109.00, 36.12, 20.32, 17.83.

GRB002 $^1$H-NMR (400 MHz, DMSO-D6) δ 10.26 (s, 1H), 8.90 (s, 1H), 8.59 (s, 1H), 7.86 (q, J=1.2 Hz, 1H), 7.48-7.51 (m, 1H), 7.28-7.35 (m, 2H), 7.17 (d, J=8.2 Hz, 1H), 6.72 (d, J=8.2 Hz, 1H), 3.45 (s, 2H); $^{13}$C-NMR (101 MHz, DMSO-D6) δ 176.21, 152.48, 140.18, 138.76, 133.11, 130.97, 130.52, 126.25, 122.79, 119.11, 118.28, 118.19, 116.42, 108.96, 36.07.

GRB022 $^1$H-NMR (400 MHz, DMSO-D6) δ 10.50 (d, J=37.6 Hz, 2H), 8.86 (s, 1H), 8.62 (s, 1H), 7.86 (s, 1H), 7.48

(d, J=8.7 Hz, 1H), 7.30 (d, J=8.2 Hz, 2H), 6.82 (s, 2H), 3.47-3.30 (OH), 2.49 (s, 1H); $^{13}$C-NMR (101 MHz, DMSO-D6) δ 155.61, 152.50, 140.20, 132.79, 131.05, 130.52, 129.94, 125.12, 122.88, 119.20, 118.24, 111.62, 108.44, 100.55.

GRB020. $^{1}$H-NMR (400 MHz, DMSO-D6) δ 10.47 (d, J=38.0 Hz, 2H), 8.91 (s, 1H), 7.86 (d, J=8.2 Hz, 2H), 7.29-7.38 (m, 3H), 6.80 (q, J=8.2 Hz, 2H), 3.33, 2.24 (d, J=11.0 Hz, 3H); $^{13}$C-NMR (101 MHz, DMSO-D6) δ 155.5, 152.5, 137.2, 133.2, 132.4, 129.9, 129.7, 128.8, 124.8, 122.1, 113.8, 110.9, 108.4, 99.9, 17.6. LRMS (ESI) $C_{15}H_{13}BrN_4O_2$ found [M+H]: 363.32.

GRB025 $^{1}$H-NMR (400 MHz, DMSO-D6) δ 10.51 (d, J=38.0 Hz, 2H), 8.91 (s, 1H), 8.67 (s, 1H), 7.96 (s, 1H), 7.65 (d, J=8.2 Hz, 1H), 7.30-7.49 (m, 3H), 6.83 (s, 2H), 3.36 (s, 2H), 2.50 (s, 1H); $^{13}$C-NMR (101 MHz, DMSO-D6) δ 155.5, 152.6, 140.9, 132.8, 130.2, 129.9, 125.1, 122.8, 120.6, 118.9, 111.6, 111.5, 108.4, 100.4. LRMS (ESI) $C_{15}H_{11}N_5O_2$ found [M+H]: 294.35.

General Procedure I:

373.0 mg (2.50 mmole) of 5-aminobenzimidazolone was dissolved in 10 mL of anhydrous tetrahydrofuran by stirring with magnetic stirrer bar. 1 mL (12.8 mmol or 5.1 equivalent mole to amine) of triethylamine was added to the solution and stirred for 10 minutes. The solution was cool to 0° C. in ice bath and 572.0 mg (3.00 mmole or 1.2 equivalent mole to amine) of sulfonyl chloride was added portion-wise with stirring. After addition, the ice bath was removed and the reaction mixture was stirred at room temperature. The reaction was monitored by TLC and upon completion, diluted with 15 mL of tetrahydrofuran. The organic solution was washed with saturated $NaHCO_3$ (2×15 mL), brine (2×15 mL) and water (2×15 mL). The organic solution was dried ($MgSO_4$), filtered and solvent removed under reduced pressure. The crude compound was purified by column chromatography.

GRB111: $^{1}$H NMR (400 MHz, DMSO-D6) δ 10.49 (s, 2H), 10.31-9.33 (1H), 7.53-7.55 (m, 2H), 7.29 (d, J=8.2 Hz, 2H), 6.72 (d, J=8.7 Hz, 1H), 6.68 (d, J=1.8 Hz, 1H), 6.60 (dd, J=8.2, 1.8 Hz, 1H), 2.30 (s, 3H); $^{13}$C NMR (101 MHz, DMSO-D6) δ 155.3, 142.9, 136.6, 130.7, 129.9, 129.5, 126.9, 126.7, 114.4, 108.5, 102.8, 20.9.

GRB112: $^{1}$H-NMR (400 MHz, DMSO-D6) δ 10.58 (s, 2H), 9.84 (d, J=17.9 Hz, 1H), 7.55-7.62 (m, 2H), 7.02 (q, J=4.1 Hz, 2H), 6.63-6.76 (m, 3H), 3.72-3.78 (m, 3H); $^{13}$C-NMR (101 MHz, DMSO-D6) δ 162.2, 155.3, 131.1, 130.8, 129.8, 128.8, 126.9, 114.5, 114.2, 108.5, 102.9, 55.6.

GRB113: $^{1}$H-NMR (400 MHz, DMSO-D6) δ 10.56 (d, J=7.8 Hz, 2H), 10.01 (s, 1H), 7.75 (dt, J=9.0, 2.1 Hz, 2H), 7.58 (dt, J=9.0, 2.1 Hz, 2H), 6.77 (d, J=8.2 Hz, 1H), 6.69 (d, J=1.8 Hz, 1H), 6.62 (dd, J=8.2, 2.3 Hz, 1H); $^{13}$C-NMR (101 MHz, DMSO-D6) δ 155.3, 138.6, 132.2, 130.1, 129.9, 128.7, 127.2, 126.5, 114.9, 108.6, 103.3.

GRB114: $^{1}$H-NMR (400 MHz, DMSO-D6) δ 10.54 (s, 2H), 9.65 (s, 1H), 7.10-7.13 (m, 3H), 6.73 (d, J=8.7 Hz, 2H), 6.67 (s, 1H), 3.84 (s, 3H), 3.67 (s, 3H); $^{13}$C-NMR (101 MHz, DMSO-D6) δ 155.3, 152.1, 150.3, 130.6, 129.8, 126.9, 126.7, 119.7, 115.1, 114.0, 113.9, 108.4, 102.5, 56.4, 55.7.

GRB115: $^{1}$H-NMR (400 MHz, DMSO-D6) δ 10.55 (d, J=5.0 Hz, 2H), 10.25 (s, 1H), 7.75 (td, J=8.6, 6.3 Hz, 1H), 7.49-7.54 (m, 1H), 7.20 (td, J=8.6, 2.1 Hz, 1H), 6.76 (d, J=8.2 Hz, 1H), 6.71 (d, J=1.8 Hz, 1H), 6.65 (dd, J=8.2, 1.8 Hz, 1H); $^{13}$C-NMR (101 MHz, DMSO-D6) δ 155.3, 132.5, 129.9, 129.6, 127.3, 123.6, 114.6, 112.2, 108.6, 106.2, 105.9, 105.6, 103.1; $^{19}$F-NMR (376 MHz, DMSO-D6) δ−101.29-−101.20 (m, 1F), −104.52 (q, J=10.6 Hz, 1F).

GRB116: $^{1}$H-NMR (400 MHz, DMSO-D6) δ 10.58 (d, J=9.2 Hz, 2H), 10.07 (s, 1H), 7.80 (d, J=11.4 Hz, 2H), 7.63 (d, J=7.8 Hz, 1H), 7.48 (t, J=7.8 Hz, 1H), 6.78 (d, J=8.2 Hz, 1H), 6.70 (s, 1H), 6.62-6.64 (m, 1H); $^{13}$C-NMR (101 MHz, DMSO-D6) δ 155.3, 141.3, 135.6, 131.4, 129.9, 129.0, 127.3, 125.7, 121.9, 115.0, 108.6, 103.3.

GRB117: $^{1}$H-NMR (400 MHz, DMSO-D6) δ 10.57 (d, J=11.0 Hz, 2H), 10.08 (s, 1H), 8.00 (d, J=7.8 Hz, 1H), 7.92 (t, J=7.6 Hz, 2H), 7.77 (t, J=7.8 Hz, 1H), 6.77 (d, J=8.2 Hz, 1H), 6.67 (s, 1H), 6.60 (dd, J=8.2, 1.4 Hz, 1H); $^{13}$C-NMR (101 MHz, DMSO-D6) δ 155.3, 140.4, 130.8, 130.7, 129.9, 129.8, 129.5, 127.5, 124.7, 123.2, 122.0, 115.2, 108.6, 103.6; $^{19}$F-NMR (376 MHz, DMSO-D6) δ −61.43 (s, 1F).

General Procedure II:

Amine (1 mmole) was added 5 mL of DMF with stirring and cooled 0° C. in an ice bath. Isocyanate (1.1 mmol) was added dropwise slowly to the solution. After addition, the resulting solution was heated to 80° C. and monitored by TLC. Upon completion of the reaction, 50 mL ice water was added into the mixture and stirred for 10 min. The mixture was filtered and was washed with water (3×20 mL). Pure product was obtained by column chromatography.

GRB121: $^{1}$H-NMR (400 MHz, DMSO-D6) δ 10.52 (s, 1H), 10.42 (s, 1H), 8.99 (s, 1H), 7.91 (d, J=20.0 Hz, 2H), 7.37 (s, 1H), 6.80 (d, J=7.6 Hz, 2H), 6.61 (s, 1H), 6.47 (s, 1H), 3.79 (d, J=50.4 Hz, 6H); $^{13}$C-NMR (101 MHz, DMSO-D6) δ 155.6, 154.8, 152.8, 149.1, 133.7, 129.9, 124.5, 122.1, 119.6, 110.7, 108.5, 104.1, 99.8, 98.8, 55.8, 55.3.

GRB122: $^{1}$H-NMR (400 MHz, DMSO-D6) δ 10.53 (s, 1H), 10.44 (s, 1H), 8.88 (s, 1H), 8.02 (s, 1H), 7.76 (d, J=7.6 Hz, 1H), 7.35 (s, 1H), 7.14 (m, 2H), 6.81 (m, 2H), 2.29 (s, 3H); $^{13}$C-NMR (101 MHz, DMSO-D6) δ 155.5, 152.7, 139.2, 133.5, 133.2, 129.9, 126.9, 126.1, 124.8, 123.4, 120.5, 110.8, 108.4, 100.0, 14.7.

GRB145: $^{1}$H-NMR (400 MHz, DMSO-D6) δ 10.24 (s, 1H), 9.16 (s, 1H), 8.15 (s, 1H), 7.85 (d, J=2.7 Hz, 1H), 7.40 (s, 1H), 7.16 (d, J=7.8 Hz, 1H), 6.90 (d, J=8.7 Hz, 1H), 6.73 (d, J=8.2 Hz, 1H), 6.46 (dd, J=8.7, 2.3 Hz, 1H), 3.82 (s, 3H), 3.68 (s, 3H), 3.46 (s, 2H); $^{13}$C-NMR (101 MHz, DMSO-D6) δ 176.4, 153.5, 152.6, 141.9, 138.6, 133.9, 130.0, 126.5, 117.7, 116.0, 111.5, 109.2, 105.4, 105.1, 56.5, 55.4.

GRB146: $^{1}$H-NMR (400 MHz, DMSO-D6) δ 10.24 (s, 1H), 9.32 (s, 1H), 8.69 (s, 1H), 8.14 (d, J=9.2 Hz, 2H), 7.63 (d, J=9.2 Hz, 2H), 7.34 (s, 1H), 7.17 (d, J=6.9 Hz, 1H), 6.71 (d, J=8.2 Hz, 1H), 3.43 (s, 2H); $^{13}$C-NMR (101 MHz, DMSO-D6) δ 176.7, 152.7, 147.1, 141.3, 139.6, 133.4, 126.9, 125.5, 119.0, 117.8, 116.9, 109.5.

GRB015: $^{1}$H-NMR (400 MHz, DMSO-D6) δ 10.23 (s, 1H), 8.37 (d, J=2.3 Hz, 2H), 7.34 (t, J=8.5 Hz, 3H), 7.15 (d, J=7.8 Hz, 1H), 6.85 (d, J=8.7 Hz, 2H), 6.71 (d, J=8.2 Hz, 1H), 3.71 (s, 3H), 3.45 (s, 2H); $^{13}$C-NMR (101 MHz, DMSO-D6) δ 176.7, 154.8, 153.5, 138.8, 134.4, 133.5, 126.7, 120.4, 118.2, 116.5, 114.5, 109.5, 55.7.

GRB147: $^{1}$H-NMR (400 MHz, DMSO-D6) δ 11.46 (s, 1H), 9.38 (s, 1H), 8.21 (s, 1H), 7.84 (d, J=2.7 Hz, 1H), 7.59 (s, 1H), 7.01 (dd, J=12.4, 8.2 Hz, 2H), 6.91 (d, J=9.2 Hz, 1H), 6.48 (dd, J=8.7, 2.7 Hz, 1H), 3.82 (s, 3H), 3.71 (d, J=22.0 Hz, 3H); $^{13}$C-NMR (101 MHz, DMSO-D6) δ 154.7, 153.3, 152.4, 143.5, 141.8, 134.6, 129.5, 124.8, 113.6, 111.4, 109.7, 105.4, 105.1, 100.8, 56.3, 55.2, 40.1, 39.9, 39.7, 39.5, 39.3, 39.1, 38.9.

GRB148: $^{1}$H-NMR (400 MHz, DMSO-D6) δ 11.45 (s, 1H), 8.95 (s, 1H), 8.17 (s, OH), 7.91 (s, 1H), 7.56 (d, J=26.1 Hz, 2H), 7.02 (s, 3H), 6.89 (s, 1H), 2.25 (s, 3H), 2.13 (s, 3H); $^{13}$C-NMR (101 MHz, DMSO-D6) δ 154.7, 153.0, 143.5, 136.9, 136.6, 134.9, 127.5, 125.2, 124.9, 124.6, 120.4, 113.6, 109.6, 100.8, 20.4, 13.6.

GRB149: $^1$H-NMR (400 MHz, DMSO-D6) δ 11.44 (s, 1H), 9.17 (s, 1H), 7.92 (q, J=7.8 Hz, 2H), 7.58 (s, 1H), 6.98 (d, J=7.3 Hz, 2H), 6.61 (d, J=5.0 Hz, 1H), 6.47 (s, 1H), 3.85 (s, 3H), 3.72 (s, 3H); $^{13}$C-NMR (101 MHz, DMSO-D6) δ 154.9, 154.7, 152.6, 149.1, 143.5, 134.9, 124.5, 121.8, 119.7, 113.4, 109.7, 104.1, 100.6, 98.8, 55.8, 55.3.

GRB150: $^1$H-NMR (400 MHz, DMSO-D6) δ 11.46 (s, 1H), 9.06 (s, 1H), 8.47 (s, OH), 8.11 (s, 1H), 7.75 (d, J=10.2 Hz, 1H), 7.59 (d, J=8.4 Hz, 1H), 7.15 (d, J=6.9 Hz, 2H), 7.01-7.06 (m, 2H), 2.28 (s, 3H); $^{13}$C-NMR (101 MHz, DMSO-D6) δ 154.6, 152.7, 143.5, 138.9, 134.5, 133.5, 126.9, 126.5, 124.8, 123.6, 120.8, 113.8, 109.7, 100.9, 14.7.

GRB151: $^1$H-NMR (400 MHz, DMSO-D6) δ 11.49 (s, 1H), 9.07 (s, 1H), 8.81 (s, 1H), 7.88 (d, J=7.8 Hz, 2H), 7.58 (s, 3H), 7.08 (d, J=8.2 Hz, 1H), 7.01 (d, J=8.2 Hz, 1H), 4.27 (q, J=6.9 Hz, 2H), 1.30 (t, J=6.6 Hz, 3H); $^{13}$C-NMR (101 MHz, DMSO-D6) δ 165.4, 154.6, 152.3, 144.3, 143.5, 134.1, 130.4, 125.2, 122.7, 117.3, 114.2, 109.6, 101.3, 60.3, 14.2.

GRB152: $^1$H-NMR (400 MHz, DMSO-D6) δ 11.66 (s, 1H), 10.00 (s, 1H), 9.86 (s, 1H), 7.87 (d, J=3.6 Hz, 1H), 7.57 (t, J=4.4 Hz, 1H), 7.45 (s, 2H), 7.05-7.09 (m, 2H); $^{13}$C-NMR (101 MHz, DMSO-D6) δ 180.0, 154.6, 142.9, 139.8, 133.3, 130.4, 130.1, 127.8, 126.0, 125.1, 123.8, 120.5, 109.4, 107.2, 40.1, 39.9, 39.7, 39.5, 39.3, 39.1, 38.9.

GRB159: $^1$H-NMR (400 MHz, DMSO-D6) δ 10.25 (s, 1H), 9.20 (s, 1H), 8.22-8.30 (m, 2H), 7.38 (s, 1H), 7.16 (d, J=8.2 Hz, 1H), 6.94-7.03 (m, 2H), 6.73 (d, J=8.2 Hz, 1H), 3.88 (s, 3H), 3.46 (s, 2H); $^{13}$C-NMR (101 MHz, DMSO-D6) δ 176.7, 152.9, 146.8, 139.1, 133.9, 130.7, 126.9, 124.9, 121.1, 118.2, 117.7, 116.4, 112.4, 109.6, 56.7.

GRB123: $^1$H-NMR (400 MHz, DMSO-D6) δ 10.56 (s, 1H), 10.45 (s, 1H), 9.24 (s, 1H), 8.12 (s, 1H), 8.02 (s, 1H), 7.29-7.35 (m, 2H), 6.82 (s, 3H), 2.28 (s, 3H); $^{13}$C-NMR (101 MHz, DMSO-D6) δ 155.5, 152.2, 137.0, 135.8, 133.0, 129.9, 128.7, 124.9, 123.7, 121.5, 118.7, 110.9, 108.5, 100.0, 20.9.

GRB124: $^1$H-NMR (400 MHz, DMSO-D6) δ 10.55 (s, 1H), 10.46 (s, 1H), 9.10 (s, 1H), 8.96 (d, J=2.3 Hz, 1H), 8.16 (s, 1H), 7.78 (dd, J=8.2, 1.8 Hz, 1H), 7.45 (d, J=8.2 Hz, 1H), 7.38 (s, 1H), 6.83 (dd, J=13.7, 8.2 Hz, 2H), 2.36 (s, 3H); $^{13}$C-NMR (101 MHz, DMSO-D6) δ 155.5, 152.5, 146.1, 138.8, 134.1, 132.8, 131.0, 129.9, 125.0, 116.4, 113.3, 111.1, 108.5, 100.1, 18.1.

GRB125: $^1$H-NMR (400 MHz, DMSO-D6) δ 10.54 (s, 1H), 10.44 (s, 1H), 9.05 (s, 1H), 8.68 (s, 1H), 8.38 (s, OH), 8.11 (s, 1H), 7.60 (s, 2H), 7.30 (s, 1H), 6.83 (s, 2H); $^{13}$C-NMR (101 MHz, DMSO-D6) δ 155.5, 152.6, 139.6, 132.6, 131.9, 129.9, 126.8, 126.5, 125.2, 122.9, 121.9, 116.6, 111.7, 108.4, 100.6; $^{19}$F-NMR (376 MHz, DMSO-D6) δ −61.38 (s, 1F).

GRB126: $^1$H-NMR (400 MHz, DMSO-D6) δ 10.56 (s, 1H), 10.45 (s, 1H), 9.24 (s, 1H), 8.29 (s, 1H), 8.23 (s, 1H), 7.34 (s, 1H), 7.01 (d, J=8.2 Hz, 1H), 6.95 (d, J=7.3 Hz, 1H), 6.83 (d, J=7.8 Hz, 1H), 6.79 (s, 1H), 3.87 (s, 3H); $^{13}$C-NMR (101 MHz, DMSO-D6) δ 155.5, 152.3, 146.2, 133.0, 130.2, 129.9, 124.9, 124.4, 120.6, 117.2, 111.9, 110.9, 108.5, 99.9, 56.1.

GRB127: $^1$H-NMR (400 MHz, DMSO-D6) δ 10.49 (s, 1H), 10.41 (s, 1H), 8.71 (s, 1H), 7.83 (s, 1H), 7.33 (d, J=9.6 Hz, 2H), 7.23 (d, J=7.3 Hz, 1H), 7.16 (t, J=7.8 Hz, 1H), 6.80 (s, 2H), 2.25 (s, 3H); $^{13}$C-NMR (101 MHz, DMSO-D6) δ 155.5, 152.9, 138.0, 134.2, 133.6, 131.7, 129.9, 129.1, 127.0, 126.8, 124.6, 110.9, 108.3, 99.9, 18.6.

GRB128: $^1$H-NMR (400 MHz, DMSO-D6) δ 10.55 (s, 1H), 10.45 (s, 1H), 8.91 (s, 1H), 8.68 (s, 1H), 8.12 (s, 1H), 8.02 (s, 1H), 7.93 (d, J=5.5 Hz, 1H), 7.58 (m, 3H), 7.44 (d, J=22.9 Hz, 2H), 6.93 (s, 2H); $^{13}$C-NMR (101 MHz, DMSO-D6) δ 155.5, 153.0, 134.5, 133.7, 133.4, 129.9, 128.4, 125.9, 125.8, 125.6, 124.8, 122.7, 121.3, 117.0, 110.9, 108.5, 100.0.

GRB129: $^1$H-NMR (400 MHz, DMSO-D6) δ 10.52 (s, 1H), 10.43 (s, 1H), 8.74 (s, 1H), 7.98 (s, 1H), 7.28 (s, 2H), 7.15 (d, J=7.3 Hz, 2H), 6.81 (s, 2H); $^{13}$C-NMR (101 MHz, DMSO-D6) δ 159.3, 155.7, 152.6, 133.2, 129.9, 126.8, 124.8, 115.5, 111.8, 111.1, 108.3, 100.1. $^{19}$F-NMR (376 MHz, DMSO-D6) δ −118.79 (s, 1F)

GRB130: $^1$H-NMR (400 MHz, DMSO-D6) δ 10.53 (s, 1H), 10.44 (s, 1H), 8.76 (s, 1H), 8.55 (s, 1H), 7.54 (d, J=9.2 Hz, 2H), 7.30 (s, 1H), 7.27 (d, J=8.2 Hz, 2H), 6.81 (s, 2H); $^{13}$C-NMR (101 MHz, DMSO-D6) δ 155.5, 152.6, 142.4, 139.2, 133.0, 129.9, 124.9, 121.7, 119.2, 111.3, 108.4, 100.3; $^{19}$F-NMR (376 MHz, DMSO-D6) δ −57.02 (s, 1F)

GRB131: $^1$H-NMR (400 MHz, DMSO-D6) δ 10.60 (s, 1H), 10.59 (s, 1H), 9.34 (s, 1H), 7.49 (s, 1H), 6.93 (s, 1H), 6.87 (d, J=8.2 Hz, 1H), 6.75 (d, J=7.8 Hz, 1H), 3.47 (s, 6H), 2.29 (d, J=6.4 Hz, 6H), 1.66 (t, J=6.4 Hz, 2H); $^{13}$C-NMR (101 MHz, DMSO-D6) δ 180.3, 155.5, 131.6, 129.8, 127.3, 117.1, 108.4, 105.7, 66.0, 56.1, 53.3, 42.8, 25.2.

GRB153: $^1$H-NMR (400 MHz, DMSO-D6) δ 10.57 (s, 1H), 10.48 (s, 1H), 9.73 (s, 1H), 9.61 (s, 1H), 8.21 (s, 1H), 8.01 (d, J=7.8 Hz, 1H), 7.33 (s, 1H), 6.99 (d, J=7.8 Hz, 1H), 6.86 (d, J=11.0 Hz, 2H), 2.38 (s, 3H); $^{13}$C-NMR (101 MHz, DMSO-D6) δ 155.52, 151.79, 146.29, 135.52, 134.80, 132.65, 129.90, 125.49, 125.26, 122.77, 121.96, 111.54, 108.43, 100.45, 21.53.

GRB154: $^1$H-NMR (400 MHz, DMSO-D6) δ 10.54 (s, 1H), 10.45 (s, 1H), 9.50 (s, 1H), 9.25 (s, 1H), 8.12 (d, J=9.2 Hz, 1H), 7.55 (s, 1H), 7.34 (d, J=8.0 Hz, 1H), 7.30 (s, 1H), 6.84 (d, J=2.7 Hz, 2H), 3.82 (s, 3H); $^{13}$C-NMR (101 MHz, DMSO-D6) δ 155.56, 153.75, 152.09, 138.62, 133.05, 130.15, 128.60, 125.10, 124.67, 121.96, 111.50, 108.48, 108.18, 100.41, 55.97.

GRB155: $^1$H-NMR (400 MHz, DMSO-D6) δ 10.51 (s, 1H), 10.43 (s, 1H), 8.54 (s, 1H), 8.46 (s, 1H), 7.32 (s, 1H), 6.79 (d, J=7.8 Hz, 2H), 6.66 (s, 2H), 6.12 (s, 1H), 3.71 (s, 6H).

GRB163: $^1$H-NMR (400 MHz, DMSO-D6) δ 10.54 (s, 1H), 10.45 (s, 1H), 8.98 (s, 1H), 8.63 (s, 1H), 7.87 (d, J=7.8 Hz, 2H), 7.57 (d, J=8.2 Hz, 2H), 7.32 (s, 1H), 6.82 (s, 2H), 4.27 (d, J=6.9 Hz, 2H), 1.30 (t, J=6.9 Hz, 3H); $^{13}$C-NMR (101 MHz, DMSO-D6) δ 165.4, 155.5, 152.3, 144.5, 132.7, 130.3, 129.9, 125.0, 122.5, 117.1, 111.4, 108.4, 100.3, 60.2, 14.2.

GRB164: $^1$H-NMR (400 MHz, DMSO-D6) δ 10.54-10.67 (m, 1H), 10.47 (d, J=14.2 Hz, 1H), 10.03-10.15 (m, 1H), 9.43-9.46 (m, 1H), 9.13-9.23 (m, 1H), 8.00 (dd, J=15.1, 9.2 Hz, 1H), 7.40-7.54 (m, 1H), 7.30-7.34 (m, 1H), 7.15 (d, J=6.0 Hz, 1H), 6.83-6.93 (m, 2H); $^{13}$C-NMR (101 MHz, DMSO-D6) δ 155.5, 152.3, 138.8, 132.9, 129.9, 126.8, 125.0, 122.9, 111.3, 109.9, 108.4, 100.3.

GRB165: $^1$H-NMR (400 MHz, DMSO-D6) δ 10.49 (s, 1H), 10.38 (s, 1H), 9.72 (s, 1H), 8.89 (s, 2H), 7.71 (s, 1H), 7.62 (d, J=8.7 Hz, 1H), 7.33 (s, 1H), 6.75-6.80 (m, 2H), 6.33 (s, 1H), 6.15 (d, J=8.2 Hz, 1H); $^{13}$C-NMR (101 MHz, DMSO-D6) δ 155.5, 153.1, 152.7, 147.2, 133.8, 129.9, 124.4, 120.5, 119.5, 110.6, 108.4, 105.5, 102.4, 99.7.

GRB166: $^1$H-NMR (400 MHz, DMSO-D6) δ 10.53 (s, 1H), 10.43 (s, 1H), 10.26 (s, 1H), 9.22 (s, 1H), 8.18 (d, J=20.6 Hz, 2H), 7.33 (s, 1H), 6.81 (br s, 4H); $^{13}$C-NMR (101 MHz, DMSO-D6) δ 155.5, 152.4, 144.2, 133.2, 129.9, 129.4, 124.8, 122.6, 120.6, 117.5, 115.2, 110.8, 108.4, 99.8.

GRB167: $^1$H-NMR (400 MHz, DMSO-D6) δ 10.50 (d, J=33.9 Hz, 2H), 9.12 (s, 1H), 8.58 (s, 1H), 8.33 (s, 2H), 8.07

(s, 1H), 7.31 (s, 1H), 6.84 (s, 2H), 3.89 (s, 6H); $^{13}$C-NMR (101 MHz, DMSO-D6) δ 165.4, 155.5, 152.6, 141.1, 132.7, 130.6, 129.9, 125.1, 122.6, 122.4, 111.7, 108.4, 100.6, 52.5.

GRB168: $^{1}$H-NMR (400 MHz, DMSO-D6) δ 12.62 (s, 1H), 10.49 (d, J=37.1 Hz, 2H), 8.97 (s, 1H), 8.65 (s, 1H), 7.84 (s, 2H), 7.55 (s, 2H), 7.32 (s, 1H), 6.82 (s, 2H), $^{13}$C-NMR (101 MHz, DMSO-D6) δ 167.1, 155.5, 152.4, 144.2, 132.8, 130.5, 129.9, 125.0, 123.4, 117.1, 111.4, 108.4, 100.3.

GRB169: $^{1}$H-NMR (400 MHz, DMSO-D6) δ 13.36-12.33 (1H), 10.55 (d, J=11.4 Hz, 1H), 10.45 (d, J=11.4 Hz, 1H), 8.83 (d, J=11.9 Hz, 1H), 8.58 (d, J=12.4 Hz, 1H), 8.11 (d, J=11.9 Hz, 1H), 7.65 (t, J=9.4 Hz, 1H), 7.52-7.57 (m, 1H), 7.31-7.43 (m, 2H), 6.84 (d, J=11.9 Hz, 2H); $^{13}$C-NMR (101 MHz, DMSO-D6) δ 167.4, 155.5, 152.7, 140.2, 133.1, 131.4, 129.9, 128.9, 124.9, 122.4, 122.2, 118.8, 111.4, 108.4, 100.3.

GRB170: $^{1}$H-NMR (400 MHz, DMSO-D6) δ 13.19 (s, 2H), 10.55 (s, 1H), 10.45 (s, 1H), 9.06 (s, 1H), 8.62 (s, 1H), 8.27 (s, 2H), 8.07 (s, 1H), 7.30 (s, 1H), 6.84 (s, 2H); $^{13}$C-NMR (101 MHz, DMSO-D6) δ 166.7, 155.5, 152.7, 140.7, 132.9, 131.7, 129.9, 125.0, 123.0, 122.6, 111.6, 108.3, 100.6.

GRB171: $^{1}$H-NMR (400 MHz, DMSO-D6) δ 10.50 (s, 1H), 10.41 (s, 1H), 8.39 (s, 2H), 7.33 (s, 1H), 7.20 (d, J=16.0 Hz, 1H), 6.82 (d, J=21.5 Hz, 4H), 3.71 (d, J=11.9 Hz, 6H); $^{13}$C-NMR (101 MHz, DMSO-D6) δ 155.5, 152.9, 148.8, 143.8, 133.6, 133.4, 129.9, 124.6, 112.5, 111.1, 109.9, 108.4, 103.8, 100.1, 55.9, 55.3.

GRB181: $^{1}$H-NMR (400 MHz, DMSO-D6) δ 10.22 (s, 1H), 8.95 (s, 1H), 7.91 (t, J=8.5 Hz, 2H), 7.38 (s, 1H), 7.15 (d, J=7.8 Hz, 1H), 6.71 (d, J=8.2 Hz, 1H), 6.60 (s, 1H), 6.46 (d, J=6.4 Hz, 1H), 3.85 (s, 3H), 3.72 (s, 3H), 3.45 (s, 2H); $^{13}$C-NMR (101 MHz, DMSO-D6) δ 176.7, 155.3, 153.3, 149.5, 138.6, 134.6, 126.8, 122.6, 120.0, 117.8, 116.1, 109.5, 104.6, 99.3, 56.3, 55.8, 36.7.

GRB185: $^{1}$H-NMR (400 MHz, DMSO-D6) δ 10.23 (s, 1H), 8.39 (d, J=17.4 Hz, 2H), 7.38 (s, 1H), 7.14-7.21 (m, 2H), 6.84 (s, 2H), 6.71 (d, J=8.2 Hz, 1H), 3.71 (d, J=11.0 Hz, 6H), 3.45 (s, 2H); $^{13}$C-NMR (101 MHz, DMSO-D6) δ 176.8, 153.4, 149.3, 144.4, 138.8, 134.3, 134.1, 126.7, 118.3, 116.6, 113.0, 110.4, 109.5, 104.2, 56.4, 55.8, 36.6.

GRB186: $^{1}$H-NMR (400 MHz, DMSO-D6) δ 10.24 (s, 1H), 8.52 (s, 1H), 8.40 (s, 1H), 7.39 (s, 1H), 7.15 (d, J=7.8 Hz, 1H), 6.70-6.78 (m, 3H), 3.73 (s, 6H), 3.60 (s, 3H), 3.45 (s, 2H); $^{13}$C-NMR (101 MHz, DMSO-D6) δ 176.8, 153.4, 153.3, 138.9, 136.6, 134.1, 132.8, 126.7, 118.4, 116.7, 109.5, 96.3, 60.6, 56.1, 36.6.

GRB187: $^{1}$H-NMR (400 MHz, DMSO-D6) δ 10.28 (s, 1H), 9.66 (d, J=38.9 Hz, 2H), 8.21 (s, 1H), 8.01 (d, J=8.2 Hz, 1H), 7.42 (s, 1H), 7.21 (d, J=7.3 Hz, 1H), 6.98 (d, J=8.2 Hz, 1H), 6.75 (d, J=7.8 Hz, 1H), 3.47 (s, 2H), 2.37 (s, 3H); $^{13}$C-NMR (101 MHz, DMSO-D6) δ 176.8, 152.4, 146.8, 139.5, 136.0, 135.3, 133.6, 126.8, 126.0, 123.3, 122.5, 118.9, 117.0, 109.6, 36.6, 22.1.

GRB188: $^{1}$H-NMR (400 MHz, DMSO-D6) δ 10.27 (s, 1H), 9.47 (s, 1H), 9.26 (s, 1H), 8.11 (d, J=8.7 Hz, 1H), 7.54 (s, 1H), 7.33-7.39 (m, 2H), 7.19 (d, J=7.3 Hz, 1H), 6.74 (d, J=7.8 Hz, 1H), 3.82 (s, 3H), 3.46 (s, 2H); $^{13}$C-NMR (101 MHz, DMSO-D6) δ 176.8, 154.3, 152.7, 139.3, 139.0, 133.8, 128.9, 126.8, 125.2, 122.9, 118.7, 116.8, 109.6, 108.7, 56.4, 36.6.

GRB147: $^{1}$H-NMR (400 MHz, DMSO-D6) δ 11.47 (s, 1H), 9.37 (d, J=12.4 Hz, 1H), 8.20 (d, J=12.4 Hz, 1H), 7.84 (d, J=2.7 Hz, 1H), 7.57 (d, J=11.0 Hz, 1H), 6.87-7.01 (m, 3H), 6.48 (d, J=5.5 Hz, 1H), 3.80 (d, J=12.8 Hz, 3H), 3.67 (d, J=12.8 Hz, 3H); $^{13}$C-NMR (101 MHz, DMSO-D6) δ 155.2, 153.8, 152.9, 144.0, 142.3, 135.1, 130.0, 125.3, 114.1, 111.9, 110.2, 105.9, 105.6, 101.3, 56.9, 55.8.

GRB161: $^{1}$H-NMR (400 MHz, DMSO-D6) δ 11.48 (s, 1H), 9.42 (s, 1H), 8.36 (s, 1H), 8.23 (s, 1H), 7.59 (s, 1H), 7.00 (dd, J=20.1, 8.7 Hz, 4H), 3.88 (s, 3H); $^{13}$C-NMR (101 MHz, DMSO-D6) δ 155.2, 152.8, 146.8, 144.0, 134.8, 130.5, 125.5, 124.9, 121.3, 117.8, 114.2, 112.5, 110.2, 101.4, 56.7.

GRB136: $^{1}$H-NMR (400 MHz, DMSO-D6) δ 10.57 (s, 1H), 10.47 (s, 1H), 9.38 (s, 1H), 8.34 (d, J=6.4 Hz, 2H), 7.49 (d, J=6.9 Hz, 1H), 7.33 (s, 1H), 7.07 (d, J=6.4 Hz, 1H), 6.82 (d, J=8.2 Hz, 2H); $^{13}$C-NMR (101 MHz, DMSO-D6) δ 156.0, 152.4, 138.0, 133.1, 132.4, 131.1, 130.5, 125.7, 122.9, 120.2, 111.7, 109.1, 100.5.

GRB041: $^{1}$H-NMR (400 MHz, DMSO-D6) δ 10.50 (d, J=38.0 Hz, 2H), 8.75 (s, 1H), 8.58 (s, 1H), 7.84-7.99 (m, 1H), 7.11-7.30 (m, 4H), 6.82 (s, 2H); $^{13}$C-NMR: (101 MHz, DMSO-D6) δ 156.1, 153.0, 142.2, 133.4, 131.2, 130.4, 125.5, 124.6, 122.2, 120.8, 117.4, 111.9, 108.9, 100.9.

GRB135: $^{1}$H-NMR (400 MHz, DMSO-D6) δ 10.44 (s, 1H), 10.34 (s, 1H), 8.20 (s, 1H), 7.25-7.33 (m, 6H), 6.71 (dd, J=25.4, 7.6 Hz, 2H), 6.46 (d, J=6.4 Hz, 1H), 4.80 (d, J=6.4 Hz, 1H), 1.37 (d, J=6.0 Hz, 3H); $^{13}$C-NMR (101 MHz, DMSO-D6) δ 155.5, 154.6, 145.3, 134.0, 130.0, 128.3, 126.6, 125.9, 124.2, 110.4, 108.3, 99.5, 48.4, 23.0.

GRB134: $^{1}$H-NMR (400 MHz, DMSO-D6) δ 10.44 (s, 1H), 10.34 (s, 1H), 8.20 (s, 1H), 7.24-7.33 (m, 6H), 6.71 (dd, J=25.6, 7.8 Hz, 2H), 6.47 (d, J=7.3 Hz, 1H), 4.81 (d, J=6.4 Hz, 1H), 1.37 (d, J=6.4 Hz, 3H); $^{13}$C-NMR (101 MHz, DMSO-D6) δ 155.5, 154.6, 145.3, 134.1, 129.9, 128.3, 126.6, 125.8, 124.1, 110.4, 108.3, 99.5, 48.7, 23.2.

GRB142: $^{1}$H-NMR (400 MHz, DMSO-D6) δ 10.54 (s, 1H), 10.44 (s, 1H), 8.84 (s, OH), 8.67 (s, 1H), 8.55 (s, 1H), 8.00 (d, J=1.8 Hz, 1H), 7.29-7.33 (m, 3H), 7.07 (q, J=7.9 Hz, 1H), 6.78-6.83 (m, 2H); $^{13}$C-NMR (101 MHz, DMSO-D6) δ 155.3, 152.2, 141.2, 132.7, 130.5, 129.9, 129.7, 125.9, 124.7, 117.1, 111.1, 108.1, 100.1, 94.6.

GRB137: $^{1}$H-NMR (400 MHz, DMSO-D6) δ 10.50 (s, 1H), 10.41 (s, 1H), 8.44 (s, 2H), 7.32 (s, 3H), 7.14 (s, 2H), 6.79 (s, 2H), 2.82 (s, 1H), 1.17 (d, J=6.0 Hz, 6H); $^{13}$C-NMR (101 MHz, DMSO-D6) δ 155.9, 153.3, 142.1, 138.0, 133.9, 130.4, 127.0, 125.2, 118.8, 111.5, 108.7, 100.6, 33.3, 24.6.

GRB143: $^{1}$H-NMR (400 MHz, DMSO-D6) δ 10.53 (s, 1H), 10.44 (s, 1H), 9.16 (s, 1H), 8.88 (s, 1H), 7.93 (s, 1H), 7.48 (d, J=8.7 Hz, 1H), 7.31 (d, J=8.2 Hz, 2H), 6.82 (t, J=1.8 Hz, 2H), 2.89 (s, OH), 2.73 (s, OH), 2.36 (s, 3H); $^{13}$C-NMR: (101 MHz, DMSO-D6) δ 155.3, 152.6, 138.1, 132.9, 132.4, 129.7, 128.0, 127.4, 125.7, 124.7, 121.1, 114.6, 111.0, 108.1, 99.9, 17.8; $^{19}$F-NMR (376 MHz, DMSO-D6) δ −60.37 (t, J=18.8 Hz, 1F).

GRB139: $^{1}$H-NMR (400 MHz, DMSO-D6) δ 10.53 (s, 1H), 10.44 (s, 1H), 8.77 (s, 1H), 8.57 (s, 1H), 7.66 (s, 1H), 7.31 (d, J=16.9 Hz, 2H), 7.10 (s, 1H), 6.81 (s, 2H); $^{13}$C-NMR (101 MHz, DMSO-D6) δ 155.7, 152.8, 137.3, 133.1, 130.1, 125.2, 117.6, 117.5, 114.4, 111.6, 108.6, 107.3, 107.1, 100.6; $^{19}$F-NMR (376 MHz, DMSO-D6) δ −137.33-−137.506 (m, 1F), −146.79-−147.30 (m, 1F).

GRB138: $^{1}$H-NMR (400 MHz, DMSO-D6) δ 10.46 (d, J=40.8 Hz, 2H), 8.38 (d, J=31.6 Hz, 2H), 7.01-7.32 (m, 4H), 6.78 (s, 2H), 2.89 (s, OH), 2.73 (s, OH), 2.16 (d, J=10.1 Hz, 6H); $^{13}$C-NMR (101 MHz, DMSO-D6) δ 155.5, 152.7, 137.5, 136.3, 133.4, 129.9, 129.6, 129.2, 124.6, 119.4, 115.6, 111.0, 108.3, 100.0, 19.7, 18.5.

GRB140: $^{1}$H-NMR (400 MHz, DMSO-D6) δ 10.56 (s, 1H), 10.48 (s, 1H), 9.34 (s, 1H), 8.77 (s, 1H), 8.17-8.23 (m, 2H), 7.66-7.73 (m, 2H), 7.31 (s, 1H), 6.84 (s, 2H); $^{13}$C-NMR (101 MHz, DMSO-D6) δ 155.7, 152.3, 146.9, 141.0, 132.6, 130.1, 125.5, 125.4, 117.5, 111.8, 108.6, 100.7.

GRB141: $^{1}$H-NMR (400 MHz, DMSO-D6) δ 10.53 (s, 1H), 10.43 (s, 1H), 8.69 (s, 1H), 8.53 (s, 1H), 7.47 (d, J=8.7 Hz, 2H), 7.31 (d, J=8.2 Hz, 3H), 6.80 (s, 2H); $^{13}$C-NMR (101 MHz, DMSO-D6) δ 155.5, 152.6, 138.9, 133.0, 129.9, 128.6, 125.1, 124.9, 119.6, 111.3, 108.4, 100.2.

GRB037: $^{1}$H-NMR (400 MHz, DMSO-D6) δ 10.45 (d, J=38.0 Hz, 2H), 8.37 (d, J=22.9 Hz, 2H), 7.31-7.34 (m, 3H), 6.76-6.86 (m, 4H), 3.71 (s, 3H); $^{13}$C-NMR (101 MHz, DMSO-D6) δ 156.0, 154.8, 153.4, 134.0, 133.5, 130.4, 125.1, 120.4, 114.5, 111.5, 108.9, 100.6, 55.7.

GRB156: $^{1}$H-NMR (400 MHz, DMSO-D6) δ 10.51 (s, 1H), 10.42 (s, 1H), 9.19 (s, 1H), 8.14 (s, 1H), 7.85 (d, J=2.7 Hz, 1H), 7.36 (s, 1H), 6.91 (d, J=8.7 Hz, 1H), 6.75-6.82 (m, 2H), 6.46 (dd, J=8.9, 3.0 Hz, 1H), 3.81 (s, 3H), 3.68 (s, 3H); $^{13}$C-NMR (101 MHz, DMSO-D6) δ 156.0, 153.8, 153.0, 142.2, 133.8, 130.5, 130.3, 125.2, 111.9, 111.3, 109.0, 105.7, 105.4, 100.3, 56.8, 55.7.

GRB182: $^{1}$H-NMR (400 MHz, DMSO-D6) δ 10.44 (s, 1H), 10.35 (s, 1H), 8.36 (s, 2H), 7.23 (s, 1H), 7.13 (s, 1H), 6.73 (s, 4H), 5.89 (s, 2H); $^{13}$C-NMR (101 MHz, DMSO-D6) δ 156.0, 153.4, 147.7, 142.4, 134.8, 133.8, 130.4, 125.2, 111.6, 111.3, 108.9, 108.6, 101.3, 100.7.

GRB189: $^{1}$H-NMR (400 MHz, DMSO-D6) δ 10.49 (d, J=35.7 Hz, 2H), 9.96 (s, 1H), 9.64 (s, 1H), 8.35 (s, 1H), 7.93 (s, 1H), 7.56 (s, 1H), 7.33 (s, 1H), 6.23-7.05 (m, 4H), 3.88 (s, 2H); $^{13}$C-NMR (101 MHz, DMSO-D6) δ 168.2, 156.0, 152.8, 142.6, 134.5, 133.6, 131.0, 130.4, 125.5, 121.4, 120.6, 115.3, 112.2, 108.9, 101.1, 52.8.

GRB174: $^{1}$H-NMR (400 MHz, DMSO-D6) δ 11.47 (d, J=11.9 Hz, 1H), 9.42 (d, J=33.9 Hz, 1H), 9.26-8.97 (1H), 8.83-8.48 (1H), 8.08 (s, 1H), 7.61 (s, 2H), 7.01 (d, J=13.3 Hz, 4H); $^{13}$C-NMR (101 MHz, DMSO-D6) δ 155.1, 153.0, 152.8, 150.5, 144.0, 138.4, 128.8, 125.1, 115.2, 114.9, 113.9, 110.2, 106.6, 101.1.

GRB175: $^{1}$H-NMR (400 MHz, DMSO-D6) δ 11.80-10.99 (1H), 10.72-9.97 (1H), 9.37-9.42 (m, 1H), 8.09-8.28 (m, 2H), 7.54-7.59 (m, 1H), 6.95-7.00 (m, 2H), 6.77-6.82 (m, 2H); $^{13}$C-NMR (101 MHz, DMSO-D6) δ 155.1, 152.9, 144.8, 144.0, 135.0, 129.7, 125.4, 123.1, 121.3, 118.0, 115.7, 114.1, 110.2, 101.3.

GRB158: $^{1}$H-NMR (400 MHz, DMSO-D6) δ 10.51 (s, 1H), 10.41 (s, 1H), 9.13 (s, 2H), 8.61 (s, 1H), 7.98 (s, 1H), 7.60 (s, 1H), 7.34 (s, 1H), 6.79 (s, 2H), 6.60 (d, J=7.3 Hz, 1H), 6.17 (d, J=7.3 Hz, 1H); $^{13}$C-NMR (101 MHz, DMSO-D6) δ 156.0, 153.1, 150.5, 138.4, 134.1, 130.4, 129.0, 125.1, 115.2, 111.2, 108.9, 107.8, 106.6, 100.3.

GRB172: $^{1}$H-NMR (400 MHz, DMSO-D6) δ 10.51 (d, J=6.9 Hz, 1H), 10.40 (d, J=6.9 Hz, 1H), 8.31 (d, J=7.3 Hz, 1H), 8.05-8.15 (m, 2H), 7.31 (d, J=7.3 Hz, 1H), 6.97 (d, J=6.9 Hz, 1H), 6.78 (t, J=8.0 Hz, 2H), 6.61 (d, J=7.3 Hz, 3H); $^{13}$C-NMR: (101 MHz, DMSO-D6) δ 156.0, 153.3, 145.6, 140.8, 134.1, 132.2, 130.4, 125.0, 116.0, 111.4, 110.0, 108.9, 107.8, 100.5.

GRB157: $^{1}$H-NMR (400 MHz, DMSO-D6) δ 10.45 (d, J=38.5 Hz, 2H), 9.03 (s, 1H), 8.34 (s, 1H), 8.19 (s, 1H), 7.25 (d, J=46.7 Hz, 3H), 6.67-6.85 (m, 4H); $^{13}$C-NMR (101 MHz, DMSO-D6) δ 156.4, 153.4, 152.7, 133.9, 131.8, 130.3, 124.9, 120.8, 115.7, 114.4, 111.4, 108.9, 100.5.

GRB173: $^{1}$H-NMR (400 MHz, DMSO-D6) δ 10.46 (dd, J=40.5, 12.1 Hz, 2H), 8.76 (d, J=12.4 Hz, 2H), 8.26 (d, J=11.9 Hz, 1H), 8.07 (d, J=12.4 Hz, 1H), 7.67 (d, J=13.3 Hz, 1H), 7.31 (d, J=11.9 Hz, 1H), 6.78 (s, 2H), 6.43 (d, J=12.8 Hz, 2H); $^{13}$C-NMR (101 MHz, DMSO-D6) δ 156.2, 153.2, 146.6, 134.1, 131.6, 130.4, 128.2, 125.0, 111.3, 108.9, 100.4, 98.6.

GRB144: $^{1}$H-NMR (400 MHz, DMSO-D6) δ 10.22 (s, 1H), 9.03 (s, 1H), 8.17-8.36 (m, 2H), 7.36 (s, 1H), 7.17 (dd, J=20.1, 8.2 Hz, 3H), 6.66-6.84 (m, 3H); $^{13}$C-NMR (101 MHz, DMSO-D6) δ 176.6, 153.5, 152.9, 138.7, 134.5, 132.0, 126.7, 120.8, 118.1, 116.3, 115.7, 109.5.

GRB160: $^{1}$H-NMR: (400 MHz, DMSO-D6) δ 10.26 (s, 2H), 9.19 (s, 1H), 8.18 (d, J=29.3 Hz, 2H), 7.38 (s, 1H), 7.16 (d, J=6.4 Hz, 1H), 6.72-6.81 (m, 3H), 3.46 (s, 2H); $^{13}$C-NMR: (101 MHz, DMSO-D6) δ 176.7, 152.9, 144.7, 138.9, 134.1, 129.9, 126.7, 123.0, 121.0, 118.1, 116.3, 115.7, 109.5.

GRB183: $^{1}$H-NMR (400 MHz, DMSO-D6) δ 10.18 (s, 1H), 9.05-9.09 (m, 2H), 8.57 (s, 1H), 7.94 (s, 1H), 7.54 (s, 1H), 7.32 (s, 1H), 7.12 (d, J=6.9 Hz, 1H), 6.67 (d, J=7.3 Hz, 1H), 6.55 (d, J=7.3 Hz, 1H), 6.12 (d, J=6.0 Hz, 1H), 3.49 (d, J=65.7 Hz, 2H); $^{13}$C-NMR (101 MHz, DMSO-D6) δ 176.7, 153.1, 150.5, 138.7, 138.4, 134.5, 129.0, 126.8, 117.9, 116.2, 115.2, 109.5, 107.8, 106.6.

GRB184: $^{1}$H-NMR (400 MHz, DMSO-D6) δ 10.23 (s, 1H), 9.90 (s, 1H), 9.10 (s, 1H), 8.00-8.06 (m, 2H), 7.39 (s, 1H), 7.17 (d, J=7.3 Hz, 1H), 6.71-6.82 (m, 4H), 3.46 (s, 2H); $^{13}$C-NMR (101 MHz, DMSO-D6) δ 176.8, 153.2, 146.0, 138.7, 134.5, 128.5, 126.8, 122.0, 119.7, 119.0 117.9 116.2 114.9 109.5.

TABLE 2

Mass spectrometry and retention times for GRB inhibitors.

| Compond ID | Formula | Found M + H | Retention Time (min) |
|---|---|---|---|
| GRB021 | $C_{15}H_{14}N_4O_2$ | 283.39 | 4.58 |
| GRB023 | $C_{14}H_{11}FN_4O_2$ | 287.27 | 2.92 |
| GRB024 | $C_{14}H_{10}F_2N_4O_2$ | 305.33 | 3.45 |
| GRB026 | $C_{16}H_{16}N_4O_2$ | 297.33 | 1.65 |
| GRB028 | $C_{14}H_{10}Cl_2N_4O_2$ | 337.31 | 4.24 |
| GRB029 | $C_{16}H_{16}N_4O_2$ | 297.23 | 2.70 |
| GRB030 | $C_{16}H_{16}N_4O_2$ | 297.30 | 3.09 |
| GRB031 | $C_{14}H_{10}ClFN_4O_2$ | 321.25 | 3.18 |
| GRB032 | $C_{17}H_{18}N_4O_5$ | 359.20 | 1.93 |
| GRB033 | $C_{16}H_{14}N_4O_4$ | 327.27 | 2.70 |
| GRB034 | $C_{15}H_{14}N_4O_3$ | 299.16 | 3.11 |
| GRB035 | $C_{15}H_{14}N_4O_2$ | 283.25 | 2.74 |
| GRB036 | $C_{15}H_{14}N_4O_2$ | 283.16 | 3.27 |
| GRB037 | $C_{15}H_{14}N_4O_3$ | 299.25 | 1.15 |
| GRB038 | $C_{14}H_{11}BrN_4O_2$ | 347.28 | 3.65 |
| GRB039 | $C_{16}H_{14}N_4O_3$ | 311.25 | 1.54 |
| GRB040 | $C_{15}H_{13}ClN_4O_2$ | 317.28 | 2.43 |
| GRB041 | $C_{14}H_{11}BrN_4O_2$ | 347.28 | 3.30 |
| GRB042 | $C_{15}H_{12}N_4O_3$ | 297.23 | 3.14 |
| GRB043 | $C_{15}H_{11}N_5O_2$ | 294.25 | 1.70 |
| GRB045 | $C_{17}H_{16}N_4O_4$ | 341.23 | 2.81 |
| GRB059 | $C_{14}H_{11}FN_4OS$ | 303.27 | 1.98 |
| GRB060 | $C_{14}H_{10}F_2N_4OS$ | 321.20 | 3.14 |
| GRB061 | $C_{15}H_{14}N_4O_2S$ | 315.19 | 1.54 |
| GRB062 | $C_{16}H_{16}N_4OS$ | 313.21 | 3.98 |
| GRB063 | $C_{15}H_{11}N_5OS$ | 310.32 | 4.37 |
| GRB064 | $C_{14}H_{12}N_4OS$ | 285.28 | 3.93 |
| GRB068 | $C_{22}H_{19}FN_4O_2S$ | 423.25 | 3.87 |
| GRB071 | $C_{21}H_{15}F_3N_4OS$ | 429.25 | 3.08 |
| GRB072 | $C_{22}H_{16}FN_5OS$ | 418.15 | 4.51 |
| GRB075 | $C_{21}H_{16}F_2N_4OS$ | 411.23 | 4.70 |
| GRB076 | $C_{16}H_{13}N_3O_3S$ | 328.30 | 4.69 |
| GRB086 | $C_{15}H_{11}Cl_2N_3OS$ | 352.25 | 3.44 |
| GRB090 | $C_{16}H_{14}ClN_3O_2$ | 316.35 | 4.65 |
| GRB101 | $C_{14}H_9Cl_2N_3O_3$ | 338.15 | 3.68 |

Example 3—Biological Data

Figures 16A, 16B:
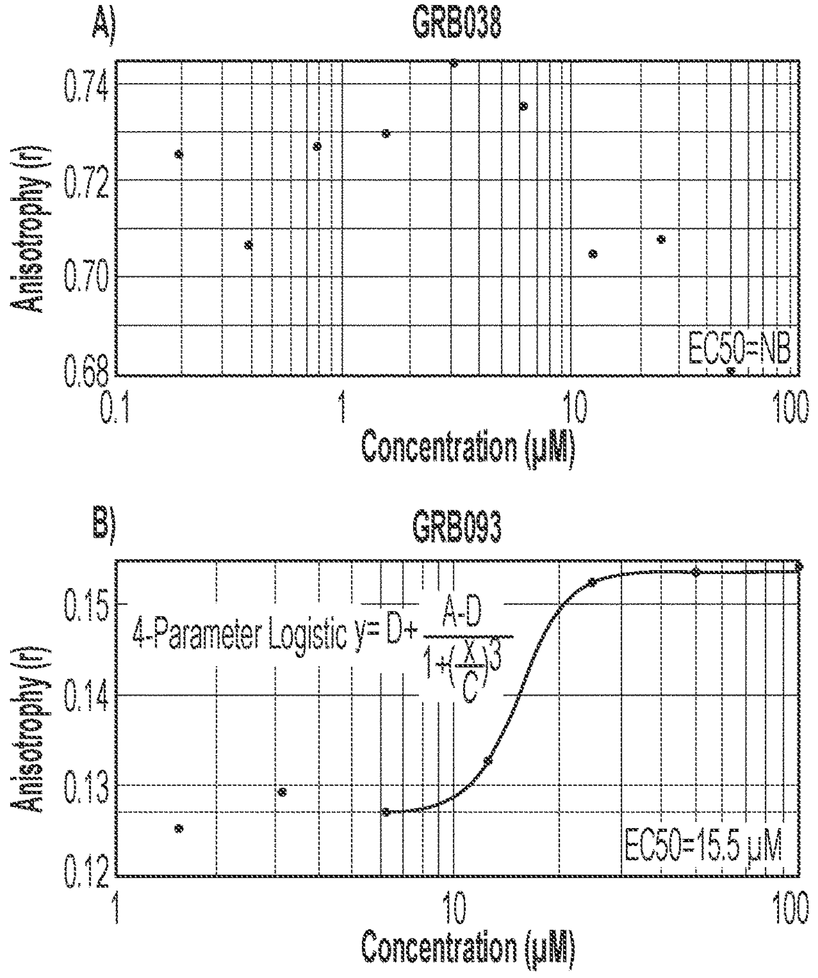
FIGS. 16A & 16B show fluorescence anisotropy assay data measuring GRB2 dimerization. 100 nM Atto488 labeled GRB2, which is below its dimer forming concentration, was used to identify compounds that induce dimerization. Dimeric GRB2 yields higher anisotropy value while the monomer displays a lower value reflecting size of the molecule. The $EC_{50}$ values corresponding to the fluorescence anisotropy assay data represent the compound induced dimerization function as opposed to binding affinity.

Table 3, below, includes fluorescence anisotropy assay data, an example of which is shown in FIG. 16. GRB2 dimerization was measured by fluorescence anisotropy assay. 100 nM Atto488 labeled GRB2, which is below its dimer forming concentration, was used to identify compounds that induce dimerization. Dimeric GRB2 yields higher anisotropy value while the monomer displays a lower value reflecting size of the molecule. The $EC_{50}$ values corresponding to the fluorescence anisotropy assay data represent the compound induced dimerization function as opposed to binding affinity. FIG. 16A shows a representative anisotropy measurement of no-binding (NB) data for compound GRB038. FIG. 16B shows a representative anisotropy measurement with GBR093 inducing GRB2 dimerization at a $EC_{50}$ of 15.5 μM. Note that NB represent compounds inability to induce GRB2 dimerization.

TABLE 3

EC50 anisotropy data for dimeric GRB2 stabilizers.

| Compound ID | $EC_{50}$ (μM) |
|---|---|
| GRB020 | 0.75 |
| GRB021 | 1 |
| GRB022 | 2.1 |
| GRB023 | 3.1 |
| GRB024 | 4.6 |
| GRB025 | 6 |
| GRB026 | 8.2 |
| GRB027 | 10.1 |
| GRB028 | 10.2 |
| GRB029 | 16.3 |
| GRB030 | 37.3 |
| GRB031 | 40.3 |
| GRB032 | >100 |
| GRB033 | >100 |
| GRB034 | 264 |
| GRB035 | NB |
| GRB036 | NB |
| GRB037 | NB |
| GRB038 | NB |
| GRB039 | NB |
| GRB040 | NB |
| GRB041 | NB |
| GRB042 | NB |
| GRB043 | NB |
| GRB044 | NB |
| GRB045 | NB |
| GRB046 | 2.0 |
| GRB047 | 9.7 |
| GRB048 | 8.3 |
| GRB049 | 11.5 |
| GRB050 | 56 |
| GRB051 | >100 |
| GRB052 | NB |
| GRB053 | NB |
| GRB054 | NB |
| GRB055 | NB |
| GRB056 | NB |
| GRB057 | NB |
| GRB058 | 2.0 |
| GRB059 | 5.0 |
| GRB060 | 2.4 |
| GRB061 | 129 |
| GRB062 | 78 |
| GRB063 | 124 |
| GRB064 | 116 |
| GRB065 | 350 |
| GRB066 | 246 |
| GRB067 | 48 |
| GRB068 | ND |
| GRB069 | ND |
| GRB070 | 128 |
| GRB071 | 225 |
| GRB072 | ND |
| GRB073 | 15 |
| GRB074 | 205 |
| GRB075 | 23 |
| GRB076 | 62 |
| GRB077 | 502 |
| GRB078 | 436 |
| GRB079 | ND |

TABLE 3-continued

EC50 anisotropy data for dimeric GRB2 stabilizers.

| Compound ID | $EC_{50}$ (μM) |
|---|---|
| GRB080 | ND |
| GRB081 | ND |
| GRB082 | ND |
| GRB083 | ND |
| GRB084 | ND |
| GRB085 | 1.1 |
| GRB086 | 1.5 |
| GRB087 | 4.6 |
| GRB088 | 8.3 |
| GRB089 | 9.1 |
| GRB090 | 13 |
| GRB091 | 13.3 |
| GRB092 | 13.8 |
| GRB093 | 15.5 |
| GRB094 | 23 |
| GRB095 | 50.9 |
| GRB096 | NB |
| GRB097 | NB |
| GRB098 | NB |
| GRB099 | NB |
| GRB100 | NB |
| GRB005 | NB |
| GRB006 | 2.7 |
| GRB010 | 3.9 |
| GRB012 | 4.5 |
| GRB009 | 5.5 |
| GRB002 | 9.4 |
| GRB003 | 9.7 |
| GRB007 | 15.7 |
| GRB004 | 26 |
| GRB001 | 49.7 |
| GRB013 | 63 |
| GRB008 | ND |
| GRB011 | ND |
| GRB014 | NB |
| GRB015 | NB |
| GRB016 | NB |
| GRB017 | NB |
| GRB018 | NB |
| GRB019 | NB |
| GRB101 | 13 |
| GRB102 | >100 |
| GRB103 | NB |
| GRB104 | 3.1 |
| GRB105 | 9.7 |
| GRB106 | NB |
| GRB107 | NB |
| GRB108 | NB |

NB = No Binding; ND = Not determined.

Figure 17:
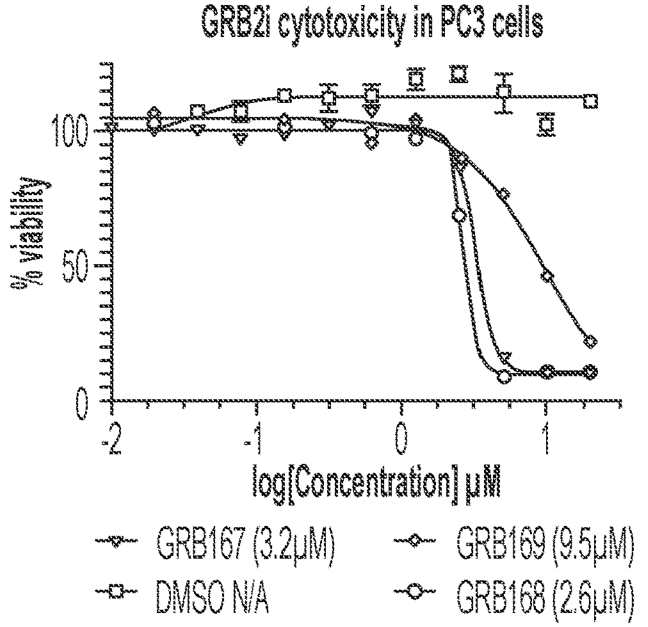
FIG. 17 shows sulforhodamine B (SRB) cytotoxicity assay to evaluate GRB167, GRB168 and GRB169 in PC3 cells. Titrating concentrations of each compounds were used to treat cells for 72 hours. The data was normalized against 100% survival at the lowest inhibitor concentration. Graphs for $IC_{50}$ were fitted to the four-parameter logistic equation using Prism8. Error bars show the percent coefficient of variation. Equivalent concentrations of DMSO were used as a negative control.

Sulforhodamine B (SRB) cytotoxicity analysis of GRB167, GRB168 and GRB169 in PC3 cells is shown in FIG. 17. SRB cytotoxicity analysis was also performed using GRB152 in HEK293T and MDA-MB-231 cells. Cells were exposed to various concentrations of compound for 72 h before viability measurements. In HEK293T cells treated with either GRB152 or GRB161 exhibited an $IC_{50}$ of 1.5±0.5 μM and >120 μM, respectively. In MDA-MB-231 cells, GRB152 exhibited an $IC_{50}$ of 12.1±1.5 μM.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

Anderson, *Practical Process Research & Development—A Guide for Organic Chemists,* $2^{nd}$ ed., Academic Press, New York, 2012.

*Handbook of Pharmaceutical Salts: Properties, and Use*, Stahl and Wermuth Eds., Verlag Helvetica Chimica Acta, 2002.

Reagan-Shaw et al., *FASEB J.,* 22(3):659-661, 2008.

Smith, *March's Advanced Organic Chemistry: Reactions, Mechanisms, and Structure,* $7^{th}$ Ed., Wiley, 2013.

Ahmed et al., *Nature,* 6(7354):1-11, 2015.

What is claimed:

1. A compound of the formula:

(I-A)

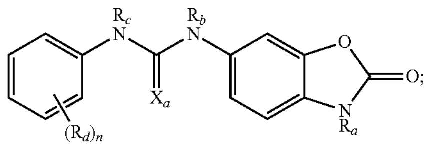

wherein:

n is 2, 3, 4, or 5;

$X_a$ is O or S;

$R_a$ is hydrogen;

$R_b$ and $R_c$ are each independently hydrogen, alkyl$_{(C\le12)}$, or substituted alkyl$_{(C\le12)}$; and $R_d$ is in each instance independently halo, hydroxy, cyano, nitro, alkyl$_{(C\le12)}$, substituted alkyl$_{(C\le12)}$, alkoxy$_{(C\le12)}$, or substituted alkoxy$_{(C\le12)}$; or a compound of the formula:

(I)

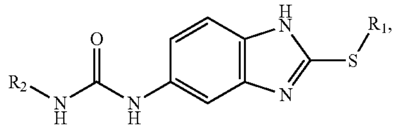

wherein:

$R_1$ is hydrogen; or alkyl$_{(C\le12)}$, aralkyl$_{(C\le12)}$, heteroaralkyl$_{(C\le12)}$, or a substituted version of any of these groups; and $R_2$ is aralkyl$_{(C\le12)}$, heteroaryl$_{(C\le12)}$, heteroaralkyl$_{(C\le12)}$, or a substituted version of any of these groups; or a group of the formula:

(Ia)

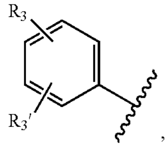

, wherein:

$R_3$ is hydrogen, hydroxy, halo, amino, nitro, cyano, carboxy, or mercapto; or alkyl$_{(C\le12)}$, alkoxy$_{(C\le12)}$, alkylamino$_{(C\le12)}$, dialkylamino$_{(C\le12)}$, acyl$_{(C\le12)}$, acyloxy$_{(C\le12)}$, amido$_{(C\le12)}$, or a substituted version of any of these groups; or —C(O)N$R_{3a}R_{3b}$, wherein:

$R_{3a}$ and $R_{3b}$ are each independently hydrogen, alkyl$_{(C\le12)}$, or substituted alkyl$_{(C\le12)}$;

$R_3$' is hydrogen, hydroxy, halo, amino, nitro, cyano, carboxy, or mercapto; or alkyl$_{(C\le12)}$, alkylamino$_{(C\le12)}$, dialkylamino$_{(C\le12)}$, acyl$_{(C\le12)}$, acyloxy$_{(C\le12)}$, amido$_{(C\le12)}$, or a substituted version of any of these groups; or —C(O)N$R_{3c}R_{3d}$, wherein:

$R_{3c}$ and $R_{3b}$ are each independently hydrogen, alkyl$_{(C\le12)}$, or substituted alkyl$_{(C\le12)}$; or $R_3$ and $R_3$' are taken together and are alkenediyl $_{(C\le12)}$ or substituted alkenediyl$_{(C\le12)}$;

or a pharmaceutically acceptable salt and/or tautomer of either of these formulae, wherein the compound is not

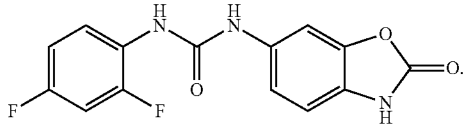 [SMILES: O=C(Nc1ccc2[nH]c(=O)oc2c1)Nc1ccc(F)cc1F]

2. The compound of claim 1, wherein the compound is further defined as:

(I-A)

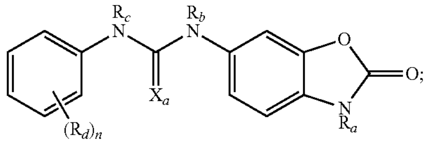

wherein:

n is 2, 3, 4, or 5;

$X_a$ is O or S;

$R_a$ is hydrogen; or alkyl$_{(C\le12)}$, aralkyl$_{(C\le12)}$, heteroaralkyl$_{(C\le12)}$, or a substituted version of any of these groups;

$R_b$ and $R_c$ are each independently hydrogen, alkyl$_{(C\le12)}$, or substituted alkyl$_{(C\le12)}$; and $R_d$ is in each instance independently halo, hydroxy, cyano, nitro, alkyl$_{(C\le12)}$, substituted alkyl$_{(C\le12)}$, alkoxy$_{(C\le12)}$, or substituted alkoxy$_{(C\le12)}$;

or a pharmaceutically acceptable salt and/or tautomer thereof.

3. The compound of claim 2, wherein the compound is defined as:

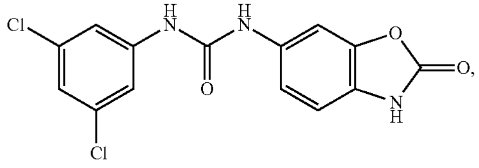

-continued

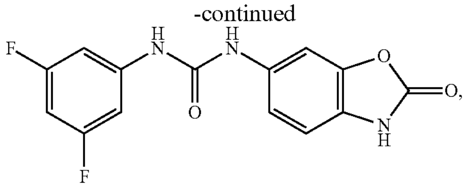,

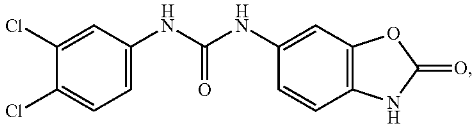,

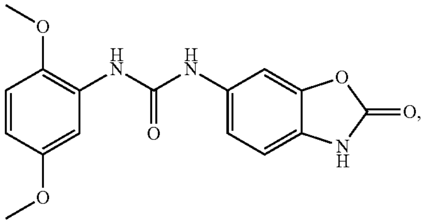,

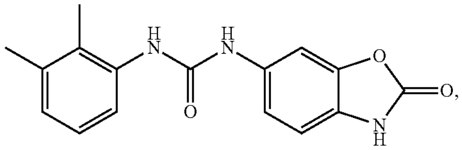,

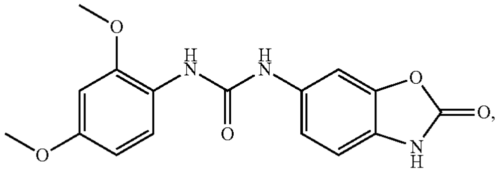,

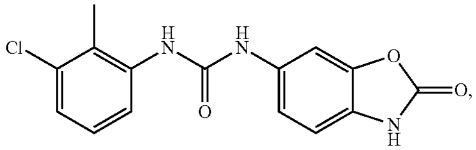,

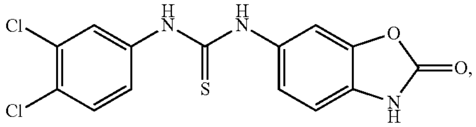,

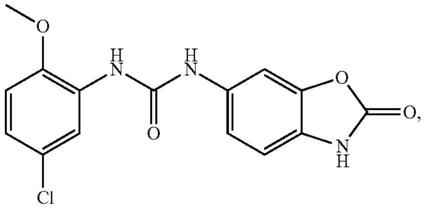,

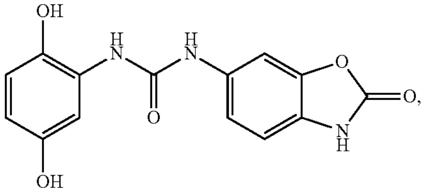, or

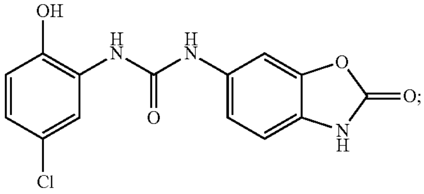;

or a pharmaceutically acceptable salt and/or tautomer thereof.

4. The compound of claim 1, wherein the compound is further defined as:

(I)

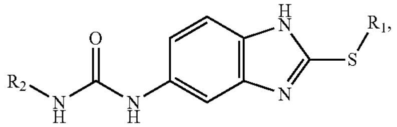

wherein:

$R_1$ is hydrogen; or alkyl$_{(C\leq12)}$, aralkyl$_{(C\leq12)}$, heteroaralkyl$_{(C\leq12)}$, or a substituted version of any of these groups; and $R_2$ is aralkyl$_{(C\leq12)}$, heteroaryl$_{(C\leq12)}$, heteroaralkyl$_{(C\leq12)}$, or a substituted version of any of these groups; or a group of the formula:

(Ia)

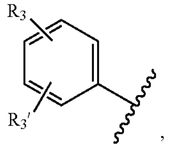

wherein:

$R_3$ is hydrogen, hydroxy, halo, amino, nitro, cyano, carboxy, or mercapto; or alkyl$_{(C\leq12)}$, alkoxy$_{(C\leq12)}$, alkylamino$_{(C\leq12)}$, dialkylamino$_{(C\leq12)}$, acyl$_{(C\leq12)}$, acyloxy$_{(C\leq12)}$, amido$_{(C\leq12)}$, or a substituted version of any of these groups; or —C(O)NR$_{3a}$R$_{3b}$, wherein:

$R_{3a}$ and $R_{3b}$ are each independently hydrogen, alkyl$_{(C\leq12)}$, or substituted alkyl$_{(C\leq12)}$;

$R_3$' is hydrogen, hydroxy, halo, amino, nitro, cyano, carboxy, or mercapto; or alkyl$_{(C\leq12)}$, alkylamino$_{(C\leq12)}$, dialkylamino$_{(C\leq12)}$, acyl$_{(C\leq12)}$, acyloxy$_{(C\leq12)}$, amido$_{(C\leq12)}$, or a substituted version of any of these groups; or —C(O)NR$_{3c}$R$_{3d}$, wherein:

$R_{3c}$ and $R_{3d}$ are each independently hydrogen, alkyl$_{(C\leq12)}$, or substituted alkyl$_{(C\leq12)}$; or $R_3$ and $R_3$' are taken together and are alkenediyl$_{(C\leq12)}$ or substituted alkenediyl$_{(C\leq12)}$;

or a pharmaceutically acceptable salt and/or tautomer thereof.

5. The compound of claim 4, wherein the compound is further defined as:

(II)

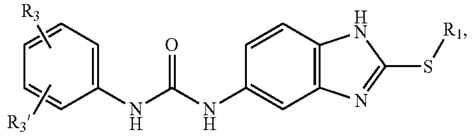

wherein:

$R_1$ is hydrogen; or alkyl$_{(C\leq 12)}$, substituted alkyl$_{(C\leq 12)}$, aralkyl$_{(C\leq 12)}$, or substituted aralkyl$_{(C\leq 12)}$; and $R_3'$ is hydrogen, hydroxy, halo, amino, nitro, cyano, carboxy, or mercapto; or alkyl$_{(C\leq 12)}$, alkoxy$_{(C\leq 12)}$, alkylamino$_{(C\leq 12)}$, dialkylamino$_{(C\leq 12)}$, acyl$_{(C\leq 12)}$, acyloxy$_{(C\leq 12)}$, amido$_{(C\leq 12)}$, or a substituted version of any of these groups; or —C(O)NR$_{3a}$R$_{3b}$, wherein:

$R_{3c}$ and $R_{3d}$ are each independently hydrogen, alkyl$_{(C\leq 12)}$, or substituted alkyl$_{(C\leq 12)}$;

$R_3'$ is hydrogen, hydroxy, halo, amino, nitro, cyano, carboxy, or mercapto; or alkyl$_{(C\leq 12)}$, alkylamino$_{(C\leq 12)}$, dialkylamino$_{(C\leq 12)}$, acyl$_{(C\leq 12)}$, acyloxy$_{(C\leq 12)}$, amido$_{(C\leq 12)}$, or a substituted version of any of these groups; or —C(O)NR$_{3c}$R$_{3d}$, wherein:

$R_{3c}$ and $R_{3d}$ are each independently hydrogen, alkyl$_{(C\leq 12)}$, or substituted alkyl$_{(C\leq 12)}$; or $R_3$ and $R_3'$ are taken together and are alkenediyl$_{(C\leq 12)}$ or substituted alkenediyl$_{(C\leq 12)}$;

or a pharmaceutically acceptable salt and/or tautomer thereof.

6. The compound of claim 4, wherein the compound is further defined as:

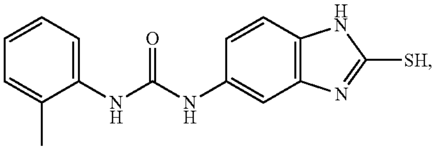

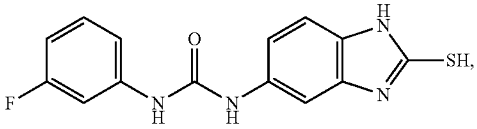

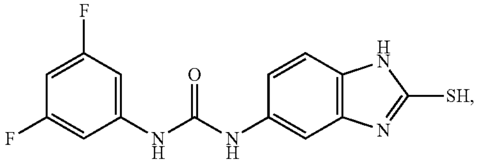

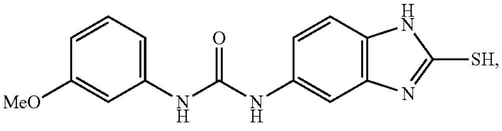

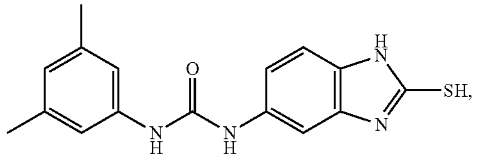

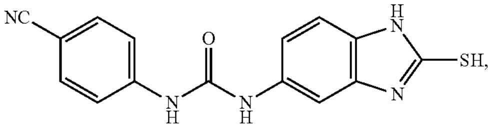

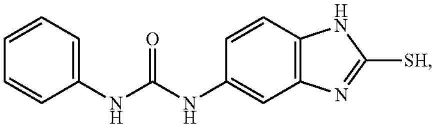

-continued

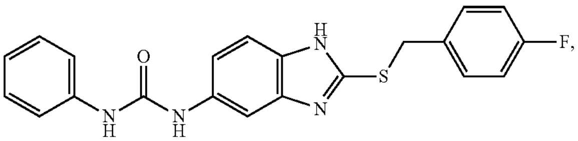

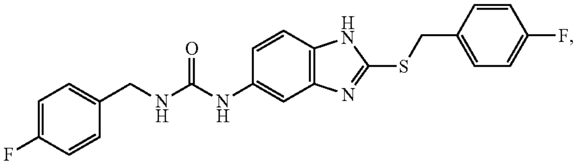

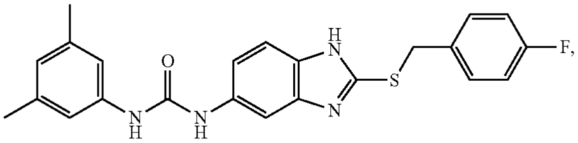

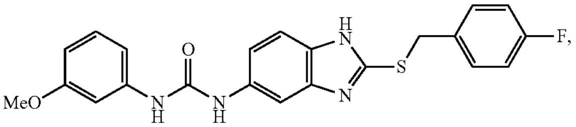

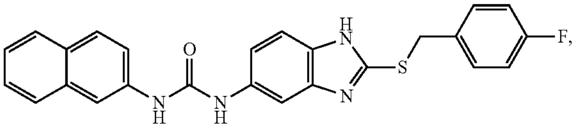

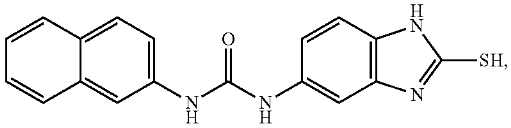

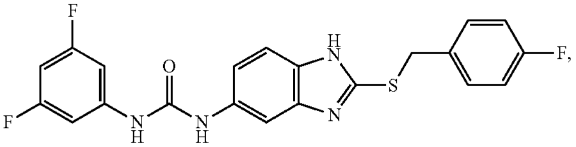

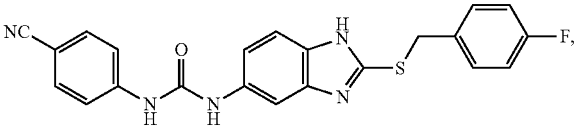

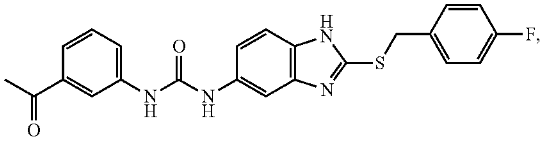

or

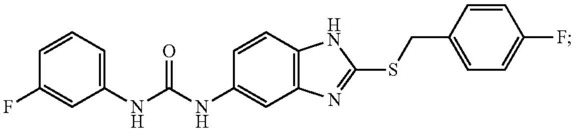

or a pharmaceutically acceptable salt and/or tautomer thereof.

7. A compound of the formula:

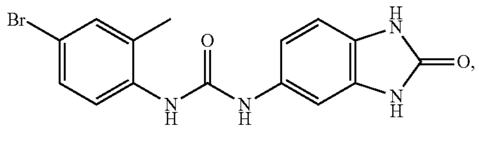

-continued
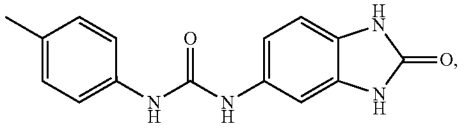
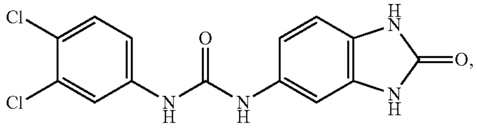
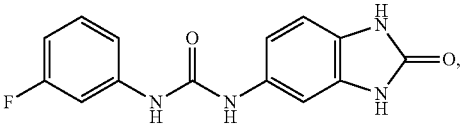
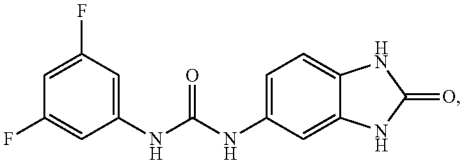
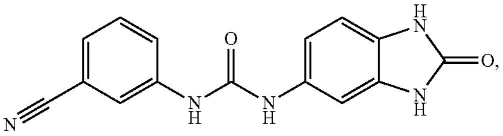
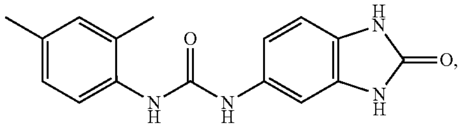
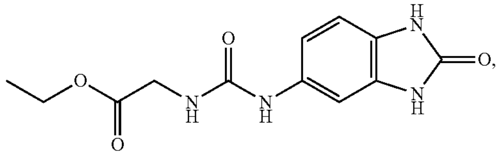
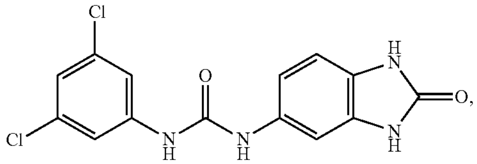
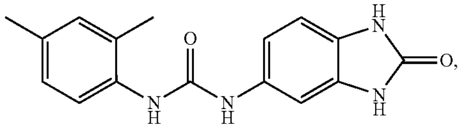
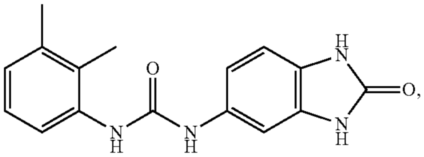
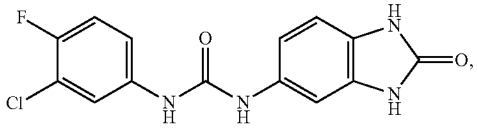
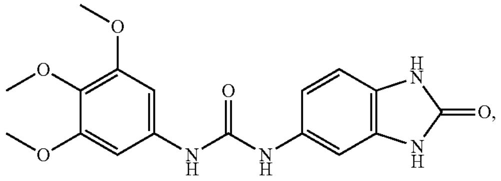
-continued
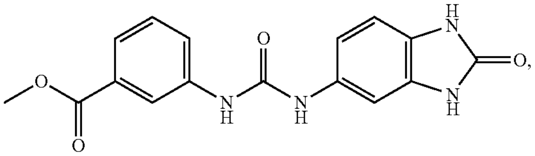
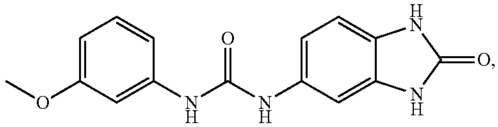
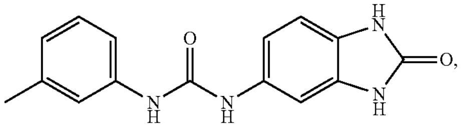
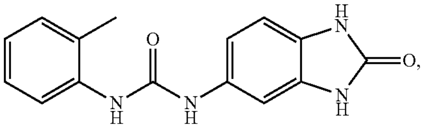
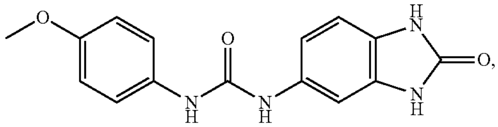
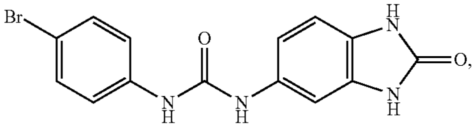
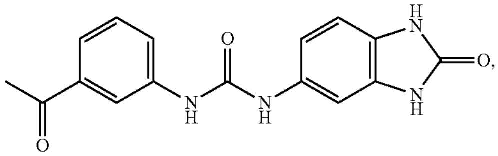
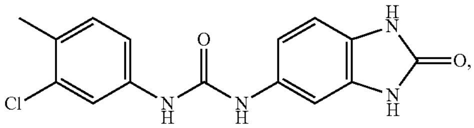
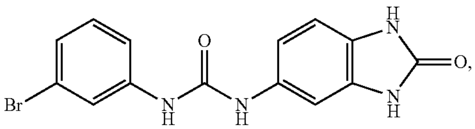
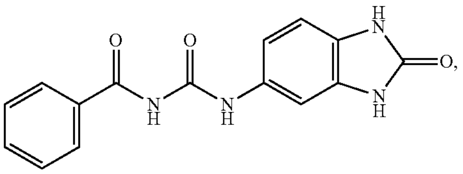
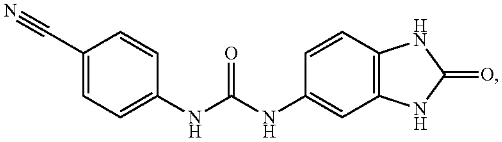
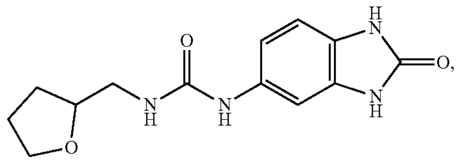

-continued
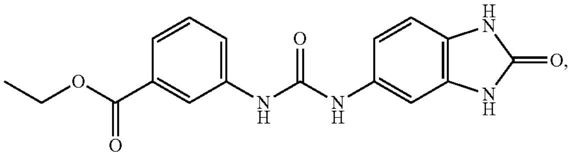
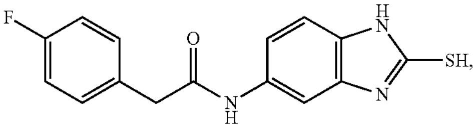
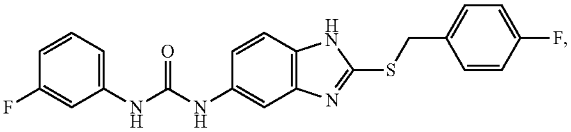
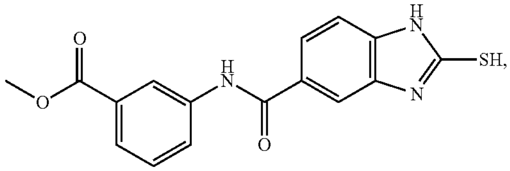
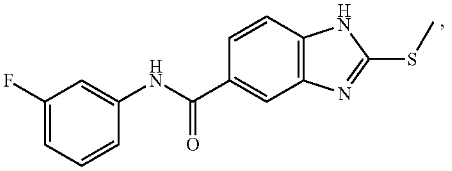
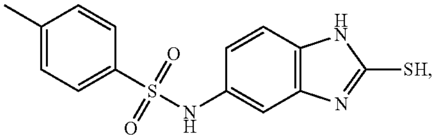
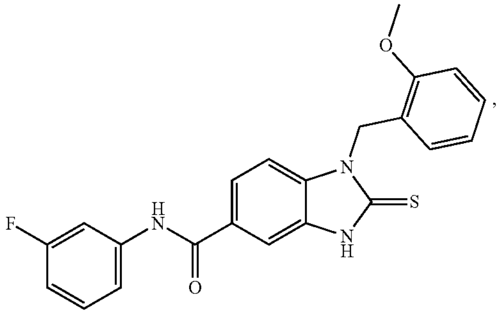
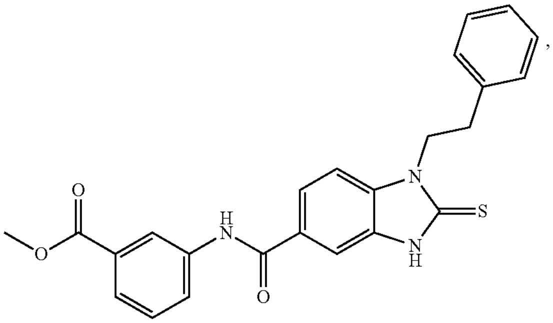
-continued
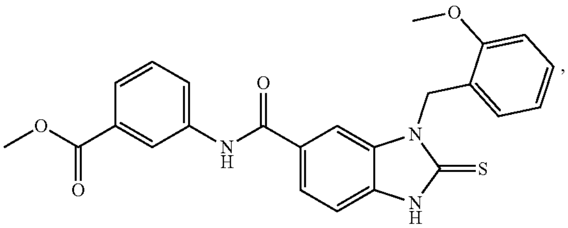
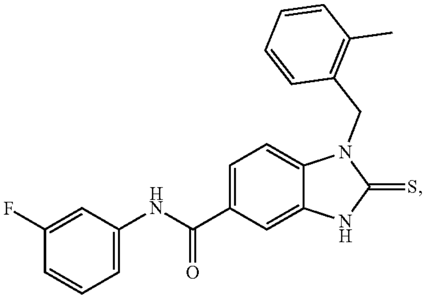
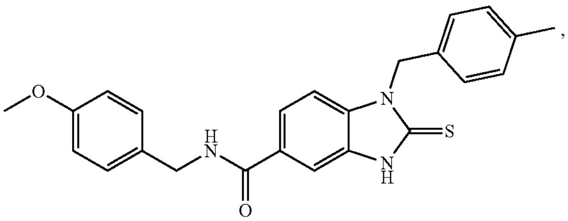
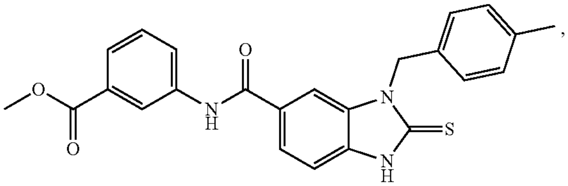
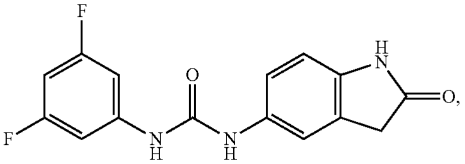
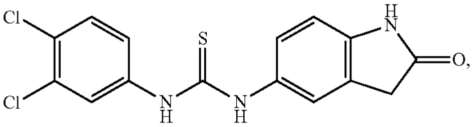
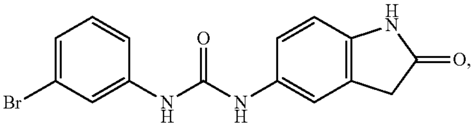
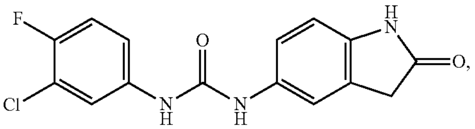
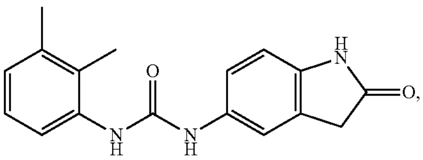

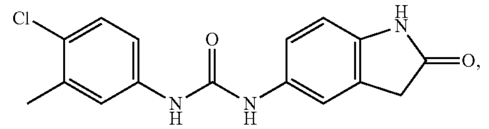
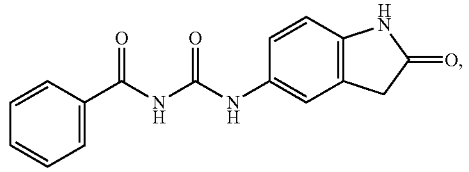
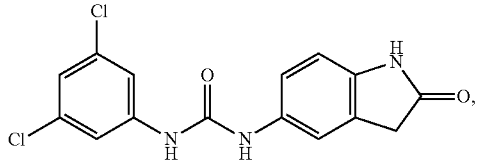
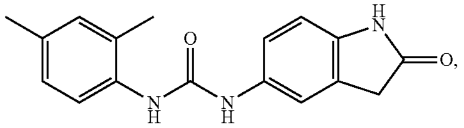
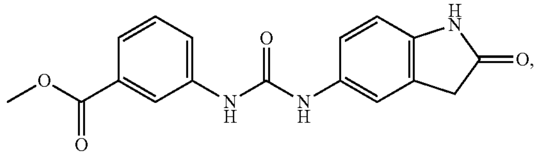
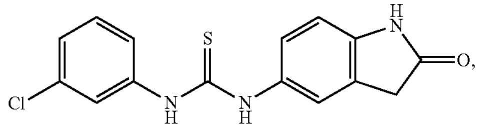
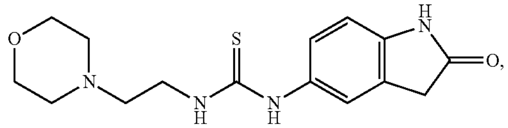
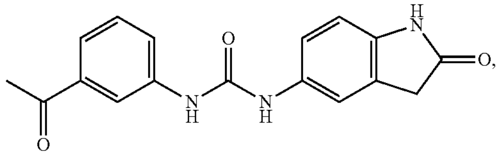
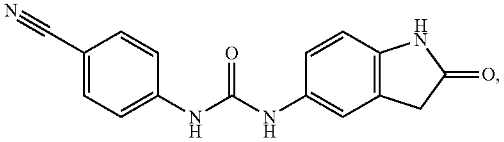
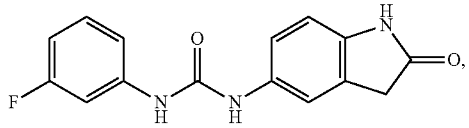
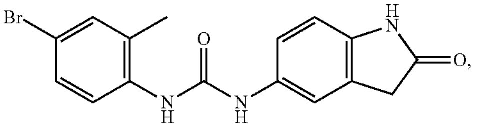
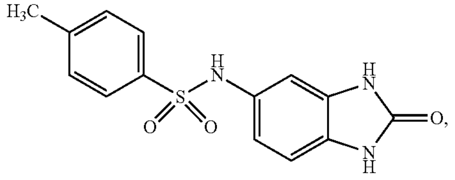
-continued
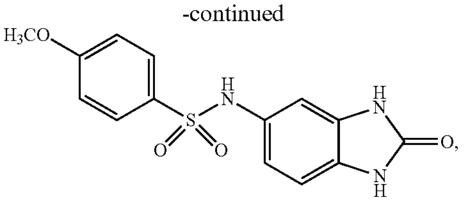
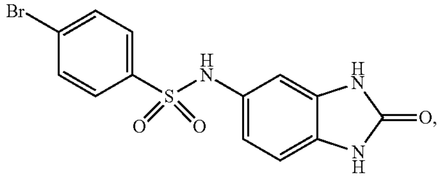
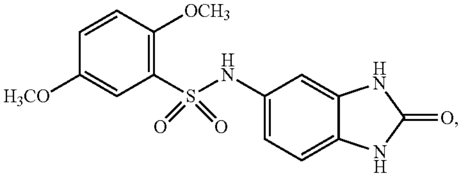
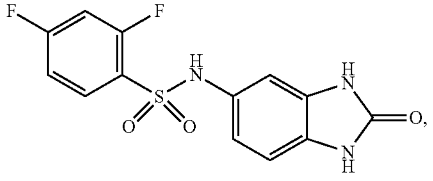
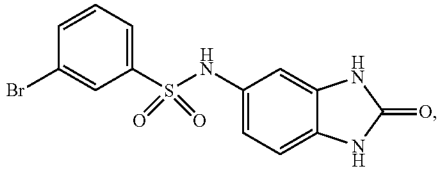
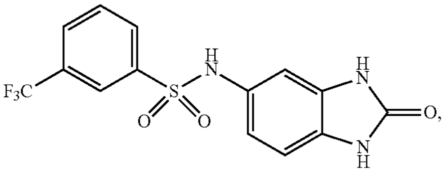
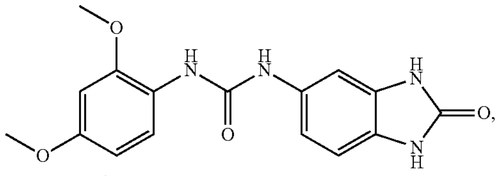
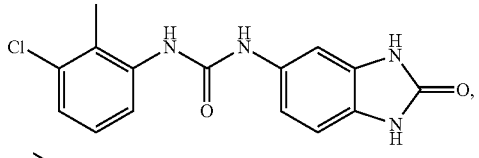
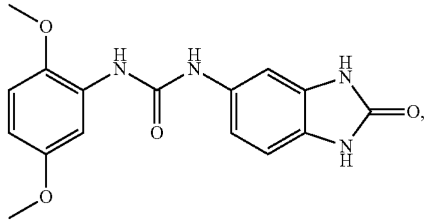
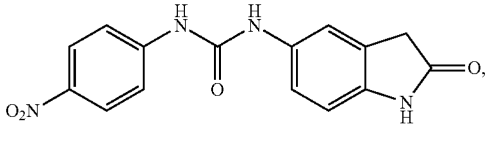

-continued
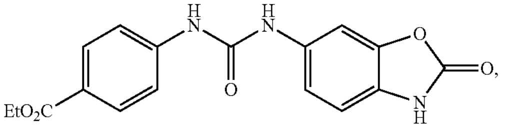
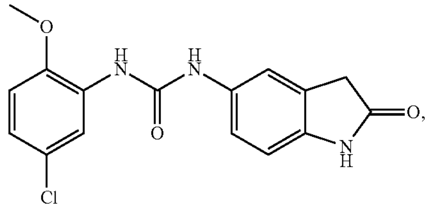
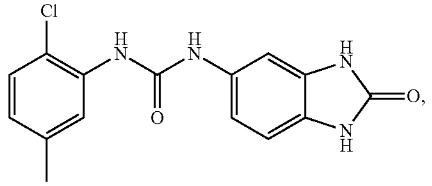
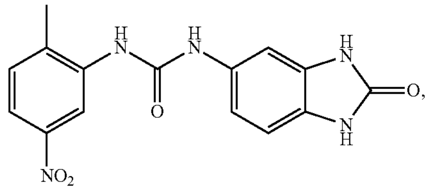
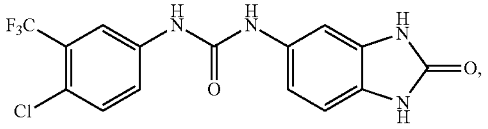
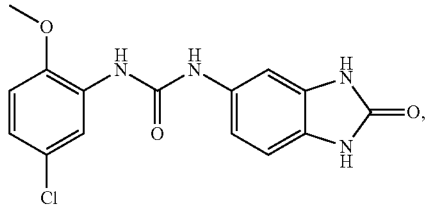
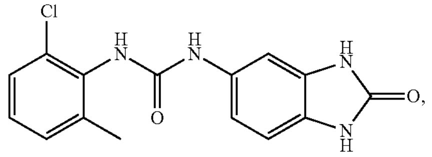
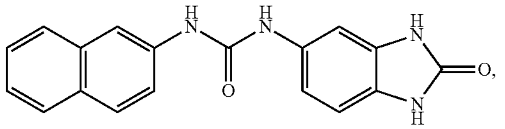
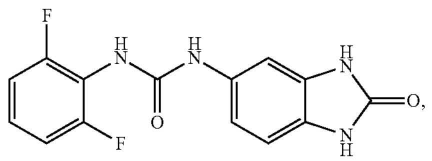
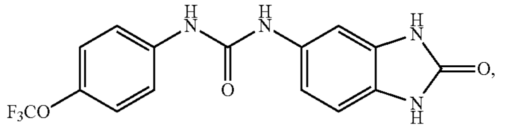
-continued
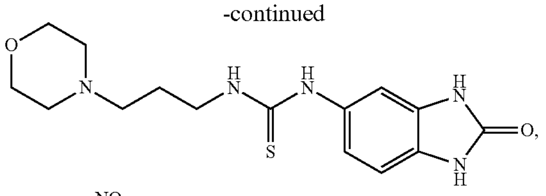
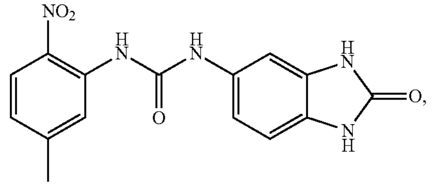
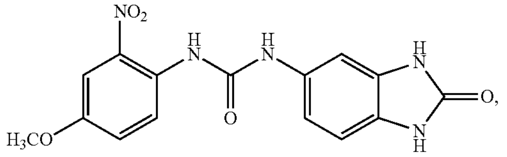
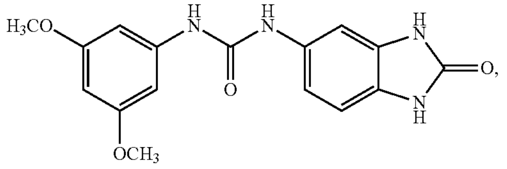
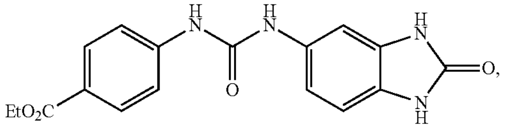
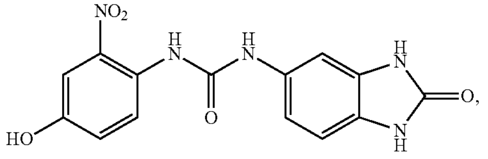
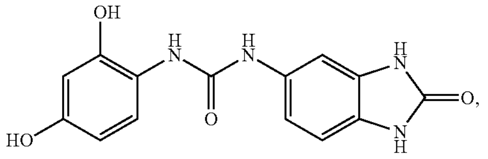
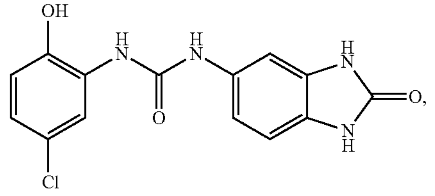
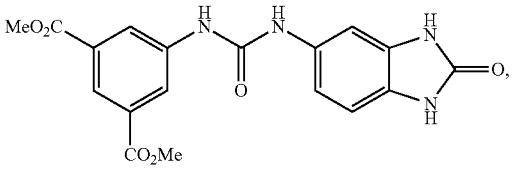
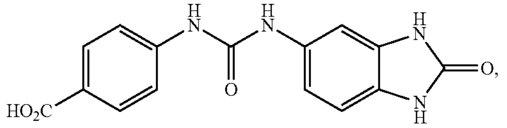
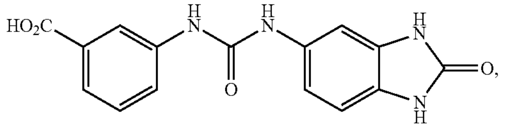

-continued
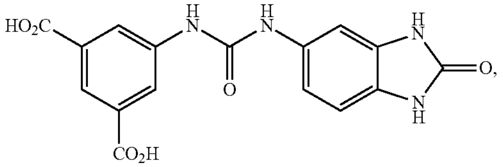
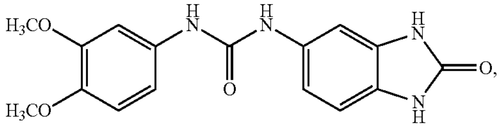
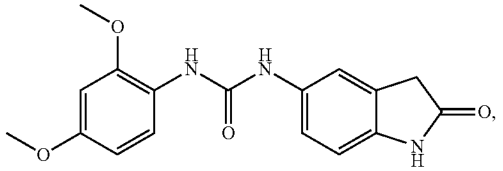
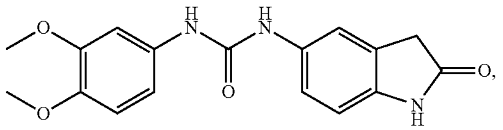
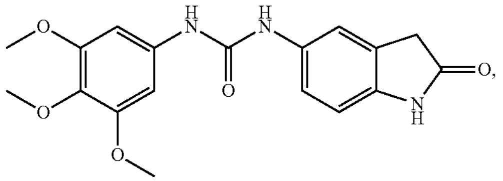
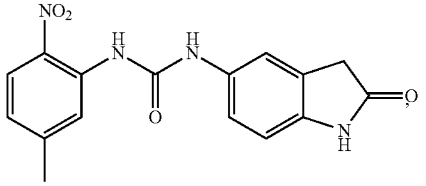
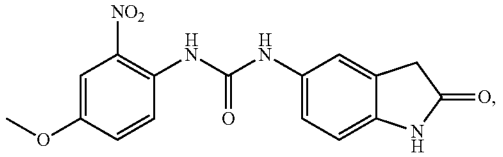
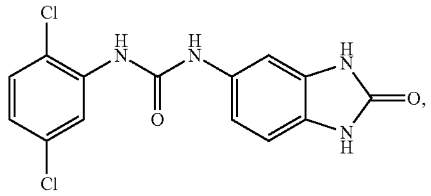
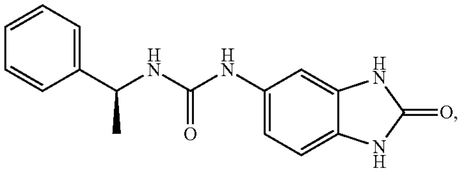
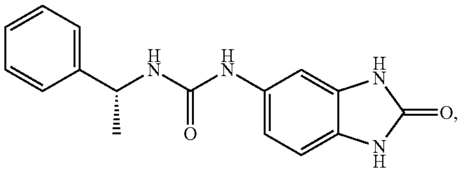
-continued
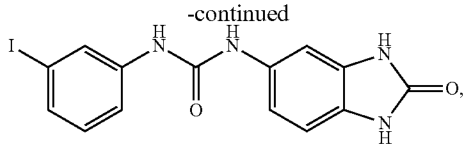
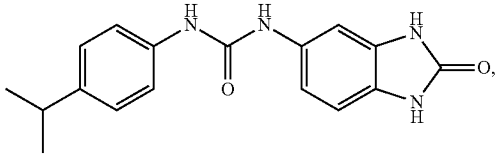
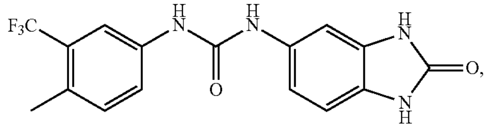
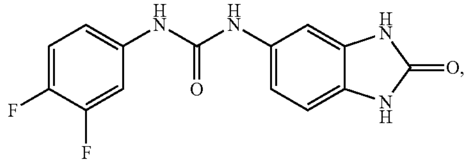
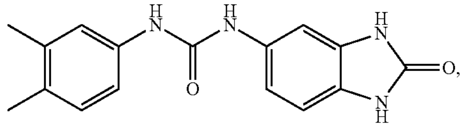
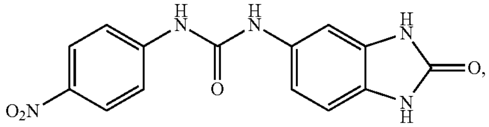
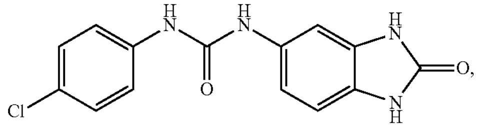
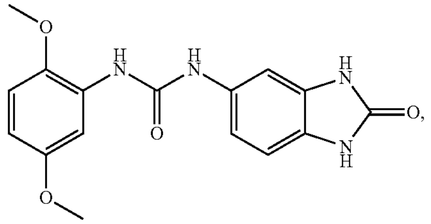
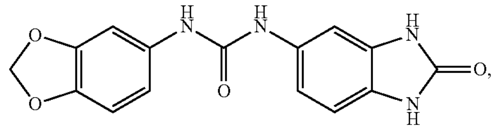
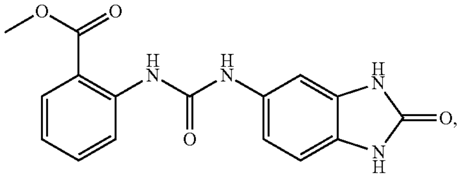
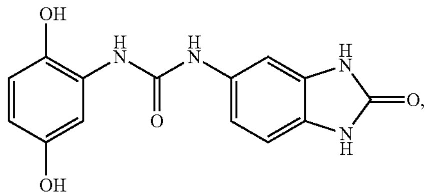

-continued

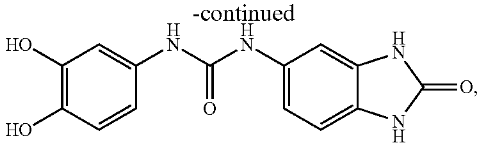

,

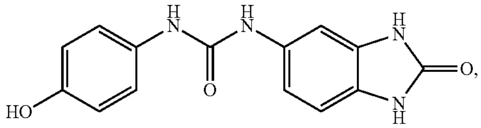

,

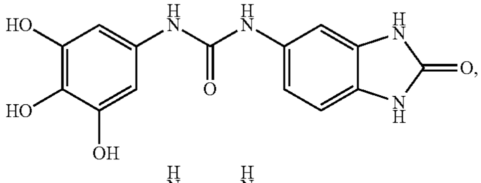

,

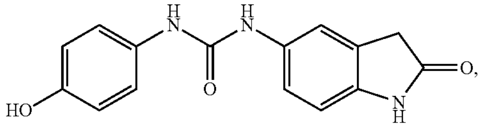

,

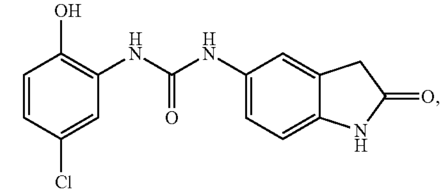

,

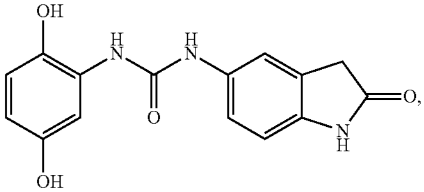

, or

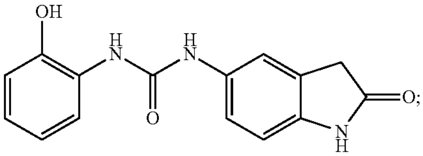

;

or a pharmaceutically acceptable salt and/or tautomer thereof.

8. A pharmaceutical composition comprising:

a) a compound of claim 1; and b) an excipient or a pharmaceutically acceptable carrier.

9. A method of treating ovarian, lung, or breast cancer in a patient in need thereof comprising administering to the patient a therapeutically effective amount of a compound of claim 1, wherein the compound stabilizes dimeric GRB2.

10. The method of claim 9, wherein the cancer is a KRAS-positive cancer.

11. The method of claim 9, wherein the cancer is triple negative breast cancer.

12. The method of claim 9, wherein the compound is a compound of the formula:

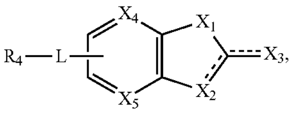

(III)

wherein:

$X_1$ is —$CH_2$—, —NH—, or —O—;

$X_2$ is —N= or —$NR_{x2}$—, wherein:

$R_{x2}$ is hydrogen; or alkyl$_{(C\leq12)}$, aralkyl$_{(C\leq12)}$, heteroaralkyl$_{(C\leq12)}$, or a substituted version of any of these groups;

$X_3$ is oxo, =S, or —$SR_{x3}$, wherein:

$R_{x3}$ is hydrogen; or alkyl$_{(C\leq12)}$, aralkyl$_{(C\leq12)}$, heteroaralkyl$_{(C\leq12)}$, or a substituted version of any of these groups;

$X_4$ and $X_5$ are each independently —CH= or —N=;

L is —NHC(O)NH—, —NHC(S)NH—, —C(O)NH—, —C(O)NHC(O)NH—, or —$S(O)_2NH$—; and $R_4$ is 1,3-benzodioxol-5-yl; or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -alkanediyl$_{(C\leq12)}$-$R_{4a}$, -arendiyl$_{(C\leq12)}$-alkoxy$_{(C\leq12)}$, or a substituted version of any of these groups, wherein:

$R_{4a}$ is carboxy; or cycloalkyl$_{(C\leq12)}$, heterocycloalkyl$_{(C\leq12)}$, —C(O)-alkoxy$_{(C\leq12)}$, or a substituted version of any of these groups;

or a pharmaceutically acceptable salt and/or tautomer thereof, wherein the compound is not

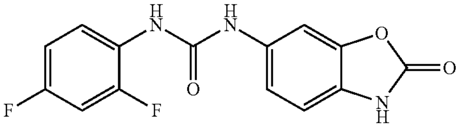

or

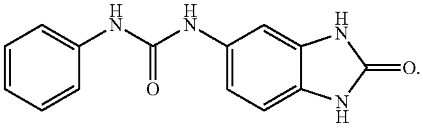

.

13. The method of claim 12, wherein the compound is further defined as:

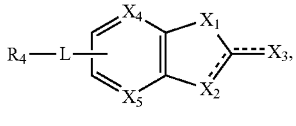

(III)

wherein:

$X_1$ is —$CH_2$—, —NH—, or —O—;

$X_2$ is —N= or —$NR_{x2}$—, wherein:

$R_{x2}$ is hydrogen; or alkyl$_{(C\leq12)}$, aralkyl$_{(C\leq12)}$, heteroaralkyl$_{(C\leq12)}$, or a substituted version of any of these groups;

$X_3$ is oxo, =S, or —$SR_{x3}$, wherein:

$R_{x3}$ is hydrogen; or alkyl$_{(C\leq12)}$, aralkyl$_{(C\leq12)}$, heteroaralkyl$_{(C\leq12)}$, or a substituted version of any of these groups;

$X_4$ and $X_5$ are each independently —CH= or —N=;

L is —NHC(O)NH—, —NHC(S)NH—, —C(O)NH—, —C(O)NHC(O)NH—, or —$S(O)_2NH$—; and $R_4$ is 1,3-benzodioxol-5-yl; or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -alkanediyl$_{(C\leq12)}$-$R_{4a}$, or a substituted version of any of these groups, wherein:

$R_{4a}$ is carboxy; or cycloalkyl$_{(C\leq 12)}$, heterocycloalkyl$_{(C\leq 12)}$, —C(O)-alkoxy$_{(C\leq 12)}$, or a substituted version of any of these groups;

or a pharmaceutically acceptable salt and/or tautomer thereof.

14. The method of claim 13, wherein the compound is further defined as:

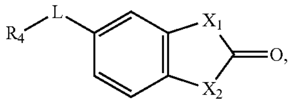

(VI)

wherein:

$X_1$ is —$CH_2$—, —NH—, or —O—;

$X_2$ is —$NR_{x2}$—, wherein:

$R_{x2}$ is hydrogen; or alkyl$_{(C\leq 12)}$, aralkyl$_{(C\leq 12)}$, heteroaralkyl$_{(C\leq 12)}$, or a substituted version of any of these groups;

L is —NHC(O)NH—, —NHC(S)NH—, —C(O)NH—, —C(O)NHC(O)NH—, or —$S(O)_2NH$—; and $R_4$ is 1,3-benzodioxol-5-yl; or alkyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, -alkanediyl$_{(C\leq 12)}$-$R_{4a}$, or a substituted version of any of these groups, wherein:

$R_{4a}$ is carboxy; or cycloalkyl$_{(C\leq 12)}$, heterocycloalkyl$_{(C\leq 12)}$, —C(O)-alkoxy$_{(C\leq 12)}$, or a substituted version of any of these groups;

or a pharmaceutically acceptable salt and/or tautomer thereof.

15. The method of claim 9, wherein the compound is further defined as:

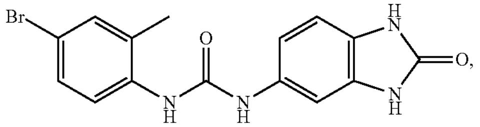

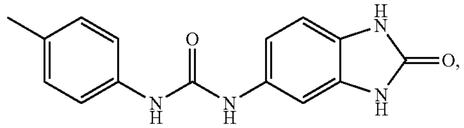

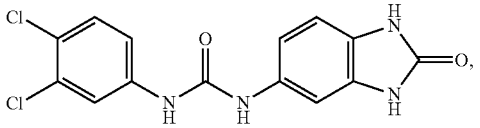

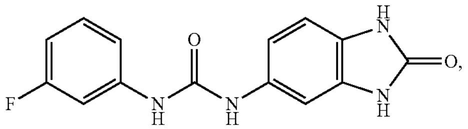

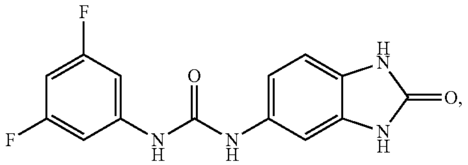

-continued

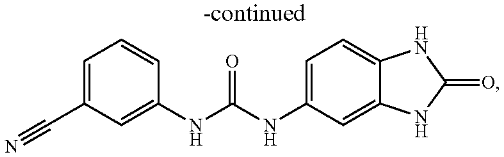

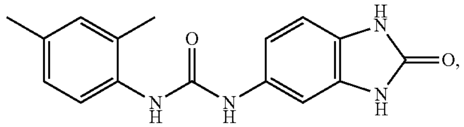

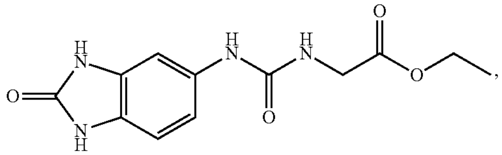

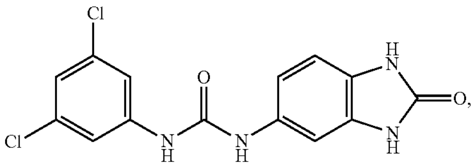

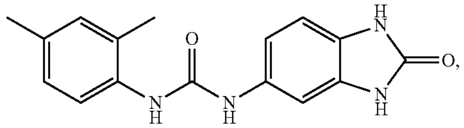

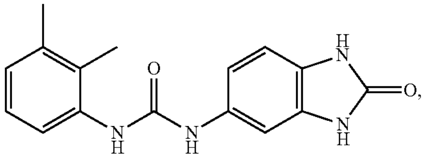

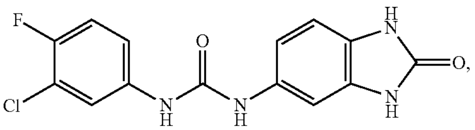

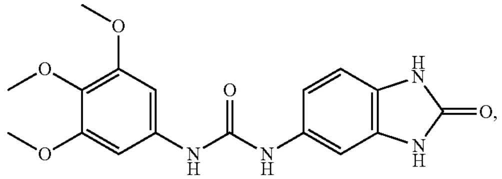

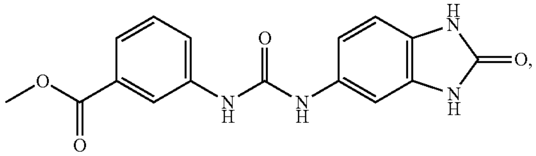

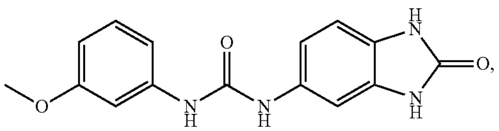

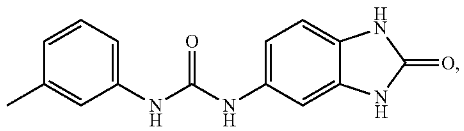

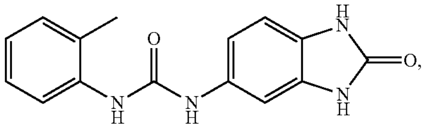

-continued
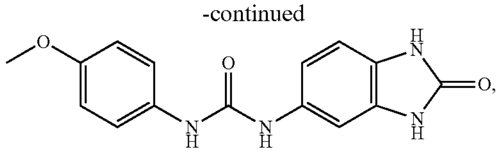
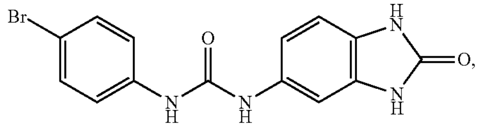
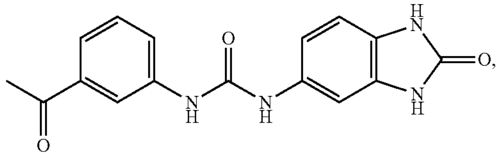
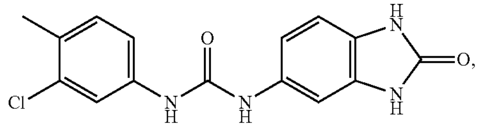
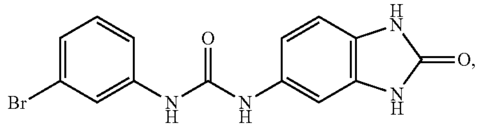
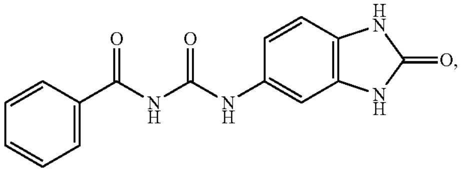
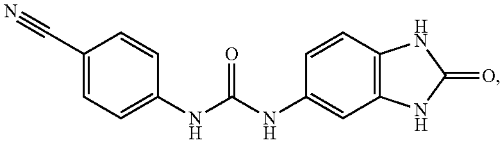
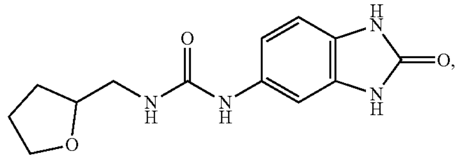
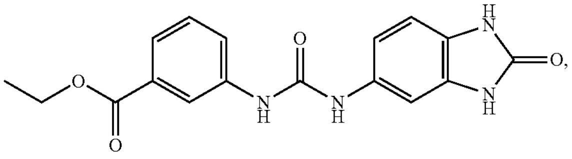
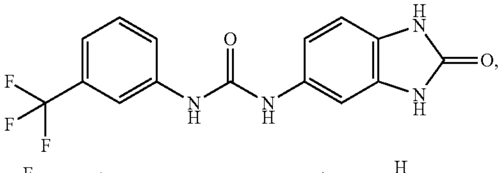
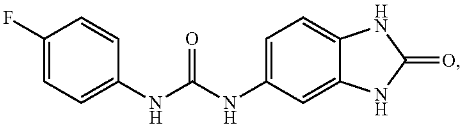
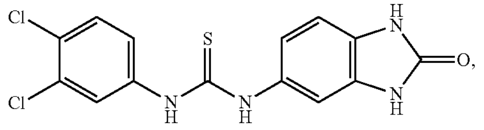
-continued
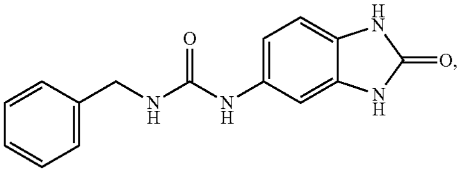
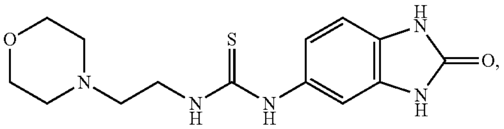
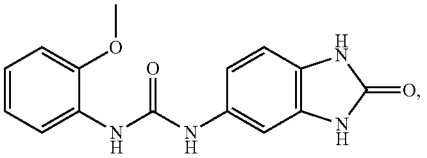
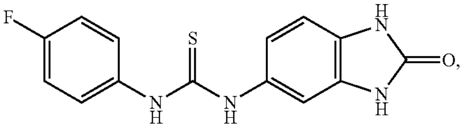
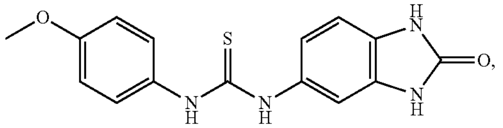
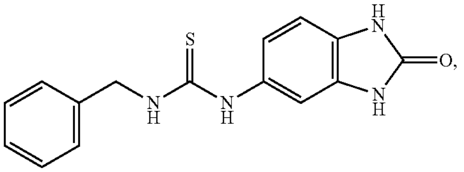
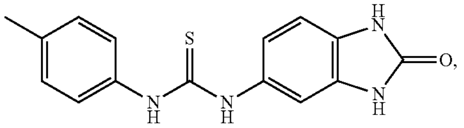
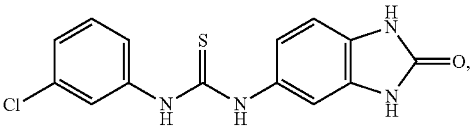
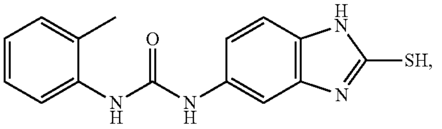
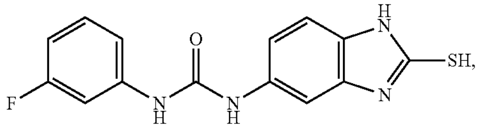
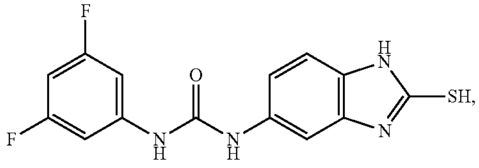
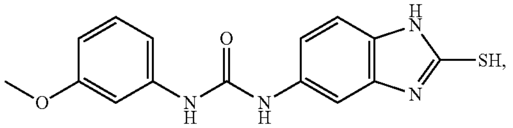

-continued
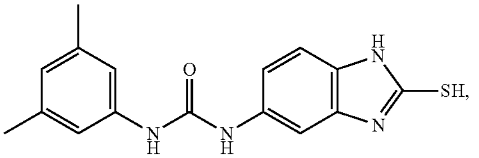
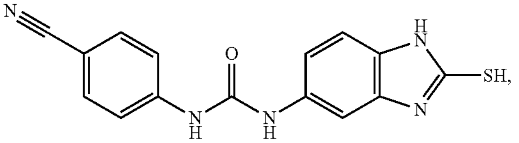
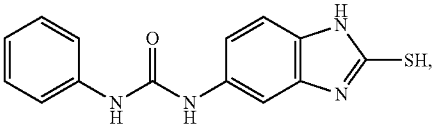
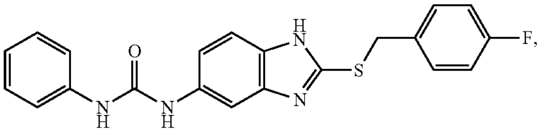
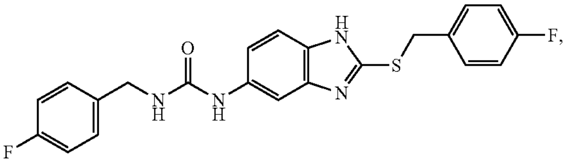
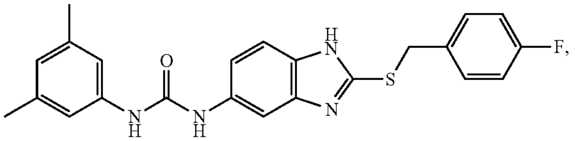
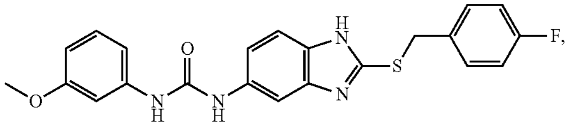
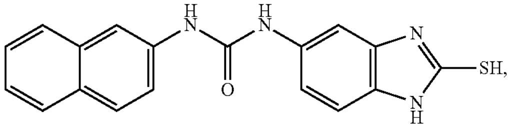
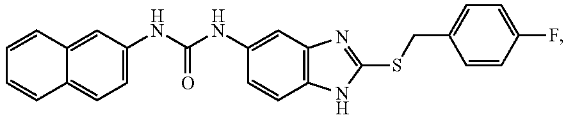
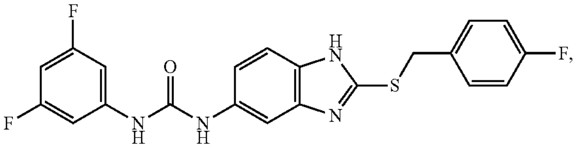
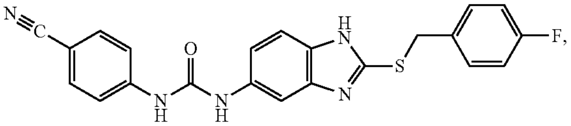
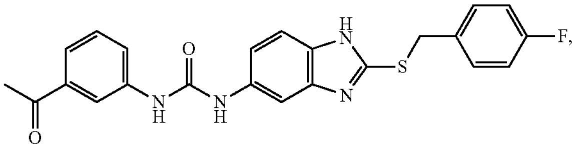
-continued
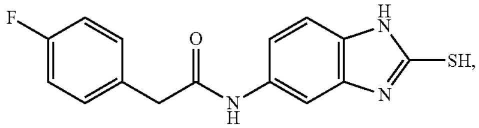
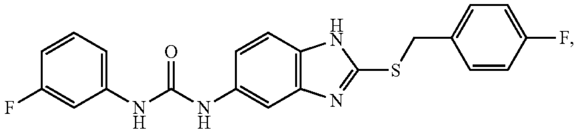
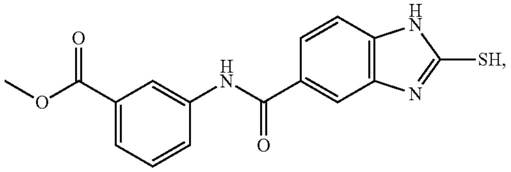
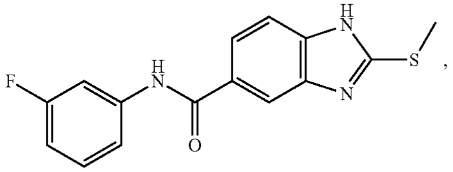
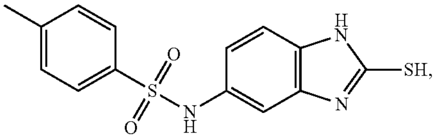
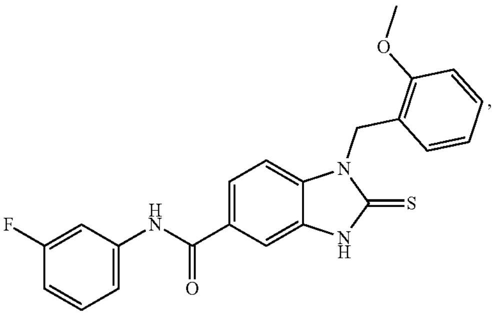
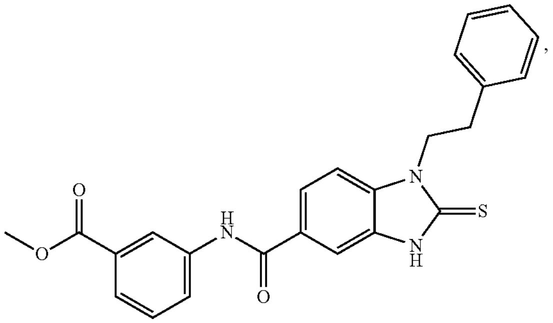
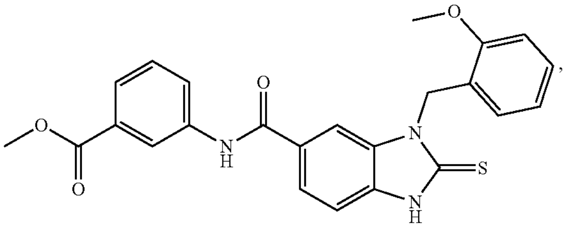

-continued
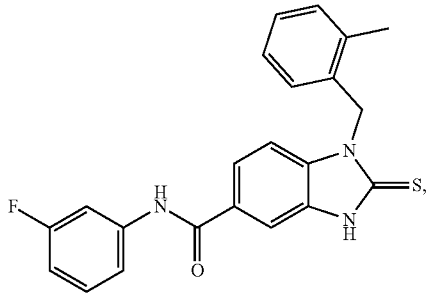,
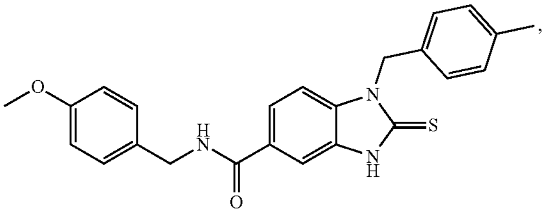,
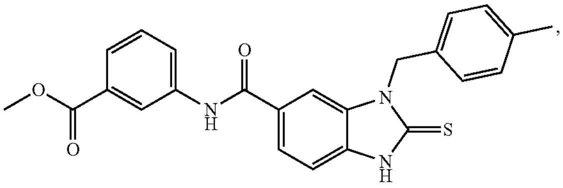,
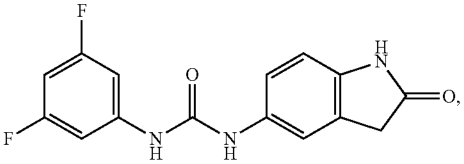,
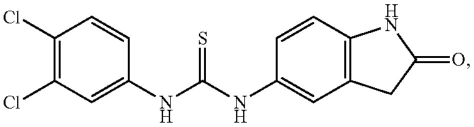,
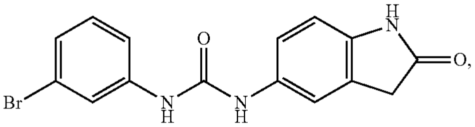,
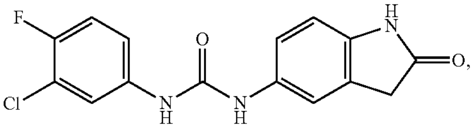,
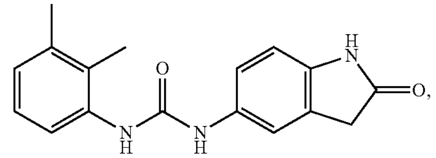,
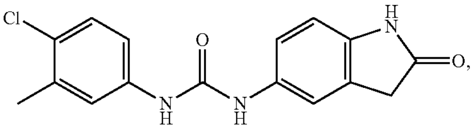,
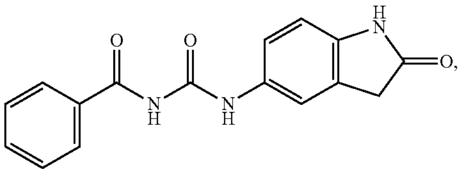,
-continued
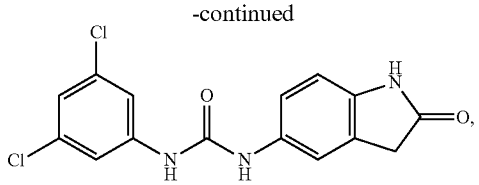,
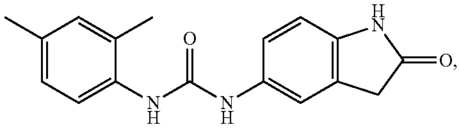,
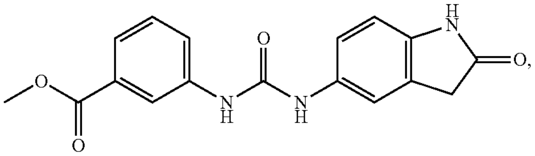,
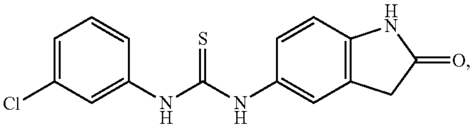,
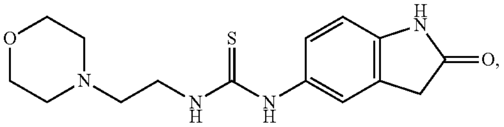,
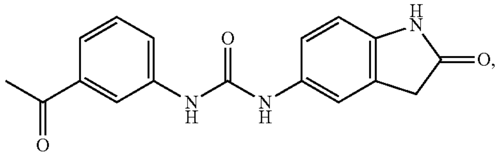,
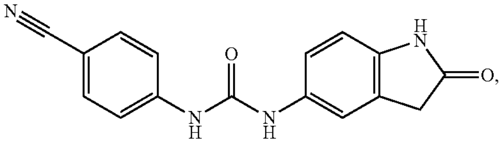,
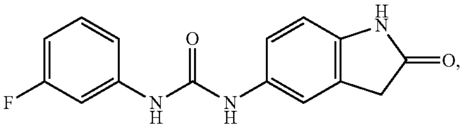,
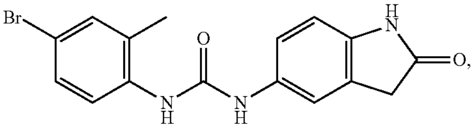,
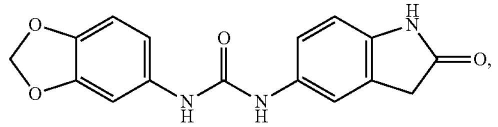,
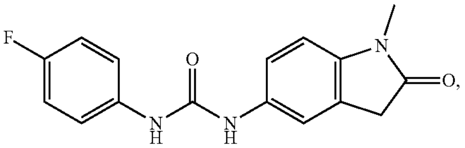,
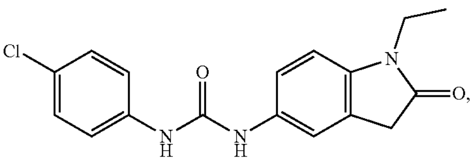, -continued
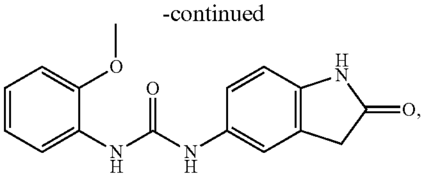
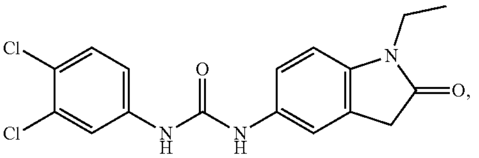
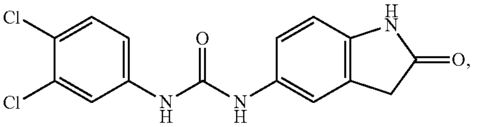
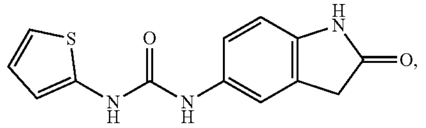
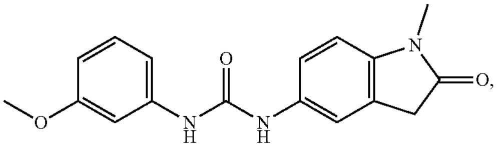
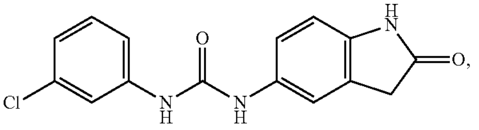
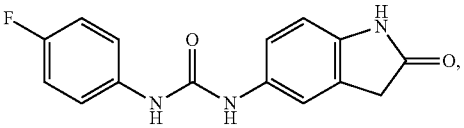
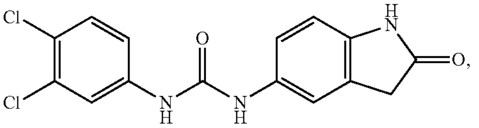
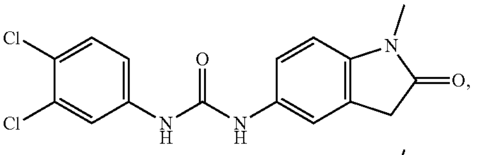
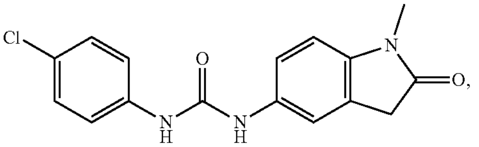
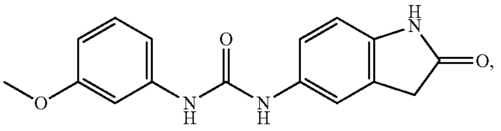
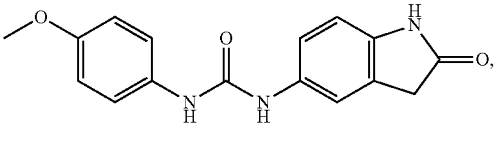
-continued
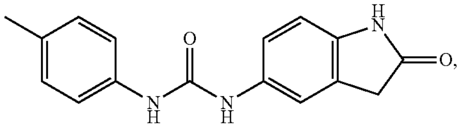
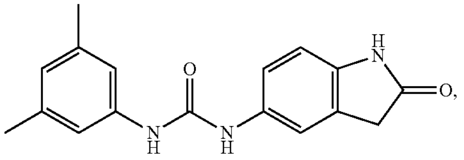
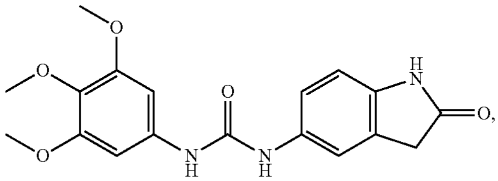
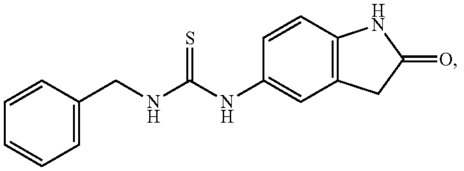
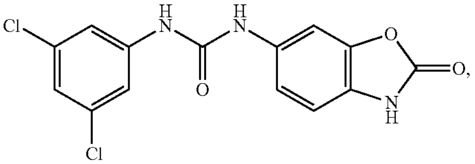
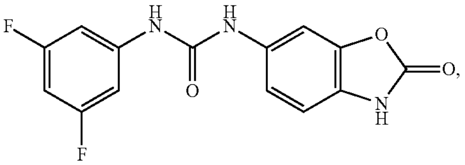
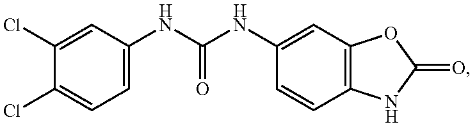
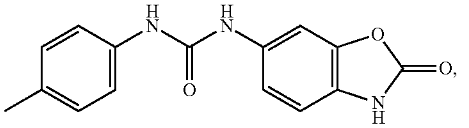
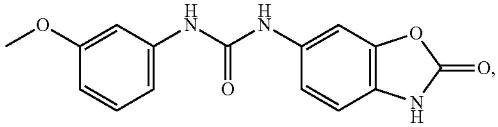
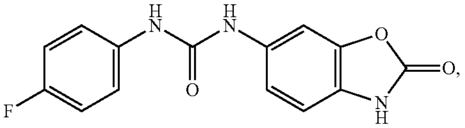
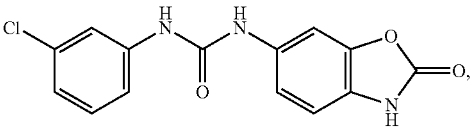

-continued
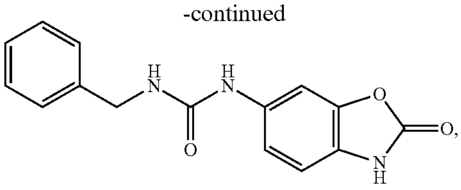,
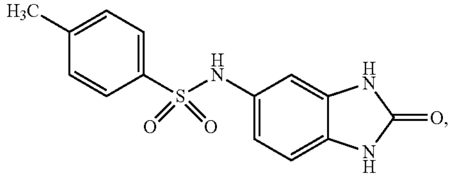,
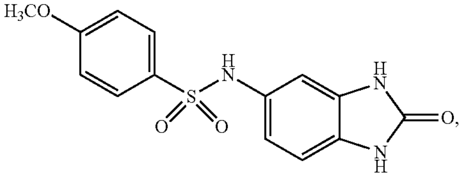,
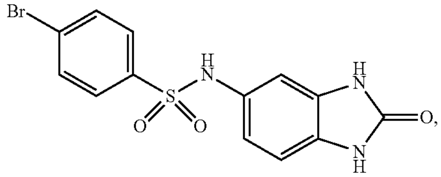,
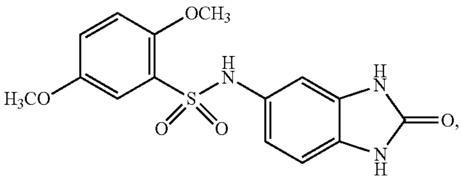,
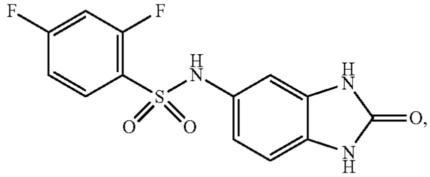,
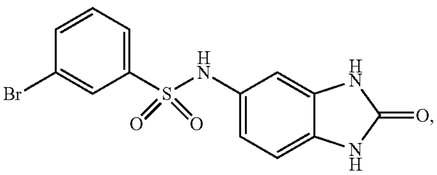,
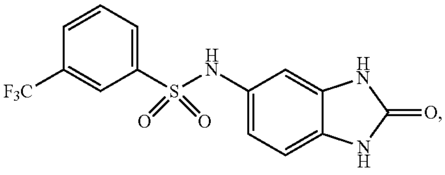,
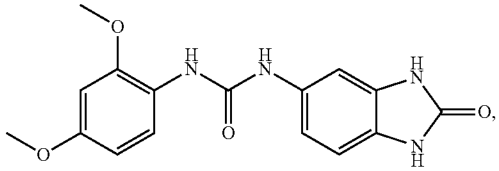,
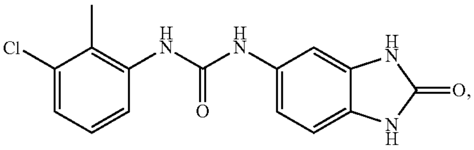,
-continued
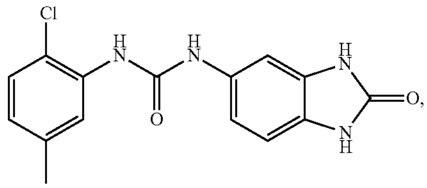,
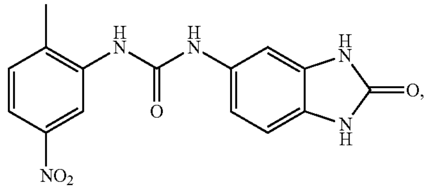,
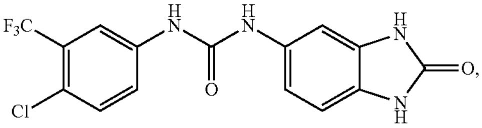,
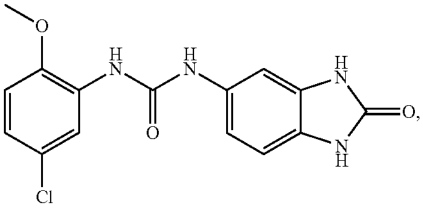,
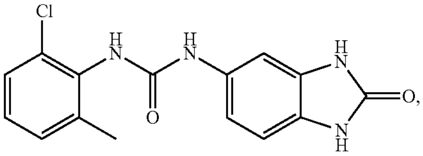,
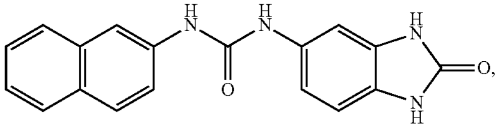,
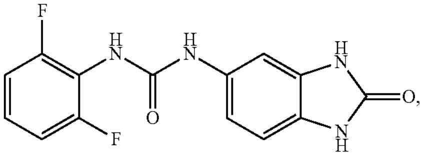,
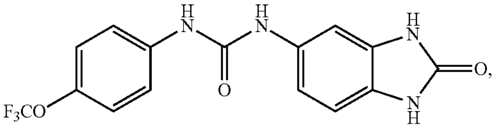,
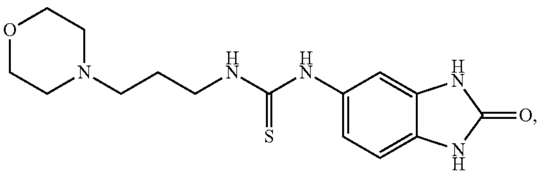,
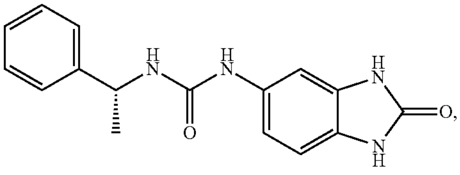, -continued
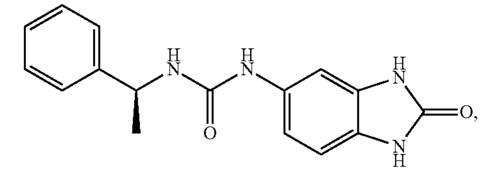
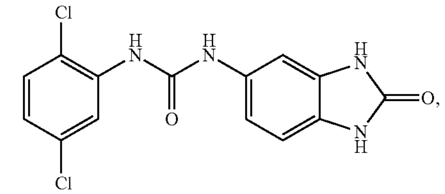
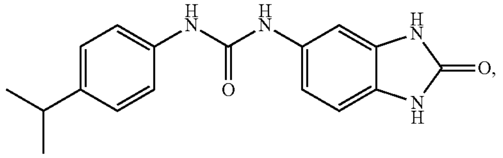
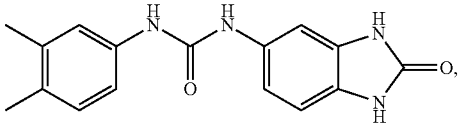
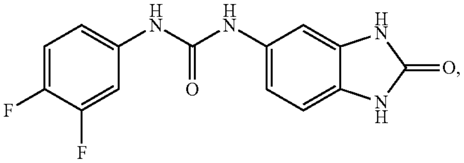
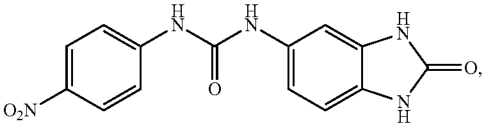
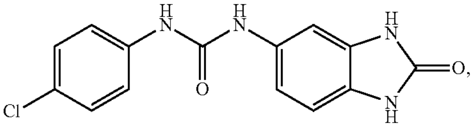
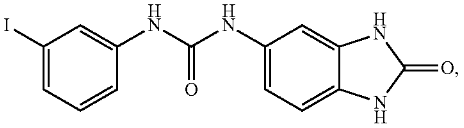
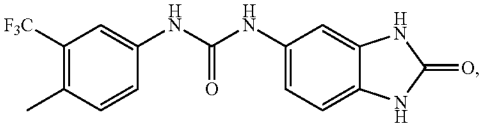
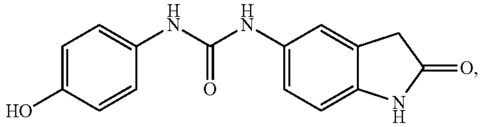
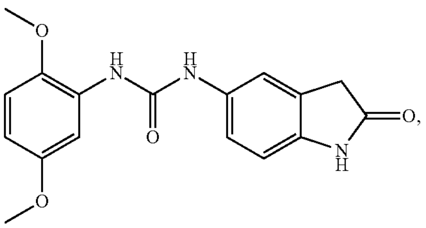
-continued
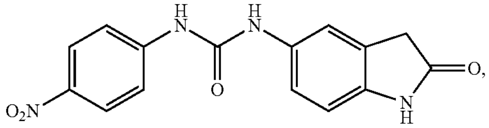
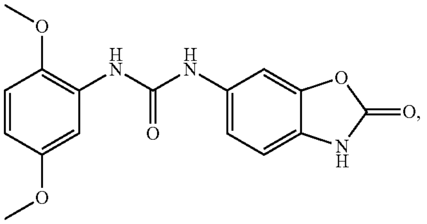
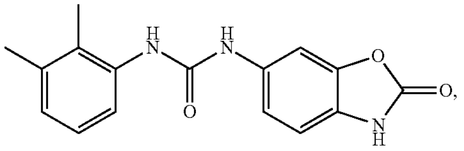
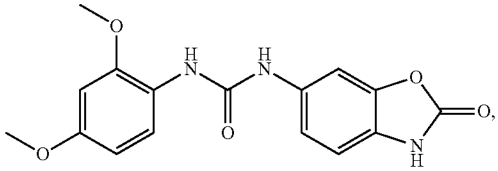
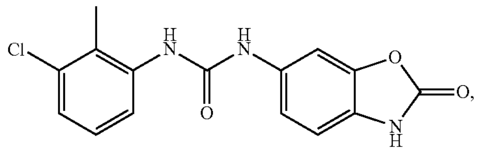
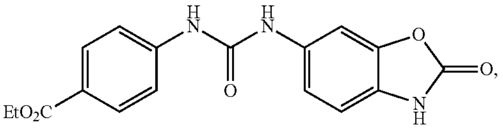
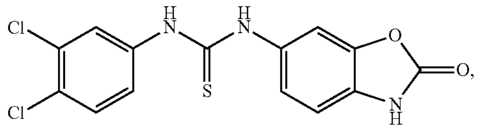
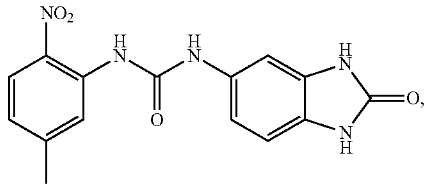
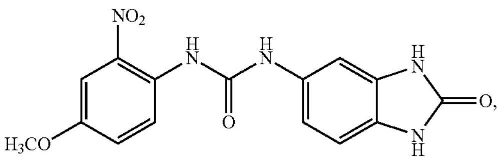
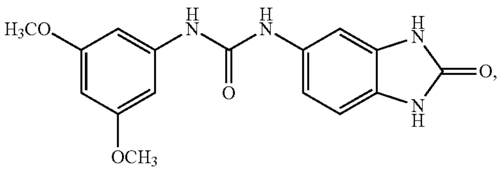

-continued
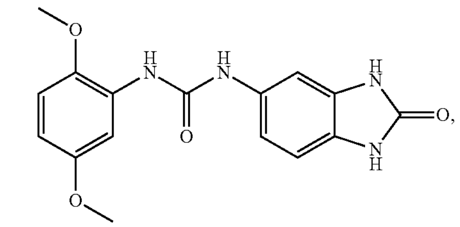
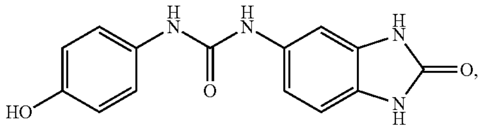
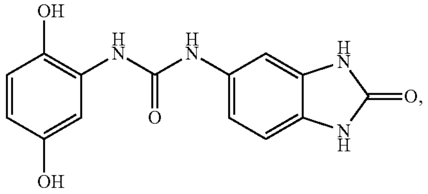
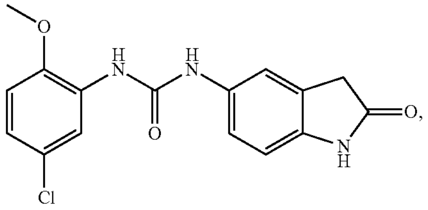
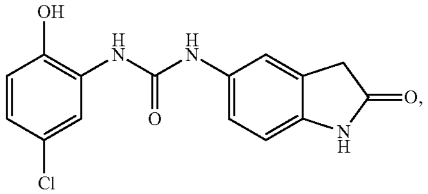
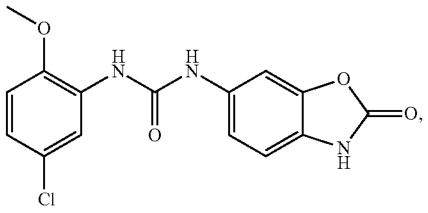
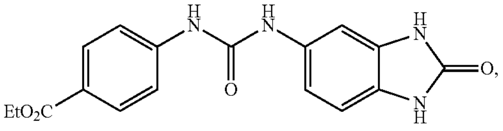
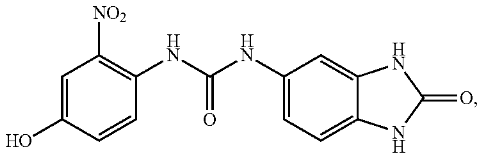
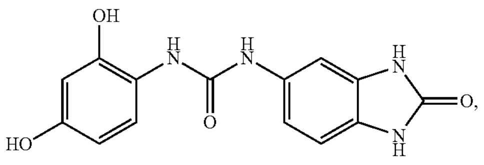
-continued
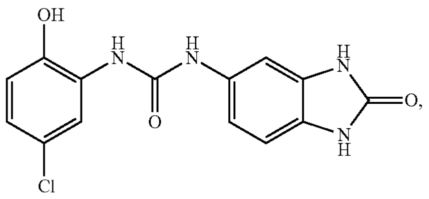
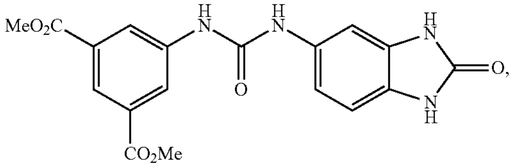
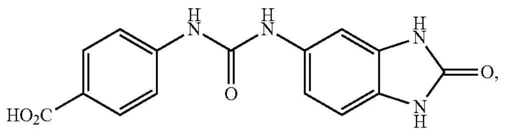
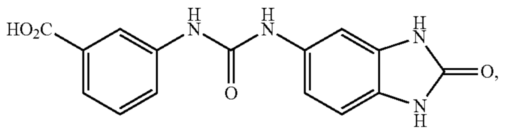
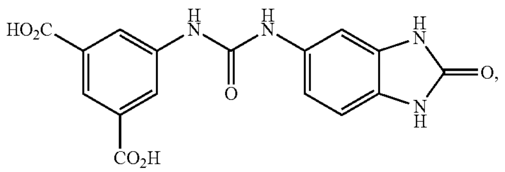
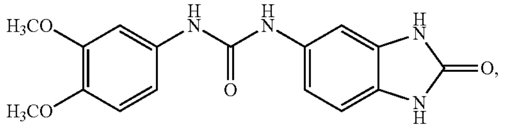
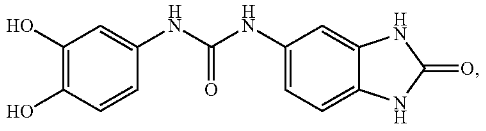
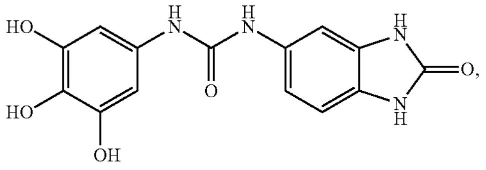
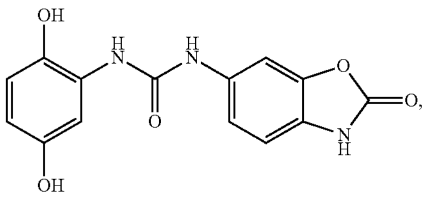
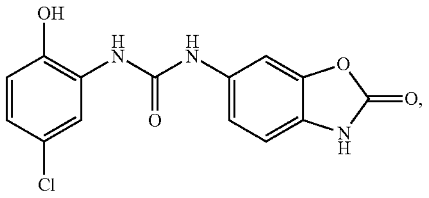

-continued
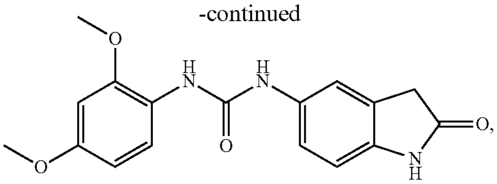
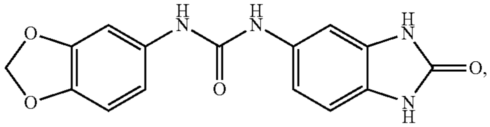
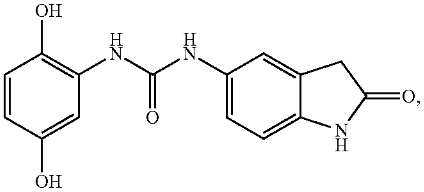
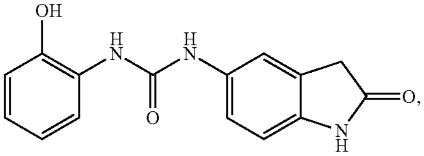
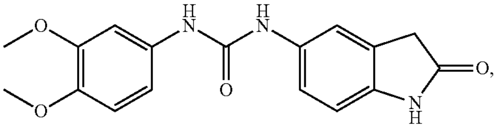
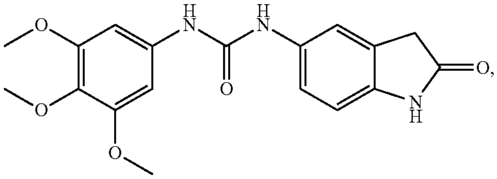
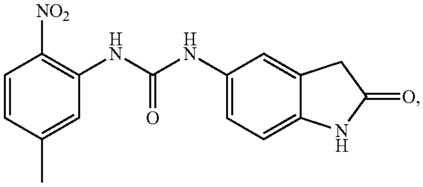
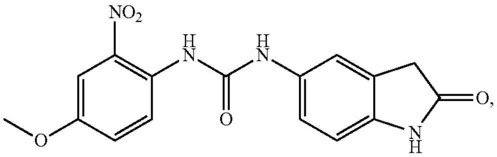
or
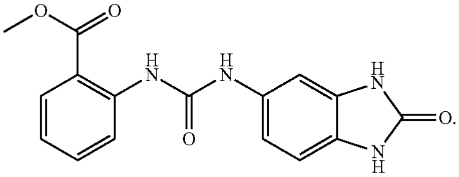
16. The method of claim 9, wherein the compound is further defined as a compound of claim 1.
* * * * *